US008247205B2

(12) United States Patent
Noel et al.

(10) Patent No.: US 8,247,205 B2
(45) Date of Patent: Aug. 21, 2012

(54) CHALCONE ISOMERASE POLYPEPTIDES AND CRYSTALS THEREOF

(75) Inventors: Joseph P Noel, San Diego, CA (US); Joseph Jez, Hayward, CA (US); Marianne E. Bowman, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 12/875,952

(22) Filed: Sep. 3, 2010

(65) Prior Publication Data

US 2011/0020895 A1    Jan. 27, 2011

Related U.S. Application Data

(62) Division of application No. 10/344,051, filed as application No. PCT/US01/27027 on Aug. 29, 2001, now Pat. No. 7,792,645.

(60) Provisional application No. 60/229,277, filed on Aug. 30, 2000.

(51) Int. Cl.
   *C12N 9/90* (2006.01)
(52) U.S. Cl. ........................................ 435/233
(58) Field of Classification Search ........................ None
   See application file for complete search history.

(56) References Cited

U.S. PATENT DOCUMENTS

| 5,790,421 | A  | 8/1998 | Osslund |
| 6,390,821 | B1 | 5/2002 | Shokat |
| 2003/0096387 | A1 | 5/2003 | Noel et al. |
| 2008/0201123 | A1 | 8/2008 | Cosgrove |

FOREIGN PATENT DOCUMENTS

| WO | WO-99/09148 | 2/1999 |
| WO | WO-00/09744 | 2/2000 |
| WO | WO-00/47763 | 8/2000 |
| WO | WO-01/07579 A2 | 2/2001 |

OTHER PUBLICATIONS

Protein Information Resource Accession No. S44371, Jan. 1995, 2 pages.*
Amersham Affinity Chromatography Handbook, 2002, pp. 42-53.*
Amersham Protein Purification Handbook, Oct. 2001, p. 59.*
Bednar et al., Biochemistry 29:3684-3690, 1990.*
Ford et al., Prot. Exp. Purif. 2:95-107, 1991.*
Abrahams & Leslie, "Methods Used in the Structure Determination of Bovine Mitochondrial F1 ATPase" Acta Crystallogr., D52:30-42, 1996.
Altschul et al., "Basic Local Alignment Search Tool" V J.Mol.Biol., 215:403-410, 1990.
Altschul et al., "Gapped BLAST and PSI-BLAST: a new generation of protein database search programs" Nuc. Acids Res., 25:3389-3402, 1977.
Bednar and Hadcock, "Purification and Characterization of Chalcone Isomerase from Soybeans" J. Biol. Chem., 263: 9582-9588, 1988.
Bednar et al., "Chemical Modification of Chalcone Isomerase by Mercurials and Tetrathionate. Evidence for a Single Cysteine Residue in the Active Site" J.Biol.Chem., 264:14272-14276, 1989.
Böhm, "The computer program LUDI: A new method for the De Novo design of enzyme inhibitors." J.Comp. Aid. Molec. Design, 6:61-78, 1992.
Brunger et al., "Crystallography & NMR System: A New Software Suite for Macromolecular Structure Determination" Acta Crystallogr., D54:905-921, 1998.
Cohen et al., "Molecular modeling software and methods for medicinal chemistry." J. Med. Chem., 33:883-894, 1990.
Davis, et al, Production of yellow color in flowers: redirection of flavonoid biosynthesis in petunia, Plant Journal, (1998), 13(2):159-266.
De la Fortelle & Bricogne, "Maximum-Likelihood Heavy-Atom Parameter Refinement for Multiple Isomorphous Replacement and Multiwavelength Anomalous Diffraction Methods" Methods Enzymol., 276:472-494, 1997.
Dixon et al., "Comparative Biochemistry of Chalcone Isomerases" Phytochemistry, 27:2801-2808, 1988.
Ferrer et al., "Structure of chalcone synthase and the molecular basis of plant polyketide biosynthesis." Nature Structural Biology, : 775-784, 1999.
Fersht, Enzyme Structure and Mechanism, 2nd Ed., W. H. Freeman & Co., New York (1985), p. 310-346.
GenBank Accession No. P28012, Jul. 1999.
Gilliland and Ladner, Crystallization of biological macromolecules for X-ray diffraction studies, Curr.Opin. Struct. Biol., 6:595-603, 1996.
Gonnet et al., "Exhaustive Matching of the Entire Protein Sequence Database" Science, 256:1443-1445, 1992.
Goodford, "A Computational Procedure for Determining Energetically Favorable Binding Sites on Biologically Important Macromolecules" J. Mol. Chem., 28:849-857, 1985.
Goodsell and Olsen, "Automated Docking of Substrates to Proteins by Simulated Annealing" Proteins: Structure, Function and Genetics, 8:195-202, 1990.
Henikoff & Henikoff, "Amino acid substitution matrices from protein blocks" Proc. Nat. Acad. Sci. USA, 89:10915, 1989.
International Search Report for application PCT/US01/27027, 3 pages, Apr. 7, 2002.
Jez et al., "Chalcone isomerase." Database PDB Online!, May 8, 2000, XP002197828, 2 pages.
Jez et al., "Dissection of malonyl-coenzyme a decarboxylation from plyketide formation in the reaction mechanism of a plant polyketide synthase." Biochemistry, 39:890-902, 2000.
Jez et al., "Structure and mechanism of the evolutionarily unique plant enzyme chalcone isomerase." Nature Structural Biology, 7:786-791, 2000.

(Continued)

*Primary Examiner* — David J Steadman
(74) *Attorney, Agent, or Firm* — Foley & Lardner LLP; Stephen E. Reiter

(57) ABSTRACT

This disclosure provides crystalline flavonoid or flavanone isomerases, isolated non-native isomerase having the structural coordinates of said crystalline isomerase, and nucleic acids encoding such non-native isomerase. Also disclosed are methods of predicting the activity and/or substrate specificity of a putative isomerase, methods of identifying potential ismerase substrates, and methods of identifying potential isomerase inhibitors.

10 Claims, 6 Drawing Sheets

OTHER PUBLICATIONS

Karlin & Altschul, "Applications and statistics for multiple high-scoring segments in molecular sequences" Proc. Nat. Acad. Sci. USA, 90:5873, 1993.

Ke and Doudna, Crystallization of RNA and RNA-protein complexes, Methods, 34:408-414, 2004.

Kierzak, et al, Biophys Chem, (2001), 91:1-20.

Kuntz et al., "A Geometric Approach to Macromolecule-Ligand Interactions" J. Mol. Biol., 161:269-288, 1982.

Laskowski et al., "PROCHECK: a program to check the stereochemical quality of protein structures." J.Appl. Crystallogr., 26 :283-291, 1993.

Martin et al., "3D Database Searching in Drug Design." J.Med. Chem., 35:2145-2154, 1992.

McKhann and Hirsch, "Isolation of chalcone synthase and chalcone isomerase cDNAs from alfalfa (Medicago sativa L.): highest transcript levels occur in young roots and root tips." Plant Molecular Biology, 24: 767-777, 1994.

McKhann et al., "Chalcone-flavone isomerase 1." (abstract) Database Swissprot Online!, Aug. 1, 1992 , XP002197826, 1 page.

McPherson, "Crystallization of Proteins from Polyethylene Glycol" J.Biol.Chem., 6300-6306, 1976.

McPherson, A., "Current Approaches to Macromolecule Crystallization" Eur. J. Biochem. 189:1-23 (1990).

Meng et al., "Automated Docking with Grid-Based Energy Evaluation" J .Comp. Chem., 13:505-524, 1992.

Miranker and Karplus, "Functionality Maps of Binding Sites: A Multiple Copy Simultaneous Search Method" Proteins: Structure, Function and Genetics, 11:29-34, 1991.

Murshudov et al, "Refinement of Macromolecular Structures by the Maximum-likelihood Method." Acta Crystallogr. D53:240-255, 1997.

Navia and Murcko, "The use of structural information in drug design." Current Opinions in Structural Biology, 2:202-210, 1992.

Nishibata and Itai, "Automatic Creation of Drug Candidate Structures Based on Receptor Structure. Starting Point for Artificial Lead Generation." Tetrahedron, 47:8985, 1991.

Noel and Tsal, "Phospholipase A2 Engineering: Design, Synthesis, and Expression of a Gene for Bovine (Pro) Phospholipase A2" J.Cell. Biochem., 40:309-320, 1989.

Office Action on 088802-8253 DTD Oct. 16, 2006, 12 pages.

Otwinowski and Minor, "Processing X-Ray Diffraction Data Collected in Oscillation Mode" Methods Enzymol., 276:307-326, 1997.

Sali and Blundell, "Comparative Protein Modelling by Satisfaction of Spatial Restraints" J.Mol.Biol., 234:779-815, 1993.

Sander & Schneider, "Database of Homology-Derived Protein Structures and the Structural Meaning of Sequence Alignment Proteins" Struct. Funct. Genet., 9:56-68, 1991.

Terwilliger & Berendzen, "Automated MAD and MIR structure solution" J. Acta Crystallogr. D55:849-861, 1999.

US Notice of Allowance dated Apr. 7, 2010 in U.S. Appl. No. 10/344,051, 5 pages.

US Office Action dated Jan. 5, 2010 in U.S. Appl. No. 10/344,051, 13 pages.

US Office Action dated Nov. 9, 2007 in U.S. Appl. No. 10/344,051, 14 pages.

US Office Action dated Feb. 1, 2009 in U.S. Appl. No. 10/344,051, 17 pages.

US Office Action dated Mar. 12, 2007 in U.S. Appl. No. 10/344,051, 8 pages.

US Office Action dated May 12, 2008 in U.S. Appl. No. 10/344,051, 20 pages.

US Office Action dated Jul. 13, 2009 in U.S. Appl. No. 10/344,051, 14 pages.

Weber, "Physical Principles of Protein Crystallization" Advances in Protein Chemistry, 41:1-36, 1991.

Wiencek, New strategies for protein crystal growth, Ann. Rev. Biomed. Eng., 1:505-534, 1999.

* cited by examiner

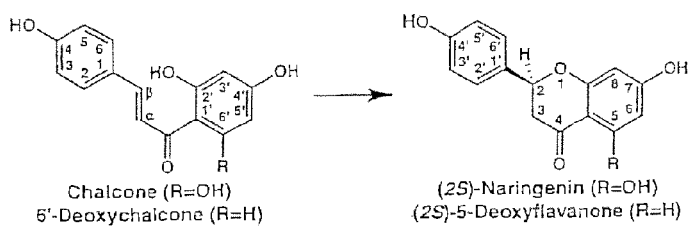
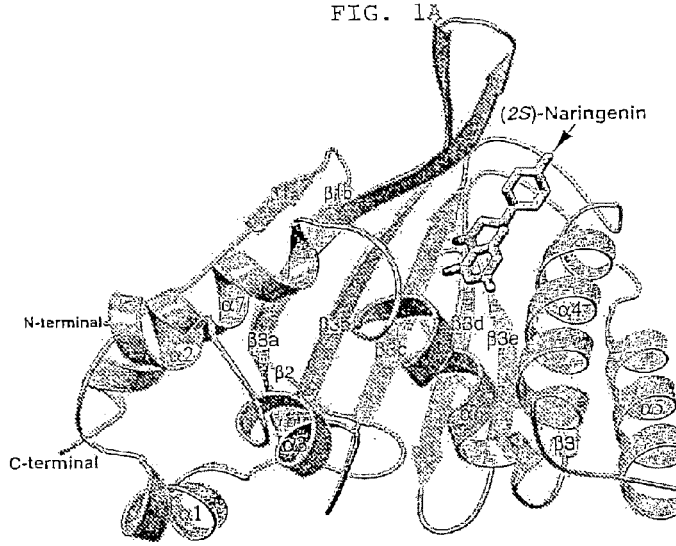
FIG. 1A
FIG. 1B
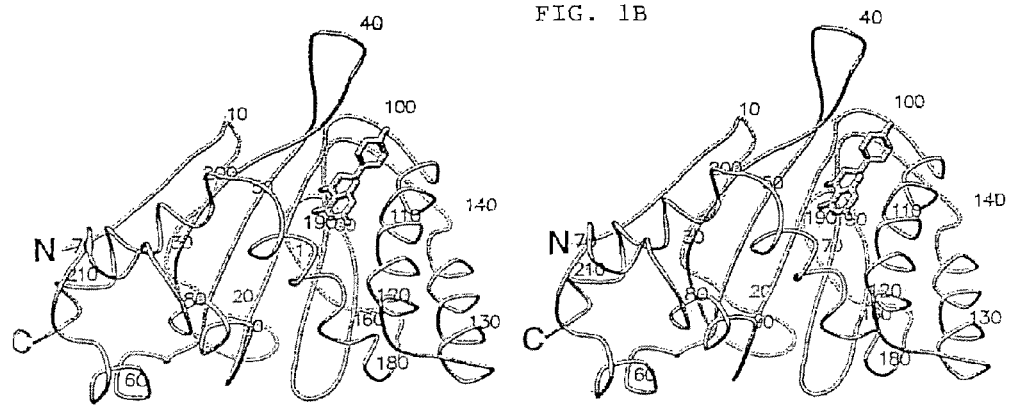
FIG. 1C

SEQUENCE LISTING

```
<160> NUMBER OF SEQ ID NOS: 11

<210> SEQ ID NO 1
<211> LENGTH: 222
<212> TYPE: PRT
<213> ORGANISM: Medicago sativa
<220> FEATURE:
<221> NAME/KEY: MOD_RES
<222> LOCATION: (36)
<223> OTHER INFORMATION: Arg, Met, Lys, Ala, His or Gln
<220> FEATURE:
<221> NAME/KEY: MOD_RES
<222> LOCATION: (38)
<223> OTHER INFORMATION: Leu or Ala
<220> FEATURE:
<221> NAME/KEY: MOD_RES
<222> LOCATION: (48)
<223> OTHER INFORMATION: Thr, Ala or Ser
<220> FEATURE:
<221> NAME/KEY: MOD_RES
<222> LOCATION: (106)
<223> OTHER INFORMATION: Tyr, Phe or Ser
<220> FEATURE:
<221> NAME/KEY: MOD_RES
<222> LOCATION: (109)
<223> OTHER INFORMATION: Lys or Met
<220> FEATURE:
<221> NAME/KEY: MOD_RES
<222> LOCATION: (110)
<223> OTHER INFORMATION: Val, Ala or Gly
<220> FEATURE:
<221> NAME/KEY: MOD_RES
<222> LOCATION: (113)
<223> OTHER INFORMATION: Asn or Ala
<220> FEATURE:
<221> NAME/KEY: MOD_RES
<222> LOCATION: (190)
<223> OTHER INFORMATION: Thr, Ser or Ala
<220> FEATURE:
<221> NAME/KEY: MOD_RES
<222> LOCATION: (191)
<223> OTHER INFORMATION: Met or Ile

<400> SEQUENCE: 1

Met Ala Ala Ser Ile Thr Ala Ile Thr Val Glu Asn Leu Glu Tyr Pro
  1               5                  10                  15

Ala Val Val Thr Ser Pro Val Thr Gly Lys Ser Tyr Phe Leu Gly Gly
             20                  25                  30

Ala Gly Glu Xaa Gly Xaa Thr Ile Glu Gly Asn Phe Ile Lys Phe Xaa
         35                  40                  45

Ala Ile Gly Val Tyr Leu Glu Asp Ile Ala Val Ala Ser Leu Ala Ala
     50                  55                  60

Lys Trp Lys Gly Lys Ser Ser Glu Glu Leu Leu Glu Thr Leu Asp Phe
 65                  70                  75                  80
```

```
Tyr Arg Asp Ile Ile Ser Gly Pro Phe Glu Lys Leu Ile Arg Gly Ser
                85                  90                  95

Lys Ile Arg Glu Leu Ser Gly Pro Glu Xaa Ser Arg Xaa Xaa Met Glu
            100                 105                 110

Xaa Cys Val Ala His Leu Lys Ser Val Gly Thr Tyr Gly Asp Ala Glu
        115                 120                 125

Ala Glu Ala Met Gln Lys Phe Ala Glu Ala Phe Lys Pro Val Asn Phe
    130                 135                 140

Pro Pro Gly Ala Ser Val Phe Tyr Arg Gln Ser Pro Asp Gly Ile Leu
145                 150                 155                 160

Gly Leu Ser Phe Ser Pro Asp Thr Ser Ile Pro Glu Lys Glu Ala Ala
                165                 170                 175

Leu Ile Glu Asn Lys Ala Val Ser Ser Ala Val Leu Glu Xaa Xaa Ile
            180                 185                 190

Gly Glu His Ala Val Ser Pro Asp Leu Lys Arg Cys Leu Ala Ala Arg
        195                 200                 205

Leu Pro Ala Leu Leu Asn Glu Gly Ala Phe Lys Ile Gly Asn
210                 215                 220

<210> SEQ ID NO 2
<211> LENGTH: 221
<212> TYPE: PRT
<213> ORGANISM: Phaseolus vulgaris

<400> SEQUENCE: 2

Met Ala Thr Ala Pro Thr Ile Thr Asp Val Gln Val Glu Phe Leu His
1               5                   10                  15

Phe Pro Ala Val Val Thr Ser Pro Ala Thr Ala Lys Thr Tyr Phe Leu
                20                  25                  30

Gly Gly Ala Gly Glu Arg Gly Leu Thr Ile Glu Gly Lys Phe Ile Lys
            35                  40                  45

Phe Thr Ala Ile Gly Val Tyr Leu Glu Asp Lys Ala Val Ala Ser Leu
        50                  55                  60

Ala Thr Lys Trp Lys Gly Lys Pro Ser Glu Glu Leu Ile Asn Thr Leu
65                  70                  75                  80

Asp Phe Tyr Arg Asp Ile Ile Ser Gly Pro Phe Glu Lys Leu Ile Arg
                85                  90                  95

Gly Ser Lys Ile Leu Gln Leu Ser Gly Thr Glu Tyr Ser Arg Lys Val
            100                 105                 110

Met Glu Asn Cys Val Ala His Leu Lys Ser Val Gly Thr Tyr Gly Asp
        115                 120                 125

Ala Glu Ala Lys Gly Ile Glu Glu Phe Ala Glu Ala Phe Lys Lys Val
    130                 135                 140

Asn Phe Pro Pro Gly Ala Ser Val Phe Tyr Arg Gln Ser Pro Asp Gly
145                 150                 155                 160

Ile Leu Gly Leu Ser Phe Ser Glu Asp Ala Thr Ile Pro Gly Glu Glu
                165                 170                 175

Ala Val Val Ile Glu Asn Lys Ala Val Ser Ala Ala Val Leu Glu Thr
            180                 185                 190

Met Ile Gly Glu His Ala Val Ser Pro Asp Leu Lys Arg Ser Leu Ala
        195                 200                 205

Ser Arg Leu Pro Ala Val Leu Asn Gly Gly Ile Ile Val
210                 215                 220

<210> SEQ ID NO 3
<211> LENGTH: 223
```

<212> TYPE: PRT
<213> ORGANISM: Pisum sativum

<400> SEQUENCE: 3

```
Met Cys Cys Ser Ile Leu His His Arg Asn Pro Arg Arg Glu His Glu
  1               5                  10                  15

Phe Pro Ala Val Val Thr Ser Pro Val Thr Glu Asn His Ile Phe Leu
                 20                  25                  30

Gly Gly Ala Gly Glu Arg Gly Leu Thr Ile Asn Gly Thr Phe Ile Lys
             35                  40                  45

Phe Thr Cys Ile Gly Val Tyr Leu Glu Asp Lys Ala Asp Lys Ser Leu
         50                  55                  60

Ala Thr Lys Trp Glu Gly Lys Leu Glu Glu Leu Leu Glu Thr Leu Asp
 65                  70                  75                  80

Phe Tyr Arg Asp Ile Ile Ser Gly Pro Phe Glu Lys Leu Ile Arg Arg
                 85                  90                  95

Ser Lys Ile Lys Glu Leu Ser Gly Pro Glu Tyr Ser Arg Lys Val Met
            100                 105                 110

Glu Asn Cys Val Ala His Leu Lys Ser Val Gly Thr Tyr Gly Asp Ala
        115                 120                 125

Glu Val Glu Ala Ile Gln Asn Leu Gln Lys Leu Ser Arg Met Leu Ile
    130                 135                 140

Phe His Leu Val Leu Leu Lys Lys Asn Arg Gln Ser Pro Asp Gly Ile
145                 150                 155                 160

Leu Gly Leu Ser Ser Ser Lys Asp Ile Ser Ile Pro Glu Lys Glu Asp
                165                 170                 175

Ala Ile Ile Glu Asn Lys Ala Ala Ser Ser Ala Val Leu Glu Thr Met
            180                 185                 190

Ile Gly Glu His Ala Val Ser Pro Asp Leu Lys Arg Cys Leu Ala Ala
        195                 200                 205

Arg Leu Pro Ala Leu Leu Asn Glu Gly Thr Phe Lys Ile Gly Asn
    210                 215                 220
```

<210> SEQ ID NO 4
<211> LENGTH: 231
<212> TYPE: PRT
<213> ORGANISM: Zea maize

<400> SEQUENCE: 4

```
Met Ala Cys Arg Arg Trp Trp Ser Thr Ala Val Val Phe Pro Pro Val
  1               5                  10                  15

Ala Arg Pro Pro Gly Ser Ala Gly Ser His Phe Leu Gly Gly Ala Gly
                 20                  25                  30

Val Arg Gly Val Glu Ile Gly Gly Asn Phe Ile Lys Phe Thr Ala Ile
             35                  40                  45

Gly Val Tyr Leu Glu Asp Ala Ala Val Pro Ala Leu Ala Lys Lys Trp
         50                  55                  60

Gly Gly Lys Thr Ala Asp Glu Leu Ala Ser Asp Ala Ala Phe Arg
 65                  70                  75                  80

Asp Val Val Thr Gly Asp Phe Glu Lys Phe Thr Arg Val Thr Met Ile
                 85                  90                  95

Leu Pro Leu Thr Gly Glu Gln Tyr Ala Glu Lys Val Thr Glu Asn Cys
            100                 105                 110

Val Ala Phe Trp Lys Ala Ala Gly Leu Tyr Thr Asp Ala Glu Gly Val
        115                 120                 125

Ala Val Glu Lys Phe Arg Glu Val Phe Lys Pro Glu Thr Phe Ala Pro
```

```
            130                 135                 140
Gly Arg Ser Ile Leu Phe Thr His Ser Pro Ala Gly Val Leu Thr Val
145                 150                 155                 160

Ala Phe Ser Lys Asp Ser Ser Val Pro Ala Ala Gly Gly Val Ala Ile
                165                 170                 175

Glu Asn Lys Arg Leu Cys Glu Ala Val Leu Glu Ser Ile Ile Gly Glu
            180                 185                 190

Arg Gly Val Ser Pro Ala Ala Lys Leu Ser Leu Ala Ala Arg Val Ser
        195                 200                 205

Glu Leu Leu Ala Lys Glu Thr Ala Ala Ala Asp Ala Pro Gln Ala
210                 215                 220

Glu Pro Val Ser Ile Thr Ala
225                 230

<210> SEQ ID NO 5
<211> LENGTH: 234
<212> TYPE: PRT
<213> ORGANISM: Vitis vinifera

<400> SEQUENCE: 5

Met Ser Gln Val Pro Ser Val Thr Ala Val Gln Val Glu Asn Val Leu
1               5                   10                  15

Phe Pro Pro Ser Val Lys Pro Pro Gly Ser Thr Asn Asp Leu Phe Leu
            20                  25                  30

Gly Gly Ala Gly Val Arg Gly Leu Glu Ile Gln Gly Lys Phe Val Lys
        35                  40                  45

Phe Thr Ala Ile Gly Val Tyr Leu Glu Asn Ser Ala Val Pro Thr Leu
    50                  55                  60

Ala Val Lys Trp Lys Gly Lys Thr Val Glu Gly Leu Ala Asp Ser Val
65                  70                  75                  80

Asp Phe Phe Arg Asp Val Val Thr Gly Pro Phe Glu Lys Phe Thr Lys
                85                  90                  95

Val Thr Thr Ile Leu Pro Leu Thr Gly Arg Gln Tyr Ser Asp Lys Val
            100                 105                 110

Ser Glu Asn Cys Val Ala Phe Trp Lys Ser Val Gly Ile Tyr Thr Asp
        115                 120                 125

Ala Glu Ala Lys Ala Ile Glu Lys Phe Asn Glu Val Leu Lys Asp Glu
    130                 135                 140

Thr Phe Pro Pro Gly Asn Ser Ile Leu Phe Thr His Ser Pro Leu Gly
145                 150                 155                 160

Ala Leu Thr Met Ser Phe Ser Lys Asp Gly Ser Leu Pro Glu Val Gly
                165                 170                 175

Asn Ala Val Ile Glu Asn Lys Leu Leu Thr Glu Ala Val Leu Glu Ser
            180                 185                 190

Ile Ile Gly Lys His Gly Val Ser Pro Glu Ala Lys Lys Ser Leu Ala
        195                 200                 205

Ala Arg Leu Ser Glu Leu Phe Cys Lys Glu Ala Gly Asp Glu Lys Ile
    210                 215                 220

Glu Ala Glu Lys Val Ala Pro Val Ala Cys
225                 230

<210> SEQ ID NO 6
<211> LENGTH: 241
<212> TYPE: PRT
<213> ORGANISM: Ipomoea purpurea

<400> SEQUENCE: 6
```

```
Met Ser Ala Pro Pro Cys Val Ala Glu Val Lys Val Glu Ser Tyr Val
1               5                   10                  15

Phe Pro Ala Thr Val Lys Pro Pro Gly Thr Ala Lys Thr Leu Ile Leu
                20                  25                  30

Gly Gly Ala Gly Ala Arg Gly Leu Asn Ile Asp Gly Lys Phe Val Lys
            35                  40                  45

Phe Thr Ala Ile Gly Val Tyr Leu Glu Ala Asp Ala Val Pro Ser Leu
        50                  55                  60

Ala Val Lys Trp Asn Gly Lys Ser Val Glu Glu Leu Thr Asp Ser Val
65                  70                  75                  80

Gln Phe Phe Arg Asp Ile Val Thr Gly Pro Phe Lys Leu Thr Arg
                85                  90                  95

Ile Thr Met Ile Leu Pro Leu Ser Gly Lys Gln Tyr Ser Glu Lys Val
                100                 105                 110

Thr Glu Asn Cys Val Ala Phe Trp Lys Ala Gly Met Tyr Gly Asp
            115                 120                 125

Ala Glu Ser Lys Ala Ile Asp Lys Phe Asn Asp Val Phe Ser Asp Gln
        130                 135                 140

Met Phe Pro Pro Gly Ala Ser Ile Phe Phe Thr Gln Ser Pro Leu Gly
145                 150                 155                 160

Ser Leu Thr Val Ser Phe Ser Lys Asp Gly Ser Met Pro Glu Ile Ala
                165                 170                 175

Ser Ala Val Ile Glu Asn Lys Pro Leu Ser Glu Ala Val Leu Glu Ser
                180                 185                 190

Ile Ile Gly Ser Lys Gly Val Ser Pro Glu Ala Lys Gln Ser Leu Ala
            195                 200                 205

Val Arg Leu Ser Glu Met Phe Ile Asn Gly Gly Asp Ala Ile Ser Gly
        210                 215                 220

Lys Val Gly Val Glu Asn Asp Val Ile Pro Gln Thr Val Val Ser
225                 230                 235                 240

Lys

<210> SEQ ID NO 7
<211> LENGTH: 241
<212> TYPE: PRT
<213> ORGANISM: Petunia hybrida

<400> SEQUENCE: 7

Met Ser Pro Pro Val Ser Val Thr Lys Met Gln Val Glu Asn Tyr Ala
1               5                   10                  15

Phe Ala Pro Thr Val Asn Pro Ala Gly Ser Thr Asn Thr Leu Phe Leu
                20                  25                  30

Ala Gly Ala Gly His Arg Gly Leu Glu Ile Glu Gly Lys Phe Val Lys
            35                  40                  45

Phe Thr Ala Ile Gly Val Tyr Leu Glu Glu Ser Ala Ile Pro Phe Leu
        50                  55                  60

Ala Glu Lys Trp Lys Gly Lys Thr Pro Gln Glu Leu Thr Asp Ser Val
65                  70                  75                  80

Glu Phe Phe Arg Asp Val Val Thr Gly Pro Phe Glu Lys Phe Thr Arg
                85                  90                  95

Val Thr Met Ile Leu Pro Leu Thr Gly Lys Gln Tyr Ser Glu Lys Val
                100                 105                 110

Ala Glu Asn Cys Val Ala His Trp Lys Gly Ile Gly Thr Tyr Thr Asp
            115                 120                 125
```

```
Asp Glu Gly Arg Ala Ile Glu Lys Phe Leu Asp Val Phe Arg Ser Glu
    130                 135                 140

Thr Phe Pro Pro Gly Ala Ser Ile Met Phe Thr Gln Ser Pro Leu Gly
145                 150                 155                 160

Leu Leu Thr Ile Ser Phe Ala Lys Asp Asp Ser Val Thr Gly Thr Ala
                165                 170                 175

Asn Ala Val Ile Glu Asn Lys Gln Leu Ser Glu Ala Val Leu Glu Ser
                180                 185                 190

Ile Ile Gly Lys His Gly Val Ser Pro Ala Ala Lys Cys Ser Val Ala
            195                 200                 205

Glu Arg Val Ala Glu Leu Leu Lys Lys Ser Tyr Ala Glu Glu Ala Ser
    210                 215                 220

Val Phe Gly Lys Pro Glu Thr Glu Lys Ser Thr Ile Pro Val Ile Gly
225                 230                 235                 240

Val

<210> SEQ ID NO 8
<211> LENGTH: 246
<212> TYPE: PRT
<213> ORGANISM: Arabidopsis thaliana

<400> SEQUENCE: 8

Met Ser Ser Asn Ala Cys Ala Ser Pro Ser Pro Phe Pro Ala Val
1               5                   10                  15

Thr Lys Leu His Val Asp Ser Val Thr Phe Val Pro Ser Val Lys Ser
                20                  25                  30

Pro Ala Ser Ser Asn Pro Leu Phe Leu Gly Gly Ala Gly Val Arg Gly
            35                  40                  45

Leu Asp Ile Gln Gly Lys Phe Val Ile Phe Thr Val Ile Gly Val Tyr
    50                  55                  60

Leu Glu Gly Asn Ala Val Pro Ser Leu Ser Val Lys Trp Lys Gly Lys
65                  70                  75                  80

Thr Thr Glu Glu Leu Thr Glu Ser Ile Pro Phe Phe Arg Glu Ile Val
                85                  90                  95

Thr Gly Ala Phe Glu Lys Phe Ile Lys Val Thr Met Lys Leu Pro Leu
            100                 105                 110

Thr Gly Gln Gln Tyr Ser Glu Lys Val Thr Glu Asn Cys Val Ala Ile
        115                 120                 125

Trp Lys Gln Leu Gly Leu Tyr Thr Asp Cys Glu Ala Lys Ala Val Glu
    130                 135                 140

Lys Phe Leu Glu Ile Phe Lys Glu Glu Thr Phe Pro Pro Gly Ser Ser
145                 150                 155                 160

Ile Leu Phe Ala Leu Ser Pro Thr Gly Ser Leu Thr Val Ala Phe Ser
                165                 170                 175

Lys Asp Asp Ser Ile Pro Glu Thr Gly Ile Ala Val Ile Glu Asn Lys
            180                 185                 190

Leu Leu Ala Glu Ala Val Leu Glu Ser Ile Ile Gly Lys Asn Gly Val
        195                 200                 205

Ser Pro Gly Thr Arg Leu Ser Val Ala Glu Arg Leu Ser Gln Leu Met
    210                 215                 220

Met Lys Asn Lys Asp Glu Lys Glu Val Ser Asp His Ser Leu Glu Glu
225                 230                 235                 240

Lys Leu Ala Lys Glu Asn
                245
```

```
<210> SEQ ID NO 9
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ser Ile Thr Ala Ile Thr Val Glu Asn Leu Glu Tyr Pro Ala Val Val
 1               5                  10                  15

Thr Ser Pro Val Thr Gly Lys Ser Tyr Phe Leu Gly Gly Ala Gly Glu
            20                  25                  30

Arg Gly Leu Thr Ile Glu Gly Asn Phe Ile Lys Phe Thr Ala Ile Gly
        35                  40                  45

Val Tyr Leu Glu Asp Ile Ala Val Ala Ser Leu Ala Ala Lys Trp Lys
    50                  55                  60

Gly Lys Ser Ser Glu Glu Leu Leu Glu Thr Leu Asp Phe Tyr Arg Asp
65                  70                  75                  80

Ile Ile Ser Gly Pro Phe Glu Lys Leu Ile Arg Gly Ser Lys Ile Arg
                85                  90                  95

Glu Leu Ser Gly Pro Glu Tyr Ser Arg Lys Val Met Glu Asn Cys Val
            100                 105                 110

Ala His Leu Lys Ser Val Gly Thr Tyr Gly Asp Ala Glu Ala Glu Ala
        115                 120                 125

Met Gln Lys Phe Ala Glu Ala Phe Lys Pro Val Asn Phe Pro Pro Gly
    130                 135                 140

Ala Ser Val Phe Tyr Arg Gln Ser Pro Asp Gly Ile Leu Gly Leu Ser
145                 150                 155                 160

Phe Ser Pro Asp Thr Ser Ile Pro Glu Lys Glu Ala Ala Leu Ile Glu
                165                 170                 175

Asn Lys Ala Val Ser Ser Ala Val Leu Glu Thr Met Ile Gly Glu His
            180                 185                 190

Ala Val Ser Pro Asp Leu Lys Arg Cys Leu Ala Ala Arg Leu Pro Ala
        195                 200                 205

Leu Leu Asn Glu
    210

<210> SEQ ID NO 10
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ser Ile Thr Ala Ile Thr Val Glu Asn Leu Glu Tyr Pro Ala Val
 1               5                  10                  15

Val Thr Ser Pro Val Thr Gly Lys Ser Tyr Phe Leu Gly Gly Ala Gly
            20                  25                  30

Glu Arg Gly Leu
        35

<210> SEQ ID NO 11
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 11

Ile Lys Phe Thr Ala Ile Gly Val Tyr Leu Glu Asp Ile Ala Val Ala
1               5                   10                  15

Ser Leu Ala Ala Lys Trp Lys Gly Lys Ser Ser Glu Glu Leu Leu Glu
                20                  25                  30

Thr Leu Asp Phe Tyr Arg Asp Ile Ile Ser Gly Pro Phe Glu Lys Leu
            35                  40                  45

Ile Arg Gly Ser Lys Ile Arg Glu Leu Ser Gly Pro Glu Tyr Ser Arg
        50                  55                  60

Lys Val Met Glu Asn Cys Val Ala His Leu Lys Ser Val Gly Thr Tyr
65                  70                  75                  80

Gly Asp Ala Glu Ala Glu Ala Met Gln Lys Phe Ala Glu Ala Phe Lys
                85                  90                  95

Pro Val Asn Phe Pro Pro Gly Ala Ser Val Phe Tyr Arg Gln Ser Pro
                100                 105                 110

Asp Gly Ile Leu Gly Leu Ser Phe Ser Pro Asp Thr Ser Ile Pro Glu
            115                 120                 125

Lys Glu Ala Ala Leu Ile Glu Asn Lys Ala Val Ser Ser Ala Val Leu
130                 135                 140

Glu Thr Met Ile Gly Glu His Ala Val Ser Pro Asp Leu Lys Arg Cys
145                 150                 155                 160

Leu Ala Ala Arg Leu Pro Ala Leu Leu Asn Glu
                165                 170
```

CHALCONE ISOMERASE POLYPEPTIDES AND CRYSTALS THEREOF

RELATED APPLICATIONS

This application is a divisional of U.S. application Ser. No. 10/344,051, filed on Nov. 24, 2003 now U.S. Pat. No. 7,792,645 which is a 371 of International Application No. PCT/US01/27027, filed Aug. 29, 2001, which claims the benefit of U.S. Application No. 60/229,277, filed Aug. 30, 2000, which is hereby incorporated by reference herein in its entirety.

ACKNOWLEDGMENT

This invention was made with United States Government support under Grant No. MCB-9982586, awarded by the National Science Foundation. The Government has certain rights in the invention.

FIELD OF INVENTION

The present invention relates to methods for designing mutant chalcone isomerases, and to predicting the activity and/or substrate specificity of native and mutant chalcone isomerases. The present invention further relates to methods for identifying chalcone isomerase substrates and/or inhibitors.

BACKGROUND

Advances in molecular biology have allowed the development of biological agents useful in modulating protein or nucleic acid activity or expression, respectively. Many of these advances are based on identifying the primary sequence of the molecule to be modulated. For example, determining the nucleic acid sequence of DNA or RNA allows the development of antisense or ribozyme molecules. Similarly, identifying other primary sequence allows for the identification of sequence that may be useful in creating monoclonal antibodies. However, often the primary sequence of a protein is insufficient to develop therapeutic or diagnostic molecules due to the secondary, tertiary or quarternary structure of the protein from which the primary sequence is obtained. The process of designing potent and specific inhibitors, activators, or novel proteins has improved with the arrival of techniques for determining the three-dimensional structure of an enzyme or polypeptide whose activity one desires to modulate.

The phenylpropanoid synthetic pathway in plants produces a class of compounds know as anthocyanins, which are used for a variety of applications. Anthocyanins are involved in pigmentation and protection against UV photodamage, synthesis of anti-microbial phytoalexins, and are flavonoid inducers of *Rhizobium* modulation genes 1-4. As medicinal natural products, the phenylpropanoids exhibit cancer chemopreventive activity, as well as anti-mitotic, estrogenic, anti-malarial, anti-oxidant, and antiasthmatic activities. The benefits of consuming red wine, which contains significant amounts of 3,4',5-trihydroxystilberte (resveratrol) and other phenylpropanoids, highlight the dietary importance of these compounds. One strategy for the generation of novel enzymatic activity in flavonoid biosynthesis uses protein-engineering methods and requires a detailed structural knowledge of enzymes within the targeted pathway.

Polyketides are a large class of compounds and include a broad range of antibiotics, immunosuppressants and anticancer agents which together account for sales of over $5 billion per year. Polyketides are molecules which are an extremely rich source of bioactivities, including antibiotics (e.g., tetracyclines and erythromycin), anti-cancer agents (e.g., daunomycin), immunosuppressants (e.g., FK506 and rapamycin), veterinary products (e.g., monensin), and the like. Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization.

Chalcone synthase (CHS), a polyketide synthase, plays an essential role in the biosynthesis of plant phenylpropanoids. CHS supplies 4,2',4',6'-tetrahydroxychalcone (chalcone) to downstream enzymes, such as chalcone isomerase (CHI), that synthesize a diverse set of flavonoid phytoalexins and anthocyanin pigments.

An improvement in the understanding of the structure/function of these enzymes would allow for a number of advances in the art, e.g., the exploitation of the synthetic capabilities of known enzymes for production of useful new chemical compounds, for the creation of novel non-native enzymes having new synthetic capabilities etc. A need exists, therefore, for a detailed understanding of the molecular basis of the chemical reactions involved in polyketide, flavanone and flavonoid synthesis. The present invention addresses this and related needs.

SUMMARY OF THE INVENTION

In accordance with the present invention there are presented crystalline chalcone isomerases (CHIs) and the three-dimensional coordinates derived therefrom. Three-dimensional coordinates have been obtained for an active form of chalcone isomerase and the active site thereof, both with and without product or product analog. Accordingly, the three-dimensional coordinates and crystal structure of a CHI provides the ability to develop novel substrates, proteins and enzymatic products of CHI. In addition, the invention provides the use of the three-dimensional structure either alone or together with the structure of polyketide synthases, such as chalcone synthase, to provide a useful template for engineering novel enzymes and enzyme pathways to diversify and modify flavonoid biosynthesis for crop and food sources, as well as providing novel flavanones for intermediates and leads in drug discovery (see WO/01/07579 A2, published Feb. 1, 2001, the disclosure of which is incorporated herein by reference in it entirety).

One aspect of the present invention made possible by the results described herein is a model of the three-dimensional properties of chalcone isomerase proteins. In particular, the invention provides the three-dimensional properties of the active site. The invention features specific coordinates of at least twelve α-carbon atoms defining the active site in three-dimensional space. R-groups attached to said α-carbons are defined such that mutants can be made by changing at least one R-group found in the isomerase active site. Such mutants have unique and useful properties. Thus, in accordance with another embodiment of the invention, there are provided isolated non-native (e.g., mutant) isomerase(s) having at least twelve active site α-carbons having the structural coordinates disclosed herein and one or more R-groups other than those found in native chalcone isomerase(s).

The chalcone isomerase used in the crystallization studies disclosed herein is a chalcone isomerase derived from *Medicago sataiva* (alfalfa). A large number of isomerase proteins from various plant species have primary amino acid sequences showing substantial homology and conservation. Thus, the three-dimensional coordinates disclosed herein can be employed in a variety of methods extending to various isomerase proteins. Accordingly, in another embodiment of the present invention, there are provided methods for predicting the activity and/or substrate specificity of a putative chalcone isomerase from a variety of species. There are further provided methods for identifying potential substrates for a chalcone isomerase, as well as inhibitors thereof.

Other aspects, embodiments, advantages, and features of the present invention will become apparent from the following specification.

BRIEF DESCRIPTION OF FIGURES

FIG. 1A shows the overall reaction catalyzed by CHI, which involves a Michael-type nucleophilic attack of the 2'-hydroxyl on the α,β-unsaturated double bond of chalcone. The numbering systems for chalcones (left) and flavanones (right) are shown.

FIG. 1B is a schematic ribbon diagram of the overall structure of chalcone isomerase (CHI). The N- and C-termini are labeled, as are the β-strands and α-helices of the structure. The position of (2S)-naringenin is also indicated.

FIG. 1C is a stereo-view of the $C_\alpha$-backbone. This orientation is the same as in (FIG. 1A). Every tenth residue is numbered. The position of (2S)-naringenin is also shown.

FIG. 2A shows a stereo-view of the SIGMAA-weighted |2Fo-Fc| electron density (1.2σ) for (2S)-naringenin.

FIG. 2B shows a stereo-view of residues in the active site cleft. (2S)-Naringenin and a water molecule are also shown. Hydrogen bond interactions are indicated with dotted lines. This view is oriented looking into the cleft. The surface corresponding to Lys 109 and Asn 113 was removed for clarity.

FIG. 2C shows a stereo-view surface representation of active site cleft showing the fit of (2S)-naringenin and a water molecule therein.

FIG. 3A shows a stereo-view of the proposed chalcone conformation leading to (2S)-naringenin formation.

FIG. 3B shows a stereo-view of the steric clash that prevents (2R)-naringenin formation.

FIG. 4A is a view of the active site hydrogen bond network. This view is oriented looking out of the active site cleft. Dotted lines indicate hydrogen bonds.

FIG. 4B is a schematic representation of the active site hydrogen bonds. Distances are indicated in Å.

FIG. 4C is a proposed cyclization reaction catalyzed by CHI. Following nucleophilic attack of the 2'-O— of the substrate on the double bond in a Michael addition, the water molecule stabilized by Tyr 106 acts as a general acid to stabilize the enolate. This results in formation of a flav-3-en-4-ol intermediate that tautomerizes into the reaction product.

DETAILED DESCRIPTION OF THE INVENTION

In flavonoid biosynthesis, chalcone isomerase (CHI, E.C. 5.5.1.6) catalyzes the cyclization of chalcone (4,2',4',6'-tetrahydroxychalcone) and 6'-deoxychalcone trihydroxychalcone) into (2S)-naringenin (5,7,4'-trihydroxyflavanone) and (2S)-5-deoxyflavanone (7,4'-dihydroxyflavanone), respectively. Since chalcone spontaneously cyclizes into (2S/2R)-naringenin, CHI guarantees formation of the biologically active (S)-isomer. (2S)-Naringenin is the precursor of anthocyanin pigments, and mutations in the gene encoding CHI are linked to changes in floral pigmentation. (2S)-Naringenin and other flavonoids also act as small molecule transcription activators that target bacterial transcription regulators governing expression of *Rhizobium* genes involved in root nodulation.

An "isomerase" or a "chalcone isomerase" includes any one of a family of isomerase enzymes that catalyze the formation of flavonoid or flavanone compounds. Chalcone isomerases are generally monomers.

Mechanistically, CHI catalyzes the cyclization of chalcone with an apparent 100,000:1 preference for the S-isomer over the R-isomer. The second-order rate constant ($k_{cat}/K_m$) for conversion of chalcone by CHI approaches the diffusion-controlled limit with an enzyme-catalyzed rate that exceeds the spontaneous conversion rate by $10^7$-fold. Combined with structural knowledge, the comparison of the spontaneous and enzyme-catalyzed reactions provides insight on how an enzyme accelerates the rate of an intramolecular chemical reaction. The present invention provides a 2.5 Å crystal structure of CHI from *Medicago sativa* (alfalfa) by multiple isomorphous replacement with anomalous scattering (MIRAS) and the 1.85 Å resolution structure of CHI complexed with (2S)-naringenin by difference Fourier analysis. Atomic resolution structures provide a molecular understanding of how CHI recognizes and catalyzes the stereospecific cyclization of chalcone and provides the ability to modulate natural product specificity and to develop novel isomerase proteins having substrate specificities.

Figure 1D:
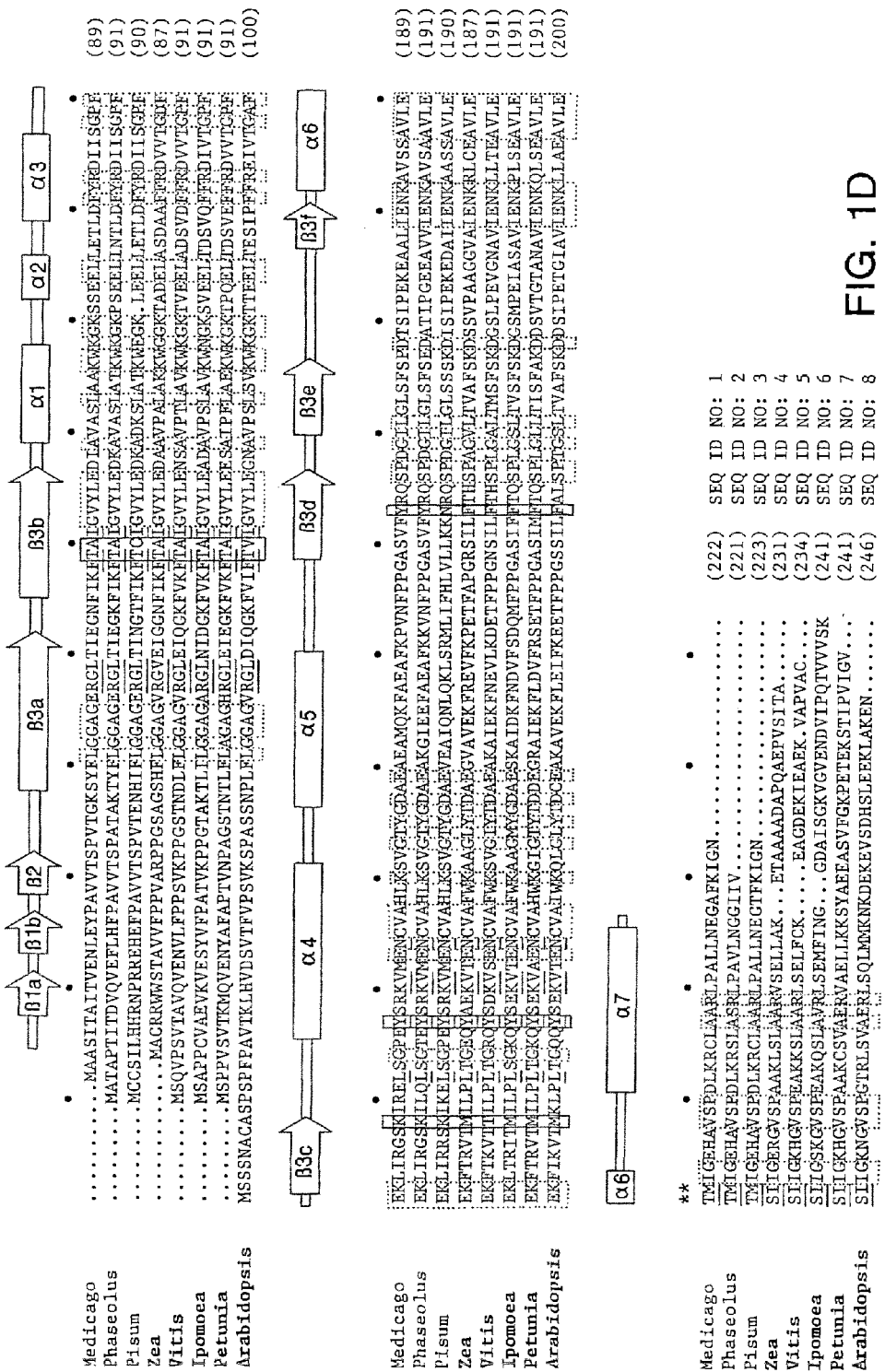
FIG. 1D is a primary and secondary structure of CHI from *Medicago sativa* (alfalfa; P28012; SEQ ID NO:1) and sequence alignment of CHIs from *Plaseolus vulgaris* (bean; P14298; SEQ ID NO:2), *Pisum sativum* (pea; P41089; SEQ ID NO:3), Zen maize (corn; S41579; SEQ ID NO:4), *Vitis vinifera* (grape; P51117; SEQ ID NO:5), *Ipomoea purpurea* (morning glory; af028238; SEQ ID NO:6), *Petunia hybrida* (P11651; SEQ ID NO:7), and *Arabidopsis thaliana* (P41088; SEQ ID NO:8). α-Helices and β-strands of CHI are indicated above the sequence and the numbering of each protein in parenthesis. Every tenth position in the alignment is dotted. Residues of the (2S)-naringenin binding cleft (underlined), residues of the active site hydrogen bond network (boxed), and other conserved residues (shaded) are indicated as noted. The residues that may influence substrate preference between chalcone and deoxychalcone are indicated with an asterisk.

CHI is a functional monomer of approximately 220 residues and has been isolated from a variety of higher plants. (Bednar, R. A. & Hadcock, J. R. J. Biol. Chem. 263:9582-9588, 1988; Dixon, et al. Phytochemistry 27:2801-2808, 1988). The present invention provides the first crystal structure for chalcone isomerase, which resembles an upside-down bouquet that adopts an open-faced β-sandwich fold (FIGS. 1B and 1C). A large β-sheet (β3α-β3f) and a layer of α-helices (α1-α7) comprise the core structure with three short β-strands (β1a, β1b, β2) on the opposite side of the large β-sheet. A search of the Protein Data Bank using DALI (Sander, C. & Schneider, R. Proteins Struct. Funct. Genet. 9:56-68, 1991) revealed no other structurally homologous folds. In addition, a PSI-BLAST search of sequence databases showed that CHI-like sequences are currently found in a number of plants and these sequences display limited homology with other proteins. These results imply that the CHI three-dimensional fold and enzymatic activity are found typically in the plant kingdom. Amino acid sequence comparison of CHIs from a variety of advanced land plants reveals high homology (49% to 82% amino acid sequence identity) with regions of conservation spread uniformly throughout the primary structure (see FIG. 1D). A conservation of residues spanning β3a, β3b, α4, and α6 in the three-dimensional structure among CHIs from different species is demonstrated by the present invention as structural elements of the active site on the protein surface.

The data demonstrates that co-localization of proteins in loosely associated macromolecular complexes is a fundamental component of cellular processes, including flavonoid biosynthesis. CHI and other flavonoid biosynthetic enzymes may associate to provide efficient channeling of substrates and products as shown recently in *Arabidopsis thaliana*. Although the three short β-strands (β1a, β1b, β2) on the backside of the CHI structure form a relatively flat surface that would be ideal for protein-protein interactions, both gel filtration and analytical ultracentrifugation failed to detect association of alfalfa CHI and alfalfa chalcone synthase 2 in vitro.

Figure 2:
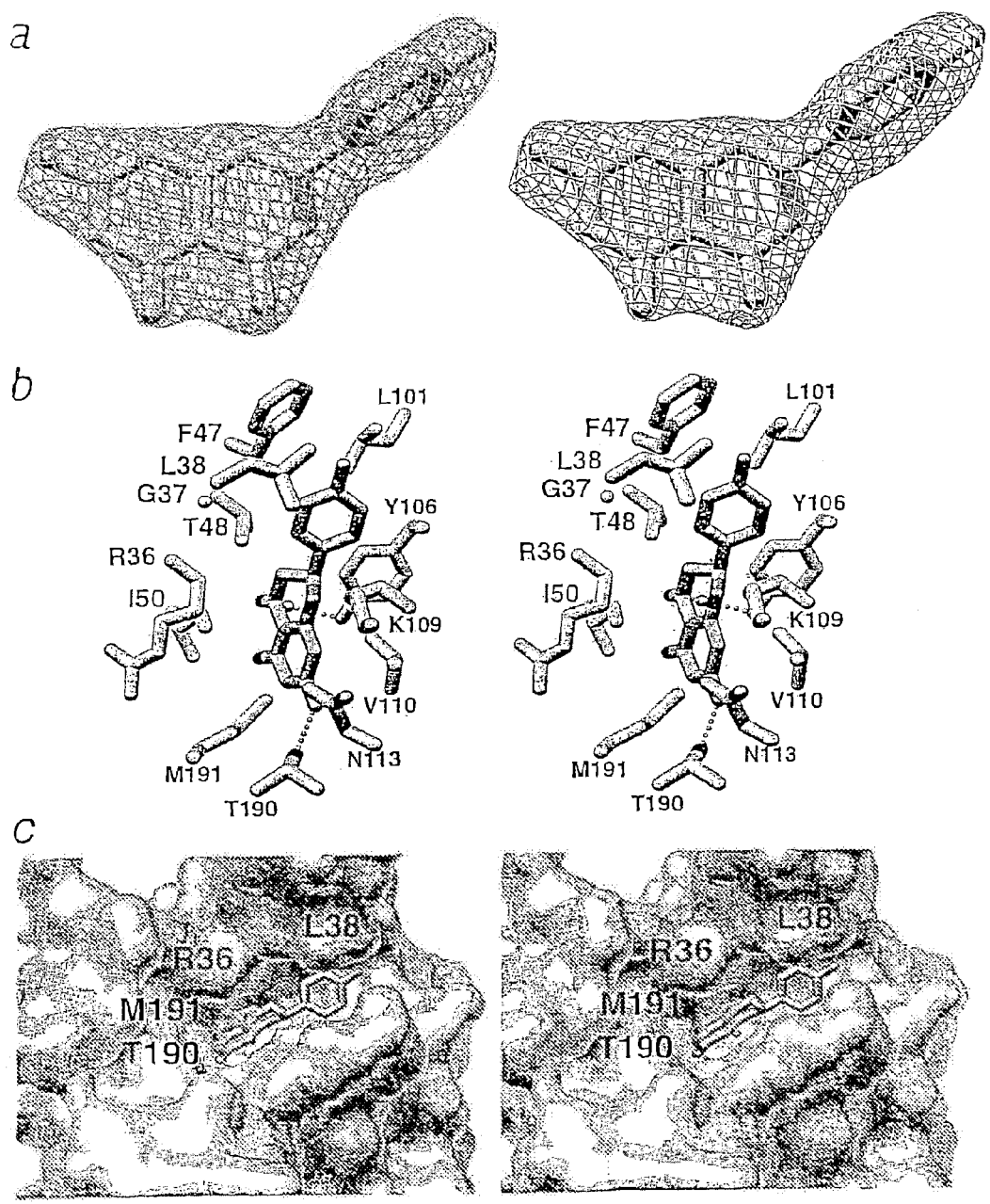
FIG. 2 collectively shows 2 (2S)-Naringenin binding and structure of the active site cleft.

For the first time the present invention identifies the active site of CHI by identifying the location of (2S)-naringenin in the CHI structure (FIG. 2). Although a commercially obtained mixture of (2S)- and (2R)-naringenin was used for co-crystallization, only the (2S)-isomer bound the CHI active site. The position of the (2S)-naringenin binding cleft is consistent with inactivation studies that suggested a cysteine residue (Cys 114 in alfalfa CHI) is proximal to the active site (Bednar et al. J. Biol. Chem. 264:14272-14276, 1989). In the CHI structure, Cys 114 is near the binding cleft but does not directly contact (2S)-naringenin. The active site cleft is largely apolar and consists of residues from β3a (Arg 36, Gly 37, Leu 38), β3b (Phe 47, Thr 48, Ile 50), α4 (Tyr 106, Lys 109, Val 110, Asn 113), and α6 (Thr 190, Met 191) (FIG. 2B). In addition, residues Ala 49, Lys 97, Leu 101, Glu 105, Glu 112, Cys 114, Tyr 152, Val 187, Asp 200 and Leu 201 contact the ligand (naringenin or deoxyflavanones) or buttress the above residues of β3a, β3b, α4, or α6. The apolar methylene carbons of Arg 36 are positioned by a restraining charge-charge interaction from the δ-guanido group to Glu 200. In addition, the methylene carbons of Lys 109 are fixed by a charge-charge interaction between the side chain amine and Glu 112. Except for Thr 190 and Met 191, the residues contacting (2S)-naringenin are identical among CHIs from different plants (FIG. 1D). Although van der Waals contacts dominate the interactions between CHI and (2S)-naringenin, two hydrogen bond interactions exist. The first is mediated by the side chain hydroxyl moiety of Thr 48 bound to the 4'-hydroxyl group of (2S)-naringenin. The second interaction is between a water molecule and the ligand ketone (FIG. 2B). This water molecule and its connected network of hydrogen bonds occupy the same position in the apoenzyme structure. The overall surface topology of the cleft tightly sequesters the (2S)-naringenin molecule (FIG. 2C). The CHI•naringenin complex explains the stereochemical preference of the cyclization reaction; moreover, it suggests why CHIs from different species show moderate selectivity for chalcone and 6'-deoxychalcone as substrates.

"Active Site" refers to a site in an isomerase defined by amino acid residues that interact with substrate and facilitate a biosynthetic reaction that allows one or more products to be produced. An active site is comprised of α-carbon atoms that are indirectly linked via peptide bonds and have the structural coordinates disclosed by the atoms of the residues found in the β3a, β3b, α4 and α6 regions of chalcone isomerase (e.g., Arg 36, Gly 37, Leu 38, Phe 47, Thr 48, Ile 50, Tyr 106, Lys 109, Val 110, Asn 113, Thr 190, and Met 191). In addition, residues Ala 49, Lys 97, Leu 101, Glu 105, Glu 112, Cys 114, Tyr 152, Val 187, Asp 200 and Leu 201 contact the ligand (naringenin or deoxyflavanones) or buttress the above residues of β3a, β3b, α4, or α6. The position in three-dimensional space of an α-carbon at the active site of an isomerase and of R-groups associated therewith can be determined using techniques such as three-dimensional modeling, X-ray crystallography, and/or techniques associated therewith.

Figure 3:
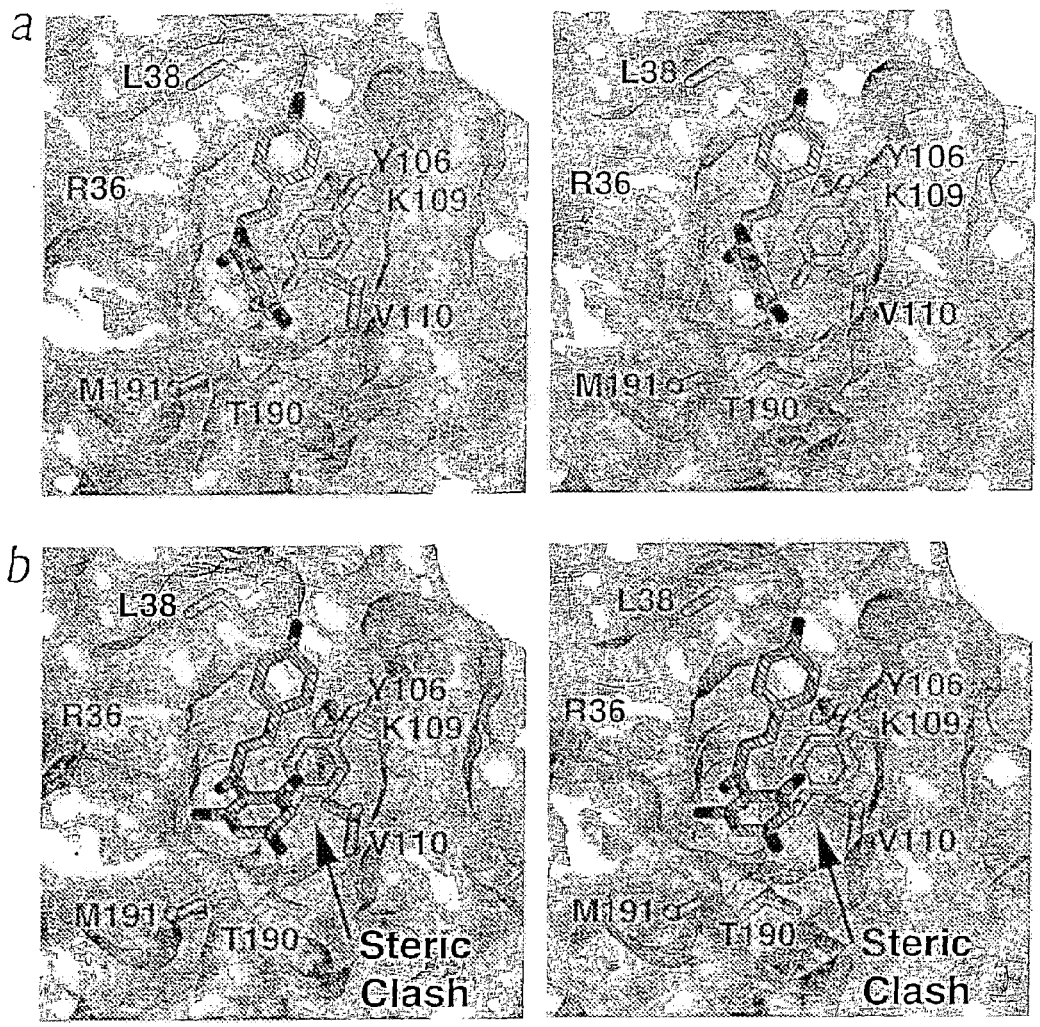
FIG. 3 collectively shows the proposed enzyme-mediated stereochemical control of the cyclization reaction. The surface of the binding cleft is transparent to show selected residues (grey). The surface associated with Lys 109 and Asn 113 has been removed for clarity. The position of chalcone (hatched) prior to cyclization has been modeled to show the formation of the new bond (dotted line). Hydrogen bond interactions are indicated by dotted lines.

Modeling of chalcone, based on the position of (2S)-naringenin, shows that a slight rotation of the trihydroxyl-ring outward in the direction of the active site opening places the 2'-hydroxyl group in position for nucleophilic attack on the α,β-unsaturated double bond of the coumaroyl moiety (FIG. 3A) This rotation preserves the position of the chalcone backbone and the hydrogen bonds between Thr 190 and the water molecule at the backside of the binding site. Formation of (2R)-naringenin would require substantial rearrangements in the active site of CHI due to significant steric clashes between the trihydroxyl-ring and CHI side chains. Although rotation of the trihydroxyl-ring away from the active site entrance could reposition the 2'-hydroxyl group for attack on the opposite face of the α,β-double bond, the side chain of Val 110 sterically prevents this movement from occurring (FIG. 3B). In addition, the opposite side of the substrate double bond could be positioned for attack by the 2'-hydroxyl group in the formation of (2R)-naringenin. This alternative cyclization would be accomplished by rotation of the coumaroyl moiety outward towards the solvent accessible active site entrance. However, Leu 38 and Lys 109 constrain the orientation of the coumaroyl moiety in the binding cleft. Architecturally, the CHI active site limits the substrate's available conformations to ensure stereospecific product formation.

Subtle variations in substrate preference reflected in the $K_m$ values for chalcone versus 6'-deoxychalcone exist between CHIs of different species (Dixon et al. Phytochemistry 27:2801-2808, 1988). CHIs from legumes, such as alfalfa, prefer 6'-deoxychalcone as a substrate but the enzymes from non-legumes, like petunia, optimally use chalcone. The structure of the CHI•naringenin complex, viewed with reference to the amino acid sequences of different CHIs, show that Thr 190 and Met 191 may partially modulate substrate preference. In the CHIs from non-legumes, a serine and an isoleucine replace Thr 190 and Met 191, respectively. These two differences may better accommodate the 6'-hydroxyl moiety of chalcone due to a modest increase in active site volume in the vicinity of the trihydroxyl ring.

The present invention provides for the first time the intramolecular reaction of CHI with its product. CHI catalyzes an intramolecular reaction utilizing a substrate-derived nucleophile and a carbon-carbon double bond as a Michael acceptor. Two reaction mechanisms have been proposed for (2S)-naringenin formation by CHI. One involves nucleophilic catalysis by an active site residue that forms a covalent intermediate that is released after a $SN_2$ displacement by the 2'-O⁻ of chalcone. The other mechanism invokes general acid-base catalysis employing an enol intermediate. The structure of CHI clearly supports the latter mechanism.

Figure 4:
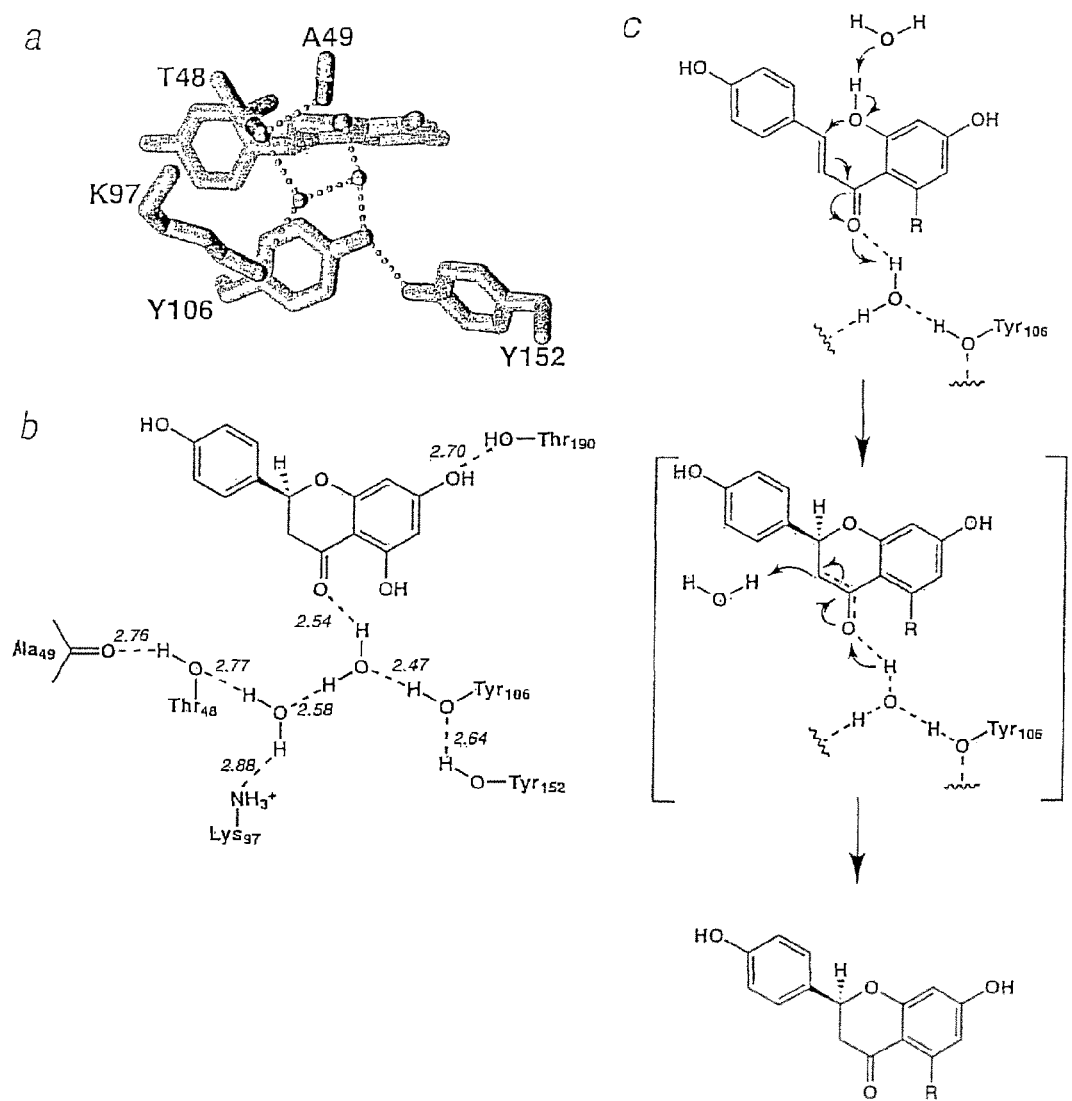
FIG. 4 collectively shows the proposed reaction mechanism of CHI.

Examination of the CHI•naringenin complex structure reveals a hydrogen bond network at the bottom of the binding cleft centered about the water molecule that contacts the ketone of (2S)-naringenin (FIGS. 4A and 4B). Of the five amino acids contributing to this network, only Thr 48 and Tyr 106 are conserved in all CHIs. The position of the water molecule between (2S)-naringenin and Tyr 106 suggests a reaction mechanism in which the tyrosine activates the water, allowing it to serve as a general acid in the cyclization reaction (FIG. 4C). In the proposed reaction mechanism, the 2'-O⁻ ($pK_a$~7-8) forms in solution as suggested by studies on the spontaneous cyclization of chalcones. The negatively charged oxygen then attacks the carbon-carbon double bond of chalcone utilizing a Michael addition with the water molecule at the backside of the active site acting as the general acid in the transient protonation of the intermediate enolate.

Accordingly, for the first time, the invention provides the ability to modulate activity of the active site of CHI to design novel enzymes to catalyze the synthesis of various flavanones. For example, Tyr 106 was substituted by phenylalanine and the properties of the mutant CHI compared to the wild-type enzyme. The present invention allows the comparison of the activities of mutants and designed mutants by computer modeling as well as by biological assays. The kinetics for the cyclization of 6'-deoxychalcone by wild-type CHI ($k_{cat}$=4384 min⁻¹; $K_m$=25.7 μM; $k_{cat}/K_m$=1.71×10⁸ M⁻¹ min⁻¹) versus those of the reaction catalyzed by the CHI Y106F mutant ($k_{cat}$=69.0 min⁻¹; $K_m$=29.1 μM; $k_{cat}/K_m$=2.37×10⁶ M⁻¹ min⁻¹) demonstrate that the tyrosine residue contributes to the stabilization of the transition state. The 100-fold reduction in reaction rate is consistent with the decrease in rate associated with the loss of a general acid. However, the observed reaction rate with the mutant remains greater than that of the uncatalyzed cyclization reaction. Thus, the present invention demonstrates that the structural complementarity of the binding cleft to the transition state of the reaction contributes additional levels of catalytic rate enhancement.

A major contribution to rate enhancement in enzymatic reactions results from bringing substrates or reactive centers in the same molecule together in space. As described above, the topology of the binding cleft limits the flexibility of chalcone and eliminates catalytically unproductive orientations by spatially, defining an optimal geometry for (2S)-naringenin formation. This effectively channels the ground state conformation of the substrate into a catalytically productive conformation. Together with contributions from general acid-base catalysis, shape complementarity between the CHI binding pocket and chalcone accelerates the cyclization of chalcone 10⁷-fold over the spontaneous reaction rate. Accordingly, the present invention, provides for the first time, the ability to design, model, and assay native CHI and mutant CHI polypeptides.

The three-dimensional structure of CHI, provided herein, together with the structure of chalcone synthase (see WO/01/07579 A2, published Feb. 1, 2001), provides a useful template for engineering experiments that aim to diversify and modify flavonoid biosynthetic pathways for crop and food sources, as well as providing novel flavanones for intermediates and leads in drug discovery.

As used herein, "naturally occurring amino acid" and "naturally occurring R-group" includes L-isomers of the twenty amino acids naturally occurring in proteins. Naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specially indicated, all amino acids referred to in this application are in the L-form.

"Unnatural, amino acid" and "unnatural R-group" includes amino acids that are not naturally found in proteins. Examples of unnatural amino acids included herein are racemic mixtures of selenocysteine and selenomethionine. In addition, unnatural amino acids include the D or L forms of, for example, nor-leucine, para-nitrophenylalanine, homophenylalanine, para-fluorophenylalanine, 3-amino-2-benzylpropionic acid, homoarginines, D-phenylalanine, and the like.

"R-group" refers to the substituent attached to the α-carbon of an amino acid residue. An R-group is an important determinant of the overall chemical character of an amino acid. There are twenty natural R-groups found in proteins, which make up the twenty naturally occurring amino acids.

"α-carbon" refers to the chiral carbon atom found in an amino acid residue. Typically, four substituents will be covalently bound to said α-carbon including an amine group, a carboxylic acid group, a hydrogen atom, and an R-group.

"Positively charged amino acid" and "positively charged R-group" includes any naturally occurring or unnatural amino acid having a positively charged side chain under normal physiological conditions. Examples of positively charged, naturally occurring amino acids include arginine, lysine, histidine, and the like.

"Negatively charged amino acid" and "negatively charged R-group" includes any naturally occurring or unnatural amino acid having a negatively charged side chain under normal physiological conditions. Examples of negatively charged, naturally occurring amino acids include aspartic acid, glutamic acid, and the like.

"Hydrophobic amino acid" and "hydrophobic R-group" includes any naturally occurring or unnatural amino acid having an uncharged, nonpolar side chain that is relatively insoluble in water. Examples of naturally occurring hydrophobic amino acids are alanine, leucine, isoleucine, valine, proline, phenylalanine, tryptophan, methionine, and the like.

"Hydrophilic amino acid" and "hydrophilic R-group" includes any naturally occurring or unnatural amino acid having a charged polar side chain that is relatively soluble in water. Examples of naturally occurring hydrophilic amino acids include serine, threonine, tyrosine, asparagine, glutamine, cysteine, and the like.

"Mutant" or "mutated isomerase" refers to an isomerase enzyme (e.g., chalcone isomerase) having one or more R-group modifications to the amino acids of a wild-type isomerase or having a substitution of one or more amino acids, either conservative or non-conservative substitutions, that result in a modification to the catalytic activity of a wild-type isomerase. For example, a mutant isomerase has an R-group on one or more α-carbon other than the prescribed arrangements of R-groups associated with one or more α-carbon of a known isolated chalcone isomerase (Accession No. 1EYP, Protein Data Bank, Table 1, SEQ ID NO:9-11). Access to the foregoing information in the Protein Data Bank can be found on the World Wide Web at the website for rcsb.org. Typically mutants refer to changes or modification to the configuration of R-groups within the active site, however mutations outside of the residues found in the active site are also considered to be mutants in light of the present invention.

"Nonmutated isomerase" includes an isomerase wherein no R-group (s) are changed relative to the active site of CHI (see, for example, PDB Accession No. 1EYP; and Table 1). A nonmutated isomerase according to the present invention may or may not have amino acid residues outside of the active site that are the same as those taught for native CHI.

The R-groups of known isolated chalcone isomerases can be readily determined by consulting sequence databases well known in the art such as, for example, GenBank. Additional R-groups found inside and/or outside of the active site may or may not be the same. R-groups may be a natural R-group, unnatural R-group, hydrophobic R-group, hydrophilic R-group, positively charged R-group, negatively charged R-group, and the like.

"Non-native" or "non-native isomerase" refers to an isomerase protein that is not found in nature, whether isolated or not. A non-native isomerase may, for example, be a mutated isomerase (see, the Examples below).

"Native" or "native isomerase" refers to isomerase proteins that are produced in nature, e.g., are not mutated (see, for example, PDB Accession No. 1EYP).

"Purified" or "isolated" refers to a protein or nucleic acid, respectively, that has been separated from its natural environment, Contaminant components of its natural environment may include enzymes, hormones, and other proteinaceous or non-proteinaceous solutes. In one embodiment, the isolated molecule, in the case of a protein, will be purified to a degree sufficient to obtain at least 15 residues of N-terminal or internal amino acid sequence or to homogeneity by SDS-PAGE under reducing or non-reducing conditions using Coomassie blue or silver stain. In the case of a nucleic acid the isolated molecule will preferably be purified to a degree sufficient to obtain a nucleic acid sequence using standard sequencing methods.

By a "substantially pure polypeptide" is meant an isomerase polypeptide (e.g., a chalcone isomerase) which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, isomerase polypeptide. A substantially pure isomerase polypeptide may be obtained, for example, by extraction from a natural source; by expression of a recombinant nucleic acid encoding an isomerase polypeptide; or by chemically synthesizing the protein. Purity can be measured by any appropriate method (e.g., column chromatography, polyacrylamide gel electrophoresis, or by HPLC analysis).

"Degenerate variations thereof" refers to changing a gene sequence using the degenerate nature of the genetic code to encode proteins having the same amino acid sequence yet having a different gene sequence. For example, a chalcone isomerase of the present invention is based on amino acid sequences. Degenerate gene variations thereof can be made encoding the same protein due to the plasticity of the genetic code, as described herein.

"Expression" refers to transcription of a gene or nucleic acid sequence, stable accumulation of nucleic acid, and the translation of that nucleic acid to a polypeptide sequence. Expression of genes also involves transcription of the gene to make RNA, processing of RNA into mRNA in eukaryotic systems, and translation of mRNA into proteins. It is not necessary for the genes to integrate into the genome of a cell in order to achieve expression. This definition in no way limits expression to a particular system or to being confined to cells or a particular cell type and is meant to include cellular, transient, in vitro, in vivo, and viral expression systems in both prokaryotic, eukaryotic cells, and the like.

"Foreign" or "heterologous" genes refers to a gene encoding a protein whose exact amino acid sequence is not normally found in the host cell.

"Promoter" and "promoter regulatory element", and the like, refers to a nucleotide sequence element within a nucleic acid fragment or gene that controls the expression of that gene. These can also include expression control sequences. Promoter regulatory elements, and the like, from a variety of sources can be used efficiently to promote gene expression. Promoter regulatory elements are meant to include constitutive, tissue-specific, developmental-specific, inducible, subgenomic promoters, and the like. Promoter regulatory elements may also include certain enhancer elements or silencing elements that improve or regulate transcriptional efficiency. Promoter regulatory elements are recognized by RNA polymerases, promote the binding thereof, and facilitate RNA transcription.

Table 1 lists the atomic structure coordinates for a chalcone isomerase (SEQ ID NOs:9-11) as derived by X-ray diffraction from a crystal of a chalcone isomerase. The data set, which may also be referred to as the "atomic coordinates" or "structure coordinates", is useful for the methods of the present invention. In addition, invention methods may use a subset or portion of the atomic coordinates contained within this data set, for example, those atomic coordinates defining the amino acid residues which comprise the enzymatic active site. The following abbreviations are used in Table 1: "Atom Type" refers to the element whose coordinates are measured. The first letter in the column defines the element; "X, Y, Z" crystallographically define the atomic position of the element measured; "B" is a thermal factor that measures movement of the atom around its atomic center; and "molecule" denoted in the table refers to the particular monomer of CHI.

TABLE 1

| Atom | Atom Type | Res | # | X | Y | Z | OCC | B | Mol. |
|---|---|---|---|---|---|---|---|---|---|
| 1 | CB | SER | 4 | 1.314 | 23.727 | 49.727 | 1.00 | 67.92 | A |
| 2 | OG | SER | 4 | 1.884 | 22.898 | 50.729 | 1.00 | 68.17 | A |
| 3 | C | SER | 4 | 2.569 | 22.924 | 47.696 | 1.00 | 67.57 | A |
| 4 | O | SER | 4 | 3.457 | 23.749 | 47.948 | 1.00 | 67.60 | A |
| 5 | N | SER | 4 | .637 | 21.623 | 48.600 | 1.00 | 67.80 | A |
| 6 | CA | SER | 4 | 1.205 | 22.987 | 48.386 | 1.00 | 67.75 | A |
| 7 | N | ILE | 5 | 2.718 | 21.924 | 46.829 | 1.00 | 67.22 | A |
| 8 | CA | ILE | 5 | 3.933 | 21.713 | 46.044 | 1.00 | 66.80 | A |
| 9 | CB | ILE | 5 | 4.100 | 20.197 | 45.707 | 1.00 | 66.89 | A |
| 10 | CG2 | ILE | 5 | 2.735 | 19.531 | 45.616 | 1.00 | 66.97 | A |
| 11 | CG1 | ILE | 5 | 4.885 | 20.005 | 44.408 | 1.00 | 66.89 | A |
| 12 | CD1 | ILE | 5 | 6.348 | 20.312 | 44.527 | 1.00 | 66.95 | A |
| 13 | C | ILE | 5 | 3.731 | 22.543 | 44.776 | 1.00 | 66.40 | A |
| 14 | O | ILE | 5 | 2.987 | 22.154 | 43.877 | 1.00 | 66.38 | A |
| 15 | N | THR | 6 | 4.382 | 23.700 | 44.723 | 1.00 | 65.89 | A |
| 16 | CA | THR | 6 | 4.247 | 24.615 | 43.594 | 1.00 | 65.37 | A |
| 17 | CB | THR | 6 | 4.518 | 26.068 | 44.030 | 1.00 | 65.36 | A |
| 18 | OG1 | THR | 6 | 5.842 | 26.163 | 44.573 | 1.00 | 65.19 | A |
| 19 | CG2 | THR | 6 | 3.510 | 26.509 | 45.078 | 1.00 | 65.29 | A |

TABLE 1-continued

| Atom | Atom Type | Res | # | X | Y | Z | OCC | B | Mol. |
|---|---|---|---|---|---|---|---|---|---|
| 20 | C | THR | 6 | 5.149 | 24.331 | 42.402 | 1.00 | 65.02 | A |
| 21 | O | THR | 6 | 5.990 | 23.432 | 42.429 | 1.00 | 64.94 | A |
| 22 | N | ALA | 7 | 4.947 | 25.113 | 41.347 | 1.00 | 64.56 | A |
| 23 | CA | ALA | 7 | 5.747 | 25.001 | 40.141 | 1.00 | 64.14 | A |
| 24 | CB | ALA | 7 | 4.900 | 25.305 | 38.911 | 1.00 | 64.10 | A |
| 25 | C | ALA | 7 | 6.848 | 26.040 | 40.294 | 1.00 | 63.80 | A |
| 26 | O | ALA | 7 | 6.735 | 26.954 | 41.114 | 1.00 | 63.75 | A |
| 27 | N | ILE | 8 | 7.917 | 25.894 | 39.524 | 1.00 | 63.43 | A |
| 28 | CA | ILE | 8 | 9.020 | 26.841 | 39.589 | 1.00 | 63.05 | A |
| 29 | CB | ILE | 8 | 10.269 | 26.220 | 40.250 | 1.00 | 62.98 | A |
| 30 | CG2 | ILE | 8 | 11.387 | 27.252 | 40.320 | 1.00 | 62.92 | A |
| 31 | CG1 | ILE | 8 | 9.926 | 25.724 | 41.654 | 1.00 | 62.91 | A |
| 32 | CD1 | ILE | 8 | 11.064 | 25.002 | 42.332 | 1.00 | 62.85 | A |
| 33 | C | ILE | 8 | 9.397 | 27.283 | 38.186 | 1.00 | 62.84 | A |
| 34 | O | ILE | 8 | 9.495 | 26.467 | 37.272 | 1.00 | 62.74 | A |
| 35 | N | THR | 9 | 9.598 | 28.581 | 38.015 | 1.00 | 62.62 | A |
| 36 | CA | THR | 9 | 9.984 | 29.104 | 36.716 | 1.00 | 62.45 | A |
| 37 | CB | THR | 9 | 9.017 | 30.206 | 36.235 | 1.00 | 62.45 | A |
| 38 | OG1 | THR | 9 | 7.720 | 29.637 | 36.021 | 1.00 | 62.47 | A |
| 39 | CG2 | THR | 9 | 9.505 | 30.817 | 34.928 | 1.00 | 62.44 | A |
| 40 | C | THR | 9 | 11.393 | 29.664 | 36.802 | 1.00 | 62.27 | A |
| 41 | O | THR | 9 | 11.708 | 30.455 | 37.689 | 1.00 | 62.24 | A |
| 42 | N | VAL | 10 | 12.244 | 29.225 | 35.885 | 1.00 | 62.10 | A |
| 43 | CA | VAL | 10 | 13.624 | 29.681 | 35.835 | 1.00 | 61.94 | A |
| 44 | CB | VAL | 10 | 14.608 | 28.509 | 36.024 | 1.00 | 61.87 | A |
| 45 | CG1 | VAL | 10 | 16.039 | 29.011 | 35.927 | 1.00 | 61.79 | A |
| 46 | CG2 | VAL | 10 | 14.369 | 27.839 | 37.370 | 1.00 | 61.80 | A |
| 47 | C | VAL | 10 | 13.863 | 30.310 | 34.469 | 1.00 | 61.89 | A |
| 48 | O | VAL | 10 | 13.782 | 29.627 | 33.448 | 1.00 | 61.89 | A |
| 49 | N | GLU | 11 | 14.148 | 31.608 | 34.453 | 1.00 | 61.82 | A |
| 50 | CA | GLU | 11 | 14.390 | 32.314 | 33.201 | 1.00 | 61.74 | A |
| 51 | CB | GLU | 11 | 15.757 | 31.931 | 32.634 | 1.00 | 61.91 | A |
| 52 | CG | GLU | 11 | 16.926 | 32.601 | 33.322 | 1.00 | 62.24 | A |
| 53 | CD | GLU | 11 | 16.947 | 34.102 | 33.095 | 1.00 | 62.41 | A |
| 54 | OE1 | GLU | 11 | 16.966 | 34.530 | 31.919 | 1.00 | 62.59 | A |
| 55 | OE2 | GLU | 11 | 16.944 | 34.851 | 34.093 | 1.00 | 62.48 | A |
| 56 | C | GLU | 11 | 13.310 | 32.001 | 32.173 | 1.00 | 61.59 | A |
| 57 | O | GLU | 11 | 13.609 | 31.632 | 31.039 | 1.00 | 61.66 | A |
| 58 | N | ASN | 12 | 12.054 | 32.132 | 32.583 | 1.00 | 61.41 | A |
| 59 | CA | ASN | 12 | 10.922 | 31.878 | 31.698 | 1.00 | 61.23 | A |
| 60 | CB | ASN | 12 | 11.060 | 32.716 | 30.426 | 1.00 | 61.51 | A |
| 61 | CG | ASN | 12 | 11.305 | 34.181 | 30.726 | 1.00 | 61.77 | A |
| 62 | OD1 | ASN | 12 | 10.511 | 34.824 | 31.417 | 1.00 | 61.95 | A |
| 63 | ND2 | ASN | 12 | 12.415 | 34.718 | 30.214 | 1.00 | 61.87 | A |
| 64 | C | ASN | 12 | 10.728 | 30.408 | 31.330 | 1.00 | 60.92 | A |
| 65 | O | ASN | 12 | 9.832 | 30.075 | 30.559 | 1.00 | 60.93 | A |
| 66 | N | LEU | 13 | 11.576 | 29.536 | 31.865 | 1.00 | 60.46 | A |
| 67 | CA | LEU | 13 | 11.451 | 28.103 | 31.612 | 1.00 | 60.03 | A |
| 68 | CB | LEU | 13 | 12.832 | 27.448 | 31.513 | 1.00 | 59.92 | A |
| 69 | CG | LEU | 13 | 13.692 | 27.886 | 30.326 | 1.00 | 59.82 | A |
| 70 | CD1 | LEU | 13 | 15.112 | 27.380 | 30.496 | 1.00 | 59.84 | A |
| 71 | CD2 | LEU | 13 | 13.082 | 27.359 | 29.041 | 1.00 | 59.83 | A |
| 72 | C | LEU | 13 | 10.690 | 27.559 | 32.813 | 1.00 | 59.78 | A |
| 73 | O | LEU | 13 | 11.206 | 27.551 | 33.930 | 1.00 | 59.74 | A |
| 74 | N | GLU | 14 | 9.460 | 27.115 | 32.595 | 1.00 | 59.52 | A |
| 75 | CA | GLU | 14 | 8.664 | 26.616 | 33.705 | 1.00 | 59.29 | A |
| 76 | CB | GLU | 14 | 7.178 | 26.915 | 33.491 | 1.00 | 59.60 | A |
| 77 | CG | GLU | 14 | 6.319 | 26.482 | 34.673 | 1.00 | 60.12 | A |
| 78 | CD | GLU | 14 | 4.845 | 26.394 | 34.340 | 1.00 | 60.47 | A |
| 79 | OE1 | GLU | 14 | 4.490 | 25.643 | 33.400 | 1.00 | 60.76 | A |
| 80 | OE2 | GLU | 14 | 4.041 | 27.067 | 35.023 | 1.00 | 60.61 | A |
| 81 | C | GLU | 14 | 8.818 | 25.133 | 33.989 | 1.00 | 58.89 | A |
| 82 | O | GLU | 14 | 8.951 | 24.315 | 33.078 | 1.00 | 58.84 | A |
| 83 | N | TYR | 15 | 8.796 | 24.811 | 35.276 | 1.00 | 58.40 | A |
| 84 | CA | TYR | 15 | 8.894 | 23.442 | 35.750 | 1.00 | 58.01 | A |
| 85 | CB | TYR | 15 | 10.107 | 23.270 | 36.663 | 1.00 | 57.57 | A |
| 86 | CG | TYR | 15 | 11.404 | 23.193 | 35.903 | 1.00 | 57.20 | A |
| 87 | CD1 | TYR | 15 | 11.998 | 24.336 | 35.373 | 1.00 | 56.96 | A |
| 88 | CE1 | TYR | 15 | 13.172 | 24.256 | 34.631 | 1.00 | 56.83 | A |
| 89 | CD2 | TYR | 15 | 12.017 | 21.964 | 35.674 | 1.00 | 56.98 | A |
| 90 | CE2 | TYR | 15 | 13.186 | 21.870 | 34.934 | 1.00 | 56.81 | A |
| 91 | CZ | TYR | 15 | 13.760 | 23.016 | 34.414 | 1.00 | 56.76 | A |
| 92 | OH | TYR | 15 | 14.919 | 22.915 | 33.679 | 1.00 | 56.45 | A |
| 93 | C | TYR | 15 | 7.618 | 23.132 | 36.516 | 1.00 | 57.93 | A |
| 94 | O | TYR | 15 | 7.439 | 23.577 | 37.647 | 1.00 | 57.80 | A |
| 95 | N | PRO | 16 | 6.703 | 22.379 | 35.891 | 1.00 | 57.97 | A |
| 96 | CD | PRO | 16 | 6.811 | 21.806 | 34.539 | 1.00 | 57.95 | A |

TABLE 1-continued

| Atom | Atom Type | Res | # | X | Y | Z | OCC | B | Mol. |
|---|---|---|---|---|---|---|---|---|---|
| 97 | CA | PRO | 16 | 5.429 | 22.005 | 36.514 | 1.00 | 58.06 | A |
| 98 | CB | PRO | 16 | 4.829 | 21.029 | 35.505 | 1.00 | 58.00 | A |
| 99 | CG | PRO | 16 | 5.373 | 21.514 | 34.206 | 1.00 | 58.02 | A |
| 100 | C | PRO | 16 | 5.666 | 21.351 | 37.872 | 1.00 | 58.14 | A |
| 101 | O | PRO | 16 | 6.686 | 20.694 | 38.081 | 1.00 | 58.11 | A |
| 102 | N | ALA | 17 | 4.722 | 21.532 | 38.789 | 1.00 | 58.25 | A |
| 103 | CA | ALA | 17 | 4.839 | 20.957 | 40.123 | 1.00 | 58.39 | A |
| 104 | CB | ALA | 17 | 3.678 | 21.419 | 40.990 | 1.00 | 58.35 | A |
| 105 | C | ALA | 17 | 4.872 | 19.435 | 40.067 | 1.00 | 58.46 | A |
| 106 | O | ALA | 17 | 5.458 | 18.786 | 40.932 | 1.00 | 58.51 | A |
| 107 | N | VAL | 18 | 4.242 | 18.872 | 39.045 | 1.00 | 58.58 | A |
| 108 | CA | VAL | 18 | 4.183 | 17.425 | 38.882 | 1.00 | 58.75 | A |
| 109 | CB | VAL | 18 | 2.849 | 16.865 | 39.448 | 1.00 | 58.76 | A |
| 110 | CG1 | VAL | 18 | 2.686 | 15.402 | 39.079 | 1.00 | 58.85 | A |
| 111 | CG2 | VAL | 18 | 2.821 | 17.025 | 40.957 | 1.00 | 58.73 | A |
| 112 | C | VAL | 18 | 4.296 | 17.049 | 37.412 | 1.00 | 58.83 | A |
| 113 | O | VAL | 18 | 3.944 | 17.835 | 36.535 | 1.00 | 58.87 | A |
| 114 | N | VAL | 19 | 4.800 | 15.850 | 37.147 | 1.00 | 58.92 | A |
| 115 | CA | VAL | 19 | 4.942 | 15.359 | 35.782 | 1.00 | 59.03 | A |
| 116 | CB | VAL | 19 | 6.300 | 15.763 | 35.148 | 1.00 | 59.07 | A |
| 117 | CG1 | VAL | 19 | 6.430 | 17.275 | 35.089 | 1.00 | 59.10 | A |
| 118 | CG2 | VAL | 19 | 7.445 | 15.160 | 35.934 | 1.00 | 59.07 | A |
| 119 | C | VAL | 19 | 4.863 | 13.841 | 35.794 | 1.00 | 59.13 | A |
| 120 | O | VAL | 19 | 5.164 | 13.207 | 36.808 | 1.00 | 59.11 | A |
| 121 | N | THR | 20 | 4.456 | 13.266 | 34.666 | 1.00 | 59.26 | A |
| 122 | CA | THR | 20 | 4.350 | 11.817 | 34.529 | 1.00 | 59.38 | A |
| 123 | CB | THR | 20 | 2.899 | 11.393 | 34.226 | 1.00 | 59.40 | A |
| 124 | OG1 | THR | 20 | 2.067 | 11.731 | 35.342 | 1.00 | 59.47 | A |
| 125 | CG2 | THR | 20 | 2.819 | 9.890 | 33.973 | 1.00 | 59.25 | A |
| 126 | C | THR | 20 | 5.258 | 11.353 | 33.395 | 1.00 | 59.42 | A |
| 127 | O | THR | 20 | 5.264 | 11.943 | 32.317 | 1.00 | 59.50 | A |
| 128 | N | SER | 21 | 6.032 | 10.301 | 33.640 | 1.00 | 59.49 | A |
| 129 | CA | SER | 21 | 6.943 | 9.784 | 32.625 | 1.00 | 59.51 | A |
| 130 | CB | SER | 21 | 8.044 | 8.942 | 33.271 | 1.00 | 59.56 | A |
| 131 | OG | SER | 21 | 8.853 | 8.329 | 32.277 | 1.00 | 59.58 | A |
| 132 | C | SER | 21 | 6.247 | 8.942 | 31.566 | 1.00 | 59.51 | A |
| 133 | O | SER | 21 | 5.539 | 7.989 | 31.884 | 1.00 | 59.49 | A |
| 134 | N | PRO | 22 | 6.427 | 9.299 | 30.287 | 1.00 | 59.53 | A |
| 135 | CD | PRO | 22 | 6.896 | 10.609 | 29.803 | 1.00 | 59.57 | A |
| 136 | CA | PRO | 22 | 5.805 | 8.540 | 29.199 | 1.00 | 59.44 | A |
| 137 | CB | PRO | 22 | 5.976 | 9.463 | 27.991 | 1.00 | 59.52 | A |
| 138 | CG | PRO | 22 | 6.003 | 10.835 | 28.609 | 1.00 | 59.57 | A |
| 139 | C | PRO | 22 | 6.576 | 7.232 | 29.029 | 1.00 | 59.35 | A |
| 140 | O | PRO | 22 | 6.142 | 6.322 | 28.321 | 1.00 | 59.29 | A |
| 141 | N | VAL | 23 | 7.722 | 7.152 | 29.701 | 1.00 | 59.24 | A |
| 142 | CA | VAL | 23 | 8.586 | 5.980 | 29.632 | 1.00 | 59.12 | A |
| 143 | CB | VAL | 23 | 10.076 | 6.383 | 29.781 | 1.00 | 59.16 | A |
| 144 | CG1 | VAL | 23 | 10.967 | 5.150 | 29.690 | 1.00 | 59.11 | A |
| 145 | CG2 | VAL | 23 | 10.450 | 7.400 | 28.709 | 1.00 | 59.19 | A |
| 146 | C | VAL | 23 | 8.272 | 4.924 | 30.689 | 1.00 | 59.03 | A |
| 147 | O | VAL | 23 | 8.253 | 3.731 | 30.393 | 1.00 | 59.06 | A |
| 148 | N | THR | 24 | 8.019 | 5.362 | 31.918 | 1.00 | 58.90 | A |
| 149 | CA | THR | 24 | 7.748 | 4.432 | 33.008 | 1.00 | 58.69 | A |
| 150 | CB | THR | 24 | 8.759 | 4.636 | 34.150 | 1.00 | 58.76 | A |
| 151 | OG1 | THR | 24 | 8.694 | 5.995 | 34.596 | 1.00 | 58.70 | A |
| 152 | CG2 | THR | 24 | 10.174 | 4.327 | 33.678 | 1.00 | 58.73 | A |
| 153 | C | THR | 24 | 6.345 | 4.544 | 33.595 | 1.00 | 58.51 | A |
| 154 | O | THR | 24 | 5.917 | 3.675 | 34.356 | 1.00 | 58.54 | A |
| 155 | N | GLY | 25 | 5.636 | 5.612 | 33.252 | 1.00 | 58.25 | A |
| 156 | CA | GLY | 25 | 4.293 | 5.791 | 33.775 | 1.00 | 57.90 | A |
| 157 | C | GLY | 25 | 4.290 | 6.303 | 35.205 | 1.00 | 57.62 | A |
| 158 | O | GLY | 25 | 3.239 | 6.623 | 35.764 | 1.00 | 57.68 | A |
| 159 | N | LYS | 26 | 5.472 | 6.383 | 35.805 | 1.00 | 57.25 | A |
| 160 | CA | LYS | 26 | 5.592 | 6.862 | 37.174 | 1.00 | 56.78 | A |
| 161 | CB | LYS | 26 | 6.977 | 6.513 | 37.720 | 1.00 | 56.84 | A |
| 162 | CG | LYS | 26 | 7.244 | 5.014 | 37.718 | 1.00 | 56.94 | A |
| 163 | CD | LYS | 26 | 8.619 | 4.652 | 38.255 | 1.00 | 57.05 | A |
| 164 | CE | LYS | 26 | 8.748 | 3.143 | 38.402 | 1.00 | 57.13 | A |
| 165 | NZ | LYS | 26 | 10.088 | 2.707 | 38.901 | 1.00 | 57.35 | A |
| 166 | C | LYS | 26 | 5.354 | 8.368 | 37.224 | 1.00 | 56.40 | A |
| 167 | O | LYS | 26 | 5.589 | 9.078 | 36.243 | 1.00 | 56.47 | A |
| 168 | N | SER | 27 | 4.860 | 8.853 | 38.357 | 1.00 | 55.84 | A |
| 169 | CA | SER | 27 | 4.607 | 10.282 | 38.512 | 1.00 | 55.24 | A |
| 170 | CB | SER | 27 | 3.182 | 10.515 | 39.021 | 1.00 | 55.40 | A |
| 171 | OG | SER | 27 | 2.947 | 9.774 | 40.205 | 1.00 | 55.82 | A |
| 172 | C | SER | 27 | 5.619 | 10.866 | 39.491 | 1.00 | 54.61 | A |
| 173 | O | SER | 27 | 6.023 | 10.197 | 40.443 | 1.00 | 54.55 | A |

TABLE 1-continued

| Atom | Atom Type | Res | # | X | Y | Z | OCC | B | Mol. |
|---|---|---|---|---|---|---|---|---|---|
| 174 | N | TYR | 28 | 6.032 | 12.108 | 39.252 | 1.00 | 53.92 | A |
| 175 | CA | TYR | 28 | 7.010 | 12.759 | 40.120 | 1.00 | 53.08 | A |
| 176 | CB | TYR | 28 | 8.364 | 12.920 | 39.414 | 1.00 | 53.09 | A |
| 177 | CG | TYR | 28 | 8.740 | 11.829 | 38.440 | 1.00 | 53.03 | A |
| 178 | CD1 | TYR | 28 | 8.118 | 11.735 | 37.199 | 1.00 | 53.08 | A |
| 179 | CE1 | TYR | 28 | 8.493 | 10.762 | 36.282 | 1.00 | 53.18 | A |
| 180 | CD2 | TYR | 28 | 9.748 | 10.915 | 38.744 | 1.00 | 53.03 | A |
| 181 | CE2 | TYR | 28 | 10.129 | 9.938 | 37.837 | 1.00 | 52.99 | A |
| 182 | CZ | TYR | 28 | 9.500 | 9.867 | 36.608 | 1.00 | 53.14 | A |
| 183 | OH | TYR | 28 | 9.874 | 8.908 | 35.701 | 1.00 | 53.23 | A |
| 184 | C | TYR | 28 | 6.550 | 14.146 | 40.541 | 1.00 | 52.56 | A |
| 185 | O | TYR | 28 | 5.671 | 14.743 | 39.916 | 1.00 | 52.53 | A |
| 186 | N | PHE | 29 | 7.155 | 14.658 | 41.606 | 1.00 | 51.84 | A |
| 187 | CA | PHE | 29 | 6.837 | 15.992 | 42.082 | 1.00 | 51.21 | A |
| 188 | CB | PHE | 29 | 6.298 | 15.937 | 43.517 | 1.00 | 51.18 | A |
| 189 | CG | PHE | 29 | 7.297 | 15.469 | 44.535 | 1.00 | 51.12 | A |
| 190 | CD1 | PHE | 29 | 8.117 | 16.379 | 45.195 | 1.00 | 51.10 | A |
| 191 | CD2 | PHE | 29 | 7.404 | 14.119 | 44.852 | 1.00 | 51.11 | A |
| 192 | CE1 | PHE | 29 | 9.030 | 15.954 | 46.160 | 1.00 | 51.04 | A |
| 193 | CE2 | PHE | 29 | 8.315 | 13.683 | 45.816 | 1.00 | 51.11 | A |
| 194 | CZ | PHE | 29 | 9.129 | 14.604 | 46.471 | 1.00 | 51.04 | A |
| 195 | C | PHE | 29 | 8.126 | 16.801 | 42.004 | 1.00 | 50.74 | A |
| 196 | O | PHE | 29 | 9.218 | 16.260 | 42.184 | 1.00 | 50.60 | A |
| 197 | N | LEU | 30 | 8.003 | 18.087 | 41.710 | 1.00 | 50.27 | A |
| 198 | CA | LEU | 30 | 9.172 | 18.951 | 41.601 | 1.00 | 49.82 | A |
| 199 | CB | LEU | 30 | 8.757 | 20.321 | 41.069 | 1.00 | 49.72 | A |
| 200 | CG | LEU | 30 | 9.886 | 21.320 | 40.830 | 1.00 | 49.58 | A |
| 201 | CD1 | LEU | 30 | 10.840 | 20.777 | 39.779 | 1.00 | 49.42 | A |
| 202 | CD2 | LEU | 30 | 9.284 | 22.653 | 40.395 | 1.00 | 49.59 | A |
| 203 | C | LEU | 30 | 9.874 | 19.111 | 42.945 | 1.00 | 49.54 | A |
| 204 | O | LEU | 30 | 9.311 | 19.671 | 43.887 | 1.00 | 49.44 | A |
| 205 | N | GLY | 31 | 11.106 | 18.613 | 43.024 | 1.00 | 49.23 | A |
| 206 | CA | GLY | 31 | 11.866 | 18.724 | 44.257 | 1.00 | 48.92 | A |
| 207 | C | GLY | 31 | 12.561 | 20.067 | 44.333 | 1.00 | 48.73 | A |
| 208 | O | GLY | 31 | 12.777 | 20.617 | 45.414 | 1.00 | 48.72 | A |
| 209 | N | GLY | 32 | 12.904 | 20.601 | 43.167 | 1.00 | 48.61 | A |
| 210 | CA | GLY | 32 | 13.571 | 21.885 | 43.091 | 1.00 | 48.42 | A |
| 211 | C | GLY | 32 | 14.033 | 22.199 | 41.681 | 1.00 | 48.30 | A |
| 212 | O | GLY | 32 | 14.156 | 21.306 | 40.841 | 1.00 | 48.08 | A |
| 213 | N | ALA | 33 | 14.278 | 23.479 | 41.422 | 1.00 | 48.27 | A |
| 214 | CA | ALA | 33 | 14.738 | 23.938 | 40.118 | 1.00 | 48.30 | A |
| 215 | CB | ALA | 33 | 13.553 | 24.384 | 39.266 | 1.00 | 48.18 | A |
| 216 | C | ALA | 33 | 15.704 | 25.094 | 40.314 | 1.00 | 48.37 | A |
| 217 | O | ALA | 33 | 15.560 | 25.884 | 41.247 | 1.00 | 48.48 | A |
| 218 | N | GLY | 34 | 16.694 | 25.186 | 39.437 | 1.00 | 48.42 | A |
| 219 | CA | GLY | 34 | 17.667 | 26.252 | 39.529 | 1.00 | 48.50 | A |
| 220 | C | GLY | 34 | 18.320 | 26.486 | 38.181 | 1.00 | 48.60 | A |
| 221 | O | GLY | 34 | 17.731 | 26.209 | 37.132 | 1.00 | 48.47 | A |
| 222 | N | GLU | 35 | 19.550 | 26.984 | 38.208 | 1.00 | 48.66 | A |
| 223 | CA | GLU | 35 | 20.268 | 27.255 | 36.980 | 1.00 | 48.81 | A |
| 224 | CB | GLU | 35 | 20.173 | 28.731 | 36.625 | 1.00 | 49.27 | A |
| 225 | CG | GLU | 35 | 19.336 | 29.521 | 37.593 | 1.00 | 50.31 | A |
| 226 | CD | GLU | 35 | 19.328 | 30.995 | 37.273 | 1.00 | 50.76 | A |
| 227 | OE1 | GLU | 35 | 19.983 | 31.383 | 36.294 | 1.00 | 51.26 | A |
| 228 | OE2 | GLU | 35 | 18.668 | 31.766 | 37.995 | 1.00 | 51.30 | A |
| 229 | C | GLU | 35 | 21.724 | 26.865 | 37.061 | 1.00 | 48.56 | A |
| 230 | O | GLU | 35 | 22.319 | 26.835 | 38.137 | 1.00 | 48.49 | A |
| 231 | N | ARG | 36 | 22.294 | 26.557 | 35.906 | 1.00 | 48.31 | A |
| 232 | CA | ARG | 36 | 23.692 | 26.184 | 35.814 | 1.00 | 48.10 | A |
| 233 | CB | ARG | 36 | 23.834 | 24.681 | 35.559 | 1.00 | 48.15 | A |
| 234 | CG | ARG | 36 | 24.466 | 23.912 | 36.716 | 1.00 | 48.32 | A |
| 235 | CD | ARG | 36 | 23.936 | 24.429 | 38.027 | 1.00 | 48.33 | A |
| 236 | NE | ARG | 36 | 23.980 | 23.448 | 39.103 | 1.00 | 48.32 | A |
| 237 | CZ | ARG | 36 | 23.172 | 23.506 | 40.153 | 1.00 | 48.28 | A |
| 238 | NH1 | ARG | 36 | 22.287 | 24.492 | 40.229 | 1.00 | 48.19 | A |
| 239 | NH2 | ARG | 36 | 23.239 | 22.590 | 41.114 | 1.00 | 48.15 | A |
| 240 | C | ARG | 36 | 24.256 | 26.954 | 34.648 | 1.00 | 48.05 | A |
| 241 | O | ARG | 36 | 23.530 | 27.321 | 33.721 | 1.00 | 47.90 | A |
| 242 | N | GLY | 37 | 25.553 | 27.201 | 34.706 | 1.00 | 47.95 | A |
| 243 | CA | GLY | 37 | 26.202 | 27.934 | 33.646 | 1.00 | 47.99 | A |
| 244 | C | GLY | 37 | 27.680 | 27.972 | 33.926 | 1.00 | 47.99 | A |
| 245 | O | GLY | 37 | 28.225 | 27.045 | 34.519 | 1.00 | 47.95 | A |
| 246 | N | LEU | 38 | 28.328 | 29.052 | 33.510 | 1.00 | 47.97 | A |
| 247 | CA | LEU | 38 | 29.757 | 29.190 | 33.723 | 1.00 | 47.98 | A |
| 248 | CB | LEU | 38 | 30.497 | 29.063 | 32.382 | 1.00 | 48.09 | A |
| 249 | CG | LEU | 38 | 30.242 | 27.777 | 31.580 | 1.00 | 48.20 | A |
| 250 | CD1 | LEU | 38 | 30.780 | 27.914 | 30.165 | 1.00 | 48.09 | A |

TABLE 1-continued

| Atom | Atom Type | Res | # | X | Y | Z | OCC | B | Mol. |
|---|---|---|---|---|---|---|---|---|---|
| 251 | CD2 | LEU | 38 | 30.894 | 26.601 | 32.287 | 1.00 | 48.21 | A |
| 252 | C | LEU | 38 | 30.071 | 30.533 | 34.361 | 1.00 | 47.94 | A |
| 253 | O | LEU | 38 | 29.368 | 31.521 | 34.145 | 1.00 | 47.77 | A |
| 254 | N | THR | 39 | 31.114 | 30.554 | 35.178 | 1.00 | 47.97 | A |
| 255 | CA | THR | 39 | 31.544 | 31.794 | 35.797 | 1.00 | 48.05 | A |
| 256 | CB | THR | 39 | 32.021 | 31.579 | 37.242 | 1.00 | 48.08 | A |
| 257 | OG1 | THR | 39 | 30.921 | 31.111 | 38.030 | 1.00 | 48.06 | A |
| 258 | CG2 | THR | 39 | 32.532 | 32.894 | 37.839 | 1.00 | 48.01 | A |
| 259 | C | THR | 39 | 32.697 | 32.254 | 34.919 | 1.00 | 48.04 | A |
| 260 | O | THR | 39 | 33.765 | 31.642 | 34.902 | 1.00 | 48.00 | A |
| 261 | N | ILE | 40 | 32.452 | 33.313 | 34.160 | 1.00 | 48.10 | A |
| 262 | CA | ILE | 40 | 33.452 | 33.854 | 33.249 | 1.00 | 48.20 | A |
| 263 | CB | ILE | 40 | 32.884 | 33.983 | 31.816 | 1.00 | 48.29 | A |
| 264 | CG2 | ILE | 40 | 33.992 | 34.369 | 30.856 | 1.00 | 48.42 | A |
| 265 | CG1 | ILE | 40 | 32.241 | 32.664 | 31.372 | 1.00 | 48.43 | A |
| 266 | CD1 | ILE | 40 | 33.229 | 31.523 | 31.159 | 1.00 | 48.46 | A |
| 267 | C | ILE | 40 | 33.858 | 35.241 | 33.732 | 1.00 | 48.15 | A |
| 268 | O | ILE | 40 | 33.030 | 36.156 | 33.785 | 1.00 | 48.07 | A |
| 269 | N | GLU | 41 | 35.131 | 35.389 | 34.085 | 1.00 | 48.08 | A |
| 270 | CA | GLU | 41 | 35.644 | 36.665 | 34.569 | 1.00 | 47.96 | A |
| 271 | CB | GLU | 41 | 35.594 | 37.711 | 33.450 | 1.00 | 48.36 | A |
| 272 | CG | GLU | 41 | 36.387 | 37.321 | 32.207 | 1.00 | 48.95 | A |
| 273 | CD | GLU | 41 | 37.889 | 37.463 | 32.393 | 1.00 | 49.41 | A |
| 274 | OE1 | GLU | 41 | 38.413 | 36.986 | 33.424 | 1.00 | 49.70 | A |
| 275 | OE2 | GLU | 41 | 38.549 | 38.051 | 31.502 | 1.00 | 49.86 | A |
| 276 | C | GLU | 41 | 34.816 | 37.137 | 35.754 | 1.00 | 47.62 | A |
| 277 | O | GLU | 41 | 34.394 | 38.290 | 35.804 | 1.00 | 47.61 | A |
| 278 | N | GLY | 42 | 34.575 | 36.234 | 36.700 | 1.00 | 47.21 | A |
| 279 | CA | GLY | 42 | 33.805 | 36.586 | 37.881 | 1.00 | 46.69 | A |
| 280 | C | GLY | 42 | 32.329 | 36.848 | 37.638 | 1.00 | 46.35 | A |
| 281 | O | GLY | 42 | 31.622 | 37.266 | 38.555 | 1.00 | 46.46 | A |
| 282 | N | ASN | 43 | 31.861 | 36.603 | 36.415 | 1.00 | 45.84 | A |
| 283 | CA | ASN | 43 | 30.458 | 36.809 | 36.057 | 1.00 | 45.29 | A |
| 284 | CB | ASN | 43 | 30.349 | 37.654 | 34.786 | 1.00 | 45.16 | A |
| 285 | CG | ASN | 43 | 30.617 | 39.121 | 35.035 | 1.00 | 45.00 | A |
| 286 | OD1 | ASN | 43 | 29.693 | 39.899 | 35.273 | 1.00 | 44.96 | A |
| 287 | ND2 | ASN | 43 | 31.886 | 39.506 | 34.990 | 1.00 | 44.74 | A |
| 288 | C | ASN | 43 | 29.760 | 35.479 | 35.813 | 1.00 | 45.05 | A |
| 289 | O | ASN | 43 | 30.271 | 34.628 | 35.083 | 1.00 | 44.95 | A |
| 290 | N | PHE | 44 | 28.592 | 35.296 | 36.421 | 1.00 | 44.77 | A |
| 291 | CA | PHE | 44 | 27.856 | 34.062 | 36.218 | 1.00 | 44.54 | A |
| 292 | CB | PHE | 44 | 26.857 | 33.801 | 37.345 | 1.00 | 44.68 | A |
| 293 | CG | PHE | 44 | 26.102 | 32.502 | 37.187 | 1.00 | 44.83 | A |
| 294 | CD1 | PHE | 44 | 26.780 | 31.286 | 37.185 | 1.00 | 44.87 | A |
| 295 | CD2 | PHE | 44 | 24.719 | 32.496 | 37.048 | 1.00 | 44.98 | A |
| 296 | CE1 | PHE | 44 | 26.092 | 30.079 | 37.050 | 1.00 | 45.03 | A |
| 297 | CE2 | PHE | 44 | 24.019 | 31.298 | 36.914 | 1.00 | 45.00 | A |
| 298 | CZ | PHE | 44 | 24.708 | 30.084 | 36.915 | 1.00 | 45.08 | A |
| 299 | C | PHE | 44 | 27.100 | 34.142 | 34.904 | 1.00 | 44.28 | A |
| 300 | O | PHE | 44 | 26.204 | 34.968 | 34.739 | 1.00 | 44.16 | A |
| 301 | N | ILE | 45 | 27.477 | 33.284 | 33.967 | 1.00 | 44.04 | A |
| 302 | CA | ILE | 45 | 26.825 | 33.245 | 32.670 | 1.00 | 43.98 | A |
| 303 | CB | ILE | 45 | 27.867 | 33.142 | 31.535 | 1.00 | 43.86 | A |
| 304 | CG2 | ILE | 45 | 27.179 | 33.253 | 30.171 | 1.00 | 43.72 | A |
| 305 | CG1 | ILE | 45 | 28.915 | 34.253 | 31.697 | 1.00 | 43.65 | A |
| 306 | CD1 | ILE | 45 | 28.339 | 35.658 | 31.718 | 1.00 | 43.39 | A |
| 307 | C | ILE | 45 | 25.924 | 32.016 | 32.678 | 1.00 | 44.04 | A |
| 308 | O | ILE | 45 | 26.402 | 30.882 | 32.703 | 1.00 | 43.96 | A |
| 309 | N | LYS | 46 | 24.620 | 32.260 | 32.685 | 1.00 | 44.19 | A |
| 310 | CA | LYS | 46 | 23.632 | 31.191 | 32.713 | 1.00 | 44.41 | A |
| 311 | CB | LYS | 46 | 22.255 | 31.745 | 33.069 | 1.00 | 44.81 | A |
| 312 | CG | LYS | 46 | 22.226 | 32.729 | 34.226 | 1.00 | 45.69 | A |
| 313 | CD | LYS | 46 | 20.797 | 33.163 | 34.535 | 1.00 | 46.28 | A |
| 314 | CE | LYS | 46 | 20.057 | 33.662 | 33.294 | 1.00 | 46.83 | A |
| 315 | NZ | LYS | 46 | 20.028 | 35.167 | 33.162 | 1.00 | 47.55 | A |
| 316 | C | LYS | 46 | 23.540 | 30.499 | 31.359 | 1.00 | 44.31 | A |
| 317 | O | LYS | 46 | 23.489 | 31.161 | 30.326 | 1.00 | 44.22 | A |
| 318 | N | PHE | 47 | 23.517 | 29.169 | 31.376 | 1.00 | 44.11 | A |
| 319 | CA | PHE | 47 | 23.410 | 28.391 | 30.151 | 1.00 | 44.14 | A |
| 320 | CB | PHE | 47 | 24.660 | 27.550 | 29.933 | 1.00 | 43.96 | A |
| 321 | CG | PHE | 47 | 25.743 | 28.279 | 29.203 | 1.00 | 44.12 | A |
| 322 | CD1 | PHE | 47 | 26.644 | 29.092 | 29.888 | 1.00 | 44.02 | A |
| 323 | CD2 | PHE | 47 | 25.827 | 28.201 | 27.815 | 1.00 | 44.07 | A |
| 324 | CE1 | PHE | 47 | 27.611 | 29.817 | 29.200 | 1.00 | 43.92 | A |
| 325 | CE2 | PHE | 47 | 26.791 | 28.923 | 27.116 | 1.00 | 43.99 | A |
| 326 | CZ | PHE | 47 | 27.686 | 29.735 | 27.811 | 1.00 | 43.99 | A |
| 327 | C | PHE | 47 | 22.194 | 27.484 | 30.150 | 1.00 | 44.13 | A |

TABLE 1-continued

| Atom | Atom Type | Res | # | X | Y | Z | OCC | B | Mol. |
|---|---|---|---|---|---|---|---|---|---|
| 328 | O | PHE | 47 | 21.664 | 27.152 | 29.086 | 1.00 | 44.05 | A |
| 329 | N | THR | 48 | 21.743 | 27.077 | 31.330 | 1.00 | 44.21 | A |
| 330 | CA | THR | 48 | 20.590 | 26.200 | 31.393 | 1.00 | 44.44 | A |
| 331 | CB | THR | 48 | 21.002 | 24.726 | 31.133 | 1.00 | 44.49 | A |
| 332 | OG1 | THR | 48 | 19.824 | 23.910 | 31.060 | 1.00 | 44.77 | A |
| 333 | CG2 | THR | 48 | 21.902 | 24.200 | 32.253 | 1.00 | 44.35 | A |
| 334 | C | THR | 48 | 19.835 | 26.247 | 32.702 | 1.00 | 44.49 | A |
| 335 | O | THR | 48 | 20.341 | 26.708 | 33.728 | 1.00 | 44.53 | A |
| 336 | N | ALA | 49 | 18.596 | 25.789 | 32.643 | 1.00 | 44.62 | A |
| 337 | CA | ALA | 49 | 17.757 | 25.700 | 33.819 | 1.00 | 44.66 | A |
| 338 | CB | ALA | 49 | 16.326 | 26.106 | 33.502 | 1.00 | 44.62 | A |
| 339 | C | ALA | 49 | 17.821 | 24.218 | 34.149 | 1.00 | 44.73 | A |
| 340 | O | ALA | 49 | 18.098 | 23.387 | 33.277 | 1.00 | 44.64 | A |
| 341 | N | ILE | 50 | 17.605 | 23.888 | 35.409 | 1.00 | 44.80 | A |
| 342 | CA | ILE | 50 | 17.630 | 22.501 | 35.823 | 1.00 | 45.04 | A |
| 343 | CB | ILE | 50 | 18.963 | 22.098 | 36.472 | 1.00 | 45.43 | A |
| 344 | CG2 | ILE | 50 | 18.916 | 20.618 | 36.842 | 1.00 | 45.46 | A |
| 345 | CG1 | ILE | 50 | 20.117 | 22.339 | 35.504 | 1.00 | 45.85 | A |
| 346 | CD1 | ILE | 50 | 21.468 | 22.096 | 36.128 | 1.00 | 46.32 | A |
| 347 | C | ILE | 50 | 16.547 | 22.281 | 36.849 | 1.00 | 44.88 | A |
| 348 | O | ILE | 50 | 16.352 | 23.097 | 37.749 | 1.00 | 44.85 | A |
| 349 | N | GLY | 51 | 15.841 | 21.174 | 36.700 | 1.00 | 44.82 | A |
| 350 | CA | GLY | 51 | 14.792 | 20.836 | 37.637 | 1.00 | 44.61 | A |
| 351 | C | GLY | 51 | 14.951 | 19.380 | 38.020 | 1.00 | 44.59 | A |
| 352 | O | GLY | 51 | 15.251 | 18.535 | 37.175 | 1.00 | 44.53 | A |
| 353 | N | VAL | 52 | 14.772 | 19.086 | 39.301 | 1.00 | 44.48 | A |
| 354 | CA | VAL | 52 | 14.881 | 17.721 | 39.780 | 1.00 | 44.45 | A |
| 355 | CB | VAL | 52 | 15.888 | 17.607 | 40.936 | 1.00 | 44.45 | A |
| 356 | CG1 | VAL | 52 | 15.957 | 16.162 | 41.424 | 1.00 | 44.49 | A |
| 357 | CG2 | VAL | 52 | 17.257 | 18.077 | 40.475 | 1.00 | 44.55 | A |
| 358 | C | VAL | 52 | 13.527 | 17.233 | 40.267 | 1.00 | 44.39 | A |
| 359 | O | VAL | 52 | 12.932 | 17.822 | 41.170 | 1.00 | 44.42 | A |
| 360 | N | TYR | 53 | 13.035 | 16.267 | 39.649 | 1.00 | 44.36 | A |
| 361 | CA | TYR | 53 | 11.764 | 15.585 | 40.053 | 1.00 | 44.38 | A |
| 362 | CB | TYR | 53 | 10.873 | 15.298 | 38.841 | 1.00 | 44.42 | A |
| 363 | CG | TYR | 53 | 10.307 | 16.543 | 38.209 | 1.00 | 44.64 | A |
| 364 | CD1 | TYR | 53 | 11.004 | 17.218 | 37.211 | 1.00 | 44.66 | A |
| 365 | CE1 | TYR | 53 | 10.510 | 18.392 | 36.656 | 1.00 | 44.85 | A |
| 366 | CD2 | TYR | 53 | 9.091 | 17.075 | 38.642 | 1.00 | 44.79 | A |
| 367 | CE2 | TYR | 53 | 8.585 | 18.256 | 38.093 | 1.00 | 44.84 | A |
| 368 | CZ | TYR | 53 | 9.300 | 18.906 | 37.102 | 1.00 | 44.90 | A |
| 369 | OH | TYR | 53 | 8.814 | 20.070 | 36.550 | 1.00 | 44.98 | A |
| 370 | C | TYR | 53 | 12.019 | 14.294 | 40.809 | 1.00 | 44.31 | A |
| 371 | O | TYR | 53 | 12.924 | 13.535 | 40.473 | 1.00 | 44.16 | A |
| 372 | N | LEU | 54 | 11.222 | 14.057 | 41.842 | 1.00 | 44.38 | A |
| 373 | CA | LEU | 54 | 11.360 | 12.846 | 42.630 | 1.00 | 44.58 | A |
| 374 | CB | LEU | 54 | 11.602 | 13.196 | 44.098 | 1.00 | 44.57 | A |
| 375 | CG | LEU | 54 | 12.821 | 14.066 | 44.413 | 1.00 | 44.65 | A |
| 376 | CD1 | LEU | 54 | 12.956 | 14.179 | 45.920 | 1.00 | 44.61 | A |
| 377 | CD2 | LEU | 54 | 14.081 | 13.457 | 43.814 | 1.00 | 44.54 | A |
| 378 | C | LEU | 54 | 10.067 | 12.055 | 42.488 | 1.00 | 44.72 | A |
| 379 | O | LEU | 54 | 8.980 | 12.634 | 42.499 | 1.00 | 44.65 | A |
| 380 | N | GLU | 55 | 10.182 | 10.740 | 42.340 | 1.00 | 44.92 | A |
| 381 | CA | GLU | 55 | 8.999 | 9.905 | 42.202 | 1.00 | 45.23 | A |
| 382 | CB | GLU | 55 | 9.388 | 8.429 | 42.108 | 1.00 | 45.30 | A |
| 383 | CG | GLU | 55 | 8.289 | 7.553 | 41.512 | 1.00 | 45.53 | A |
| 384 | CD | GLU | 55 | 8.682 | 6.094 | 41.412 | 1.00 | 45.70 | A |
| 385 | OE1 | GLU | 55 | 9.897 | 5.791 | 41.434 | 1.00 | 45.76 | A |
| 386 | OE2 | GLU | 55 | 7.773 | 5.245 | 41.297 | 1.00 | 45.91 | A |
| 387 | C | GLU | 55 | 8.118 | 10.141 | 43.422 | 1.00 | 45.38 | A |
| 388 | O | GLU | 55 | 8.619 | 10.341 | 44.528 | 1.00 | 45.30 | A |
| 389 | N | ASP | 56 | 6.805 | 10.133 | 43.221 | 1.00 | 45.67 | A |
| 390 | CA | ASP | 56 | 5.875 | 10.365 | 44.320 | 1.00 | 45.96 | A |
| 391 | CB | ASP | 56 | 4.433 | 10.122 | 43.847 | 1.00 | 46.66 | A |
| 392 | CG | ASP | 56 | 4.256 | 8.790 | 43.135 | 1.00 | 47.25 | A |
| 393 | OD1 | ASP | 56 | 3.175 | 8.582 | 42.539 | 1.00 | 47.89 | A |
| 394 | OD2 | ASP | 56 | 5.180 | 7.946 | 43.162 | 1.00 | 47.80 | A |
| 395 | C | ASP | 56 | 6.178 | 9.531 | 45.565 | 1.00 | 45.79 | A |
| 396 | O | ASP | 56 | 6.049 | 10.014 | 46.690 | 1.00 | 45.83 | A |
| 397 | N | ILE | 57 | 6.605 | 8.290 | 45.371 | 1.00 | 45.59 | A |
| 398 | CA | ILE | 57 | 6.904 | 7.422 | 46.505 | 1.00 | 45.50 | A |
| 399 | CB | ILE | 57 | 7.136 | 5.975 | 46.039 | 1.00 | 45.50 | A |
| 400 | CG2 | ILE | 57 | 5.880 | 5.456 | 45.326 | 1.00 | 45.59 | A |
| 401 | CG1 | ILE | 57 | 8.342 | 5.915 | 45.097 | 1.00 | 45.25 | A |
| 402 | CD1 | ILE | 57 | 8.695 | 4.520 | 44.636 | 1.00 | 45.00 | A |
| 403 | C | ILE | 57 | 8.107 | 7.875 | 47.339 | 1.00 | 45.50 | A |
| 404 | O | ILE | 57 | 8.345 | 7.355 | 48.428 | 1.00 | 45.45 | A |

TABLE 1-continued

| Atom | Atom Type | Res | # | X | Y | Z | OCC | B | Mol. |
|---|---|---|---|---|---|---|---|---|---|
| 405 | N | ALA | 58 | 8.861 | 8.847 | 46.837 | 1.00 | 45.47 | A |
| 406 | CA | ALA | 58 | 10.025 | 9.338 | 47.569 | 1.00 | 45.46 | A |
| 407 | CB | ALA | 58 | 10.709 | 10.441 | 46.777 | 1.00 | 45.36 | A |
| 408 | C | ALA | 58 | 9.636 | 9.852 | 48.956 | 1.00 | 45.54 | A |
| 409 | O | ALA | 58 | 10.403 | 9.735 | 49.915 | 1.00 | 45.38 | A |
| 410 | N | VAL | 59 | 8.433 | 10.414 | 49.053 | 1.00 | 45.66 | A |
| 411 | CA | VAL | 59 | 7.933 | 10.963 | 50.310 | 1.00 | 45.90 | A |
| 412 | CB | VAL | 59 | 6.510 | 11.543 | 50.125 | 1.00 | 45.96 | A |
| 413 | CG1 | VAL | 59 | 6.036 | 12.200 | 51.414 | 1.00 | 46.02 | A |
| 414 | CG2 | VAL | 59 | 6.513 | 12.547 | 48.981 | 1.00 | 46.03 | A |
| 415 | C | VAL | 59 | 7.911 | 9.917 | 51.418 | 1.00 | 45.95 | A |
| 416 | O | VAL | 59 | 8.474 | 10.132 | 52.493 | 1.00 | 46.04 | A |
| 417 | N | ALA | 60 | 7.259 | 8.789 | 51.156 | 1.00 | 46.03 | A |
| 418 | CA | ALA | 60 | 7.176 | 7.706 | 52.132 | 1.00 | 46.13 | A |
| 419 | CB | ALA | 60 | 6.321 | 6.570 | 51.576 | 1.00 | 46.10 | A |
| 420 | C | ALA | 60 | 8.567 | 7.181 | 52.487 | 1.00 | 46.26 | A |
| 421 | O | ALA | 60 | 8.842 | 6.844 | 53.642 | 1.00 | 46.27 | A |
| 422 | N | SER | 61 | 9.441 | 7.105 | 51.487 | 1.00 | 46.37 | A |
| 423 | CA | SER | 61 | 10.800 | 6.613 | 51.695 | 1.00 | 46.45 | A |
| 424 | CB | SER | 61 | 11.505 | 6.442 | 50.348 | 1.00 | 46.27 | A |
| 425 | OG | SER | 61 | 12.858 | 6.065 | 50.529 | 1.00 | 45.97 | A |
| 426 | C | SER | 61 | 11.634 | 7.534 | 52.584 | 1.00 | 46.70 | A |
| 427 | O | SER | 61 | 12.381 | 7.074 | 53.445 | 1.00 | 46.61 | A |
| 428 | N | LEU | 62 | 11.504 | 8.838 | 52.366 | 1.00 | 47.06 | A |
| 429 | CA | LEU | 62 | 12.264 | 9.824 | 53.124 | 1.00 | 47.50 | A |
| 430 | CB | LEU | 62 | 12.423 | 11.094 | 52.281 | 1.00 | 47.29 | A |
| 431 | CG | LEU | 62 | 13.216 | 10.963 | 50.974 | 1.00 | 47.14 | A |
| 432 | CD1 | LEU | 62 | 12.898 | 12.134 | 50.065 | 1.00 | 47.11 | A |
| 433 | CD2 | LEU | 62 | 14.707 | 10.901 | 51.269 | 1.00 | 47.05 | A |
| 434 | C | LEU | 62 | 11.645 | 10.181 | 54.475 | 1.00 | 47.94 | A |
| 435 | O | LEU | 62 | 12.342 | 10.636 | 55.382 | 1.00 | 47.96 | A |
| 436 | N | ALA | 63 | 10.341 | 9.959 | 54.606 | 1.00 | 48.47 | A |
| 437 | CA | ALA | 63 | 9.609 | 10.281 | 55.829 | 1.00 | 49.01 | A |
| 438 | CB | ALA | 63 | 8.182 | 9.738 | 55.735 | 1.00 | 48.91 | A |
| 439 | C | ALA | 63 | 10.248 | 9.812 | 57.134 | 1.00 | 49.39 | A |
| 440 | O | ALA | 63 | 10.470 | 10.619 | 58.043 | 1.00 | 49.51 | A |
| 441 | N | ALA | 64 | 10.545 | 8.523 | 57.227 | 1.00 | 49.79 | A |
| 442 | CA | ALA | 64 | 11.123 | 7.954 | 58.441 | 1.00 | 50.27 | A |
| 443 | CB | ALA | 64 | 11.583 | 6.537 | 58.170 | 1.00 | 50.33 | A |
| 444 | C | ALA | 64 | 12.273 | 8.767 | 59.020 | 1.00 | 50.57 | A |
| 445 | O | ALA | 64 | 12.213 | 9.230 | 60.164 | 1.00 | 50.74 | A |
| 446 | N | LYS | 65 | 13.314 | 8.954 | 58.226 | 1.00 | 50.78 | A |
| 447 | CA | LYS | 65 | 14.484 | 9.686 | 58.684 | 1.00 | 51.02 | A |
| 448 | CB | LYS | 65 | 15.705 | 9.308 | 57.832 | 1.00 | 50.84 | A |
| 449 | CG | LYS | 65 | 16.145 | 7.871 | 57.945 | 1.00 | 50.72 | A |
| 450 | CD | LYS | 65 | 17.253 | 7.556 | 56.959 | 1.00 | 50.55 | A |
| 451 | CE | LYS | 65 | 18.469 | 8.455 | 57.174 | 1.00 | 50.54 | A |
| 452 | NZ | LYS | 65 | 19.582 | 8.084 | 56.260 | 1.00 | 50.34 | A |
| 453 | C | LYS | 65 | 14.371 | 11.204 | 58.691 | 1.00 | 51.29 | A |
| 454 | O | LYS | 65 | 15.004 | 11.858 | 59.510 | 1.00 | 51.21 | A |
| 455 | N | TRP | 66 | 13.559 | 11.768 | 57.803 | 1.00 | 51.71 | A |
| 456 | CA | TRP | 66 | 13.510 | 13.224 | 57.702 | 1.00 | 52.27 | A |
| 457 | CB | TRP | 66 | 13.947 | 13.625 | 56.284 | 1.00 | 52.00 | A |
| 458 | CG | TRP | 66 | 15.219 | 12.925 | 55.918 | 1.00 | 51.86 | A |
| 459 | CD2 | TRP | 66 | 16.500 | 13.127 | 56.532 | 1.00 | 51.78 | A |
| 460 | CE2 | TRP | 66 | 17.380 | 12.174 | 55.983 | 1.00 | 51.69 | A |
| 461 | CE3 | TRP | 66 | 16.983 | 14.018 | 57.494 | 1.00 | 51.76 | A |
| 462 | CD1 | TRP | 66 | 15.376 | 11.897 | 55.039 | 1.00 | 51.80 | A |
| 463 | NE1 | TRP | 66 | 16.676 | 11.435 | 55.075 | 1.00 | 51.70 | A |
| 464 | CZ2 | TRP | 66 | 18.720 | 12.086 | 56.368 | 1.00 | 51.68 | A |
| 465 | CZ3 | TRP | 66 | 18.316 | 13.928 | 57.878 | 1.00 | 51.76 | A |
| 466 | CH2 | TRP | 66 | 19.166 | 12.964 | 57.310 | 1.00 | 51.70 | A |
| 467 | C | TRP | 66 | 12.265 | 14.000 | 58.099 | 1.00 | 52.82 | A |
| 468 | O | TRP | 66 | 12.299 | 15.230 | 58.109 | 1.00 | 52.83 | A |
| 469 | N | LYS | 67 | 11.172 | 13.321 | 58.418 | 1.00 | 53.49 | A |
| 470 | CA | LYS | 67 | 9.981 | 14.049 | 58.824 | 1.00 | 54.21 | A |
| 471 | CB | LYS | 67 | 8.819 | 13.085 | 59.067 | 1.00 | 54.43 | A |
| 472 | CG | LYS | 67 | 7.514 | 13.802 | 59.389 | 1.00 | 54.89 | A |
| 473 | CD | LYS | 67 | 6.372 | 12.831 | 59.655 | 1.00 | 55.21 | A |
| 474 | CE | LYS | 67 | 5.123 | 13.565 | 60.154 | 1.00 | 55.51 | A |
| 475 | NZ | LYS | 67 | 4.004 | 12.622 | 60.451 | 1.00 | 55.72 | A |
| 476 | C | LYS | 67 | 10.302 | 14.817 | 60.107 | 1.00 | 54.57 | A |
| 477 | O | LYS | 67 | 11.158 | 14.397 | 60.888 | 1.00 | 54.62 | A |
| 478 | N | GLY | 68 | 9.633 | 15.945 | 60.313 | 1.00 | 54.97 | A |
| 479 | CA | GLY | 68 | 9.881 | 16.714 | 61.517 | 1.00 | 55.48 | A |
| 480 | C | GLY | 68 | 11.142 | 17.567 | 61.493 | 1.00 | 55.79 | A |
| 481 | O | GLY | 68 | 11.321 | 18.427 | 62.351 | 1.00 | 55.94 | A |

TABLE 1-continued

| Atom | Atom Type | Res | # | X | Y | Z | OCC | B | Mol. |
|---|---|---|---|---|---|---|---|---|---|
| 482 | N | LYS | 69 | 12.024 | 17.344 | 60.528 | 1.00 | 56.06 | A |
| 483 | CA | LYS | 69 | 13.254 | 18.128 | 60.433 | 1.00 | 56.28 | A |
| 484 | CB | LYS | 69 | 14.303 | 17.396 | 59.586 | 1.00 | 56.40 | A |
| 485 | CG | LYS | 69 | 14.711 | 16.012 | 60.072 | 1.00 | 56.61 | A |
| 486 | CD | LYS | 69 | 15.423 | 16.035 | 61.404 | 1.00 | 56.82 | A |
| 487 | CE | LYS | 69 | 16.014 | 14.669 | 61.680 | 1.00 | 56.88 | A |
| 488 | NZ | LYS | 69 | 14.926 | 13.657 | 61.657 | 1.00 | 57.06 | A |
| 489 | C | LYS | 69 | 12.947 | 19.472 | 59.773 | 1.00 | 56.39 | A |
| 490 | O | LYS | 69 | 12.129 | 19.539 | 58.854 | 1.00 | 56.43 | A |
| 491 | N | SER | 70 | 13.599 | 20.539 | 60.224 | 1.00 | 56.49 | A |
| 492 | CA | SER | 70 | 13.356 | 21.849 | 59.627 | 1.00 | 56.59 | A |
| 493 | CB | SER | 70 | 13.750 | 22.963 | 60.596 | 1.00 | 56.59 | A |
| 494 | OG | SER | 70 | 15.159 | 23.074 | 60.709 | 1.00 | 56.59 | A |
| 495 | C | SER | 70 | 14.163 | 21.992 | 58.336 | 1.00 | 56.69 | A |
| 496 | O | SER | 70 | 15.172 | 21.303 | 58.149 | 1.00 | 56.70 | A |
| 497 | N | SER | 71 | 13.722 | 22.883 | 57.450 | 1.00 | 56.67 | A |
| 498 | CA | SER | 71 | 14.433 | 23.106 | 56.193 | 1.00 | 56.71 | A |
| 499 | CB | SER | 71 | 13.802 | 24.252 | 55.401 | 1.00 | 56.61 | A |
| 500 | OG | SER | 71 | 12.457 | 23.959 | 55.072 | 1.00 | 56.71 | A |
| 501 | C | SER | 71 | 15.888 | 23.440 | 56.476 | 1.00 | 56.73 | A |
| 502 | O | SER | 71 | 16.792 | 22.941 | 55.805 | 1.00 | 56.77 | A |
| 503 | N | GLU | 72 | 16.107 | 24.277 | 57.483 | 1.00 | 56.79 | A |
| 504 | CA | GLU | 72 | 17.450 | 24.693 | 57.849 | 1.00 | 56.88 | A |
| 505 | CB | GLU | 72 | 17.402 | 25.690 | 59.012 | 1.00 | 57.38 | A |
| 506 | CG | GLU | 72 | 16.430 | 26.852 | 58.823 | 1.00 | 58.18 | A |
| 507 | CD | GLU | 72 | 14.973 | 26.428 | 58.943 | 1.00 | 58.60 | A |
| 508 | OE1 | GLU | 72 | 14.677 | 25.517 | 59.756 | 1.00 | 59.03 | A |
| 509 | OE2 | GLU | 72 | 14.113 | 27.010 | 58.239 | 1.00 | 58.90 | A |
| 510 | C | GLU | 72 | 18.281 | 23.479 | 58.246 | 1.00 | 56.65 | A |
| 511 | O | GLU | 72 | 19.474 | 23.402 | 57.934 | 1.00 | 56.67 | A |
| 512 | N | GLU | 73 | 17.645 | 22.534 | 58.931 | 1.00 | 56.31 | A |
| 513 | CA | GLU | 73 | 18.327 | 21.321 | 59.373 | 1.00 | 55.99 | A |
| 514 | CB | GLU | 73 | 17.479 | 20.596 | 60.411 | 1.00 | 56.34 | A |
| 515 | CG | GLU | 73 | 18.198 | 19.447 | 61.076 | 1.00 | 56.94 | A |
| 516 | CD | GLU | 73 | 17.366 | 18.786 | 62.153 | 1.00 | 57.34 | A |
| 517 | OE1 | GLU | 73 | 16.262 | 19.308 | 62.478 | 1.00 | 57.53 | A |
| 518 | OE2 | GLU | 73 | 17.826 | 17.741 | 62.678 | 1.00 | 57.51 | A |
| 519 | C | GLU | 73 | 18.623 | 20.382 | 58.204 | 1.00 | 55.46 | A |
| 520 | O | GLU | 73 | 19.726 | 19.846 | 58.093 | 1.00 | 55.44 | A |
| 521 | N | LEU | 74 | 17.640 | 20.188 | 57.332 | 1.00 | 54.85 | A |
| 522 | CA | LEU | 74 | 17.834 | 19.320 | 56.179 | 1.00 | 54.21 | A |
| 523 | CB | LEU | 74 | 16.557 | 19.230 | 55.341 | 1.00 | 54.21 | A |
| 524 | CG | LEU | 74 | 15.374 | 18.505 | 55.982 | 1.00 | 54.26 | A |
| 525 | CD1 | LEU | 74 | 14.218 | 18.545 | 55.015 | 1.00 | 54.12 | A |
| 526 | CD2 | LEU | 74 | 15.741 | 17.073 | 56.313 | 1.00 | 54.10 | A |
| 527 | C | LEU | 74 | 18.966 | 19.869 | 55.327 | 1.00 | 53.75 | A |
| 528 | O | LEU | 74 | 19.890 | 19.141 | 54.975 | 1.00 | 53.62 | A |
| 529 | N | LEU | 75 | 18.917 | 21.165 | 55.041 | 1.00 | 53.20 | A |
| 530 | CA | LEU | 75 | 19.934 | 21.792 | 54.203 | 1.00 | 52.62 | A |
| 531 | CB | LEU | 75 | 19.693 | 23.306 | 54.085 | 1.00 | 52.66 | A |
| 532 | CG | LEU | 75 | 20.678 | 24.078 | 53.193 | 1.00 | 52.68 | A |
| 533 | CD1 | LEU | 75 | 20.657 | 23.565 | 51.765 | 1.00 | 52.54 | A |
| 534 | CD2 | LEU | 75 | 20.293 | 25.542 | 53.215 | 1.00 | 52.73 | A |
| 535 | C | LEU | 75 | 21.367 | 21.539 | 54.654 | 1.00 | 52.18 | A |
| 536 | O | LEU | 75 | 22.246 | 21.360 | 53.821 | 1.00 | 52.13 | A |
| 537 | N | GLU | 76 | 21.604 | 21.498 | 55.960 | 1.00 | 51.70 | A |
| 538 | CA | GLU | 76 | 22.960 | 21.288 | 56.468 | 1.00 | 51.14 | A |
| 539 | CB | GLU | 76 | 23.139 | 22.025 | 57.805 | 1.00 | 51.69 | A |
| 540 | CG | GLU | 76 | 22.263 | 21.456 | 58.919 | 1.00 | 52.39 | A |
| 541 | CD | GLU | 76 | 22.485 | 22.120 | 60.274 | 1.00 | 52.91 | A |
| 542 | OE1 | GLU | 76 | 23.297 | 23.078 | 60.349 | 1.00 | 53.16 | A |
| 543 | OE2 | GLU | 76 | 21.840 | 21.683 | 61.267 | 1.00 | 53.17 | A |
| 544 | C | GLU | 76 | 23.295 | 19.810 | 56.670 | 1.00 | 50.46 | A |
| 545 | O | GLU | 76 | 24.387 | 19.481 | 57.134 | 1.00 | 50.48 | A |
| 546 | N | THR | 77 | 22.376 | 18.916 | 56.316 | 1.00 | 49.52 | A |
| 547 | CA | THR | 77 | 22.608 | 17.482 | 56.517 | 1.00 | 48.55 | A |
| 548 | CB | THR | 77 | 21.393 | 16.832 | 57.210 | 1.00 | 48.64 | A |
| 549 | OG1 | THR | 77 | 21.011 | 17.623 | 58.341 | 1.00 | 48.63 | A |
| 550 | CG2 | THR | 77 | 21.737 | 15.424 | 57.678 | 1.00 | 48.51 | A |
| 551 | C | THR | 77 | 22.905 | 16.709 | 55.232 | 1.00 | 47.86 | A |
| 552 | O | THR | 77 | 21.999 | 16.427 | 54.447 | 1.00 | 47.69 | A |
| 553 | N | LEU | 78 | 24.176 | 16.369 | 55.026 | 1.00 | 46.95 | A |
| 554 | CA | LEU | 78 | 24.590 | 15.635 | 53.835 | 1.00 | 46.11 | A |
| 555 | CB | LEU | 78 | 26.095 | 15.337 | 53.877 | 1.00 | 46.00 | A |
| 556 | CG | LEU | 78 | 27.036 | 16.539 | 53.810 | 1.00 | 45.95 | A |
| 557 | CD1 | LEU | 78 | 28.458 | 16.058 | 53.908 | 1.00 | 45.93 | A |
| 558 | CD2 | LEU | 78 | 26.831 | 17.293 | 52.524 | 1.00 | 45.83 | A |

TABLE 1-continued

| Atom | Atom Type | Res | # | X | Y | Z | OCC | B | Mol. |
|---|---|---|---|---|---|---|---|---|---|
| 559 | C | LEU | 78 | 23.825 | 14.322 | 53.664 | 1.00 | 45.56 | A |
| 560 | O | LEU | 78 | 23.487 | 13.936 | 52.548 | 1.00 | 45.41 | A |
| 561 | N | ASP | 79 | 23.553 | 13.646 | 54.775 | 1.00 | 44.78 | A |
| 562 | CA | ASP | 79 | 22.845 | 12.377 | 54.739 | 1.00 | 44.19 | A |
| 563 | CB | ASP | 79 | 22.620 | 11.853 | 56.160 | 1.00 | 44.07 | A |
| 564 | CG | ASP | 79 | 22.214 | 10.395 | 56.183 | 1.00 | 43.85 | A |
| 565 | OD1 | ASP | 79 | 21.292 | 10.057 | 56.945 | 1.00 | 43.81 | A |
| 566 | OD2 | ASP | 79 | 22.827 | 9.591 | 55.452 | 1.00 | 43.55 | A |
| 567 | C | ASP | 79 | 21.507 | 12.534 | 54.029 | 1.00 | 43.87 | A |
| 568 | O | ASP | 79 | 21.081 | 11.650 | 53.287 | 1.00 | 43.79 | A |
| 569 | N | PHE | 80 | 20.847 | 13.663 | 54.268 | 1.00 | 43.46 | A |
| 570 | CA | PHE | 80 | 19.559 | 13.946 | 53.649 | 1.00 | 43.12 | A |
| 571 | CB | PHE | 80 | 19.080 | 15.339 | 54.050 | 1.00 | 43.22 | A |
| 572 | CG | PHE | 80 | 17.830 | 15.779 | 53.339 | 1.00 | 43.41 | A |
| 573 | CD1 | PHE | 80 | 17.794 | 17.000 | 52.664 | 1.00 | 43.41 | A |
| 574 | CD2 | PHE | 80 | 16.686 | 14.984 | 53.355 | 1.00 | 43.40 | A |
| 575 | CE1 | PHE | 80 | 16.633 | 17.428 | 52.011 | 1.00 | 43.56 | A |
| 576 | CE2 | PHE | 80 | 15.517 | 15.397 | 52.707 | 1.00 | 43.61 | A |
| 577 | CZ | PHE | 80 | 15.490 | 16.624 | 52.033 | 1.00 | 43.59 | A |
| 578 | C | PHE | 80 | 19.677 | 13.870 | 52.131 | 1.00 | 42.88 | A |
| 579 | O | PHE | 80 | 18.904 | 13.168 | 51.463 | 1.00 | 42.77 | A |
| 580 | N | TYR | 81 | 20.652 | 14.592 | 51.591 | 1.00 | 42.41 | A |
| 581 | CA | TYR | 81 | 20.863 | 14.605 | 50.156 | 1.00 | 42.04 | A |
| 582 | CB | TYR | 81 | 21.844 | 15.722 | 49.789 | 1.00 | 42.05 | A |
| 583 | CG | TYR | 81 | 21.238 | 17.071 | 50.098 | 1.00 | 42.06 | A |
| 584 | CD1 | TYR | 81 | 21.532 | 17.740 | 51.288 | 1.00 | 42.06 | A |
| 585 | CE1 | TYR | 81 | 20.858 | 18.913 | 51.637 | 1.00 | 42.06 | A |
| 586 | CD2 | TYR | 81 | 20.262 | 17.615 | 49.261 | 1.00 | 41.96 | A |
| 587 | CE2 | TYR | 81 | 19.587 | 18.776 | 49.598 | 1.00 | 41.95 | A |
| 588 | CZ | TYR | 81 | 19.884 | 19.421 | 50.785 | 1.00 | 42.02 | A |
| 589 | OH | TYR | 81 | 19.190 | 20.562 | 51.121 | 1.00 | 42.06 | A |
| 590 | C | TYR | 81 | 21.316 | 13.254 | 49.635 | 1.00 | 41.73 | A |
| 591 | O | TYR | 81 | 21.047 | 12.914 | 48.484 | 1.00 | 41.56 | A |
| 592 | N | ARG | 82 | 21.989 | 12.472 | 50.476 | 1.00 | 41.49 | A |
| 593 | CA | ARG | 82 | 22.416 | 11.146 | 50.043 | 1.00 | 41.39 | A |
| 594 | CB | ARG | 82 | 23.368 | 10.501 | 51.053 | 1.00 | 41.56 | A |
| 595 | CG | ARG | 82 | 24.743 | 11.152 | 51.094 | 1.00 | 41.85 | A |
| 596 | CD | ARG | 82 | 25.827 | 10.159 | 51.476 | 1.00 | 41.94 | A |
| 597 | NE | ARG | 82 | 27.135 | 10.810 | 51.497 | 1.00 | 42.20 | A |
| 598 | CZ | ARG | 82 | 27.610 | 11.489 | 52.535 | 1.00 | 42.16 | A |
| 599 | NH1 | ARG | 82 | 26.889 | 11.597 | 53.642 | 1.00 | 42.08 | A |
| 600 | NH2 | ARG | 82 | 28.798 | 12.079 | 52.456 | 1.00 | 42.21 | A |
| 601 | C | ARG | 82 | 21.189 | 10.261 | 49.861 | 1.00 | 41.18 | A |
| 602 | O | ARG | 82 | 21.137 | 9.456 | 48.935 | 1.00 | 41.19 | A |
| 603 | N | ASP | 83 | 20.207 | 10.405 | 50.745 | 1.00 | 40.88 | A |
| 604 | CA | ASP | 83 | 18.989 | 9.610 | 50.631 | 1.00 | 40.73 | A |
| 605 | CB | ASP | 83 | 18.086 | 9.794 | 51.848 | 1.00 | 40.55 | A |
| 606 | CG | ASP | 83 | 18.582 | 9.036 | 53.055 | 1.00 | 40.56 | A |
| 607 | OD1 | ASP | 83 | 19.253 | 8.002 | 52.869 | 1.00 | 40.49 | A |
| 608 | OD2 | ASP | 83 | 18.289 | 9.464 | 54.189 | 1.00 | 40.67 | A |
| 609 | C | ASP | 83 | 18.236 | 10.017 | 49.377 | 1.00 | 40.62 | A |
| 610 | O | ASP | 83 | 17.642 | 9.182 | 48.709 | 1.00 | 40.71 | A |
| 611 | N | ILE | 84 | 18.259 | 11.303 | 49.055 | 1.00 | 40.36 | A |
| 612 | CA | ILE | 84 | 17.582 | 11.765 | 47.857 | 1.00 | 40.35 | A |
| 613 | CB | ILE | 84 | 17.556 | 13.302 | 47.774 | 1.00 | 40.35 | A |
| 614 | CG2 | ILE | 84 | 17.102 | 13.737 | 46.387 | 1.00 | 40.17 | A |
| 615 | CG1 | ILE | 84 | 16.619 | 13.860 | 48.840 | 1.00 | 40.41 | A |
| 616 | CD1 | ILE | 84 | 16.633 | 15.367 | 48.925 | 1.00 | 40.76 | A |
| 617 | C | ILE | 84 | 18.278 | 11.238 | 46.607 | 1.00 | 40.24 | A |
| 618 | O | ILE | 84 | 17.624 | 10.773 | 45.669 | 1.00 | 40.39 | A |
| 619 | N | ILE | 85 | 19.605 | 11.309 | 46.598 | 1.00 | 39.99 | A |
| 620 | CA | ILE | 85 | 20.393 | 10.872 | 45.454 | 1.00 | 39.77 | A |
| 621 | CB | ILE | 85 | 21.885 | 11.237 | 45.632 | 1.00 | 39.66 | A |
| 622 | CG2 | ILE | 85 | 22.722 | 10.612 | 44.517 | 1.00 | 39.42 | A |
| 623 | CG1 | ILE | 85 | 22.051 | 12.762 | 45.654 | 1.00 | 39.65 | A |
| 624 | CD1 | ILE | 85 | 23.433 | 13.217 | 46.110 | 1.00 | 39.43 | A |
| 625 | C | ILE | 85 | 20.306 | 9.377 | 45.202 | 1.00 | 39.75 | A |
| 626 | O | ILE | 85 | 20.106 | 8.936 | 44.067 | 1.00 | 39.69 | A |
| 627 | N | SER | 86 | 20.458 | 8.600 | 46.266 | 1.00 | 39.72 | A |
| 628 | CA | SER | 86 | 20.446 | 7.149 | 46.152 | 1.00 | 39.80 | A |
| 629 | CB | SER | 86 | 21.688 | 6.589 | 46.841 | 1.00 | 39.86 | A |
| 630 | OG | SER | 86 | 22.853 | 7.094 | 46.221 | 1.00 | 40.14 | A |
| 631 | C | SER | 86 | 19.209 | 6.478 | 46.725 | 1.00 | 39.65 | A |
| 632 | O | SER | 86 | 19.219 | 5.278 | 46.986 | 1.00 | 39.70 | A |
| 633 | N | GLY | 87 | 18.148 | 7.251 | 46.917 | 1.00 | 39.62 | A |
| 634 | CA | GLY | 87 | 16.922 | 6.701 | 47.468 | 1.00 | 39.42 | A |
| 635 | C | GLY | 87 | 16.271 | 5.701 | 46.537 | 1.00 | 39.31 | A |

TABLE 1-continued

| Atom | Atom Type | Res | # | X | Y | Z | OCC | B | Mol. |
|---|---|---|---|---|---|---|---|---|---|
| 636 | O | GLY | 87 | 16.462 | 5.760 | 45.323 | 1.00 | 39.13 | A |
| 637 | N | PRO | 88 | 15.490 | 4.762 | 47.089 | 1.00 | 39.33 | A |
| 638 | CD | PRO | 88 | 15.214 | 4.644 | 48.532 | 1.00 | 39.36 | A |
| 639 | CA | PRO | 88 | 14.787 | 3.719 | 46.342 | 1.00 | 39.36 | A |
| 640 | CB | PRO | 88 | 14.417 | 2.723 | 47.435 | 1.00 | 39.34 | A |
| 641 | CG | PRO | 88 | 14.090 | 3.626 | 48.575 | 1.00 | 39.38 | A |
| 642 | C | PRO | 88 | 13.568 | 4.264 | 45.603 | 1.00 | 39.39 | A |
| 643 | O | PRO | 88 | 12.429 | 3.862 | 45.851 | 1.00 | 39.44 | A |
| 644 | N | PHE | 89 | 13.814 | 5.200 | 44.700 | 1.00 | 39.46 | A |
| 645 | CA | PHE | 89 | 12.755 | 5.799 | 43.909 | 1.00 | 39.53 | A |
| 646 | CB | PHE | 89 | 11.944 | 6.787 | 44.753 | 1.00 | 39.50 | A |
| 647 | CG | PHE | 89 | 12.782 | 7.703 | 45.591 | 1.00 | 39.55 | A |
| 648 | CD1 | PHE | 89 | 13.426 | 8.803 | 45.020 | 1.00 | 39.59 | A |
| 649 | CD2 | PHE | 89 | 12.937 | 7.465 | 46.957 | 1.00 | 39.49 | A |
| 650 | CE1 | PHE | 89 | 14.211 | 9.653 | 45.796 | 1.00 | 39.50 | A |
| 651 | CE2 | PHE | 89 | 13.723 | 8.309 | 47.745 | 1.00 | 39.56 | A |
| 652 | CZ | PHE | 89 | 14.362 | 9.409 | 47.156 | 1.00 | 39.51 | A |
| 653 | C | PHE | 89 | 13.394 | 6.486 | 42.721 | 1.00 | 39.68 | A |
| 654 | O | PHE | 89 | 14.564 | 6.878 | 42.764 | 1.00 | 39.78 | A |
| 655 | N | GLU | 90 | 12.631 | 6.623 | 41.651 | 1.00 | 39.59 | A |
| 656 | CA | GLU | 90 | 13.148 | 7.230 | 40.449 | 1.00 | 39.72 | A |
| 657 | CB | GLU | 90 | 12.242 | 6.863 | 39.281 | 1.00 | 39.81 | A |
| 658 | CG | GLU | 90 | 12.930 | 6.874 | 37.953 | 1.00 | 40.17 | A |
| 659 | CD | GLU | 90 | 12.091 | 6.233 | 36.879 | 1.00 | 40.25 | A |
| 660 | OE1 | GLU | 90 | 11.068 | 6.830 | 36.495 | 1.00 | 40.45 | A |
| 661 | OE2 | GLU | 90 | 12.453 | 5.131 | 36.424 | 1.00 | 40.31 | A |
| 662 | C | GLU | 90 | 13.265 | 8.740 | 40.574 | 1.00 | 39.72 | A |
| 663 | O | GLU | 90 | 12.461 | 9.383 | 41.245 | 1.00 | 39.73 | A |
| 664 | N | LYS | 91 | 14.302 | 9.298 | 39.963 | 1.00 | 39.62 | A |
| 665 | CA | LYS | 91 | 14.475 | 10.743 | 39.958 | 1.00 | 39.59 | A |
| 666 | CB | LYS | 91 | 15.810 | 11.171 | 40.594 | 1.00 | 39.42 | A |
| 667 | CG | LYS | 91 | 16.011 | 10.724 | 42.039 | 1.00 | 39.26 | A |
| 668 | CD | LYS | 91 | 16.765 | 9.392 | 42.103 | 1.00 | 38.93 | A |
| 669 | CE | LYS | 91 | 16.814 | 8.844 | 43.521 | 1.00 | 38.82 | A |
| 670 | NZ | LYS | 91 | 17.615 | 7.592 | 43.607 | 1.00 | 38.74 | A |
| 671 | C | LYS | 91 | 14.460 | 11.137 | 38.487 | 1.00 | 39.68 | A |
| 672 | O | LYS | 91 | 14.992 | 10.425 | 37.641 | 1.00 | 39.50 | A |
| 673 | N | LEU | 92 | 13.821 | 12.254 | 38.174 | 1.00 | 39.83 | A |
| 674 | CA | LEU | 92 | 13.783 | 12.718 | 36.800 | 1.00 | 40.17 | A |
| 675 | CB | LEU | 92 | 12.336 | 12.747 | 36.283 | 1.00 | 40.40 | A |
| 676 | CG | LEU | 92 | 12.157 | 13.210 | 34.837 | 1.00 | 40.65 | A |
| 677 | CD1 | LEU | 92 | 12.849 | 12.250 | 33.875 | 1.00 | 40.70 | A |
| 678 | CD2 | LEU | 92 | 10.666 | 13.288 | 34.530 | 1.00 | 40.99 | A |
| 679 | C | LEU | 92 | 14.390 | 14.119 | 36.785 | 1.00 | 40.17 | A |
| 680 | O | LEU | 92 | 13.913 | 15.010 | 37.485 | 1.00 | 40.31 | A |
| 681 | N | ILE | 93 | 15.463 | 14.301 | 36.022 | 1.00 | 40.18 | A |
| 682 | CA | ILE | 93 | 16.112 | 15.600 | 35.945 | 1.00 | 40.24 | A |
| 683 | CB | ILE | 93 | 17.638 | 15.520 | 36.226 | 1.00 | 40.35 | A |
| 684 | CG2 | ILE | 93 | 18.256 | 16.909 | 36.135 | 1.00 | 40.08 | A |
| 685 | CG1 | ILE | 93 | 17.904 | 14.954 | 37.623 | 1.00 | 40.48 | A |
| 686 | CD1 | ILE | 93 | 17.779 | 13.466 | 37.716 | 1.00 | 40.93 | A |
| 687 | C | ILE | 93 | 15.920 | 16.207 | 34.565 | 1.00 | 40.31 | A |
| 688 | O | ILE | 93 | 16.262 | 15.596 | 33.549 | 1.00 | 40.16 | A |
| 689 | N | ARG | 94 | 15.362 | 17.408 | 34.523 | 1.00 | 40.41 | A |
| 690 | CA | ARG | 94 | 15.163 | 18.061 | 33.244 | 1.00 | 40.74 | A |
| 691 | CB | ARG | 94 | 13.698 | 18.427 | 33.008 | 1.00 | 41.08 | A |
| 692 | CG | ARG | 94 | 13.453 | 18.908 | 31.576 | 1.00 | 41.68 | A |
| 693 | CD | ARG | 94 | 13.049 | 20.373 | 31.509 | 1.00 | 42.37 | A |
| 694 | NE | ARG | 94 | 11.673 | 20.578 | 31.942 | 1.00 | 42.92 | A |
| 695 | CZ | ARG | 94 | 11.073 | 21.762 | 32.013 | 1.00 | 43.32 | A |
| 696 | NH1 | ARG | 94 | 11.724 | 22.867 | 31.680 | 1.00 | 43.61 | A |
| 697 | NH2 | ARG | 94 | 9.814 | 21.844 | 32.423 | 1.00 | 43.78 | A |
| 698 | C | ARG | 94 | 15.991 | 19.318 | 33.126 | 1.00 | 40.74 | A |
| 699 | O | ARG | 94 | 15.840 | 20.255 | 33.913 | 1.00 | 40.65 | A |
| 700 | N | GLY | 95 | 16.884 | 19.316 | 32.145 | 1.00 | 40.68 | A |
| 701 | CA | GLY | 95 | 17.710 | 20.477 | 31.890 | 1.00 | 40.71 | A |
| 702 | C | GLY | 95 | 17.156 | 21.129 | 30.639 | 1.00 | 40.71 | A |
| 703 | O | GLY | 95 | 16.993 | 20.470 | 29.612 | 1.00 | 40.76 | A |
| 704 | N | SER | 96 | 16.822 | 22.410 | 30.729 | 1.00 | 40.71 | A |
| 705 | CA | SER | 96 | 16.301 | 23.142 | 29.582 | 1.00 | 40.80 | A |
| 706 | CB | SER | 96 | 14.893 | 23.661 | 29.860 | 1.00 | 40.81 | A |
| 707 | OG | SER | 96 | 13.985 | 22.583 | 29.977 | 1.00 | 40.67 | A |
| 708 | C | SER | 96 | 17.244 | 24.306 | 29.336 | 1.00 | 40.89 | A |
| 709 | O | SER | 96 | 17.483 | 25.122 | 30.230 | 1.00 | 40.93 | A |
| 710 | N | LYS | 97 | 17.776 | 24.378 | 28.124 | 1.00 | 40.80 | A |
| 711 | CA | LYS | 97 | 18.731 | 25.416 | 27.786 | 1.00 | 40.86 | A |
| 712 | CB | LYS | 97 | 19.381 | 25.103 | 26.433 | 1.00 | 40.68 | A |

TABLE 1-continued

| Atom | Atom Type | Res | # | X | Y | Z | OCC | B | Mol. |
|---|---|---|---|---|---|---|---|---|---|
| 713 | CG | LYS | 97 | 20.573 | 24.152 | 26.517 | 1.00 | 40.35 | A |
| 714 | CD | LYS | 97 | 20.226 | 22.849 | 27.248 | 1.00 | 40.01 | A |
| 715 | CE | LYS | 97 | 21.422 | 21.914 | 27.291 | 1.00 | 39.84 | A |
| 716 | NZ | LYS | 97 | 21.064 | 20.548 | 27.771 | 1.00 | 39.74 | A |
| 717 | C | LYS | 97 | 18.224 | 26.854 | 27.789 | 1.00 | 40.95 | A |
| 718 | O | LYS | 97 | 17.078 | 27.145 | 27.423 | 1.00 | 40.98 | A |
| 719 | N | ILE | 98 | 19.106 | 27.743 | 28.236 | 1.00 | 40.96 | A |
| 720 | CA | ILE | 98 | 18.844 | 29.173 | 28.271 | 1.00 | 41.07 | A |
| 721 | CB | ILE | 98 | 19.338 | 29.790 | 29.600 | 1.00 | 41.05 | A |
| 722 | CG2 | ILE | 98 | 19.259 | 31.320 | 29.545 | 1.00 | 41.10 | A |
| 723 | CG1 | ILE | 98 | 18.487 | 29.242 | 30.755 | 1.00 | 40.95 | A |
| 724 | CD1 | ILE | 98 | 18.976 | 29.640 | 32.139 | 1.00 | 40.81 | A |
| 725 | C | ILE | 98 | 19.650 | 29.702 | 27.089 | 1.00 | 41.19 | A |
| 726 | O | ILE | 98 | 19.202 | 30.575 | 26.349 | 1.00 | 41.33 | A |
| 727 | N | ARG | 99 | 20.847 | 29.154 | 26.919 | 1.00 | 41.28 | A |
| 728 | CA | ARG | 99 | 21.717 | 29.509 | 25.807 | 1.00 | 41.49 | A |
| 729 | CB | ARG | 99 | 23.057 | 30.052 | 26.305 | 1.00 | 41.83 | A |
| 730 | CG | ARG | 99 | 22.983 | 31.464 | 26.849 | 1.00 | 42.32 | A |
| 731 | CD | ARG | 99 | 24.379 | 31.981 | 27.150 | 1.00 | 42.87 | A |
| 732 | NE | ARG | 99 | 24.403 | 33.442 | 27.207 | 1.00 | 43.34 | A |
| 733 | CZ | ARG | 99 | 23.935 | 34.157 | 28.220 | 1.00 | 43.48 | A |
| 734 | NH1 | ARG | 99 | 23.402 | 33.560 | 29.277 | 1.00 | 43.60 | A |
| 735 | NH2 | ARG | 99 | 23.999 | 35.474 | 28.176 | 1.00 | 43.71 | A |
| 736 | C | ARG | 99 | 21.948 | 28.230 | 25.004 | 1.00 | 41.43 | A |
| 737 | O | ARG | 99 | 22.027 | 27.139 | 25.578 | 1.00 | 41.31 | A |
| 738 | N | GLU | 100 | 22.070 | 28.370 | 23.687 | 1.00 | 41.29 | A |
| 739 | CA | GLU | 100 | 22.257 | 27.220 | 22.814 | 1.00 | 41.18 | A |
| 740 | CB | GLU | 100 | 22.101 | 27.635 | 21.339 | 1.00 | 41.57 | A |
| 741 | CG | GLU | 100 | 22.404 | 26.510 | 20.338 | 1.00 | 42.34 | A |
| 742 | CD | GLU | 100 | 21.843 | 26.775 | 18.940 | 1.00 | 42.90 | A |
| 743 | OE1 | GLU | 100 | 22.205 | 26.045 | 17.987 | 1.00 | 43.25 | A |
| 744 | OE2 | GLU | 100 | 21.026 | 27.707 | 18.790 | 1.00 | 43.46 | A |
| 745 | C | GLU | 100 | 23.567 | 26.476 | 23.004 | 1.00 | 40.83 | A |
| 746 | O | GLU | 100 | 24.650 | 27.054 | 22.948 | 1.00 | 40.71 | A |
| 747 | N | LEU | 101 | 23.451 | 25.170 | 23.217 | 1.00 | 40.45 | A |
| 748 | CA | LEU | 101 | 24.609 | 24.306 | 23.400 | 1.00 | 40.16 | A |
| 749 | CB | LEU | 101 | 24.737 | 23.901 | 24.866 | 1.00 | 40.01 | A |
| 750 | CG | LEU | 101 | 25.155 | 24.932 | 25.909 | 1.00 | 39.88 | A |
| 751 | CD1 | LEU | 101 | 24.950 | 24.343 | 27.309 | 1.00 | 39.74 | A |
| 752 | CD2 | LEU | 101 | 26.617 | 25.317 | 25.683 | 1.00 | 39.74 | A |
| 753 | C | LEU | 101 | 24.440 | 23.043 | 22.564 | 1.00 | 40.00 | A |
| 754 | O | LEU | 101 | 23.346 | 22.482 | 22.499 | 1.00 | 39.93 | A |
| 755 | N | SER | 102 | 25.510 | 22.592 | 21.925 | 1.00 | 39.88 | A |
| 756 | CA | SER | 102 | 25.426 | 21.370 | 21.145 | 1.00 | 39.84 | A |
| 757 | CB | SER | 102 | 26.591 | 21.267 | 20.169 | 1.00 | 39.80 | A |
| 758 | OG | SER | 102 | 27.791 | 20.981 | 20.859 | 1.00 | 39.80 | A |
| 759 | C | SER | 102 | 25.511 | 20.231 | 22.158 | 1.00 | 39.87 | A |
| 760 | O | SER | 102 | 25.879 | 20.451 | 23.317 | 1.00 | 39.66 | A |
| 761 | N | GLY | 103 | 25.161 | 19.024 | 21.727 | 1.00 | 39.84 | A |
| 762 | CA | GLY | 103 | 25.224 | 17.883 | 22.621 | 1.00 | 39.93 | A |
| 763 | C | GLY | 103 | 26.632 | 17.705 | 23.161 | 1.00 | 40.16 | A |
| 764 | O | GLY | 103 | 26.818 | 17.520 | 24.361 | 1.00 | 39.95 | A |
| 765 | N | PRO | 104 | 27.652 | 17.743 | 22.288 | 1.00 | 40.42 | A |
| 766 | CD | PRO | 104 | 27.560 | 17.647 | 20.819 | 1.00 | 40.48 | A |
| 767 | CA | PRO | 104 | 29.041 | 17.584 | 22.731 | 1.00 | 40.70 | A |
| 768 | CB | PRO | 104 | 29.826 | 17.659 | 21.424 | 1.00 | 40.56 | A |
| 769 | CG | PRO | 104 | 28.893 | 17.020 | 20.452 | 1.00 | 40.54 | A |
| 770 | C | PRO | 104 | 29.455 | 18.676 | 23.720 | 1.00 | 40.97 | A |
| 771 | O | PRO | 104 | 30.128 | 18.399 | 24.714 | 1.00 | 40.96 | A |
| 772 | N | GLU | 105 | 29.048 | 19.914 | 23.444 | 1.00 | 41.22 | A |
| 773 | CA | GLU | 105 | 29.388 | 21.042 | 24.306 | 1.00 | 41.61 | A |
| 774 | CB | GLU | 105 | 28.878 | 22.354 | 23.702 | 1.00 | 41.92 | A |
| 775 | CG | GLU | 105 | 29.707 | 22.892 | 22.535 | 1.00 | 42.68 | A |
| 776 | CD | GLU | 105 | 29.090 | 24.149 | 21.916 | 1.00 | 43.02 | A |
| 777 | OE1 | GLU | 105 | 29.835 | 24.943 | 21.305 | 1.00 | 43.62 | A |
| 778 | OE2 | GLU | 105 | 27.863 | 24.345 | 22.030 | 1.00 | 43.13 | A |
| 779 | C | GLU | 105 | 28.794 | 20.870 | 25.698 | 1.00 | 41.62 | A |
| 780 | O | GLU | 105 | 29.488 | 20.994 | 26.708 | 1.00 | 41.58 | A |
| 781 | N | TYR | 106 | 27.497 | 20.600 | 25.742 | 1.00 | 41.60 | A |
| 782 | CA | TYR | 106 | 26.804 | 20.411 | 27.001 | 1.00 | 41.79 | A |
| 783 | CB | TYR | 106 | 25.310 | 20.229 | 26.750 | 1.00 | 41.53 | A |
| 784 | CG | TYR | 106 | 24.564 | 19.746 | 27.967 | 1.00 | 41.25 | A |
| 785 | CD1 | TYR | 106 | 24.233 | 20.623 | 29.000 | 1.00 | 41.04 | A |
| 786 | CE1 | TYR | 106 | 23.595 | 20.167 | 30.155 | 1.00 | 40.92 | A |
| 787 | CD2 | TYR | 106 | 24.237 | 18.396 | 28.114 | 1.00 | 41.14 | A |
| 788 | CE2 | TYR | 106 | 23.602 | 17.932 | 29.261 | 1.00 | 40.81 | A |
| 789 | CZ | TYR | 106 | 23.285 | 18.819 | 30.273 | 1.00 | 40.79 | A |

TABLE 1-continued

| Atom | Atom Type | Res | # | X | Y | Z | OCC | B | Mol. |
|---|---|---|---|---|---|---|---|---|---|
| 790 | OH | TYR | 106 | 22.664 | 18.357 | 31.404 | 1.00 | 40.49 | A |
| 791 | C | TYR | 106 | 27.332 | 19.202 | 27.768 | 1.00 | 42.09 | A |
| 792 | O | TYR | 106 | 27.694 | 19.306 | 28.938 | 1.00 | 42.10 | A |
| 793 | N | SER | 107 | 27.386 | 18.057 | 27.100 | 1.00 | 42.42 | A |
| 794 | CA | SER | 107 | 27.829 | 16.823 | 27.737 | 1.00 | 42.92 | A |
| 795 | CB | SER | 107 | 27.668 | 15.640 | 26.774 | 1.00 | 42.84 | A |
| 796 | OG | SER | 107 | 28.508 | 15.765 | 25.645 | 1.00 | 42.92 | A |
| 797 | C | SER | 107 | 29.257 | 16.878 | 28.254 | 1.00 | 43.18 | A |
| 798 | O | SER | 107 | 29.586 | 16.220 | 29.242 | 1.00 | 42.97 | A |
| 799 | N | ARG | 108 | 30.112 | 17.668 | 27.615 | 1.00 | 43.61 | A |
| 800 | CA | ARG | 108 | 31.502 | 17.763 | 28.027 | 1.00 | 44.18 | A |
| 801 | CB | ARG | 108 | 32.250 | 18.796 | 27.185 | 1.00 | 44.91 | A |
| 802 | CG | ARG | 108 | 33.755 | 18.799 | 27.407 | 1.00 | 46.10 | A |
| 803 | CD | ARG | 108 | 34.408 | 19.994 | 26.733 | 1.00 | 47.26 | A |
| 804 | NE | ARG | 108 | 35.852 | 20.020 | 26.944 | 1.00 | 48.40 | A |
| 805 | CZ | ARG | 108 | 36.722 | 19.304 | 26.240 | 1.00 | 49.05 | A |
| 806 | NH1 | ARG | 108 | 36.292 | 18.501 | 25.275 | 1.00 | 49.36 | A |
| 807 | NH2 | ARG | 108 | 38.019 | 19.390 | 26.501 | 1.00 | 49.37 | A |
| 808 | C | ARG | 108 | 31.607 | 18.104 | 29.503 | 1.00 | 44.06 | A |
| 809 | O | ARG | 108 | 32.292 | 17.405 | 30.263 | 1.00 | 44.00 | A |
| 810 | N | LYS | 109 | 30.958 | 19.181 | 29.940 | 1.00 | 44.03 | A |
| 811 | CA | LYS | 109 | 31.033 | 19.603 | 31.331 | 1.00 | 44.10 | A |
| 812 | CB | LYS | 109 | 30.403 | 20.985 | 31.507 | 1.00 | 44.72 | A |
| 813 | CG | LYS | 109 | 31.074 | 22.080 | 30.693 | 1.00 | 45.65 | A |
| 814 | CD | LYS | 109 | 32.449 | 22.414 | 31.248 | 1.00 | 46.30 | A |
| 815 | CE | LYS | 109 | 33.269 | 23.210 | 30.245 | 1.00 | 46.72 | A |
| 816 | NZ | LYS | 109 | 34.617 | 23.551 | 30.776 | 1.00 | 47.36 | A |
| 817 | C | LYS | 109 | 30.359 | 18.590 | 32.248 | 1.00 | 43.77 | A |
| 818 | O | LYS | 109 | 30.894 | 18.272 | 33.314 | 1.00 | 43.65 | A |
| 819 | N | VAL | 110 | 29.189 | 18.088 | 31.867 | 1.00 | 43.35 | A |
| 820 | CA | VAL | 110 | 28.498 | 17.111 | 32.707 | 1.00 | 42.90 | A |
| 821 | CB | VAL | 110 | 27.146 | 16.668 | 32.087 | 1.00 | 42.83 | A |
| 822 | CG1 | VAL | 110 | 26.512 | 15.580 | 32.945 | 1.00 | 42.48 | A |
| 823 | CG2 | VAL | 110 | 26.210 | 17.869 | 31.980 | 1.00 | 42.55 | A |
| 824 | C | VAL | 110 | 29.373 | 15.884 | 32.921 | 1.00 | 42.75 | A |
| 825 | O | VAL | 110 | 29.565 | 15.434 | 34.052 | 1.00 | 42.30 | A |
| 826 | N | MET | 111 | 29.914 | 15.350 | 31.834 | 1.00 | 42.78 | A |
| 827 | CA | MET | 111 | 30.765 | 14.176 | 31.919 | 1.00 | 42.98 | A |
| 828 | CB | MET | 111 | 31.184 | 13.709 | 30.523 | 1.00 | 43.15 | A |
| 829 | CG | MET | 111 | 30.008 | 13.332 | 29.614 | 1.00 | 43.57 | A |
| 830 | SD | MET | 111 | 30.531 | 12.486 | 28.103 | 1.00 | 44.26 | A |
| 831 | CE | MET | 111 | 31.374 | 13.836 | 27.227 | 1.00 | 44.12 | A |
| 832 | C | MET | 111 | 32.003 | 14.449 | 32.770 | 1.00 | 43.03 | A |
| 833 | O | MET | 111 | 32.434 | 13.585 | 33.533 | 1.00 | 43.04 | A |
| 834 | N | GLU | 112 | 32.579 | 15.644 | 32.637 | 1.00 | 42.98 | A |
| 835 | CA | GLU | 112 | 33.766 | 15.999 | 33.418 | 1.00 | 42.93 | A |
| 836 | CB | GLU | 112 | 34.186 | 17.449 | 33.153 | 1.00 | 43.27 | A |
| 837 | CG | GLU | 112 | 34.872 | 17.649 | 31.820 | 1.00 | 44.06 | A |
| 838 | CD | GLU | 112 | 35.236 | 19.101 | 31.547 | 1.00 | 44.44 | A |
| 839 | OE1 | GLU | 112 | 34.995 | 19.967 | 32.423 | 1.00 | 44.81 | A |
| 840 | OE2 | GLU | 112 | 35.766 | 19.368 | 30.444 | 1.00 | 44.92 | A |
| 841 | C | GLU | 112 | 33.473 | 15.834 | 34.897 | 1.00 | 42.51 | A |
| 842 | O | GLU | 112 | 34.205 | 15.157 | 35.614 | 1.00 | 42.29 | A |
| 843 | N | ASN | 113 | 32.392 | 16.466 | 35.339 | 1.00 | 42.25 | A |
| 844 | CA | ASN | 113 | 31.976 | 16.403 | 36.732 | 1.00 | 42.06 | A |
| 845 | CB | ASN | 113 | 30.792 | 17.336 | 36.953 | 1.00 | 42.02 | A |
| 846 | CG | ASN | 113 | 31.160 | 18.778 | 36.713 | 1.00 | 42.12 | A |
| 847 | OD1 | ASN | 113 | 32.324 | 19.080 | 36.443 | 1.00 | 41.97 | A |
| 848 | ND2 | ASN | 113 | 30.184 | 19.677 | 36.810 | 1.00 | 41.88 | A |
| 849 | C | ASN | 113 | 31.624 | 14.992 | 37.174 | 1.00 | 42.00 | A |
| 850 | O | ASN | 113 | 31.921 | 14.598 | 38.309 | 1.00 | 41.99 | A |
| 851 | N | CYS | 114 | 30.992 | 14.228 | 36.286 | 1.00 | 41.78 | A |
| 852 | CA | CYS | 114 | 30.626 | 12.862 | 36.622 | 1.00 | 41.74 | A |
| 853 | CB | CYS | 114 | 29.749 | 12.244 | 35.522 | 1.00 | 41.53 | A |
| 854 | SG | CYS | 114 | 28.039 | 12.830 | 35.584 | 1.00 | 41.30 | A |
| 855 | C | CYS | 114 | 31.884 | 12.037 | 36.815 | 1.00 | 41.88 | A |
| 856 | O | CYS | 114 | 32.001 | 11.280 | 37.775 | 1.00 | 41.78 | A |
| 857 | N | VAL | 115 | 32.836 | 12.196 | 35.907 | 1.00 | 42.06 | A |
| 858 | CA | VAL | 115 | 34.075 | 11.447 | 35.999 | 1.00 | 42.47 | A |
| 859 | CB | VAL | 115 | 34.954 | 11.695 | 34.757 | 1.00 | 42.46 | A |
| 860 | CG1 | VAL | 115 | 36.291 | 10.987 | 34.909 | 1.00 | 42.38 | A |
| 861 | CG2 | VAL | 115 | 34.226 | 11.195 | 33.514 | 1.00 | 42.49 | A |
| 862 | C | VAL | 115 | 34.854 | 11.801 | 37.268 | 1.00 | 42.74 | A |
| 863 | O | VAL | 115 | 35.393 | 10.920 | 37.933 | 1.00 | 42.62 | A |
| 864 | N | ALA | 116 | 34.908 | 13.088 | 37.599 | 1.00 | 43.18 | A |
| 865 | CA | ALA | 116 | 35.618 | 13.535 | 38.795 | 1.00 | 43.74 | A |
| 866 | CB | ALA | 116 | 35.552 | 15.063 | 38.913 | 1.00 | 43.60 | A |

TABLE 1-continued

| Atom | Atom Type | Res | # | X | Y | Z | OCC | B | Mol. |
|---|---|---|---|---|---|---|---|---|---|
| 867 | C | ALA | 116 | 34.972 | 12.883 | 40.015 | 1.00 | 44.09 | A |
| 868 | O | ALA | 116 | 35.653 | 12.348 | 40.892 | 1.00 | 44.07 | A |
| 869 | N | HIS | 117 | 33.648 | 12.929 | 40.071 | 1.00 | 44.53 | A |
| 870 | CA | HIS | 117 | 32.950 | 12.315 | 41.189 | 1.00 | 44.95 | A |
| 871 | CB | HIS | 117 | 31.433 | 12.446 | 41.032 | 1.00 | 45.11 | A |
| 872 | CG | HIS | 117 | 30.664 | 11.576 | 41.979 | 1.00 | 45.31 | A |
| 873 | CD2 | HIS | 117 | 29.919 | 10.467 | 41.762 | 1.00 | 45.38 | A |
| 874 | ND1 | HIS | 117 | 30.687 | 11.763 | 43.346 | 1.00 | 45.33 | A |
| 875 | CE1 | HIS | 117 | 29.992 | 10.803 | 43.929 | 1.00 | 45.43 | A |
| 876 | NE2 | HIS | 117 | 29.516 | 10.002 | 42.991 | 1.00 | 45.53 | A |
| 877 | C | HIS | 117 | 33.306 | 10.838 | 41.285 | 1.00 | 45.24 | A |
| 878 | O | HIS | 117 | 33.764 | 10.369 | 42.323 | 1.00 | 45.23 | A |
| 879 | N | LEU | 118 | 33.101 | 10.112 | 40.192 | 1.00 | 45.60 | A |
| 880 | CA | LEU | 118 | 33.368 | 8.679 | 40.161 | 1.00 | 46.15 | A |
| 881 | CB | LEU | 118 | 33.093 | 8.129 | 38.765 | 1.00 | 46.02 | A |
| 882 | CG | LEU | 118 | 31.624 | 8.251 | 38.350 | 1.00 | 46.10 | A |
| 883 | CD1 | LEU | 118 | 31.475 | 7.974 | 36.859 | 1.00 | 46.01 | A |
| 884 | CD2 | LEU | 118 | 30.779 | 7.286 | 39.180 | 1.00 | 46.11 | A |
| 885 | C | LEU | 118 | 34.774 | 8.306 | 40.610 | 1.00 | 46.58 | A |
| 886 | O | LEU | 118 | 34.943 | 7.379 | 41.403 | 1.00 | 46.56 | A |
| 887 | N | LYS | 119 | 35.779 | 9.010 | 40.097 | 1.00 | 47.09 | A |
| 888 | CA | LYS | 119 | 37.159 | 8.740 | 40.492 | 1.00 | 47.62 | A |
| 889 | CB | LYS | 119 | 38.133 | 9.573 | 39.655 | 1.00 | 47.78 | A |
| 890 | CG | LYS | 119 | 38.212 | 9.155 | 38.205 | 1.00 | 48.15 | A |
| 891 | CD | LYS | 119 | 39.222 | 9.999 | 37.451 | 1.00 | 48.55 | A |
| 892 | CE | LYS | 119 | 39.383 | 9.510 | 36.029 | 1.00 | 48.80 | A |
| 893 | NZ | LYS | 119 | 40.542 | 10.166 | 35.376 | 1.00 | 49.23 | A |
| 894 | C | LYS | 119 | 37.296 | 9.109 | 41.966 | 1.00 | 47.88 | A |
| 895 | O | LYS | 119 | 37.943 | 8.407 | 42.737 | 1.00 | 48.10 | A |
| 896 | N | SER | 120 | 36.665 | 10.212 | 42.352 | 1.00 | 48.12 | A |
| 897 | CA | SER | 120 | 36.700 | 10.680 | 43.731 | 1.00 | 48.39 | A |
| 898 | CB | SER | 120 | 35.782 | 11.894 | 43.887 | 1.00 | 48.60 | A |
| 899 | OG | SER | 120 | 35.518 | 12.166 | 45.253 | 1.00 | 49.22 | A |
| 900 | C | SER | 120 | 36.283 | 9.603 | 44.731 | 1.00 | 48.39 | A |
| 901 | O | SER | 120 | 36.952 | 9.388 | 45.745 | 1.00 | 48.52 | A |
| 902 | N | VAL | 121 | 35.180 | 8.922 | 44.441 | 1.00 | 48.23 | A |
| 903 | CA | VAL | 121 | 34.667 | 7.886 | 45.332 | 1.00 | 48.06 | A |
| 904 | CB | VAL | 121 | 33.126 | 7.883 | 45.325 | 1.00 | 48.03 | A |
| 905 | CG1 | VAL | 121 | 32.608 | 9.247 | 45.771 | 1.00 | 48.02 | A |
| 906 | CG2 | VAL | 121 | 32.609 | 7.555 | 43.927 | 1.00 | 48.00 | A |
| 907 | C | VAL | 121 | 35.172 | 6.483 | 45.000 | 1.00 | 47.91 | A |
| 908 | O | VAL | 121 | 34.633 | 5.493 | 45.491 | 1.00 | 47.99 | A |
| 909 | N | GLY | 122 | 36.200 | 6.403 | 44.163 | 1.00 | 47.73 | A |
| 910 | CA | GLY | 122 | 36.774 | 5.116 | 43.804 | 1.00 | 47.44 | A |
| 911 | C | GLY | 122 | 35.947 | 4.142 | 42.981 | 1.00 | 47.28 | A |
| 912 | O | GLY | 122 | 36.156 | 2.935 | 43.070 | 1.00 | 47.24 | A |
| 913 | N | THR | 123 | 35.012 | 4.641 | 42.178 | 1.00 | 47.14 | A |
| 914 | CA | THR | 123 | 34.200 | 3.759 | 41.347 | 1.00 | 46.98 | A |
| 915 | CB | THR | 123 | 32.724 | 3.717 | 41.805 | 1.00 | 46.91 | A |
| 916 | OG1 | THR | 123 | 32.113 | 4.994 | 41.583 | 1.00 | 46.66 | A |
| 917 | CG2 | THR | 123 | 32.639 | 3.353 | 43.281 | 1.00 | 46.84 | A |
| 918 | C | THR | 123 | 34.238 | 4.205 | 39.890 | 1.00 | 46.97 | A |
| 919 | O | THR | 123 | 33.216 | 4.571 | 39.306 | 1.00 | 46.92 | A |
| 920 | N | TYR | 124 | 35.429 | 4.195 | 39.308 | 1.00 | 46.84 | A |
| 921 | CA | TYR | 124 | 35.564 | 4.576 | 37.917 | 1.00 | 46.66 | A |
| 922 | CB | TYR | 124 | 36.176 | 5.971 | 37.774 | 1.00 | 46.86 | A |
| 923 | CG | TYR | 124 | 36.098 | 6.477 | 36.347 | 1.00 | 47.23 | A |
| 924 | CD1 | TYR | 124 | 34.862 | 6.719 | 35.747 | 1.00 | 47.38 | A |
| 925 | CE1 | TYR | 124 | 34.768 | 7.134 | 34.425 | 1.00 | 47.54 | A |
| 926 | CD2 | TYR | 124 | 37.251 | 6.669 | 35.580 | 1.00 | 47.35 | A |
| 927 | CE2 | TYR | 124 | 37.168 | 7.086 | 34.245 | 1.00 | 47.53 | A |
| 928 | CZ | TYR | 124 | 35.923 | 7.315 | 33.679 | 1.00 | 47.66 | A |
| 929 | OH | TYR | 124 | 35.823 | 7.719 | 32.368 | 1.00 | 47.86 | A |
| 930 | C | TYR | 124 | 36.444 | 3.558 | 37.227 | 1.00 | 46.44 | A |
| 931 | O | TYR | 124 | 37.627 | 3.798 | 36.999 | 1.00 | 46.53 | A |
| 932 | N | GLY | 125 | 35.858 | 2.409 | 36.912 | 1.00 | 46.10 | A |
| 933 | CA | GLY | 125 | 36.589 | 1.354 | 36.239 | 1.00 | 45.74 | A |
| 934 | C | GLY | 125 | 36.263 | 1.351 | 34.761 | 1.00 | 45.52 | A |
| 935 | O | GLY | 125 | 35.666 | 2.302 | 34.249 | 1.00 | 45.43 | A |
| 936 | N | ASP | 126 | 36.648 | .284 | 34.068 | 1.00 | 45.30 | A |
| 937 | CA | ASP | 126 | 36.388 | .191 | 32.643 | 1.00 | 45.09 | A |
| 938 | CB | ASP | 126 | 36.925 | −1.128 | 32.079 | 1.00 | 45.36 | A |
| 939 | CG | ASP | 126 | 38.446 | −1.241 | 32.192 | 1.00 | 45.63 | A |
| 940 | OD1 | ASP | 126 | 39.137 | −.197 | 32.225 | 1.00 | 45.67 | A |
| 941 | OD2 | ASP | 126 | 38.950 | −2.382 | 32.233 | 1.00 | 45.82 | A |
| 942 | C | ASP | 126 | 34.897 | .304 | 32.358 | 1.00 | 44.81 | A |
| 943 | O | ASP | 126 | 34.483 | 1.018 | 31.444 | 1.00 | 44.67 | A |

TABLE 1-continued

| Atom | Atom Type | Res | # | X | Y | Z | OCC | B | Mol. |
|---|---|---|---|---|---|---|---|---|---|
| 944 | N | ALA | 127 | 34.091 | −.394 | 33.152 | 1.00 | 44.39 | A |
| 945 | CA | ALA | 127 | 32.648 | −.361 | 32.967 | 1.00 | 44.02 | A |
| 946 | CB | ALA | 127 | 31.956 | −1.222 | 34.028 | 1.00 | 43.92 | A |
| 947 | C | ALA | 127 | 32.130 | 1.074 | 33.024 | 1.00 | 43.76 | A |
| 948 | O | ALA | 127 | 31.348 | 1.487 | 32.166 | 1.00 | 43.61 | A |
| 949 | N | GLU | 128 | 32.572 | 1.843 | 34.014 | 1.00 | 43.55 | A |
| 950 | CA | GLU | 128 | 32.111 | 3.224 | 34.126 | 1.00 | 43.62 | A |
| 951 | CB | GLU | 128 | 32.531 | 3.845 | 35.463 | 1.00 | 43.55 | A |
| 952 | CG | GLU | 128 | 31.788 | 3.279 | 36.678 | 1.00 | 43.55 | A |
| 953 | CD | GLU | 128 | 32.126 | 1.824 | 36.941 | 1.00 | 43.58 | A |
| 954 | OE1 | GLU | 128 | 33.327 | 1.508 | 37.052 | 1.00 | 43.53 | A |
| 955 | OE2 | GLU | 128 | 31.201 | .991 | 37.042 | 1.00 | 43.62 | A |
| 956 | C | GLU | 128 | 32.620 | 4.086 | 32.972 | 1.00 | 43.60 | A |
| 957 | O | GLU | 128 | 31.911 | 4.971 | 32.500 | 1.00 | 43.55 | A |
| 958 | N | ALA | 129 | 33.844 | 3.827 | 32.523 | 1.00 | 43.63 | A |
| 959 | CA | ALA | 129 | 34.422 | 4.585 | 31.412 | 1.00 | 43.86 | A |
| 960 | CB | ALA | 129 | 35.885 | 4.182 | 31.194 | 1.00 | 43.78 | A |
| 961 | C | ALA | 129 | 33.606 | 4.302 | 30.159 | 1.00 | 43.88 | A |
| 962 | O | ALA | 129 | 33.249 | 5.210 | 29.415 | 1.00 | 43.98 | A |
| 963 | N | GLU | 130 | 33.305 | 3.032 | 29.930 | 1.00 | 44.01 | A |
| 964 | CA | GLU | 130 | 32.517 | 2.656 | 28.774 | 1.00 | 44.23 | A |
| 965 | CB | GLU | 130 | 32.422 | 1.135 | 28.683 | 1.00 | 44.93 | A |
| 966 | CG | GLU | 130 | 33.741 | .489 | 28.282 | 1.00 | 46.16 | A |
| 967 | CD | GLU | 130 | 33.736 | −1.016 | 28.465 | 1.00 | 47.06 | A |
| 968 | OE1 | GLU | 130 | 32.695 | −1.650 | 28.167 | 1.00 | 47.65 | A |
| 969 | OE2 | GLU | 130 | 34.778 | −1.569 | 28.896 | 1.00 | 47.67 | A |
| 970 | C | GLU | 130 | 31.128 | 3.280 | 28.859 | 1.00 | 43.90 | A |
| 971 | O | GLU | 130 | 30.576 | 3.718 | 27.849 | 1.00 | 43.72 | A |
| 972 | N | ALA | 131 | 30.568 | 3.329 | 30.065 | 1.00 | 43.53 | A |
| 973 | CA | ALA | 131 | 29.249 | 3.919 | 30.254 | 1.00 | 43.31 | A |
| 974 | CB | ALA | 131 | 28.762 | 3.709 | 31.688 | 1.00 | 43.09 | A |
| 975 | C | ALA | 131 | 29.308 | 5.407 | 29.931 | 1.00 | 43.19 | A |
| 976 | O | ALA | 131 | 28.388 | 5.952 | 29.318 | 1.00 | 43.03 | A |
| 977 | N | MET | 132 | 30.389 | 6.066 | 30.337 | 1.00 | 43.13 | A |
| 978 | CA | MET | 132 | 30.530 | 7.492 | 30.060 | 1.00 | 43.23 | A |
| 979 | CB | MET | 132 | 31.697 | 8.086 | 30.849 | 1.00 | 43.34 | A |
| 980 | CG | MET | 132 | 31.472 | 8.107 | 32.353 | 1.00 | 43.56 | A |
| 981 | SD | MET | 132 | 29.878 | 8.840 | 32.809 | 1.00 | 43.96 | A |
| 982 | CE | MET | 132 | 30.021 | 10.478 | 32.064 | 1.00 | 43.50 | A |
| 983 | C | MET | 132 | 30.721 | 7.754 | 28.565 | 1.00 | 43.26 | A |
| 984 | O | MET | 132 | 30.315 | 8.802 | 28.058 | 1.00 | 43.15 | A |
| 985 | N | GLN | 133 | 31.337 | 6.806 | 27.862 | 1.00 | 43.25 | A |
| 986 | CA | GLN | 133 | 31.539 | 6.956 | 26.420 | 1.00 | 43.48 | A |
| 987 | CB | GLN | 133 | 32.523 | 5.903 | 25.893 | 1.00 | 43.88 | A |
| 988 | CG | GLN | 133 | 32.779 | 5.983 | 24.384 | 1.00 | 44.76 | A |
| 989 | CD | GLN | 133 | 33.188 | 7.381 | 23.923 | 1.00 | 45.33 | A |
| 990 | OE1 | GLN | 133 | 34.118 | 7.984 | 24.469 | 1.00 | 45.84 | A |
| 991 | NE2 | GLN | 133 | 32.494 | 7.901 | 22.913 | 1.00 | 45.68 | A |
| 992 | C | GLN | 133 | 30.180 | 6.794 | 25.748 | 1.00 | 43.22 | A |
| 993 | O | GLN | 133 | 29.849 | 7.509 | 24.798 | 1.00 | 43.19 | A |
| 994 | N | LYS | 134 | 29.383 | 5.859 | 26.257 | 1.00 | 42.89 | A |
| 995 | CA | LYS | 134 | 28.054 | 5.646 | 25.704 | 1.00 | 42.64 | A |
| 996 | CB | LYS | 134 | 27.389 | 4.436 | 26.360 | 1.00 | 42.74 | A |
| 997 | CG | LYS | 134 | 26.011 | 4.115 | 25.805 | 1.00 | 42.92 | A |
| 998 | CD | LYS | 134 | 25.502 | 2.779 | 26.345 | 1.00 | 43.17 | A |
| 999 | CE | LYS | 134 | 24.109 | 2.464 | 25.830 | 1.00 | 43.26 | A |
| 1000 | NZ | LYS | 134 | 23.665 | 1.122 | 26.298 | 1.00 | 43.66 | A |
| 1001 | C | LYS | 134 | 27.250 | 6.912 | 25.985 | 1.00 | 42.33 | A |
| 1002 | O | LYS | 134 | 26.435 | 7.349 | 25.173 | 1.00 | 42.13 | A |
| 1003 | N | PHE | 135 | 27.496 | 7.499 | 27.149 | 1.00 | 42.17 | A |
| 1004 | CA | PHE | 135 | 26.825 | 8.728 | 27.543 | 1.00 | 41.95 | A |
| 1005 | CB | PHE | 135 | 27.363 | 9.173 | 28.905 | 1.00 | 41.89 | A |
| 1006 | CG | PHE | 135 | 26.648 | 10.357 | 29.503 | 1.00 | 41.74 | A |
| 1007 | CD1 | PHE | 135 | 25.641 | 10.173 | 30.439 | 1.00 | 41.59 | A |
| 1008 | CD2 | PHE | 135 | 27.025 | 11.656 | 29.170 | 1.00 | 41.62 | A |
| 1009 | CE1 | PHE | 135 | 25.021 | 11.265 | 31.047 | 1.00 | 41.62 | A |
| 1010 | CE2 | PHE | 135 | 26.412 | 12.752 | 29.771 | 1.00 | 41.54 | A |
| 1011 | CZ | PHE | 135 | 25.410 | 12.555 | 30.713 | 1.00 | 41.53 | A |
| 1012 | C | PHE | 135 | 27.154 | 9.770 | 26.465 | 1.00 | 41.96 | A |
| 1013 | O | PHE | 135 | 26.262 | 10.364 | 25.858 | 1.00 | 41.77 | A |
| 1014 | N | ALA | 136 | 28.448 | 9.965 | 26.223 | 1.00 | 42.04 | A |
| 1015 | CA | ALA | 136 | 28.922 | 10.931 | 25.229 | 1.00 | 42.27 | A |
| 1016 | CB | ALA | 136 | 30.444 | 10.863 | 25.125 | 1.00 | 42.09 | A |
| 1017 | C | ALA | 136 | 28.307 | 10.689 | 23.858 | 1.00 | 42.41 | A |
| 1018 | O | ALA | 136 | 27.848 | 11.618 | 23.193 | 1.00 | 42.42 | A |
| 1019 | N | GLU | 137 | 28.303 | 9.430 | 23.440 | 1.00 | 42.64 | A |
| 1020 | CA | GLU | 137 | 27.767 | 9.061 | 22.141 | 1.00 | 43.03 | A |

TABLE 1-continued

| Atom | Atom Type | Res | # | X | Y | Z | OCC | B | Mol. |
|---|---|---|---|---|---|---|---|---|---|
| 1021 | CB | GLU | 137 | 27.875 | 7.550 | 21.951 | 1.00 | 43.75 | A |
| 1022 | CG | GLU | 137 | 28.505 | 7.155 | 20.644 | 1.00 | 45.13 | A |
| 1023 | CD | GLU | 137 | 29.983 | 7.466 | 20.611 | 1.00 | 45.82 | A |
| 1024 | OE1 | GLU | 137 | 30.723 | 6.842 | 21.406 | 1.00 | 46.56 | A |
| 1025 | OE2 | GLU | 137 | 30.400 | 8.329 | 19.801 | 1.00 | 46.16 | A |
| 1026 | C | GLU | 137 | 26.317 | 9.488 | 21.970 | 1.00 | 42.71 | A |
| 1027 | O | GLU | 137 | 25.917 | 9.950 | 20.899 | 1.00 | 42.80 | A |
| 1028 | N | ALA | 138 | 25.527 | 9.332 | 23.025 | 1.00 | 42.31 | A |
| 1029 | CA | ALA | 138 | 24.116 | 9.691 | 22.962 | 1.00 | 41.96 | A |
| 1030 | CB | ALA | 138 | 23.417 | 9.279 | 24.254 | 1.00 | 41.98 | A |
| 1031 | C | ALA | 138 | 23.894 | 11.181 | 22.707 | 1.00 | 41.72 | A |
| 1032 | O | ALA | 138 | 22.880 | 11.571 | 22.128 | 1.00 | 41.54 | A |
| 1033 | N | PHE | 139 | 24.837 | 12.012 | 23.140 | 1.00 | 41.34 | A |
| 1034 | CA | PHE | 139 | 24.700 | 13.455 | 22.965 | 1.00 | 41.15 | A |
| 1035 | CB | PHE | 139 | 25.381 | 14.213 | 24.111 | 1.00 | 40.74 | A |
| 1036 | CG | PHE | 139 | 24.588 | 14.245 | 25.387 | 1.00 | 40.50 | A |
| 1037 | CD1 | PHE | 139 | 24.687 | 13.214 | 26.315 | 1.00 | 40.18 | A |
| 1038 | CD2 | PHE | 139 | 23.760 | 15.329 | 25.672 | 1.00 | 40.30 | A |
| 1039 | CE1 | PHE | 139 | 23.978 | 13.264 | 27.512 | 1.00 | 40.10 | A |
| 1040 | CE2 | PHE | 139 | 23.042 | 15.388 | 26.872 | 1.00 | 40.16 | A |
| 1041 | CZ | PHE | 139 | 23.154 | 14.354 | 27.791 | 1.00 | 40.04 | A |
| 1042 | C | PHE | 139 | 25.240 | 14.010 | 21.655 | 1.00 | 41.14 | A |
| 1043 | O | PHE | 139 | 24.835 | 15.085 | 21.238 | 1.00 | 41.08 | A |
| 1044 | N | LYS | 140 | 26.148 | 13.289 | 21.006 | 1.00 | 41.32 | A |
| 1045 | CA | LYS | 140 | 26.745 | 13.779 | 19.764 | 1.00 | 41.72 | A |
| 1046 | CB | LYS | 140 | 27.740 | 12.752 | 19.212 | 1.00 | 41.92 | A |
| 1047 | CG | LYS | 140 | 28.978 | 12.587 | 20.086 | 1.00 | 42.34 | A |
| 1048 | CD | LYS | 140 | 29.990 | 11.644 | 19.460 | 1.00 | 42.79 | A |
| 1049 | CE | LYS | 140 | 31.231 | 11.518 | 20.342 | 1.00 | 43.20 | A |
| 1050 | NZ | LYS | 140 | 32.244 | 10.587 | 19.749 | 1.00 | 43.64 | A |
| 1051 | C | LYS | 140 | 25.807 | 14.230 | 18.641 | 1.00 | 41.79 | A |
| 1052 | O | LYS | 140 | 26.063 | 15.245 | 17.992 | 1.00 | 41.89 | A |
| 1053 | N | PRO | 141 | 24.714 | 13.494 | 18.393 | 1.00 | 41.82 | A |
| 1054 | CD | PRO | 141 | 24.354 | 12.156 | 18.903 | 1.00 | 41.97 | A |
| 1055 | CA | PRO | 141 | 23.803 | 13.904 | 17.318 | 1.00 | 41.80 | A |
| 1056 | CB | PRO | 141 | 23.155 | 12.585 | 16.913 | 1.00 | 41.90 | A |
| 1057 | CG | PRO | 141 | 23.005 | 11.898 | 18.229 | 1.00 | 41.95 | A |
| 1058 | C | PRO | 141 | 22.765 | 14.931 | 17.748 | 1.00 | 41.71 | A |
| 1059 | O | PRO | 141 | 21.848 | 15.254 | 16.995 | 1.00 | 41.61 | A |
| 1060 | N | VAL | 142 | 22.915 | 15.456 | 18.955 | 1.00 | 41.56 | A |
| 1061 | CA | VAL | 142 | 21.938 | 16.397 | 19.466 | 1.00 | 41.56 | A |
| 1062 | CB | VAL | 142 | 21.417 | 15.924 | 20.850 | 1.00 | 41.66 | A |
| 1063 | CG1 | VAL | 142 | 20.292 | 16.833 | 21.335 | 1.00 | 41.67 | A |
| 1064 | CG2 | VAL | 142 | 20.936 | 14.473 | 20.755 | 1.00 | 41.81 | A |
| 1065 | C | VAL | 142 | 22.427 | 17.832 | 19.606 | 1.00 | 41.50 | A |
| 1066 | O | VAL | 142 | 23.612 | 18.089 | 19.826 | 1.00 | 41.47 | A |
| 1067 | N | ASN | 143 | 21.496 | 18.762 | 19.447 | 1.00 | 41.33 | A |
| 1068 | CA | ASN | 143 | 21.794 | 20.168 | 19.626 | 1.00 | 41.38 | A |
| 1069 | CB | ASN | 143 | 21.789 | 20.935 | 18.302 | 1.00 | 41.38 | A |
| 1070 | CG | ASN | 143 | 22.159 | 22.406 | 18.491 | 1.00 | 41.39 | A |
| 1071 | OD1 | ASN | 143 | 23.181 | 22.719 | 19.103 | 1.00 | 41.27 | A |
| 1072 | ND2 | ASN | 143 | 21.330 | 23.306 | 17.972 | 1.00 | 41.22 | A |
| 1073 | C | ASN | 143 | 20.704 | 20.702 | 20.533 | 1.00 | 41.38 | A |
| 1074 | O | ASN | 143 | 19.545 | 20.281 | 20.442 | 1.00 | 41.22 | A |
| 1075 | N | PHE | 144 | 21.070 | 21.615 | 21.422 | 1.00 | 41.46 | A |
| 1076 | CA | PHE | 144 | 20.097 | 22.179 | 22.342 | 1.00 | 41.70 | A |
| 1077 | CB | PHE | 144 | 20.501 | 21.926 | 23.801 | 1.00 | 41.45 | A |
| 1078 | CG | PHE | 144 | 20.604 | 20.471 | 24.174 | 1.00 | 41.40 | A |
| 1079 | CD1 | PHE | 144 | 21.843 | 19.843 | 24.239 | 1.00 | 41.20 | A |
| 1080 | CD2 | PHE | 144 | 19.458 | 19.739 | 24.498 | 1.00 | 41.26 | A |
| 1081 | CE1 | PHE | 144 | 21.952 | 18.504 | 24.625 | 1.00 | 41.32 | A |
| 1082 | CE2 | PHE | 144 | 19.550 | 18.398 | 24.884 | 1.00 | 41.35 | A |
| 1083 | CZ | PHE | 144 | 20.798 | 17.779 | 24.949 | 1.00 | 41.26 | A |
| 1084 | C | PHE | 144 | 19.880 | 23.677 | 22.174 | 1.00 | 41.98 | A |
| 1085 | O | PHE | 144 | 20.526 | 24.486 | 22.847 | 1.00 | 41.96 | A |
| 1086 | N | PRO | 145 | 18.991 | 24.073 | 21.255 | 1.00 | 42.28 | A |
| 1087 | CD | PRO | 145 | 18.284 | 23.323 | 20.200 | 1.00 | 42.24 | A |
| 1088 | CA | PRO | 145 | 18.770 | 25.512 | 21.117 | 1.00 | 42.29 | A |
| 1089 | CB | PRO | 145 | 17.942 | 25.611 | 19.836 | 1.00 | 42.43 | A |
| 1090 | CG | PRO | 145 | 17.196 | 24.295 | 19.807 | 1.00 | 42.47 | A |
| 1091 | C | PRO | 145 | 17.990 | 25.933 | 22.367 | 1.00 | 42.41 | A |
| 1092 | O | PRO | 145 | 17.510 | 25.075 | 23.124 | 1.00 | 42.42 | A |
| 1093 | N | PRO | 146 | 17.863 | 27.247 | 22.616 | 1.00 | 42.40 | A |
| 1094 | CD | PRO | 146 | 18.349 | 28.400 | 21.833 | 1.00 | 42.37 | A |
| 1095 | CA | PRO | 146 | 17.126 | 27.687 | 23.802 | 1.00 | 42.32 | A |
| 1096 | CB | PRO | 146 | 16.937 | 29.180 | 23.554 | 1.00 | 42.35 | A |
| 1097 | CG | PRO | 146 | 18.196 | 29.542 | 22.812 | 1.00 | 42.35 | A |

TABLE 1-continued

| Atom | Atom Type | Res | # | X | Y | Z | OCC | B | Mol. |
|---|---|---|---|---|---|---|---|---|---|
| 1098 | C | PRO | 146 | 15.795 | 26.957 | 23.938 | 1.00 | 42.26 | A |
| 1099 | O | PRO | 146 | 15.071 | 26.794 | 22.963 | 1.00 | 42.31 | A |
| 1100 | N | GLY | 147 | 15.476 | 26.517 | 25.148 | 1.00 | 42.22 | A |
| 1101 | CA | GLY | 147 | 14.221 | 25.819 | 25.360 | 1.00 | 42.03 | A |
| 1102 | C | GLY | 147 | 14.317 | 24.318 | 25.147 | 1.00 | 41.85 | A |
| 1103 | O | GLY | 147 | 13.484 | 23.572 | 25.668 | 1.00 | 41.83 | A |
| 1104 | N | ALA | 148 | 15.312 | 23.879 | 24.375 | 1.00 | 41.67 | A |
| 1105 | CA | ALA | 148 | 15.515 | 22.452 | 24.116 | 1.00 | 41.47 | A |
| 1106 | CB | ALA | 148 | 16.627 | 22.240 | 23.091 | 1.00 | 41.48 | A |
| 1107 | C | ALA | 148 | 15.889 | 21.814 | 25.446 | 1.00 | 41.43 | A |
| 1108 | O | ALA | 148 | 16.473 | 22.472 | 26.317 | 1.00 | 41.33 | A |
| 1109 | N | SER | 149 | 15.571 | 20.533 | 25.608 | 1.00 | 41.17 | A |
| 1110 | CA | SER | 149 | 15.833 | 19.884 | 26.881 | 1.00 | 40.92 | A |
| 1111 | CB | SER | 149 | 14.532 | 19.772 | 27.668 | 1.00 | 40.88 | A |
| 1112 | OG | SER | 149 | 13.888 | 21.022 | 27.774 | 1.00 | 41.22 | A |
| 1113 | C | SER | 149 | 16.467 | 18.513 | 26.856 | 1.00 | 40.65 | A |
| 1114 | O | SER | 149 | 16.417 | 17.788 | 25.860 | 1.00 | 40.68 | A |
| 1115 | N | VAL | 150 | 17.069 | 18.171 | 27.986 | 1.00 | 40.32 | A |
| 1116 | CA | VAL | 150 | 17.665 | 16.865 | 28.172 | 1.00 | 39.84 | A |
| 1117 | CB | VAL | 150 | 19.185 | 16.939 | 28.436 | 1.00 | 39.89 | A |
| 1118 | CG1 | VAL | 150 | 19.479 | 17.829 | 29.651 | 1.00 | 39.70 | A |
| 1119 | CG2 | VAL | 150 | 19.724 | 15.533 | 28.670 | 1.00 | 39.82 | A |
| 1120 | C | VAL | 150 | 16.960 | 16.328 | 29.404 | 1.00 | 39.59 | A |
| 1121 | O | VAL | 150 | 16.746 | 17.058 | 30.374 | 1.00 | 39.45 | A |
| 1122 | N | PHE | 151 | 16.560 | 15.063 | 29.351 | 1.00 | 39.30 | A |
| 1123 | CA | PHE | 151 | 15.891 | 14.440 | 30.480 | 1.00 | 38.87 | A |
| 1124 | CB | PHE | 151 | 14.508 | 13.928 | 30.077 | 1.00 | 39.13 | A |
| 1125 | CG | PHE | 151 | 13.509 | 15.015 | 29.823 | 1.00 | 39.25 | A |
| 1126 | CD1 | PHE | 151 | 12.636 | 15.420 | 30.826 | 1.00 | 39.37 | A |
| 1127 | CD2 | PHE | 151 | 13.438 | 15.632 | 28.578 | 1.00 | 39.36 | A |
| 1128 | CE1 | PHE | 151 | 11.699 | 16.425 | 30.597 | 1.00 | 39.52 | A |
| 1129 | CE2 | PHE | 151 | 12.503 | 16.641 | 28.336 | 1.00 | 39.54 | A |
| 1130 | CZ | PHE | 151 | 11.634 | 17.037 | 29.345 | 1.00 | 39.45 | A |
| 1131 | C | PHE | 151 | 16.724 | 13.270 | 30.973 | 1.00 | 38.58 | A |
| 1132 | O | PHE | 151 | 17.062 | 12.366 | 30.205 | 1.00 | 38.41 | A |
| 1133 | N | TYR | 152 | 17.076 | 13.308 | 32.252 | 1.00 | 38.13 | A |
| 1134 | CA | TYR | 152 | 17.834 | 12.227 | 32.857 | 1.00 | 37.88 | A |
| 1135 | CB | TYR | 152 | 18.949 | 12.746 | 33.768 | 1.00 | 37.88 | A |
| 1136 | CG | TYR | 152 | 20.021 | 13.550 | 33.079 | 1.00 | 37.74 | A |
| 1137 | CD1 | TYR | 152 | 19.977 | 14.945 | 33.066 | 1.00 | 37.66 | A |
| 1138 | CE1 | TYR | 152 | 20.986 | 15.689 | 32.447 | 1.00 | 37.66 | A |
| 1139 | CD2 | TYR | 152 | 21.092 | 12.917 | 32.459 | 1.00 | 37.76 | A |
| 1140 | CE2 | TYR | 152 | 22.101 | 13.644 | 31.841 | 1.00 | 37.59 | A |
| 1141 | CZ | TYR | 152 | 22.043 | 15.029 | 31.841 | 1.00 | 37.66 | A |
| 1142 | OH | TYR | 152 | 23.056 | 15.750 | 31.251 | 1.00 | 37.80 | A |
| 1143 | C | TYR | 152 | 16.857 | 11.465 | 33.729 | 1.00 | 37.79 | A |
| 1144 | O | TYR | 152 | 16.323 | 12.020 | 34.695 | 1.00 | 37.55 | A |
| 1145 | N | ARG | 153 | 16.597 | 10.210 | 33.387 | 1.00 | 37.54 | A |
| 1146 | CA | ARG | 153 | 15.711 | 9.416 | 34.221 | 1.00 | 37.53 | A |
| 1147 | CB | ARG | 153 | 14.763 | 8.555 | 33.384 | 1.00 | 37.44 | A |
| 1148 | CG | ARG | 153 | 13.813 | 7.728 | 34.245 | 1.00 | 37.32 | A |
| 1149 | CD | ARG | 153 | 12.827 | 6.961 | 33.373 | 1.00 | 37.28 | A |
| 1150 | NE | ARG | 153 | 13.515 | 6.054 | 32.462 | 1.00 | 37.30 | A |
| 1151 | CZ | ARG | 153 | 13.946 | 4.839 | 32.786 | 1.00 | 37.33 | A |
| 1152 | NH1 | ARG | 153 | 13.758 | 4.361 | 34.013 | 1.00 | 37.43 | A |
| 1153 | NH2 | ARG | 153 | 14.574 | 4.107 | 31.878 | 1.00 | 37.25 | A |
| 1154 | C | ARG | 153 | 16.626 | 8.519 | 35.030 | 1.00 | 37.57 | A |
| 1155 | O | ARG | 153 | 17.244 | 7.603 | 34.487 | 1.00 | 37.45 | A |
| 1156 | N | GLN | 154 | 16.741 | 8.798 | 36.321 | 1.00 | 37.63 | A |
| 1157 | CA | GLN | 154 | 17.597 | 7.988 | 37.173 | 1.00 | 37.90 | A |
| 1158 | CB | GLN | 154 | 18.270 | 8.850 | 38.247 | 1.00 | 37.95 | A |
| 1159 | CG | GLN | 154 | 19.330 | 8.096 | 39.051 | 1.00 | 38.05 | A |
| 1160 | CD | GLN | 154 | 19.810 | 8.881 | 40.260 | 1.00 | 38.19 | A |
| 1161 | OE1 | GLN | 154 | 19.877 | 10.110 | 40.226 | 1.00 | 38.28 | A |
| 1162 | NE2 | GLN | 154 | 20.153 | 8.175 | 41.330 | 1.00 | 38.08 | A |
| 1163 | C | GLN | 154 | 16.766 | 6.901 | 37.841 | 1.00 | 38.01 | A |
| 1164 | O | GLN | 154 | 16.024 | 7.159 | 38.790 | 1.00 | 37.91 | A |
| 1165 | N | SER | 155 | 16.886 | 5.688 | 37.320 | 1.00 | 38.27 | A |
| 1166 | CA | SER | 155 | 16.167 | 4.545 | 37.852 | 1.00 | 38.62 | A |
| 1167 | CB | SER | 155 | 16.046 | 3.470 | 36.784 | 1.00 | 38.57 | A |
| 1168 | OG | SER | 155 | 15.731 | 2.229 | 37.378 | 1.00 | 39.38 | A |
| 1169 | C | SER | 155 | 16.936 | 3.993 | 39.042 | 1.00 | 38.76 | A |
| 1170 | O | SER | 155 | 18.162 | 3.876 | 39.000 | 1.00 | 38.81 | A |
| 1171 | N | PRO | 156 | 16.227 | 3.633 | 40.120 | 1.00 | 38.88 | A |
| 1172 | CD | PRO | 156 | 14.770 | 3.655 | 40.339 | 1.00 | 38.95 | A |
| 1173 | CA | PRO | 156 | 16.928 | 3.098 | 41.288 | 1.00 | 38.90 | A |
| 1174 | CB | PRO | 156 | 15.835 | 3.050 | 42.349 | 1.00 | 38.90 | A |

TABLE 1-continued

| Atom | Atom Type | Res | # | X | Y | Z | OCC | B | Mol. |
|---|---|---|---|---|---|---|---|---|---|
| 1175 | CG | PRO | 156 | 14.612 | 2.752 | 41.539 | 1.00 | 38.97 | A |
| 1176 | C | PRO | 156 | 17.544 | 1.734 | 40.996 | 1.00 | 38.81 | A |
| 1177 | O | PRO | 156 | 18.340 | 1.219 | 41.782 | 1.00 | 38.90 | A |
| 1178 | N | ASP | 157 | 17.180 | 1.160 | 39.854 | 1.00 | 38.77 | A |
| 1179 | CA | ASP | 157 | 17.699 | −.144 | 39.457 | 1.00 | 38.75 | A |
| 1180 | CB | ASP | 157 | 16.699 | −.854 | 38.538 | 1.00 | 39.02 | A |
| 1181 | CG | ASP | 157 | 15.319 | −.949 | 39.150 | 1.00 | 39.26 | A |
| 1182 | OD1 | ASP | 157 | 15.225 | −1.296 | 40.345 | 1.00 | 39.28 | A |
| 1183 | OD2 | ASP | 157 | 14.326 | −.680 | 38.436 | 1.00 | 39.64 | A |
| 1184 | C | ASP | 157 | 19.065 | −.048 | 38.764 | 1.00 | 38.67 | A |
| 1185 | O | ASP | 157 | 19.506 | −.991 | 38.111 | 1.00 | 38.65 | A |
| 1186 | N | GLY | 158 | 19.721 | 1.102 | 38.893 | 1.00 | 38.54 | A |
| 1187 | CA | GLY | 158 | 21.042 | 1.269 | 38.312 | 1.00 | 38.54 | A |
| 1188 | C | GLY | 158 | 21.105 | 1.553 | 36.826 | 1.00 | 38.44 | A |
| 1189 | O | GLY | 158 | 22.040 | 1.132 | 36.143 | 1.00 | 38.40 | A |
| 1190 | N | ILE | 159 | 20.115 | 2.275 | 36.321 | 1.00 | 38.42 | A |
| 1191 | CA | ILE | 159 | 20.074 | 2.619 | 34.909 | 1.00 | 38.43 | A |
| 1192 | CB | ILE | 159 | 18.963 | 1.846 | 34.159 | 1.00 | 38.57 | A |
| 1193 | CG2 | ILE | 159 | 18.839 | 2.368 | 32.726 | 1.00 | 38.58 | A |
| 1194 | CG1 | ILE | 159 | 19.270 | .346 | 34.174 | 1.00 | 38.75 | A |
| 1195 | CD1 | ILE | 159 | 18.225 | −.505 | 33.457 | 1.00 | 39.00 | A |
| 1196 | C | ILE | 159 | 19.786 | 4.099 | 34.784 | 1.00 | 38.38 | A |
| 1197 | O | ILE | 159 | 19.019 | 4.663 | 35.565 | 1.00 | 38.19 | A |
| 1198 | N | LEU | 160 | 20.426 | 4.731 | 33.812 | 1.00 | 38.40 | A |
| 1199 | CA | LEU | 160 | 20.214 | 6.148 | 33.582 | 1.00 | 38.59 | A |
| 1200 | CB | LEU | 160 | 21.539 | 6.910 | 33.673 | 1.00 | 38.58 | A |
| 1201 | CG | LEU | 160 | 21.456 | 8.411 | 33.380 | 1.00 | 38.62 | A |
| 1202 | CD1 | LEU | 160 | 20.672 | 9.103 | 34.482 | 1.00 | 38.51 | A |
| 1203 | CD2 | LEU | 160 | 22.867 | 8.990 | 33.278 | 1.00 | 38.65 | A |
| 1204 | C | LEU | 160 | 19.633 | 6.275 | 32.185 | 1.00 | 38.66 | A |
| 1205 | O | LEU | 160 | 20.296 | 5.950 | 31.204 | 1.00 | 38.58 | A |
| 1206 | N | GLY | 161 | 18.384 | 6.714 | 32.100 | 1.00 | 38.88 | A |
| 1207 | CA | GLY | 161 | 17.765 | 6.872 | 30.799 | 1.00 | 39.27 | A |
| 1208 | C | GLY | 161 | 17.975 | 8.281 | 30.278 | 1.00 | 39.47 | A |
| 1209 | O | GLY | 161 | 17.758 | 9.249 | 31.004 | 1.00 | 39.35 | A |
| 1210 | N | LEU | 162 | 18.407 | 8.393 | 29.027 | 1.00 | 39.76 | A |
| 1211 | CA | LEU | 162 | 18.636 | 9.694 | 28.406 | 1.00 | 40.16 | A |
| 1212 | CB | LEU | 162 | 20.042 | 9.757 | 27.805 | 1.00 | 40.00 | A |
| 1213 | CG | LEU | 162 | 21.192 | 9.511 | 28.786 | 1.00 | 39.96 | A |
| 1214 | CD1 | LEU | 162 | 22.527 | 9.575 | 28.044 | 1.00 | 39.90 | A |
| 1215 | CD2 | LEU | 162 | 21.135 | 10.546 | 29.900 | 1.00 | 39.77 | A |
| 1216 | C | LEU | 162 | 17.618 | 10.018 | 27.315 | 1.00 | 40.55 | A |
| 1217 | O | LEU | 162 | 17.444 | 9.253 | 26.368 | 1.00 | 40.35 | A |
| 1218 | N | SER | 163 | 16.958 | 11.160 | 27.464 | 1.00 | 41.13 | A |
| 1219 | CA | SER | 163 | 15.974 | 11.631 | 26.497 | 1.00 | 41.76 | A |
| 1220 | CB | SER | 163 | 14.566 | 11.585 | 27.086 | 1.00 | 41.76 | A |
| 1221 | OG | SER | 163 | 14.176 | 10.256 | 27.345 | 1.00 | 42.44 | A |
| 1222 | C | SER | 163 | 16.298 | 13.067 | 26.097 | 1.00 | 42.06 | A |
| 1223 | O | SER | 163 | 16.758 | 13.863 | 26.917 | 1.00 | 41.82 | A |
| 1224 | N | PHE | 164 | 16.049 | 13.386 | 24.834 | 1.00 | 42.54 | A |
| 1225 | CA | PHE | 164 | 16.306 | 14.720 | 24.304 | 1.00 | 43.18 | A |
| 1226 | CB | PHE | 164 | 17.444 | 14.662 | 23.294 | 1.00 | 43.12 | A |
| 1227 | CG | PHE | 164 | 18.655 | 13.945 | 23.800 | 1.00 | 43.17 | A |
| 1228 | CD1 | PHE | 164 | 19.087 | 12.771 | 23.194 | 1.00 | 43.26 | A |
| 1229 | CD2 | PHE | 164 | 19.362 | 14.436 | 24.896 | 1.00 | 43.19 | A |
| 1230 | CE1 | PHE | 164 | 20.209 | 12.095 | 23.672 | 1.00 | 43.22 | A |
| 1231 | CE2 | PHE | 164 | 20.482 | 13.771 | 25.383 | 1.00 | 43.14 | A |
| 1232 | CZ | PHE | 164 | 20.908 | 12.601 | 24.772 | 1.00 | 43.37 | A |
| 1233 | C | PHE | 164 | 15.049 | 15.255 | 23.639 | 1.00 | 43.78 | A |
| 1234 | O | PHE | 164 | 14.379 | 14.540 | 22.893 | 1.00 | 43.65 | A |
| 1235 | N | SER | 165 | 14.731 | 16.513 | 23.919 | 1.00 | 44.59 | A |
| 1236 | CA | SER | 165 | 13.551 | 17.150 | 23.355 | 1.00 | 45.52 | A |
| 1237 | CB | SER | 165 | 12.523 | 17.403 | 24.458 | 1.00 | 45.60 | A |
| 1238 | OG | SER | 165 | 11.409 | 18.123 | 23.962 | 1.00 | 45.95 | A |
| 1239 | C | SER | 165 | 13.912 | 18.470 | 22.678 | 1.00 | 46.18 | A |
| 1240 | O | SER | 165 | 14.866 | 19.143 | 23.081 | 1.00 | 46.10 | A |
| 1241 | N | PRO | 166 | 13.160 | 18.849 | 21.625 | 1.00 | 46.85 | A |
| 1242 | CD | PRO | 166 | 12.093 | 18.064 | 20.982 | 1.00 | 46.97 | A |
| 1243 | CA | PRO | 166 | 13.396 | 20.098 | 20.890 | 1.00 | 47.32 | A |
| 1244 | CB | PRO | 166 | 12.488 | 19.971 | 19.664 | 1.00 | 47.26 | A |
| 1245 | CG | PRO | 166 | 12.218 | 18.495 | 19.556 | 1.00 | 47.29 | A |
| 1246 | C | PRO | 166 | 12.965 | 21.264 | 21.766 | 1.00 | 47.81 | A |
| 1247 | O | PRO | 166 | 13.396 | 22.400 | 21.573 | 1.00 | 47.92 | A |
| 1248 | N | ASP | 167 | 12.083 | 20.964 | 22.714 | 1.00 | 48.36 | A |
| 1249 | CA | ASP | 167 | 11.566 | 21.955 | 23.643 | 1.00 | 48.95 | A |
| 1250 | CB | ASP | 167 | 10.156 | 22.381 | 23.236 | 1.00 | 49.26 | A |
| 1251 | CG | ASP | 167 | 9.263 | 21.204 | 22.919 | 1.00 | 49.70 | A |

TABLE 1-continued

| Atom | Atom Type | Res | # | X | Y | Z | OCC | B | Mol. |
|---|---|---|---|---|---|---|---|---|---|
| 1252 | OD1 | ASP | 167 | 9.256 | 20.227 | 23.704 | 1.00 | 49.86 | A |
| 1253 | OD2 | ASP | 167 | 8.562 | 21.260 | 21.882 | 1.00 | 49.98 | A |
| 1254 | C | ASP | 167 | 11.549 | 21.378 | 25.052 | 1.00 | 49.23 | A |
| 1255 | O | ASP | 167 | 12.371 | 20.520 | 25.381 | 1.00 | 49.23 | A |
| 1256 | N | THR | 168 | 10.608 | 21.825 | 25.878 | 1.00 | 49.60 | A |
| 1257 | CA | THR | 168 | 10.537 | 21.366 | 27.259 | 1.00 | 50.10 | A |
| 1258 | CB | THR | 168 | 10.070 | 22.504 | 28.192 | 1.00 | 50.15 | A |
| 1259 | OG1 | THR | 168 | 8.771 | 22.947 | 27.781 | 1.00 | 50.34 | A |
| 1260 | CG2 | THR | 168 | 11.047 | 23.678 | 28.142 | 1.00 | 50.15 | A |
| 1261 | C | THR | 168 | 9.632 | 20.159 | 27.496 | 1.00 | 50.41 | A |
| 1262 | O | THR | 168 | 9.537 | 19.672 | 28.621 | 1.00 | 50.48 | A |
| 1263 | N | SER | 169 | 8.970 | 19.673 | 26.452 | 1.00 | 50.70 | A |
| 1264 | CA | SER | 169 | 8.081 | 18.529 | 26.619 | 1.00 | 51.03 | A |
| 1265 | CB | SER | 169 | 7.083 | 18.458 | 25.461 | 1.00 | 51.11 | A |
| 1266 | OG | SER | 169 | 7.740 | 18.288 | 24.216 | 1.00 | 51.50 | A |
| 1267 | C | SER | 169 | 8.888 | 17.234 | 26.707 | 1.00 | 51.10 | A |
| 1268 | O | SER | 169 | 9.896 | 17.081 | 26.013 | 1.00 | 51.14 | A |
| 1269 | N | ILE | 170 | 8.453 | 16.301 | 27.551 | 1.00 | 51.18 | A |
| 1270 | CA | ILE | 170 | 9.126 | 15.021 | 27.726 | 1.00 | 51.37 | A |
| 1271 | CB | ILE | 170 | 8.594 | 14.235 | 28.915 | 1.00 | 51.51 | A |
| 1272 | CG2 | ILE | 170 | 9.475 | 13.025 | 29.174 | 1.00 | 51.59 | A |
| 1273 | CG1 | ILE | 170 | 8.538 | 15.144 | 30.150 | 1.00 | 51.79 | A |
| 1274 | CD1 | ILE | 170 | 7.897 | 14.447 | 31.361 | 1.00 | 52.03 | A |
| 1275 | C | ILE | 170 | 8.967 | 14.132 | 26.527 | 1.00 | 51.28 | A |
| 1276 | O | ILE | 170 | 7.856 | 13.844 | 26.074 | 1.00 | 51.32 | A |
| 1277 | N | PRO | 171 | 10.076 | 13.654 | 25.972 | 1.00 | 51.20 | A |
| 1278 | CD | PRO | 171 | 11.504 | 13.961 | 26.221 | 1.00 | 51.19 | A |
| 1279 | CA | PRO | 171 | 9.868 | 12.800 | 24.800 | 1.00 | 51.10 | A |
| 1280 | CB | PRO | 171 | 11.266 | 12.621 | 24.192 | 1.00 | 51.16 | A |
| 1281 | CG | PRO | 171 | 12.262 | 13.161 | 25.172 | 1.00 | 51.18 | A |
| 1282 | C | PRO | 171 | 9.230 | 11.482 | 25.188 | 1.00 | 51.04 | A |
| 1283 | O | PRO | 171 | 9.411 | 11.000 | 26.316 | 1.00 | 50.87 | A |
| 1284 | N | GLU | 172 | 8.491 | 10.897 | 24.253 | 1.00 | 50.95 | A |
| 1285 | CA | GLU | 172 | 7.807 | 9.624 | 24.481 | 1.00 | 50.86 | A |
| 1286 | CB | GLU | 172 | 6.855 | 9.351 | 23.309 | 1.00 | 51.49 | A |
| 1287 | CG | GLU | 172 | 5.612 | 10.220 | 23.369 | 1.00 | 52.62 | A |
| 1288 | CD | GLU | 172 | 4.708 | 9.847 | 24.542 | 1.00 | 53.33 | A |
| 1289 | OE1 | GLU | 172 | 4.950 | 8.791 | 25.189 | 1.00 | 53.96 | A |
| 1290 | OE2 | GLU | 172 | 3.737 | 10.599 | 24.818 | 1.00 | 53.74 | A |
| 1291 | C | GLU | 172 | 8.801 | 8.469 | 24.653 | 1.00 | 50.31 | A |
| 1292 | O | GLU | 172 | 8.588 | 7.577 | 25.471 | 1.00 | 50.24 | A |
| 1293 | N | LYS | 173 | 9.895 | 8.512 | 23.897 | 1.00 | 49.72 | A |
| 1294 | CA | LYS | 173 | 10.902 | 7.457 | 23.987 | 1.00 | 49.12 | A |
| 1295 | CB | LYS | 173 | 11.030 | 6.736 | 22.644 | 1.00 | 49.50 | A |
| 1296 | CG | LYS | 173 | 9.745 | 6.060 | 22.171 | 1.00 | 50.05 | A |
| 1297 | CD | LYS | 173 | 10.013 | 5.108 | 20.993 | 1.00 | 50.55 | A |
| 1298 | CE | LYS | 173 | 8.762 | 4.310 | 20.583 | 1.00 | 50.91 | A |
| 1299 | NZ | LYS | 173 | 9.021 | 3.315 | 19.486 | 1.00 | 51.32 | A |
| 1300 | C | LYS | 173 | 12.270 | 7.989 | 24.405 | 1.00 | 48.50 | A |
| 1301 | O | LYS | 173 | 12.581 | 9.157 | 24.174 | 1.00 | 48.43 | A |
| 1302 | N | GLU | 174 | 13.092 | 7.130 | 25.003 | 1.00 | 47.59 | A |
| 1303 | CA | GLU | 174 | 14.421 | 7.554 | 25.418 | 1.00 | 46.78 | A |
| 1304 | CB | GLU | 174 | 14.842 | 6.858 | 26.714 | 1.00 | 46.63 | A |
| 1305 | CG | GLU | 174 | 13.877 | 7.093 | 27.860 | 1.00 | 46.41 | A |
| 1306 | CD | GLU | 174 | 14.385 | 6.543 | 29.171 | 1.00 | 46.39 | A |
| 1307 | OE1 | GLU | 174 | 14.706 | 5.330 | 29.226 | 1.00 | 46.38 | A |
| 1308 | OE2 | GLU | 174 | 14.457 | 7.319 | 30.151 | 1.00 | 46.26 | A |
| 1309 | C | GLU | 174 | 15.416 | 7.264 | 24.315 | 1.00 | 46.31 | A |
| 1310 | O | GLU | 174 | 15.264 | 6.300 | 23.565 | 1.00 | 46.29 | A |
| 1311 | N | ALA | 175 | 16.426 | 8.119 | 24.208 | 1.00 | 45.59 | A |
| 1312 | CA | ALA | 175 | 17.449 | 7.971 | 23.185 | 1.00 | 44.97 | A |
| 1313 | CB | ALA | 175 | 18.133 | 9.315 | 22.939 | 1.00 | 44.96 | A |
| 1314 | C | ALA | 175 | 18.488 | 6.912 | 23.553 | 1.00 | 44.55 | A |
| 1315 | O | ALA | 175 | 19.097 | 6.301 | 22.679 | 1.00 | 44.28 | A |
| 1316 | N | ALA | 176 | 18.701 | 6.701 | 24.847 | 1.00 | 44.10 | A |
| 1317 | CA | ALA | 176 | 19.678 | 5.707 | 25.279 | 1.00 | 43.81 | A |
| 1318 | CB | ALA | 176 | 21.095 | 6.236 | 25.069 | 1.00 | 43.77 | A |
| 1319 | C | ALA | 176 | 19.485 | 5.310 | 26.729 | 1.00 | 43.51 | A |
| 1320 | O | ALA | 176 | 18.808 | 6.002 | 27.492 | 1.00 | 43.44 | A |
| 1321 | N | LEU | 177 | 20.077 | 4.177 | 27.093 | 1.00 | 43.22 | A |
| 1322 | CA | LEU | 177 | 20.012 | 3.657 | 28.452 | 1.00 | 42.98 | A |
| 1323 | CB | LEU | 177 | 19.184 | 2.366 | 28.509 | 1.00 | 43.12 | A |
| 1324 | CG | LEU | 177 | 17.671 | 2.444 | 28.282 | 1.00 | 43.23 | A |
| 1325 | CD1 | LEU | 177 | 17.081 | 1.029 | 28.344 | 1.00 | 43.35 | A |
| 1326 | CD2 | LEU | 177 | 17.026 | 3.324 | 29.344 | 1.00 | 43.13 | A |
| 1327 | C | LEU | 177 | 21.428 | 3.354 | 28.897 | 1.00 | 42.67 | A |
| 1328 | O | LEU | 177 | 22.101 | 2.514 | 28.305 | 1.00 | 42.82 | A |

TABLE 1-continued

| Atom | Atom Type | Res | # | X | Y | Z | OCC | B | Mol. |
|---|---|---|---|---|---|---|---|---|---|
| 1329 | N | ILE | 178 | 21.891 | 4.046 | 29.928 | 1.00 | 42.22 | A |
| 1330 | CA | ILE | 178 | 23.233 | 3.810 | 30.430 | 1.00 | 41.67 | A |
| 1331 | CB | ILE | 178 | 23.907 | 5.121 | 30.894 | 1.00 | 41.77 | A |
| 1332 | CG2 | ILE | 178 | 25.384 | 4.874 | 31.188 | 1.00 | 41.56 | A |
| 1333 | CG1 | ILE | 178 | 23.762 | 6.197 | 29.812 | 1.00 | 41.63 | A |
| 1334 | CD1 | ILE | 178 | 24.386 | 5.833 | 28.476 | 1.00 | 41.74 | A |
| 1335 | C | ILE | 178 | 23.042 | 2.879 | 31.614 | 1.00 | 41.43 | A |
| 1336 | O | ILE | 178 | 22.576 | 3.287 | 32.683 | 1.00 | 41.40 | A |
| 1337 | N | GLU | 179 | 23.388 | 1.618 | 31.411 | 1.00 | 40.99 | A |
| 1338 | CA | GLU | 179 | 23.225 | .616 | 32.448 | 1.00 | 40.66 | A |
| 1339 | CB | GLU | 179 | 22.782 | −.695 | 31.801 | 1.00 | 41.14 | A |
| 1340 | CG | GLU | 179 | 21.535 | −.493 | 30.947 | 1.00 | 42.12 | A |
| 1341 | CD | GLU | 179 | 20.907 | −1.784 | 30.475 | 1.00 | 42.79 | A |
| 1342 | OE1 | GLU | 179 | 19.833 | −1.715 | 29.832 | 1.00 | 43.53 | A |
| 1343 | OE2 | GLU | 179 | 21.475 | −2.865 | 30.742 | 1.00 | 43.30 | A |
| 1344 | C | GLU | 179 | 24.496 | .440 | 33.263 | 1.00 | 40.04 | A |
| 1345 | O | GLU | 179 | 25.349 | −.388 | 32.951 | 1.00 | 39.95 | A |
| 1346 | N | ASN | 180 | 24.609 | 1.251 | 34.306 | 1.00 | 39.27 | A |
| 1347 | CA | ASN | 180 | 25.758 | 1.226 | 35.205 | 1.00 | 38.73 | A |
| 1348 | CB | ASN | 180 | 26.945 | 1.954 | 34.566 | 1.00 | 38.45 | A |
| 1349 | CG | ASN | 180 | 28.172 | 1.941 | 35.451 | 1.00 | 38.27 | A |
| 1350 | OD1 | ASN | 180 | 28.282 | 2.728 | 36.390 | 1.00 | 38.08 | A |
| 1351 | ND2 | ASN | 180 | 29.094 | 1.030 | 35.167 | 1.00 | 38.09 | A |
| 1352 | C | ASN | 180 | 25.322 | 1.920 | 36.493 | 1.00 | 38.31 | A |
| 1353 | O | ASN | 180 | 24.881 | 3.071 | 36.467 | 1.00 | 38.24 | A |
| 1354 | N | LYS | 181 | 25.434 | 1.218 | 37.614 | 1.00 | 37.95 | A |
| 1355 | CA | LYS | 181 | 24.994 | 1.760 | 38.900 | 1.00 | 37.61 | A |
| 1356 | CB | LYS | 181 | 25.182 | .718 | 40.012 | 1.00 | 37.74 | A |
| 1357 | CG | LYS | 181 | 24.609 | 1.126 | 41.380 | 1.00 | 37.69 | A |
| 1358 | CD | LYS | 181 | 23.125 | 1.471 | 41.280 | 1.00 | 37.99 | A |
| 1359 | CE | LYS | 181 | 22.459 | 1.584 | 42.654 | 1.00 | 38.20 | A |
| 1360 | NZ | LYS | 181 | 20.974 | 1.744 | 42.544 | 1.00 | 38.41 | A |
| 1361 | C | LYS | 181 | 25.670 | 3.062 | 39.309 | 1.00 | 37.43 | A |
| 1362 | O | LYS | 181 | 24.995 | 4.061 | 39.588 | 1.00 | 37.26 | A |
| 1363 | N | ALA | 182 | 26.998 | 3.053 | 39.341 | 1.00 | 37.18 | A |
| 1364 | CA | ALA | 182 | 27.757 | 4.231 | 39.747 | 1.00 | 37.12 | A |
| 1365 | CB | ALA | 182 | 29.259 | 3.938 | 39.679 | 1.00 | 37.14 | A |
| 1366 | C | ALA | 182 | 27.415 | 5.430 | 38.885 | 1.00 | 36.99 | A |
| 1367 | O | ALA | 182 | 27.093 | 6.504 | 39.394 | 1.00 | 37.05 | A |
| 1368 | N | VAL | 183 | 27.468 | 5.238 | 37.574 | 1.00 | 36.87 | A |
| 1369 | CA | VAL | 183 | 27.173 | 6.319 | 36.653 | 1.00 | 36.72 | A |
| 1370 | CB | VAL | 183 | 27.500 | 5.896 | 35.200 | 1.00 | 36.81 | A |
| 1371 | CG1 | VAL | 183 | 27.086 | 6.986 | 34.212 | 1.00 | 36.71 | A |
| 1372 | CG2 | VAL | 183 | 28.997 | 5.613 | 35.082 | 1.00 | 36.81 | A |
| 1373 | C | VAL | 183 | 25.723 | 6.773 | 36.749 | 1.00 | 36.58 | A |
| 1374 | O | VAL | 183 | 25.438 | 7.970 | 36.636 | 1.00 | 36.33 | A |
| 1375 | N | SER | 184 | 24.808 | 5.836 | 37.001 | 1.00 | 36.47 | A |
| 1376 | CA | SER | 184 | 23.394 | 6.199 | 37.057 | 1.00 | 36.55 | A |
| 1377 | CB | SER | 184 | 22.513 | 4.974 | 37.364 | 1.00 | 36.41 | A |
| 1378 | OG | SER | 184 | 22.561 | 4.611 | 38.731 | 1.00 | 36.53 | A |
| 1379 | C | SER | 184 | 23.087 | 7.326 | 38.036 | 1.00 | 36.59 | A |
| 1380 | O | SER | 184 | 22.214 | 8.149 | 37.767 | 1.00 | 36.57 | A |
| 1381 | N | SER | 185 | 23.794 | 7.382 | 39.163 | 1.00 | 36.79 | A |
| 1382 | CA | SER | 185 | 23.545 | 8.446 | 40.133 | 1.00 | 37.20 | A |
| 1383 | CB | SER | 185 | 23.538 | 7.891 | 41.565 | 1.00 | 37.17 | A |
| 1384 | OG | SER | 185 | 24.832 | 7.467 | 41.965 | 1.00 | 37.40 | A |
| 1385 | C | SER | 185 | 24.549 | 9.603 | 40.047 | 1.00 | 37.45 | A |
| 1386 | O | SER | 185 | 24.365 | 10.633 | 40.696 | 1.00 | 37.51 | A |
| 1387 | N | ALA | 186 | 25.589 | 9.440 | 39.234 | 1.00 | 37.65 | A |
| 1388 | CA | ALA | 186 | 26.622 | 10.469 | 39.097 | 1.00 | 37.89 | A |
| 1389 | CB | ALA | 186 | 27.687 | 10.009 | 38.106 | 1.00 | 37.74 | A |
| 1390 | C | ALA | 186 | 26.083 | 11.833 | 38.681 | 1.00 | 37.97 | A |
| 1391 | O | ALA | 186 | 26.485 | 12.861 | 39.229 | 1.00 | 38.04 | A |
| 1392 | N | VAL | 187 | 25.171 | 11.850 | 37.717 | 1.00 | 38.08 | A |
| 1393 | CA | VAL | 187 | 24.621 | 13.111 | 37.252 | 1.00 | 38.22 | A |
| 1394 | CB | VAL | 187 | 23.591 | 12.892 | 36.118 | 1.00 | 38.21 | A |
| 1395 | CG1 | VAL | 187 | 23.066 | 14.230 | 35.629 | 1.00 | 38.05 | A |
| 1396 | CG2 | VAL | 187 | 24.235 | 12.126 | 34.973 | 1.00 | 37.92 | A |
| 1397 | C | VAL | 187 | 23.965 | 13.884 | 38.385 | 1.00 | 38.42 | A |
| 1398 | O | VAL | 187 | 24.307 | 15.040 | 38.632 | 1.00 | 38.34 | A |
| 1399 | N | LEU | 188 | 23.030 | 13.248 | 39.086 | 1.00 | 38.62 | A |
| 1400 | CA | LEU | 188 | 22.339 | 13.916 | 40.181 | 1.00 | 38.82 | A |
| 1401 | CB | LEU | 188 | 21.223 | 13.024 | 40.739 | 1.00 | 38.68 | A |
| 1402 | CG | LEU | 188 | 20.362 | 13.651 | 41.840 | 1.00 | 38.63 | A |
| 1403 | CD1 | LEU | 188 | 19.699 | 14.929 | 41.332 | 1.00 | 38.43 | A |
| 1404 | CD2 | LEU | 188 | 19.311 | 12.642 | 42.285 | 1.00 | 38.52 | A |
| 1405 | C | LEU | 188 | 23.320 | 14.288 | 41.293 | 1.00 | 39.05 | A |

TABLE 1-continued

| Atom | Atom Type | Res | # | X | Y | Z | OCC | B | Mol. |
|---|---|---|---|---|---|---|---|---|---|
| 1406 | O | LEU | 188 | 23.174 | 15.321 | 41.936 | 1.00 | 39.02 | A |
| 1407 | N | GLU | 189 | 24.316 | 13.439 | 41.512 | 1.00 | 39.35 | A |
| 1408 | CA | GLU | 189 | 25.335 | 13.690 | 42.524 | 1.00 | 39.94 | A |
| 1409 | CB | GLU | 189 | 26.382 | 12.573 | 42.487 | 1.00 | 40.24 | A |
| 1410 | CG | GLU | 189 | 27.439 | 12.639 | 43.569 | 1.00 | 41.00 | A |
| 1411 | CD | GLU | 189 | 26.921 | 12.218 | 44.942 | 1.00 | 41.45 | A |
| 1412 | OE1 | GLU | 189 | 26.265 | 11.155 | 45.041 | 1.00 | 41.52 | A |
| 1413 | OE2 | GLU | 189 | 27.185 | 12.943 | 45.927 | 1.00 | 41.70 | A |
| 1414 | C | GLU | 189 | 26.021 | 15.041 | 42.271 | 1.00 | 40.13 | A |
| 1415 | O | GLU | 189 | 26.260 | 15.808 | 43.204 | 1.00 | 39.98 | A |
| 1416 | N | THR | 190 | 26.320 | 15.335 | 41.006 | 1.00 | 40.31 | A |
| 1417 | CA | THR | 190 | 26.992 | 16.582 | 40.661 | 1.00 | 40.75 | A |
| 1418 | CB | THR | 190 | 27.578 | 16.539 | 39.233 | 1.00 | 40.62 | A |
| 1419 | OG1 | THR | 190 | 26.515 | 16.440 | 38.276 | 1.00 | 40.54 | A |
| 1420 | CG2 | THR | 190 | 28.510 | 15.345 | 39.077 | 1.00 | 40.51 | A |
| 1421 | C | THR | 190 | 26.053 | 17.775 | 40.761 | 1.00 | 41.14 | A |
| 1422 | O | THR | 190 | 26.474 | 18.917 | 40.617 | 1.00 | 41.18 | A |
| 1423 | N | MET | 191 | 24.780 | 17.511 | 41.016 | 1.00 | 41.50 | A |
| 1424 | CA | MET | 191 | 23.812 | 18.591 | 41.125 | 1.00 | 42.08 | A |
| 1425 | CB | MET | 191 | 22.542 | 18.231 | 40.356 | 1.00 | 42.19 | A |
| 1426 | CG | MET | 191 | 22.790 | 17.885 | 38.900 | 1.00 | 42.52 | A |
| 1427 | SD | MET | 191 | 21.284 | 17.304 | 38.120 | 1.00 | 42.98 | A |
| 1428 | CE | MET | 191 | 21.674 | 17.510 | 36.378 | 1.00 | 43.11 | A |
| 1429 | C | MET | 191 | 23.460 | 18.926 | 42.573 | 1.00 | 42.40 | A |
| 1430 | O | MET | 191 | 23.313 | 20.099 | 42.920 | 1.00 | 42.43 | A |
| 1431 | N | ILE | 192 | 23.330 | 17.905 | 43.415 | 1.00 | 42.74 | A |
| 1432 | CA | ILE | 192 | 22.972 | 18.124 | 44.815 | 1.00 | 43.28 | A |
| 1433 | CB | ILE | 192 | 21.499 | 17.754 | 45.064 | 1.00 | 43.18 | A |
| 1434 | CG2 | ILE | 192 | 20.596 | 18.639 | 44.219 | 1.00 | 43.15 | A |
| 1435 | CG1 | ILE | 192 | 21.269 | 16.276 | 44.731 | 1.00 | 43.06 | A |
| 1436 | CD1 | ILE | 192 | 19.848 | 15.798 | 45.004 | 1.00 | 42.93 | A |
| 1437 | C | ILE | 192 | 23.831 | 17.349 | 45.809 | 1.00 | 43.79 | A |
| 1438 | O | ILE | 192 | 23.538 | 17.324 | 47.004 | 1.00 | 43.59 | A |
| 1439 | N | GLY | 193 | 24.882 | 16.710 | 45.310 | 1.00 | 44.53 | A |
| 1440 | CA | GLY | 193 | 25.765 | 15.951 | 46.173 | 1.00 | 45.57 | A |
| 1441 | C | GLY | 193 | 26.611 | 16.876 | 47.032 | 1.00 | 46.48 | A |
| 1442 | O | GLY | 193 | 26.524 | 18.104 | 46.910 | 1.00 | 46.38 | A |
| 1443 | N | GLU | 194 | 27.437 | 16.290 | 47.893 | 1.00 | 47.30 | A |
| 1444 | CA | GLU | 194 | 28.286 | 17.064 | 48.795 | 1.00 | 48.24 | A |
| 1445 | CB | GLU | 194 | 29.124 | 16.130 | 49.672 | 1.00 | 48.33 | A |
| 1446 | CG | GLU | 194 | 30.122 | 16.877 | 50.545 | 1.00 | 48.74 | A |
| 1447 | CD | GLU | 194 | 31.022 | 15.953 | 51.341 | 1.00 | 49.05 | A |
| 1448 | OE1 | GLU | 194 | 31.022 | 14.731 | 51.068 | 1.00 | 49.21 | A |
| 1449 | OE2 | GLU | 194 | 31.739 | 16.452 | 52.235 | 1.00 | 49.15 | A |
| 1450 | C | GLU | 194 | 29.221 | 18.018 | 48.064 | 1.00 | 48.72 | A |
| 1451 | O | GLU | 194 | 29.404 | 19.168 | 48.487 | 1.00 | 48.83 | A |
| 1452 | N | HIS | 195 | 29.820 | 17.542 | 46.976 | 1.00 | 49.39 | A |
| 1453 | CA | HIS | 195 | 30.745 | 18.365 | 46.214 | 1.00 | 50.10 | A |
| 1454 | CB | HIS | 195 | 31.890 | 17.516 | 45.694 | 1.00 | 50.52 | A |
| 1455 | CG | HIS | 195 | 32.670 | 16.884 | 46.798 | 1.00 | 50.96 | A |
| 1456 | CD2 | HIS | 195 | 33.358 | 17.433 | 47.828 | 1.00 | 51.16 | A |
| 1457 | ND1 | HIS | 195 | 32.695 | 15.523 | 46.999 | 1.00 | 51.15 | A |
| 1458 | CE1 | HIS | 195 | 33.367 | 15.256 | 48.107 | 1.00 | 51.27 | A |
| 1459 | NE2 | HIS | 195 | 33.781 | 16.398 | 48.628 | 1.00 | 51.39 | A |
| 1460 | C | HIS | 195 | 30.137 | 19.185 | 45.105 | 1.00 | 50.36 | A |
| 1461 | O | HIS | 195 | 30.821 | 19.604 | 44.172 | 1.00 | 50.51 | A |
| 1462 | N | ALA | 196 | 28.834 | 19.412 | 45.213 | 1.00 | 50.55 | A |
| 1463 | CA | ALA | 196 | 28.152 | 20.260 | 44.251 | 1.00 | 50.75 | A |
| 1464 | CB | ALA | 196 | 26.732 | 19.779 | 43.998 | 1.00 | 50.64 | A |
| 1465 | C | ALA | 196 | 28.135 | 21.636 | 44.926 | 1.00 | 50.88 | A |
| 1466 | O | ALA | 196 | 27.440 | 21.850 | 45.924 | 1.00 | 50.94 | A |
| 1467 | N | VAL | 197 | 28.899 | 22.570 | 44.377 | 1.00 | 51.05 | A |
| 1468 | CA | VAL | 197 | 28.957 | 23.906 | 44.954 | 1.00 | 51.23 | A |
| 1469 | CB | VAL | 197 | 30.044 | 24.754 | 44.263 | 1.00 | 51.40 | A |
| 1470 | CG1 | VAL | 197 | 30.208 | 26.092 | 44.990 | 1.00 | 51.42 | A |
| 1471 | CG2 | VAL | 197 | 31.362 | 23.995 | 44.264 | 1.00 | 51.45 | A |
| 1472 | C | VAL | 197 | 27.626 | 24.658 | 44.920 | 1.00 | 51.21 | A |
| 1473 | O | VAL | 197 | 27.168 | 25.152 | 45.958 | 1.00 | 51.19 | A |
| 1474 | N | SER | 198 | 27.012 | 24.751 | 43.741 | 1.00 | 51.08 | A |
| 1475 | CA | SER | 198 | 25.734 | 25.444 | 43.597 | 1.00 | 51.00 | A |
| 1476 | CB | SER | 198 | 25.172 | 25.243 | 42.190 | 1.00 | 51.05 | A |
| 1477 | OG | SER | 198 | 26.092 | 25.680 | 41.209 | 1.00 | 51.19 | A |
| 1478 | C | SER | 198 | 24.737 | 24.911 | 44.615 | 1.00 | 50.92 | A |
| 1479 | O | SER | 198 | 24.475 | 23.715 | 44.673 | 1.00 | 50.96 | A |
| 1480 | N | PRO | 199 | 24.162 | 25.802 | 45.433 | 1.00 | 50.81 | A |
| 1481 | CD | PRO | 199 | 24.663 | 27.150 | 45.771 | 1.00 | 50.78 | A |
| 1482 | CA | PRO | 199 | 23.199 | 25.347 | 46.436 | 1.00 | 50.69 | A |

TABLE 1-continued

| Atom | Atom Type | Res | # | X | Y | Z | OCC | B | Mol. |
|---|---|---|---|---|---|---|---|---|---|
| 1483 | CB | PRO | 199 | 23.581 | 26.178 | 47.649 | 1.00 | 50.77 | A |
| 1484 | CG | PRO | 199 | 23.840 | 27.514 | 47.010 | 1.00 | 50.73 | A |
| 1485 | C | PRO | 199 | 21.729 | 25.538 | 46.083 | 1.00 | 50.57 | A |
| 1486 | O | PRO | 199 | 20.871 | 25.108 | 46.845 | 1.00 | 50.55 | A |
| 1487 | N | ASP | 200 | 21.427 | 26.163 | 44.945 | 1.00 | 50.43 | A |
| 1488 | CA | ASP | 200 | 20.029 | 26.416 | 44.601 | 1.00 | 50.41 | A |
| 1489 | CB | ASP | 200 | 19.900 | 27.138 | 43.241 | 1.00 | 50.39 | A |
| 1490 | CG | ASP | 200 | 20.503 | 26.363 | 42.078 | 1.00 | 50.36 | A |
| 1491 | OD1 | ASP | 200 | 21.013 | 25.231 | 42.272 | 1.00 | 50.44 | A |
| 1492 | OD2 | ASP | 200 | 20.469 | 26.895 | 40.945 | 1.00 | 50.25 | A |
| 1493 | C | ASP | 200 | 19.117 | 25.193 | 44.653 | 1.00 | 50.34 | A |
| 1494 | O | ASP | 200 | 18.030 | 25.260 | 45.232 | 1.00 | 50.33 | A |
| 1495 | N | LEU | 201 | 19.550 | 24.081 | 44.073 | 1.00 | 50.31 | A |
| 1496 | CA | LEU | 201 | 18.737 | 22.870 | 44.083 | 1.00 | 50.30 | A |
| 1497 | CB | LEU | 201 | 19.338 | 21.825 | 43.140 | 1.00 | 50.26 | A |
| 1498 | CG | LEU | 201 | 18.675 | 21.571 | 41.782 | 1.00 | 50.37 | A |
| 1499 | CD1 | LEU | 201 | 18.002 | 22.802 | 41.250 | 1.00 | 50.33 | A |
| 1500 | CD2 | LEU | 201 | 19.740 | 21.082 | 40.827 | 1.00 | 50.15 | A |
| 1501 | C | LEU | 201 | 18.649 | 22.320 | 45.505 | 1.00 | 50.30 | A |
| 1502 | O | LEU | 201 | 17.581 | 21.896 | 45.947 | 1.00 | 50.16 | A |
| 1503 | N | LYS | 202 | 19.764 | 22.339 | 46.226 | 1.00 | 50.41 | A |
| 1504 | CA | LYS | 202 | 19.757 | 21.839 | 47.594 | 1.00 | 50.68 | A |
| 1505 | CB | LYS | 202 | 21.153 | 21.899 | 48.212 | 1.00 | 50.62 | A |
| 1506 | CG | LYS | 202 | 22.165 | 20.990 | 47.549 | 1.00 | 50.62 | A |
| 1507 | CD | LYS | 202 | 23.545 | 21.212 | 48.135 | 1.00 | 50.63 | A |
| 1508 | CE | LYS | 202 | 24.597 | 20.387 | 47.416 | 1.00 | 50.71 | A |
| 1509 | NZ | LYS | 202 | 25.982 | 20.706 | 47.872 | 1.00 | 50.72 | A |
| 1510 | C | LYS | 202 | 18.795 | 22.657 | 48.442 | 1.00 | 50.90 | A |
| 1511 | O | LYS | 202 | 18.030 | 22.102 | 49.227 | 1.00 | 50.78 | A |
| 1512 | N | ARG | 203 | 18.825 | 23.973 | 48.273 | 1.00 | 51.26 | A |
| 1513 | CA | ARG | 203 | 17.953 | 24.848 | 49.042 | 1.00 | 51.71 | A |
| 1514 | CB | ARG | 203 | 18.305 | 26.315 | 48.792 | 1.00 | 52.21 | A |
| 1515 | CG | ARG | 203 | 19.695 | 26.687 | 49.302 | 1.00 | 53.05 | A |
| 1516 | CD | ARG | 203 | 20.058 | 28.139 | 49.001 | 1.00 | 53.78 | A |
| 1517 | NE | ARG | 203 | 21.449 | 28.417 | 49.352 | 1.00 | 54.50 | A |
| 1518 | CZ | ARG | 203 | 22.082 | 29.556 | 49.091 | 1.00 | 54.85 | A |
| 1519 | NH1 | ARG | 203 | 21.457 | 30.554 | 48.470 | 1.00 | 55.02 | A |
| 1520 | NH2 | ARG | 203 | 23.356 | 29.690 | 49.444 | 1.00 | 55.05 | A |
| 1521 | C | ARG | 203 | 16.483 | 24.595 | 48.738 | 1.00 | 51.75 | A |
| 1522 | O | ARG | 203 | 15.657 | 24.598 | 49.647 | 1.00 | 51.66 | A |
| 1523 | N | CYS | 204 | 16.149 | 24.379 | 47.469 | 1.00 | 51.79 | A |
| 1524 | CA | CYS | 204 | 14.761 | 24.105 | 47.112 | 1.00 | 51.94 | A |
| 1525 | CB | CYS | 204 | 14.626 | 23.899 | 45.607 | 1.00 | 52.01 | A |
| 1526 | SG | CYS | 204 | 14.550 | 25.400 | 44.646 | 1.00 | 52.24 | A |
| 1527 | C | CYS | 204 | 14.276 | 22.847 | 47.820 | 1.00 | 52.00 | A |
| 1528 | O | CYS | 204 | 13.200 | 22.833 | 48.413 | 1.00 | 51.91 | A |
| 1529 | N | LEU | 205 | 15.087 | 21.794 | 47.739 | 1.00 | 52.10 | A |
| 1530 | CA | LEU | 205 | 14.769 | 20.507 | 48.347 | 1.00 | 52.26 | A |
| 1531 | CB | LEU | 205 | 15.884 | 19.495 | 48.065 | 1.00 | 51.94 | A |
| 1532 | CG | LEU | 205 | 15.926 | 18.961 | 46.632 | 1.00 | 51.67 | A |
| 1533 | CD1 | LEU | 205 | 17.242 | 18.276 | 46.391 | 1.00 | 51.47 | A |
| 1534 | CD2 | LEU | 205 | 14.782 | 18.004 | 46.408 | 1.00 | 51.46 | A |
| 1535 | C | LEU | 205 | 14.549 | 20.632 | 49.848 | 1.00 | 52.57 | A |
| 1536 | O | LEU | 205 | 13.590 | 20.082 | 50.387 | 1.00 | 52.54 | A |
| 1537 | N | ALA | 206 | 15.429 | 21.367 | 50.516 | 1.00 | 52.95 | A |
| 1538 | CA | ALA | 206 | 15.311 | 21.549 | 51.956 | 1.00 | 53.42 | A |
| 1539 | CB | ALA | 206 | 16.546 | 22.241 | 52.501 | 1.00 | 53.35 | A |
| 1540 | C | ALA | 206 | 14.064 | 22.357 | 52.294 | 1.00 | 53.82 | A |
| 1541 | O | ALA | 206 | 13.402 | 22.091 | 53.295 | 1.00 | 53.77 | A |
| 1542 | N | ALA | 207 | 13.732 | 23.322 | 51.444 | 1.00 | 54.28 | A |
| 1543 | CA | ALA | 207 | 12.568 | 24.165 | 51.679 | 1.00 | 54.86 | A |
| 1544 | CB | ALA | 207 | 12.703 | 25.463 | 50.894 | 1.00 | 54.81 | A |
| 1545 | C | ALA | 207 | 11.254 | 23.482 | 51.330 | 1.00 | 55.29 | A |
| 1546 | O | ALA | 207 | 10.261 | 23.645 | 52.032 | 1.00 | 55.37 | A |
| 1547 | N | ARG | 208 | 11.257 | 22.692 | 50.266 | 1.00 | 55.79 | A |
| 1548 | CA | ARG | 208 | 10.044 | 22.023 | 49.813 | 1.00 | 56.35 | A |
| 1549 | CB | ARG | 208 | 10.118 | 21.775 | 48.308 | 1.00 | 56.32 | A |
| 1550 | CG | ARG | 208 | 10.421 | 23.006 | 47.500 | 1.00 | 56.51 | A |
| 1551 | CD | ARG | 208 | 10.328 | 22.726 | 46.018 | 1.00 | 56.57 | A |
| 1552 | NE | ARG | 208 | 9.498 | 23.740 | 45.392 | 1.00 | 56.83 | A |
| 1553 | CZ | ARG | 208 | 8.566 | 23.498 | 44.487 | 1.00 | 56.83 | A |
| 1554 | NH1 | ARG | 208 | 8.326 | 22.264 | 44.071 | 1.00 | 56.75 | A |
| 1555 | NH2 | ARG | 208 | 7.844 | 24.509 | 44.029 | 1.00 | 57.04 | A |
| 1556 | C | ARG | 208 | 9.652 | 20.711 | 50.475 | 1.00 | 56.77 | A |
| 1557 | O | ARG | 208 | 8.472 | 20.463 | 50.682 | 1.00 | 56.73 | A |
| 1558 | N | LEU | 209 | 10.628 | 19.868 | 50.789 | 1.00 | 57.33 | A |
| 1559 | CA | LEU | 209 | 10.340 | 18.561 | 51.371 | 1.00 | 57.96 | A |

TABLE 1-continued

| Atom | Atom Type | Res | # | X | Y | Z | OCC | B | Mol. |
|---|---|---|---|---|---|---|---|---|---|
| 1560 | CB | LEU | 209 | 11.627 | 17.731 | 51.446 | 1.00 | 57.90 | A |
| 1561 | CG | LEU | 209 | 11.988 | 16.846 | 50.241 | 1.00 | 57.92 | A |
| 1562 | CD1 | LEU | 209 | 10.950 | 15.745 | 50.075 | 1.00 | 57.91 | A |
| 1563 | CD2 | LEU | 209 | 12.082 | 17.681 | 48.988 | 1.00 | 57.85 | A |
| 1564 | C | LEU | 209 | 9.626 | 18.478 | 52.720 | 1.00 | 58.48 | A |
| 1565 | O | LEU | 209 | 8.736 | 17.651 | 52.891 | 1.00 | 58.48 | A |
| 1566 | N | PRO | 210 | 10.006 | 19.321 | 53.693 | 1.00 | 59.04 | A |
| 1567 | CD | PRO | 210 | 11.051 | 20.359 | 53.644 | 1.00 | 59.19 | A |
| 1568 | CA | PRO | 210 | 9.373 | 19.289 | 55.017 | 1.00 | 59.61 | A |
| 1569 | CB | PRO | 210 | 9.895 | 20.561 | 55.671 | 1.00 | 59.46 | A |
| 1570 | CG | PRO | 210 | 11.277 | 20.653 | 55.115 | 1.00 | 59.29 | A |
| 1571 | C | PRO | 210 | 7.848 | 19.211 | 55.011 | 1.00 | 60.18 | A |
| 1572 | O | PRO | 210 | 7.261 | 18.404 | 55.731 | 1.00 | 60.18 | A |
| 1573 | N | ALA | 211 | 7.208 | 20.043 | 54.197 | 1.00 | 60.93 | A |
| 1574 | CA | ALA | 211 | 5.752 | 20.055 | 54.118 | 1.00 | 61.74 | A |
| 1575 | CB | ALA | 211 | 5.293 | 21.111 | 53.126 | 1.00 | 61.76 | A |
| 1576 | C | ALA | 211 | 5.216 | 18.690 | 53.707 | 1.00 | 62.31 | A |
| 1577 | O | ALA | 211 | 4.278 | 18.174 | 54.318 | 1.00 | 62.36 | A |
| 1578 | N | LEU | 212 | 5.815 | 18.112 | 52.670 | 1.00 | 63.00 | A |
| 1579 | CA | LEU | 212 | 5.400 | 16.805 | 52.169 | 1.00 | 63.72 | A |
| 1580 | CB | LEU | 212 | 6.117 | 16.493 | 50.854 | 1.00 | 63.70 | A |
| 1581 | CG | LEU | 212 | 5.865 | 17.446 | 49.687 | 1.00 | 63.70 | A |
| 1582 | CD1 | LEU | 212 | 6.695 | 17.016 | 48.492 | 1.00 | 63.67 | A |
| 1583 | CD2 | LEU | 212 | 4.386 | 17.446 | 49.338 | 1.00 | 63.66 | A |
| 1584 | C | LEU | 212 | 5.680 | 15.694 | 53.175 | 1.00 | 64.26 | A |
| 1585 | O | LEU | 212 | 4.844 | 14.819 | 53.400 | 1.00 | 64.29 | A |
| 1586 | N | LEU | 213 | 6.860 | 15.734 | 53.781 | 1.00 | 64.95 | A |
| 1587 | CA | LEU | 213 | 7.242 | 14.724 | 54.756 | 1.00 | 65.72 | A |
| 1588 | CB | LEU | 213 | 8.704 | 14.917 | 55.171 | 1.00 | 65.66 | A |
| 1589 | CG | LEU | 213 | 9.750 | 14.821 | 54.056 | 1.00 | 65.62 | A |
| 1590 | CD1 | LEU | 213 | 11.138 | 14.973 | 54.653 | 1.00 | 65.58 | A |
| 1591 | CD2 | LEU | 213 | 9.620 | 13.486 | 53.337 | 1.00 | 65.62 | A |
| 1592 | C | LEU | 213 | 6.348 | 14.750 | 55.991 | 1.00 | 66.31 | A |
| 1593 | O | LEU | 213 | 6.182 | 13.732 | 56.661 | 1.00 | 66.41 | A |
| 1594 | N | ASN | 214 | 5.767 | 15.908 | 56.290 | 1.00 | 67.00 | A |
| 1595 | CA | ASN | 214 | 4.900 | 16.033 | 57.457 | 1.00 | 67.73 | A |
| 1596 | CB | ASN | 214 | 4.786 | 17.497 | 57.883 | 1.00 | 67.80 | A |
| 1597 | CG | ASN | 214 | 5.957 | 17.939 | 58.733 | 1.00 | 68.01 | A |
| 1598 | OD1 | ASN | 214 | 6.342 | 17.245 | 59.676 | 1.00 | 68.12 | A |
| 1599 | ND2 | ASN | 214 | 6.526 | 19.099 | 58.415 | 1.00 | 68.17 | A |
| 1600 | C | ASN | 214 | 3.508 | 15.439 | 57.273 | 1.00 | 68.14 | A |
| 1601 | O | ASN | 214 | 2.852 | 15.078 | 58.249 | 1.00 | 68.29 | A |
| 1602 | N | GLU | 215 | 3.055 | 15.336 | 56.029 | 1.00 | 68.60 | A |
| 1603 | CA | GLU | 215 | 1.743 | 14.765 | 55.751 | 1.00 | 69.03 | A |
| 1604 | CB | GLU | 215 | .833 | 15.809 | 55.097 | 1.00 | 69.33 | A |
| 1605 | CG | GLU | 215 | 1.427 | 16.486 | 53.877 | 1.00 | 69.76 | A |
| 1606 | CD | GLU | 215 | .434 | 17.403 | 53.188 | 1.00 | 70.11 | A |
| 1607 | OE1 | GLU | 215 | −.103 | 18.312 | 53.865 | 1.00 | 70.24 | A |
| 1608 | OE2 | GLU | 215 | .193 | 17.212 | 51.972 | 1.00 | 70.24 | A |
| 1609 | C | GLU | 215 | 1.853 | 13.531 | 54.856 | 1.00 | 69.16 | A |
| 1610 | OT1 | GLU | 215 | 1.410 | 13.597 | 53.686 | 1.00 | 69.27 | A |
| 1611 | OT2 | GLU | 215 | 2.391 | 12.510 | 55.340 | 1.00 | 69.25 | A |
| 1612 | CB | SER | 4 | 13.836 | −22.661 | 42.351 | 1.00 | 61.80 | B |
| 1613 | OG | SER | 4 | 13.171 | −21.446 | 42.663 | 1.00 | 61.99 | B |
| 1614 | C | SER | 4 | 15.637 | −22.063 | 43.963 | 1.00 | 61.58 | B |
| 1615 | O | SER | 4 | 14.784 | −22.189 | 44.844 | 1.00 | 61.68 | B |
| 1616 | N | SER | 4 | 16.030 | −23.817 | 42.279 | 1.00 | 61.77 | B |
| 1617 | CA | SER | 4 | 15.348 | −22.517 | 42.541 | 1.00 | 61.72 | B |
| 1618 | N | ILE | 5 | 16.847 | −21.548 | 44.176 | 1.00 | 61.27 | B |
| 1619 | CA | ILE | 5 | 17.287 | −21.062 | 45.481 | 1.00 | 60.86 | B |
| 1620 | CB | ILE | 5 | 16.681 | −19.642 | 45.772 | 1.00 | 60.98 | B |
| 1621 | CG2 | ILE | 5 | 15.161 | −19.701 | 45.822 | 1.00 | 61.01 | B |
| 1622 | CG1 | ILE | 5 | 17.242 | −19.080 | 47.078 | 1.00 | 60.98 | B |
| 1623 | CD1 | ILE | 5 | 16.423 | −19.415 | 48.290 | 1.00 | 61.06 | B |
| 1624 | C | ILE | 5 | 16.992 | −22.049 | 46.619 | 1.00 | 60.46 | B |
| 1625 | O | ILE | 5 | 15.847 | −22.254 | 47.032 | 1.00 | 60.42 | B |
| 1626 | N | THR | 6 | 18.060 | −22.663 | 47.116 | 1.00 | 59.93 | B |
| 1627 | CA | THR | 6 | 17.977 | −23.649 | 48.182 | 1.00 | 59.38 | B |
| 1628 | CB | THR | 6 | 18.791 | −24.895 | 47.824 | 1.00 | 59.37 | B |
| 1629 | OG1 | THR | 6 | 20.152 | −24.511 | 47.588 | 1.00 | 59.31 | B |
| 1630 | CG2 | THR | 6 | 18.235 | −25.557 | 46.581 | 1.00 | 59.31 | B |
| 1631 | C | THR | 6 | 18.530 | −23.116 | 49.497 | 1.00 | 58.99 | B |
| 1632 | O | THR | 6 | 19.154 | −22.057 | 49.540 | 1.00 | 58.84 | B |
| 1633 | N | ALA | 7 | 18.301 | −23.867 | 50.569 | 1.00 | 58.52 | B |
| 1634 | CA | ALA | 7 | 18.805 | −23.488 | 51.874 | 1.00 | 58.11 | B |
| 1635 | CB | ALA | 7 | 18.091 | −24.278 | 52.966 | 1.00 | 58.10 | B |
| 1636 | C | ALA | 7 | 20.291 | −23.824 | 51.861 | 1.00 | 57.82 | B |

TABLE 1-continued

| Atom | Atom Type | Res | # | X | Y | Z | OCC | B | Mol. |
|---|---|---|---|---|---|---|---|---|---|
| 1637 | O | ALA | 7 | 20.740 | −24.647 | 51.063 | 1.00 | 57.74 | B |
| 1638 | N | ILE | 8 | 21.055 | −23.172 | 52.726 | 1.00 | 57.49 | B |
| 1639 | CA | ILE | 8 | 22.484 | −23.426 | 52.807 | 1.00 | 57.18 | B |
| 1640 | CB | ILE | 8 | 23.315 | −22.263 | 52.234 | 1.00 | 57.11 | B |
| 1641 | CG2 | ILE | 8 | 24.796 | −22.544 | 52.429 | 1.00 | 57.06 | B |
| 1642 | CG1 | ILE | 8 | 23.003 | −22.070 | 50.750 | 1.00 | 57.03 | B |
| 1643 | CD1 | ILE | 8 | 23.673 | −20.848 | 50.148 | 1.00 | 57.04 | B |
| 1644 | C | ILE | 8 | 22.861 | −23.583 | 54.263 | 1.00 | 57.06 | B |
| 1645 | O | ILE | 8 | 22.430 | −22.803 | 55.113 | 1.00 | 56.94 | B |
| 1646 | N | THR | 9 | 23.667 | −24.594 | 54.549 | 1.00 | 56.98 | B |
| 1647 | CA | THR | 9 | 24.107 | −24.828 | 55.912 | 1.00 | 56.95 | B |
| 1648 | CB | THR | 9 | 23.763 | −26.256 | 56.374 | 1.00 | 56.98 | B |
| 1649 | OG1 | THR | 9 | 22.338 | −26.427 | 56.349 | 1.00 | 57.05 | B |
| 1650 | CG2 | THR | 9 | 24.273 | −26.498 | 57.799 | 1.00 | 56.95 | B |
| 1651 | C | THR | 9 | 25.606 | −24.611 | 55.993 | 1.00 | 56.90 | B |
| 1652 | O | THR | 9 | 26.365 | −25.122 | 55.172 | 1.00 | 56.86 | B |
| 1653 | N | VAL | 10 | 26.021 | −23.823 | 56.974 | 1.00 | 56.82 | B |
| 1654 | CA | VAL | 10 | 27.431 | −23.534 | 57.178 | 1.00 | 56.83 | B |
| 1655 | CB | VAL | 10 | 27.713 | −22.017 | 57.053 | 1.00 | 56.70 | B |
| 1656 | CG1 | VAL | 10 | 29.183 | −21.726 | 57.328 | 1.00 | 56.57 | B |
| 1657 | CG2 | VAL | 10 | 27.325 | −21.535 | 55.669 | 1.00 | 56.63 | B |
| 1658 | C | VAL | 10 | 27.784 | −24.000 | 58.582 | 1.00 | 56.92 | B |
| 1659 | O | VAL | 10 | 27.317 | −23.428 | 59.565 | 1.00 | 56.96 | B |
| 1660 | N | GLU | 11 | 28.588 | −25.053 | 58.675 | 1.00 | 57.03 | B |
| 1661 | CA | GLU | 11 | 28.989 | −25.578 | 59.978 | 1.00 | 57.08 | B |
| 1662 | CB | GLU | 11 | 29.940 | −24.596 | 60.663 | 1.00 | 57.41 | B |
| 1663 | CG | GLU | 11 | 31.291 | −24.455 | 59.983 | 1.00 | 57.98 | B |
| 1664 | CD | GLU | 11 | 32.137 | −25.704 | 60.119 | 1.00 | 58.33 | B |
| 1665 | OE1 | GLU | 11 | 32.355 | −26.142 | 61.269 | 1.00 | 58.58 | B |
| 1666 | OE2 | GLU | 11 | 32.585 | −26.246 | 59.084 | 1.00 | 58.64 | B |
| 1667 | C | GLU | 11 | 27.785 | −25.833 | 60.879 | 1.00 | 56.87 | B |
| 1668 | O | GLU | 11 | 27.719 | −25.335 | 62.005 | 1.00 | 56.92 | B |
| 1669 | N | ASN | 12 | 26.829 | −26.603 | 60.374 | 1.00 | 56.59 | B |
| 1670 | CA | ASN | 12 | 25.631 | −26.936 | 61.135 | 1.00 | 56.21 | B |
| 1671 | CB | ASN | 12 | 26.020 | −27.661 | 62.428 | 1.00 | 56.68 | B |
| 1672 | CG | ASN | 12 | 26.858 | −28.903 | 62.165 | 1.00 | 57.06 | B |
| 1673 | OD1 | ASN | 12 | 26.479 | −29.765 | 61.364 | 1.00 | 57.33 | B |
| 1674 | ND2 | ASN | 12 | 28.003 | −29.000 | 62.834 | 1.00 | 57.28 | B |
| 1675 | C | ASN | 12 | 24.733 | −25.738 | 61.449 | 1.00 | 55.73 | B |
| 1676 | O | ASN | 12 | 23.795 | −25.854 | 62.234 | 1.00 | 55.69 | B |
| 1677 | N | LEU | 13 | 25.027 | −24.592 | 60.840 | 1.00 | 55.07 | B |
| 1678 | CA | LEU | 13 | 24.212 | −23.398 | 61.026 | 1.00 | 54.34 | B |
| 1679 | CB | LEU | 13 | 25.093 | −22.165 | 61.255 | 1.00 | 54.30 | B |
| 1680 | CG | LEU | 13 | 25.882 | −22.163 | 62.568 | 1.00 | 54.24 | B |
| 1681 | CD1 | LEU | 13 | 26.883 | −21.027 | 62.565 | 1.00 | 54.22 | B |
| 1682 | CD2 | LEU | 13 | 24.925 | −22.033 | 63.745 | 1.00 | 54.27 | B |
| 1683 | C | LEU | 13 | 23.398 | −23.256 | 59.744 | 1.00 | 53.90 | B |
| 1684 | O | LEU | 13 | 23.912 | −22.871 | 58.694 | 1.00 | 53.87 | B |
| 1685 | N | GLU | 14 | 22.122 | −23.589 | 59.839 | 1.00 | 53.26 | B |
| 1686 | CA | GLU | 14 | 21.244 | −23.546 | 58.683 | 1.00 | 52.74 | B |
| 1687 | CB | GLU | 14 | 20.074 | −24.504 | 58.910 | 1.00 | 53.34 | B |
| 1688 | CG | GLU | 14 | 18.709 | −23.907 | 58.609 | 1.00 | 54.36 | B |
| 1689 | CD | GLU | 14 | 17.572 | −24.812 | 59.041 | 1.00 | 54.97 | B |
| 1690 | OE1 | GLU | 14 | 17.799 | −26.045 | 59.135 | 1.00 | 55.41 | B |
| 1691 | OE2 | GLU | 14 | 16.455 | −24.288 | 59.276 | 1.00 | 55.26 | B |
| 1692 | C | GLU | 14 | 20.707 | −22.166 | 58.320 | 1.00 | 51.88 | B |
| 1693 | O | GLU | 14 | 20.326 | −21.376 | 59.188 | 1.00 | 51.76 | B |
| 1694 | N | TYR | 15 | 20.672 | −21.900 | 57.016 | 1.00 | 50.85 | B |
| 1695 | CA | TYR | 15 | 20.145 | −20.658 | 56.469 | 1.00 | 49.85 | B |
| 1696 | CB | TYR | 15 | 21.212 | −19.904 | 55.672 | 1.00 | 49.70 | B |
| 1697 | CG | TYR | 15 | 22.216 | −19.181 | 56.531 | 1.00 | 49.56 | B |
| 1698 | CD1 | TYR | 15 | 23.274 | −19.862 | 57.130 | 1.00 | 49.49 | B |
| 1699 | CE1 | TYR | 15 | 24.177 | −19.197 | 57.954 | 1.00 | 49.40 | B |
| 1700 | CD2 | TYR | 15 | 22.086 | −17.814 | 56.776 | 1.00 | 49.56 | B |
| 1701 | CE2 | TYR | 15 | 22.976 | −17.144 | 57.594 | 1.00 | 49.37 | B |
| 1702 | CZ | TYR | 15 | 24.020 | −17.836 | 58.180 | 1.00 | 49.43 | B |
| 1703 | OH | TYR | 15 | 24.898 | −17.155 | 58.991 | 1.00 | 49.23 | B |
| 1704 | C | TYR | 15 | 18.998 | −21.040 | 55.542 | 1.00 | 49.19 | B |
| 1705 | O | TYR | 15 | 19.220 | −21.455 | 54.409 | 1.00 | 49.13 | B |
| 1706 | N | PRO | 16 | 17.754 | −20.927 | 56.020 | 1.00 | 48.65 | B |
| 1707 | CD | PRO | 16 | 17.283 | −20.460 | 57.334 | 1.00 | 48.52 | B |
| 1708 | CA | PRO | 16 | 16.626 | −21.286 | 55.155 | 1.00 | 48.15 | B |
| 1709 | CB | PRO | 16 | 15.404 | −20.973 | 56.023 | 1.00 | 48.28 | B |
| 1710 | CG | PRO | 16 | 15.914 | −19.956 | 57.002 | 1.00 | 48.46 | B |
| 1711 | C | PRO | 16 | 16.638 | −20.517 | 53.836 | 1.00 | 47.65 | B |
| 1712 | O | PRO | 16 | 17.183 | −19.413 | 53.745 | 1.00 | 47.40 | B |
| 1713 | N | ALA | 17 | 16.034 | −21.120 | 52.819 | 1.00 | 47.10 | B |

TABLE 1-continued

| Atom | Atom Type | Res | # | X | Y | Z | OCC | B | Mol. |
|---|---|---|---|---|---|---|---|---|---|
| 1714 | CA | ALA | 17 | 15.980 | −20.533 | 51.488 | 1.00 | 46.55 | B |
| 1715 | CB | ALA | 17 | 15.310 | −21.513 | 50.523 | 1.00 | 46.52 | B |
| 1716 | C | ALA | 17 | 15.227 | −19.214 | 51.495 | 1.00 | 46.25 | B |
| 1717 | O | ALA | 17 | 15.556 | −18.293 | 50.745 | 1.00 | 46.11 | B |
| 1718 | N | VAL | 18 | 14.219 | −19.118 | 52.349 | 1.00 | 45.82 | B |
| 1719 | CA | VAL | 18 | 13.421 | −17.906 | 52.421 | 1.00 | 45.55 | B |
| 1720 | CB | VAL | 18 | 12.079 | −18.095 | 51.659 | 1.00 | 45.68 | B |
| 1721 | CG1 | VAL | 18 | 11.269 | −19.207 | 52.300 | 1.00 | 45.77 | B |
| 1722 | CG2 | VAL | 18 | 11.279 | −16.800 | 51.644 | 1.00 | 45.93 | B |
| 1723 | C | VAL | 18 | 13.128 | −17.518 | 53.862 | 1.00 | 45.24 | B |
| 1724 | O | VAL | 18 | 13.072 | −18.374 | 54.753 | 1.00 | 45.26 | B |
| 1725 | N | VAL | 19 | 12.978 | −16.224 | 54.098 | 1.00 | 44.65 | B |
| 1726 | CA | VAL | 19 | 12.663 | −15.758 | 55.435 | 1.00 | 44.13 | B |
| 1727 | CB | VAL | 19 | 13.926 | −15.336 | 56.272 | 1.00 | 44.19 | B |
| 1728 | CG1 | VAL | 19 | 14.885 | −16.498 | 56.411 | 1.00 | 44.28 | B |
| 1729 | CG2 | VAL | 19 | 14.611 | −14.157 | 55.633 | 1.00 | 44.26 | B |
| 1730 | C | VAL | 19 | 11.764 | −14.556 | 55.344 | 1.00 | 43.70 | B |
| 1731 | O | VAL | 19 | 11.831 | −13.779 | 54.386 | 1.00 | 43.46 | B |
| 1732 | N | THR | 20 | 10.915 | −14.421 | 56.350 | 1.00 | 43.23 | B |
| 1733 | CA | THR | 20 | 10.018 | −13.294 | 56.448 | 1.00 | 43.00 | B |
| 1734 | CB | THR | 20 | 8.565 | −13.743 | 56.490 | 1.00 | 43.00 | B |
| 1735 | OG1 | THR | 20 | 8.244 | −14.391 | 55.257 | 1.00 | 42.95 | B |
| 1736 | CG2 | THR | 20 | 7.646 | −12.540 | 56.691 | 1.00 | 42.85 | B |
| 1737 | C | THR | 20 | 10.368 | −12.563 | 57.723 | 1.00 | 42.81 | B |
| 1738 | O | THR | 20 | 10.469 | −13.157 | 58.791 | 1.00 | 42.81 | B |
| 1739 | N | SER | 21 | 10.560 | −11.262 | 57.603 | 1.00 | 42.69 | B |
| 1740 | CA | SER | 21 | 10.938 | −10.454 | 58.746 | 1.00 | 42.56 | B |
| 1741 | CB | SER | 21 | 11.586 | −9.148 | 58.277 | 1.00 | 42.51 | B |
| 1742 | OG | SER | 21 | 11.680 | −8.226 | 59.347 | 1.00 | 42.51 | B |
| 1743 | C | SER | 21 | 9.843 | −10.101 | 59.728 | 1.00 | 42.46 | B |
| 1744 | O | SER | 21 | 8.838 | −9.512 | 59.352 | 1.00 | 42.41 | B |
| 1745 | N | PRO | 22 | 10.022 | −10.464 | 61.004 | 1.00 | 42.42 | B |
| 1746 | CD | PRO | 22 | 10.998 | −11.374 | 61.631 | 1.00 | 42.39 | B |
| 1747 | CA | PRO | 22 | 8.974 | −10.107 | 61.959 | 1.00 | 42.32 | B |
| 1748 | CB | PRO | 22 | 9.361 | −10.890 | 63.208 | 1.00 | 42.38 | B |
| 1749 | CG | PRO | 22 | 10.839 | −11.014 | 63.087 | 1.00 | 42.48 | B |
| 1750 | C | PRO | 22 | 9.035 | −8.595 | 62.180 | 1.00 | 42.18 | B |
| 1751 | O | PRO | 22 | 8.143 | −8.013 | 62.780 | 1.00 | 42.18 | B |
| 1752 | N | VAL | 23 | 10.100 | −7.971 | 61.687 | 1.00 | 41.99 | B |
| 1753 | CA | VAL | 23 | 10.272 | −6.532 | 61.845 | 1.00 | 41.75 | B |
| 1754 | CB | VAL | 23 | 11.781 | −6.106 | 61.828 | 1.00 | 41.80 | B |
| 1755 | CG1 | VAL | 23 | 11.887 | −4.592 | 61.992 | 1.00 | 41.65 | B |
| 1756 | CG2 | VAL | 23 | 12.534 | −6.795 | 62.950 | 1.00 | 41.65 | B |
| 1757 | C | VAL | 23 | 9.561 | −5.743 | 60.754 | 1.00 | 41.72 | B |
| 1758 | O | VAL | 23 | 8.772 | −4.839 | 61.039 | 1.00 | 41.65 | B |
| 1759 | N | THR | 24 | 9.839 | −6.076 | 59.500 | 1.00 | 41.57 | B |
| 1760 | CA | THR | 24 | 9.249 | −5.340 | 58.386 | 1.00 | 41.68 | B |
| 1761 | CB | THR | 24 | 10.304 | −4.993 | 57.325 | 1.00 | 41.54 | B |
| 1762 | OG1 | THR | 24 | 10.806 | −6.209 | 56.755 | 1.00 | 41.46 | B |
| 1763 | CG2 | THR | 24 | 11.457 | −4.206 | 57.946 | 1.00 | 41.58 | B |
| 1764 | C | THR | 24 | 8.135 | −6.074 | 57.652 | 1.00 | 41.71 | B |
| 1765 | O | THR | 24 | 7.444 | −5.478 | 56.825 | 1.00 | 41.85 | B |
| 1766 | N | GLY | 25 | 7.978 | −7.358 | 57.934 | 1.00 | 41.81 | B |
| 1767 | CA | GLY | 25 | 6.951 | −8.127 | 57.253 | 1.00 | 41.91 | B |
| 1768 | C | GLY | 25 | 7.378 | −8.465 | 55.836 | 1.00 | 42.03 | B |
| 1769 | O | GLY | 25 | 6.656 | −9.152 | 55.115 | 1.00 | 41.88 | B |
| 1770 | N | LYS | 26 | 8.552 | −7.994 | 55.426 | 1.00 | 42.07 | B |
| 1771 | CA | LYS | 26 | 9.050 | −8.268 | 54.081 | 1.00 | 42.16 | B |
| 1772 | CB | LYS | 26 | 10.130 | −7.250 | 53.684 | 1.00 | 42.37 | B |
| 1773 | CG | LYS | 26 | 9.616 | −5.819 | 53.685 | 1.00 | 42.59 | B |
| 1774 | CD | LYS | 26 | 10.656 | −4.795 | 53.250 | 1.00 | 42.92 | B |
| 1775 | CE | LYS | 26 | 10.030 | −3.404 | 53.240 | 1.00 | 43.24 | B |
| 1776 | NZ | LYS | 26 | 10.919 | −2.330 | 52.711 | 1.00 | 43.72 | B |
| 1777 | C | LYS | 26 | 9.614 | −9.674 | 54.008 | 1.00 | 42.21 | B |
| 1778 | O | LYS | 26 | 10.023 | −10.238 | 55.022 | 1.00 | 42.21 | B |
| 1779 | N | SER | 27 | 9.623 | −10.235 | 52.803 | 1.00 | 42.25 | B |
| 1780 | CA | SER | 27 | 10.142 | −11.575 | 52.590 | 1.00 | 42.37 | B |
| 1781 | CB | SER | 27 | 9.086 | −12.447 | 51.901 | 1.00 | 42.48 | B |
| 1782 | OG | SER | 27 | 7.938 | −12.588 | 52.732 | 1.00 | 42.80 | B |
| 1783 | C | SER | 27 | 11.406 | −11.512 | 51.748 | 1.00 | 42.40 | B |
| 1784 | O | SER | 27 | 11.514 | −10.697 | 50.829 | 1.00 | 42.23 | B |
| 1785 | N | TYR | 28 | 12.358 | −12.379 | 52.064 | 1.00 | 42.45 | B |
| 1786 | CA | TYR | 28 | 13.621 | −12.408 | 51.351 | 1.00 | 42.71 | B |
| 1787 | CB | TYR | 28 | 14.770 | −11.927 | 52.243 | 1.00 | 42.79 | B |
| 1788 | CG | TYR | 28 | 14.444 | −10.811 | 53.208 | 1.00 | 42.90 | B |
| 1789 | CD1 | TYR | 28 | 13.798 | −11.073 | 54.416 | 1.00 | 43.14 | B |
| 1790 | CE1 | TYR | 28 | 13.564 | −10.052 | 55.344 | 1.00 | 43.31 | B |

TABLE 1-continued

| Atom | Atom Type | Res | # | X | Y | Z | OCC | B | Mol. |
|---|---|---|---|---|---|---|---|---|---|
| 1791 | CD2 | TYR | 28 | 14.839 | −9.500 | 52.943 | 1.00 | 42.89 | B |
| 1792 | CE2 | TYR | 28 | 14.609 | −8.477 | 53.855 | 1.00 | 42.94 | B |
| 1793 | CZ | TYR | 28 | 13.977 | −8.756 | 55.054 | 1.00 | 43.14 | B |
| 1794 | OH | TYR | 28 | 13.790 | −7.753 | 55.976 | 1.00 | 43.15 | B |
| 1795 | C | TYR | 28 | 13.957 | −13.815 | 50.933 | 1.00 | 42.80 | B |
| 1796 | O | TYR | 28 | 13.404 | −14.783 | 51.455 | 1.00 | 42.85 | B |
| 1797 | N | PHE | 29 | 14.883 | −13.924 | 49.994 | 1.00 | 42.97 | B |
| 1798 | CA | PHE | 29 | 15.349 | −15.224 | 49.551 | 1.00 | 43.23 | B |
| 1799 | CB | PHE | 29 | 15.030 | −15.442 | 48.070 | 1.00 | 42.93 | B |
| 1800 | CG | PHE | 29 | 15.706 | −14.477 | 47.153 | 1.00 | 42.69 | B |
| 1801 | CD1 | PHE | 29 | 16.988 | −14.731 | 46.678 | 1.00 | 42.62 | B |
| 1802 | CD2 | PHE | 29 | 15.056 | −13.313 | 46.750 | 1.00 | 42.65 | B |
| 1803 | CE1 | PHE | 29 | 17.615 | −13.840 | 45.814 | 1.00 | 42.52 | B |
| 1804 | CE2 | PHE | 29 | 15.678 | −12.415 | 45.886 | 1.00 | 42.52 | B |
| 1805 | CZ | PHE | 29 | 16.959 | −12.684 | 45.416 | 1.00 | 42.46 | B |
| 1806 | C | PHE | 29 | 16.848 | −15.224 | 49.810 | 1.00 | 43.57 | B |
| 1807 | O | PHE | 29 | 17.490 | −14.175 | 49.766 | 1.00 | 43.42 | B |
| 1808 | N | LEU | 30 | 17.396 | −16.394 | 50.106 | 1.00 | 44.16 | B |
| 1809 | CA | LEU | 30 | 18.815 | −16.522 | 50.390 | 1.00 | 44.89 | B |
| 1810 | CB | LEU | 30 | 19.104 | −17.902 | 50.977 | 1.00 | 44.66 | B |
| 1811 | CG | LEU | 30 | 20.547 | −18.188 | 51.383 | 1.00 | 44.61 | B |
| 1812 | CD1 | LEU | 30 | 20.981 | −17.233 | 52.491 | 1.00 | 44.49 | B |
| 1813 | CD2 | LEU | 30 | 20.650 | −19.638 | 51.855 | 1.00 | 44.61 | B |
| 1814 | C | LEU | 30 | 19.673 | −16.302 | 49.149 | 1.00 | 45.58 | B |
| 1815 | O | LEU | 30 | 19.652 | −17.102 | 48.212 | 1.00 | 45.50 | B |
| 1816 | N | GLY | 31 | 20.428 | −15.209 | 49.150 | 1.00 | 46.38 | B |
| 1817 | CA | GLY | 31 | 21.290 | −14.909 | 48.022 | 1.00 | 47.43 | B |
| 1818 | C | GLY | 31 | 22.575 | −15.705 | 48.108 | 1.00 | 48.27 | B |
| 1819 | O | GLY | 31 | 23.185 | −16.041 | 47.091 | 1.00 | 48.24 | B |
| 1820 | N | GLY | 32 | 22.988 | −16.013 | 49.333 | 1.00 | 49.11 | B |
| 1821 | CA | GLY | 32 | 24.204 | −16.777 | 49.533 | 1.00 | 50.38 | B |
| 1822 | C | GLY | 32 | 24.594 | −16.853 | 50.994 | 1.00 | 51.37 | B |
| 1823 | O | GLY | 32 | 24.123 | −16.066 | 51.813 | 1.00 | 51.30 | B |
| 1824 | N | ALA | 33 | 25.449 | −17.809 | 51.326 | 1.00 | 52.42 | B |
| 1825 | CA | ALA | 33 | 25.904 | −17.972 | 52.698 | 1.00 | 53.70 | B |
| 1826 | CB | ALA | 33 | 25.011 | −18.956 | 53.440 | 1.00 | 53.52 | B |
| 1827 | C | ALA | 33 | 27.332 | −18.481 | 52.671 | 1.00 | 54.67 | B |
| 1828 | O | ALA | 33 | 27.717 | −19.217 | 51.767 | 1.00 | 54.78 | B |
| 1829 | N | GLY | 34 | 28.119 | −18.081 | 53.658 | 1.00 | 55.80 | B |
| 1830 | CA | GLY | 34 | 29.496 | −18.525 | 53.712 | 1.00 | 57.28 | B |
| 1831 | C | GLY | 34 | 30.030 | −18.472 | 55.124 | 1.00 | 58.38 | B |
| 1832 | O | GLY | 34 | 29.268 | −18.376 | 56.085 | 1.00 | 58.39 | B |
| 1833 | N | GLU | 35 | 31.348 | −18.537 | 55.250 | 1.00 | 59.51 | B |
| 1834 | CA | GLU | 35 | 31.990 | −18.491 | 56.552 | 1.00 | 60.71 | B |
| 1835 | CB | GLU | 35 | 32.602 | −19.853 | 56.878 | 1.00 | 60.83 | B |
| 1836 | CG | GLU | 35 | 33.477 | −20.406 | 55.770 | 1.00 | 61.20 | B |
| 1837 | CD | GLU | 35 | 33.783 | −21.883 | 55.949 | 1.00 | 61.39 | B |
| 1838 | OE1 | GLU | 35 | 33.051 | −22.562 | 56.704 | 1.00 | 61.47 | B |
| 1839 | OE2 | GLU | 35 | 34.746 | −22.369 | 55.319 | 1.00 | 61.58 | B |
| 1840 | C | GLU | 35 | 33.064 | −17.415 | 56.576 | 1.00 | 61.50 | B |
| 1841 | O | GLU | 35 | 33.589 | −17.021 | 55.533 | 1.00 | 61.60 | B |
| 1842 | N | ARG | 36 | 33.362 | −16.932 | 57.774 | 1.00 | 62.40 | B |
| 1843 | CA | ARG | 36 | 34.377 | −15.913 | 57.984 | 1.00 | 63.41 | B |
| 1844 | CB | ARG | 36 | 33.736 | −14.531 | 58.136 | 1.00 | 63.24 | B |
| 1845 | CG | ARG | 36 | 33.101 | −13.984 | 56.863 | 1.00 | 63.15 | B |
| 1846 | CD | ARG | 36 | 34.152 | −13.434 | 55.898 | 1.00 | 63.03 | B |
| 1847 | NE | ARG | 36 | 33.553 | −12.696 | 54.787 | 1.00 | 62.88 | B |
| 1848 | CZ | ARG | 36 | 32.857 | −13.251 | 53.804 | 1.00 | 62.80 | B |
| 1849 | NH1 | ARG | 36 | 32.666 | −14.559 | 53.785 | 1.00 | 62.66 | B |
| 1850 | NH2 | ARG | 36 | 32.357 | −12.491 | 52.838 | 1.00 | 62.73 | B |
| 1851 | C | ARG | 36 | 35.102 | −16.282 | 59.267 | 1.00 | 64.23 | B |
| 1852 | O | ARG | 36 | 34.516 | −16.898 | 60.160 | 1.00 | 64.34 | B |
| 1853 | N | GLY | 37 | 36.372 | −15.916 | 59.367 | 1.00 | 65.15 | B |
| 1854 | CA | GLY | 37 | 37.123 | −16.241 | 60.564 | 1.00 | 66.33 | B |
| 1855 | C | GLY | 37 | 38.520 | −15.667 | 60.540 | 1.00 | 67.19 | B |
| 1856 | O | GLY | 37 | 38.719 | −14.513 | 60.155 | 1.00 | 67.22 | B |
| 1857 | N | LEU | 38 | 39.489 | −16.473 | 60.961 | 1.00 | 68.07 | B |
| 1858 | CA | LEU | 38 | 40.879 | −16.044 | 60.985 | 1.00 | 69.00 | B |
| 1859 | CB | LEU | 38 | 41.364 | −15.882 | 62.429 | 1.00 | 69.01 | B |
| 1860 | CG | LEU | 38 | 40.616 | −14.884 | 63.320 | 1.00 | 69.15 | B |
| 1861 | CD1 | LEU | 38 | 41.184 | −14.969 | 64.719 | 1.00 | 69.20 | B |
| 1862 | CD2 | LEU | 38 | 40.743 | −13.466 | 62.797 | 1.00 | 69.12 | B |
| 1863 | C | LEU | 38 | 41.768 | −17.052 | 60.267 | 1.00 | 69.61 | B |
| 1864 | O | LEU | 38 | 41.450 | −17.525 | 59.172 | 1.00 | 69.83 | B |
| 1865 | N | THR | 39 | 42.885 | −17.363 | 60.908 | 1.00 | 70.30 | B |
| 1866 | CA | THR | 39 | 43.903 | −18.295 | 60.432 | 1.00 | 70.92 | B |
| 1867 | CB | THR | 39 | 44.605 | −17.816 | 59.125 | 1.00 | 71.00 | B |

TABLE 1-continued

| Atom | Atom Type | Res | # | X | Y | Z | OCC | B | Mol. |
|---|---|---|---|---|---|---|---|---|---|
| 1868 | OG1 | THR | 39 | 44.875 | −16.413 | 59.212 | 1.00 | 71.11 | B |
| 1869 | CG2 | THR | 39 | 43.750 | −18.112 | 57.893 | 1.00 | 71.08 | B |
| 1870 | C | THR | 39 | 44.933 | −18.276 | 61.550 | 1.00 | 71.28 | B |
| 1871 | O | THR | 39 | 45.518 | −17.230 | 61.849 | 1.00 | 71.39 | B |
| 1872 | N | ILE | 40 | 45.138 | −19.414 | 62.191 | 1.00 | 71.65 | B |
| 1873 | CA | ILE | 40 | 46.104 | −19.475 | 63.272 | 1.00 | 71.98 | B |
| 1874 | CB | ILE | 40 | 45.397 | −19.519 | 64.649 | 1.00 | 72.07 | B |
| 1875 | CG2 | ILE | 40 | 46.437 | −19.577 | 65.768 | 1.00 | 72.13 | B |
| 1876 | CG1 | ILE | 40 | 44.484 | −18.293 | 64.789 | 1.00 | 72.16 | B |
| 1877 | CD1 | ILE | 40 | 43.676 | −18.247 | 66.072 | 1.00 | 72.19 | B |
| 1878 | C | ILE | 40 | 46.996 | −20.695 | 63.113 | 1.00 | 72.13 | B |
| 1879 | O | ILE | 40 | 46.515 | −21.829 | 63.098 | 1.00 | 72.14 | B |
| 1880 | N | GLU | 41 | 48.296 | −20.445 | 62.990 | 1.00 | 72.27 | B |
| 1881 | CA | GLU | 41 | 49.280 | −21.508 | 62.829 | 1.00 | 72.37 | B |
| 1882 | CB | GLU | 41 | 49.115 | −22.567 | 63.924 | 1.00 | 72.66 | B |
| 1883 | CG | GLU | 41 | 49.074 | −22.029 | 65.342 | 1.00 | 73.09 | B |
| 1884 | CD | GLU | 41 | 48.860 | −23.131 | 66.370 | 1.00 | 73.44 | B |
| 1885 | OE1 | GLU | 41 | 48.404 | −24.239 | 65.982 | 1.00 | 73.61 | B |
| 1886 | OE2 | GLU | 41 | 49.131 | −22.891 | 67.573 | 1.00 | 73.57 | B |
| 1887 | C | GLU | 41 | 49.104 | −22.154 | 61.461 | 1.00 | 72.24 | B |
| 1888 | O | GLU | 41 | 49.422 | −23.333 | 61.284 | 1.00 | 72.33 | B |
| 1889 | N | GLY | 42 | 48.573 | −21.388 | 60.509 | 1.00 | 72.00 | B |
| 1890 | CA | GLY | 42 | 48.378 | −21.897 | 59.163 | 1.00 | 71.65 | B |
| 1891 | C | GLY | 42 | 47.039 | −22.578 | 58.912 | 1.00 | 71.39 | B |
| 1892 | O | GLY | 42 | 46.765 | −23.036 | 57.800 | 1.00 | 71.45 | B |
| 1893 | N | ASN | 43 | 46.198 | −22.651 | 59.940 | 1.00 | 71.01 | B |
| 1894 | CA | ASN | 43 | 44.884 | −23.285 | 59.808 | 1.00 | 70.49 | B |
| 1895 | CB | ASN | 43 | 44.699 | −24.372 | 60.883 | 1.00 | 70.75 | B |
| 1896 | CG | ASN | 43 | 45.721 | −24.277 | 62.002 | 1.00 | 70.91 | B |
| 1897 | OD1 | ASN | 43 | 45.379 | −24.076 | 63.167 | 1.00 | 71.10 | B |
| 1898 | ND2 | ASN | 43 | 46.993 | −24.420 | 61.651 | 1.00 | 70.99 | B |
| 1899 | C | ASN | 43 | 43.755 | −22.266 | 59.908 | 1.00 | 69.94 | B |
| 1900 | O | ASN | 43 | 43.570 | −21.639 | 60.955 | 1.00 | 69.92 | B |
| 1901 | N | PHE | 44 | 43.009 | −22.091 | 58.819 | 1.00 | 69.17 | B |
| 1902 | CA | PHE | 44 | 41.893 | −21.147 | 58.803 | 1.00 | 68.34 | B |
| 1903 | CB | PHE | 44 | 41.182 | −21.163 | 57.449 | 1.00 | 68.55 | B |
| 1904 | CG | PHE | 44 | 40.096 | −20.129 | 57.331 | 1.00 | 68.73 | B |
| 1905 | CD1 | PHE | 44 | 40.406 | −18.811 | 57.018 | 1.00 | 68.84 | B |
| 1906 | CD2 | PHE | 44 | 38.767 | −20.457 | 57.583 | 1.00 | 68.82 | B |
| 1907 | CE1 | PHE | 44 | 39.410 | −17.832 | 56.961 | 1.00 | 68.92 | B |
| 1908 | CE2 | PHE | 44 | 37.766 | −19.482 | 57.527 | 1.00 | 68.87 | B |
| 1909 | CZ | PHE | 44 | 38.091 | −18.170 | 57.218 | 1.00 | 68.89 | B |
| 1910 | C | PHE | 44 | 40.886 | −21.537 | 59.878 | 1.00 | 67.59 | B |
| 1911 | O | PHE | 44 | 40.255 | −22.590 | 59.785 | 1.00 | 67.65 | B |
| 1912 | N | ILE | 45 | 40.721 | −20.692 | 60.891 | 1.00 | 66.57 | B |
| 1913 | CA | ILE | 45 | 39.779 | −21.003 | 61.958 | 1.00 | 65.46 | B |
| 1914 | CB | ILE | 45 | 40.346 | −20.598 | 63.336 | 1.00 | 65.65 | B |
| 1915 | CG2 | ILE | 45 | 39.326 | −20.907 | 64.432 | 1.00 | 65.67 | B |
| 1916 | CG1 | ILE | 45 | 41.658 | −21.348 | 63.592 | 1.00 | 65.76 | B |
| 1917 | CD1 | ILE | 45 | 42.299 | −21.037 | 64.924 | 1.00 | 65.89 | B |
| 1918 | C | ILE | 45 | 38.444 | −20.306 | 61.731 | 1.00 | 64.50 | B |
| 1919 | O | ILE | 45 | 38.384 | −19.080 | 61.627 | 1.00 | 64.36 | B |
| 1920 | N | LYS | 46 | 37.383 | −21.098 | 61.644 | 1.00 | 63.35 | B |
| 1921 | CA | LYS | 46 | 36.040 | −20.569 | 61.422 | 1.00 | 62.15 | B |
| 1922 | CB | LYS | 46 | 35.113 | −21.672 | 60.915 | 1.00 | 62.34 | B |
| 1923 | CG | LYS | 46 | 35.632 | −22.408 | 59.702 | 1.00 | 62.53 | B |
| 1924 | CD | LYS | 46 | 34.607 | −23.414 | 59.218 | 1.00 | 62.79 | B |
| 1925 | CE | LYS | 46 | 35.092 | −24.169 | 57.994 | 1.00 | 62.95 | B |
| 1926 | NZ | LYS | 46 | 33.999 | −24.987 | 57.410 | 1.00 | 63.14 | B |
| 1927 | C | LYS | 46 | 35.451 | −19.992 | 62.702 | 1.00 | 61.12 | B |
| 1928 | O | LYS | 46 | 35.401 | −20.669 | 63.727 | 1.00 | 61.07 | B |
| 1929 | N | PHE | 47 | 34.997 | −18.747 | 62.635 | 1.00 | 59.85 | B |
| 1930 | CA | PHE | 47 | 34.398 | −18.101 | 63.793 | 1.00 | 58.58 | B |
| 1931 | CB | PHE | 47 | 35.069 | −16.763 | 64.080 | 1.00 | 58.88 | B |
| 1932 | CG | PHE | 47 | 36.336 | −16.882 | 64.871 | 1.00 | 59.15 | B |
| 1933 | CD1 | PHE | 47 | 37.512 | −17.303 | 64.263 | 1.00 | 59.24 | B |
| 1934 | CD2 | PHE | 47 | 36.352 | −16.579 | 66.230 | 1.00 | 59.25 | B |
| 1935 | CE1 | PHE | 47 | 38.691 | −17.420 | 64.996 | 1.00 | 59.37 | B |
| 1936 | CE2 | PHE | 47 | 37.530 | −16.694 | 66.976 | 1.00 | 59.38 | B |
| 1937 | CZ | PHE | 47 | 38.702 | −17.115 | 66.354 | 1.00 | 59.40 | B |
| 1938 | C | PHE | 47 | 32.909 | −17.860 | 63.626 | 1.00 | 57.53 | B |
| 1939 | O | PHE | 47 | 32.149 | −17.967 | 64.585 | 1.00 | 57.43 | B |
| 1940 | N | THR | 48 | 32.493 | −17.526 | 62.411 | 1.00 | 56.23 | B |
| 1941 | CA | THR | 48 | 31.094 | −17.242 | 62.153 | 1.00 | 54.89 | B |
| 1942 | CB | THR | 48 | 30.805 | −15.740 | 62.306 | 1.00 | 54.93 | B |
| 1943 | OG1 | THR | 48 | 31.464 | −15.023 | 61.255 | 1.00 | 54.77 | B |
| 1944 | CG2 | THR | 48 | 31.316 | −15.221 | 63.639 | 1.00 | 54.93 | B |

TABLE 1-continued

| Atom | Atom Type | Res | # | X | Y | Z | OCC | B | Mol. |
|---|---|---|---|---|---|---|---|---|---|
| 1945 | C | THR | 48 | 30.647 | −17.628 | 60.753 | 1.00 | 53.91 | B |
| 1946 | O | THR | 48 | 31.458 | −17.826 | 59.848 | 1.00 | 53.77 | B |
| 1947 | N | ALA | 49 | 29.337 | −17.736 | 60.594 | 1.00 | 52.68 | B |
| 1948 | CA | ALA | 49 | 28.736 | −18.034 | 59.309 | 1.00 | 51.46 | B |
| 1949 | CB | ALA | 49 | 27.720 | −19.153 | 59.445 | 1.00 | 51.35 | B |
| 1950 | C | ALA | 49 | 28.044 | −16.722 | 58.953 | 1.00 | 50.62 | B |
| 1951 | O | ALA | 49 | 27.607 | −15.989 | 59.844 | 1.00 | 50.37 | B |
| 1952 | N | ILE | 50 | 27.969 | −16.412 | 57.667 | 1.00 | 49.66 | B |
| 1953 | CA | ILE | 50 | 27.323 | −15.186 | 57.238 | 1.00 | 48.82 | B |
| 1954 | CB | ILE | 50 | 28.373 | −14.144 | 56.789 | 1.00 | 49.03 | B |
| 1955 | CG2 | ILE | 50 | 28.981 | −14.557 | 55.462 | 1.00 | 49.23 | B |
| 1956 | CG1 | ILE | 50 | 27.737 | −12.761 | 56.694 | 1.00 | 49.22 | B |
| 1957 | CD1 | ILE | 50 | 27.425 | −12.141 | 58.065 | 1.00 | 49.28 | B |
| 1958 | C | ILE | 50 | 26.387 | −15.529 | 56.086 | 1.00 | 48.02 | B |
| 1959 | O | ILE | 50 | 26.752 | −16.270 | 55.179 | 1.00 | 48.00 | B |
| 1960 | N | GLY | 51 | 25.164 | −15.023 | 56.154 | 1.00 | 47.11 | B |
| 1961 | CA | GLY | 51 | 24.206 | −15.278 | 55.096 | 1.00 | 45.93 | B |
| 1962 | C | GLY | 51 | 23.618 | −13.957 | 54.652 | 1.00 | 45.12 | B |
| 1963 | O | GLY | 51 | 23.386 | −13.062 | 55.472 | 1.00 | 45.09 | B |
| 1964 | N | VAL | 52 | 23.388 | −13.819 | 53.354 | 1.00 | 44.10 | B |
| 1965 | CA | VAL | 52 | 22.827 | −12.590 | 52.826 | 1.00 | 43.04 | B |
| 1966 | CB | VAL | 52 | 23.757 | −11.940 | 51.777 | 1.00 | 43.10 | B |
| 1967 | CG1 | VAL | 52 | 23.093 | −10.694 | 51.196 | 1.00 | 42.81 | B |
| 1968 | CG2 | VAL | 52 | 25.092 | −11.592 | 52.410 | 1.00 | 42.98 | B |
| 1969 | C | VAL | 52 | 21.489 | −12.863 | 52.173 | 1.00 | 42.37 | B |
| 1970 | O | VAL | 52 | 21.397 | −13.662 | 51.241 | 1.00 | 42.33 | B |
| 1971 | N | TYR | 53 | 20.456 | −12.202 | 52.678 | 1.00 | 41.49 | B |
| 1972 | CA | TYR | 53 | 19.118 | −12.339 | 52.134 | 1.00 | 40.80 | B |
| 1973 | CB | TYR | 53 | 18.089 | −12.557 | 53.247 | 1.00 | 40.46 | B |
| 1974 | CG | TYR | 53 | 18.154 | −13.924 | 53.872 | 1.00 | 40.32 | B |
| 1975 | CD1 | TYR | 53 | 19.024 | −14.190 | 54.929 | 1.00 | 40.13 | B |
| 1976 | CE1 | TYR | 53 | 19.104 | −15.465 | 55.492 | 1.00 | 40.11 | B |
| 1977 | CD2 | TYR | 53 | 17.361 | −14.969 | 53.388 | 1.00 | 40.22 | B |
| 1978 | CE2 | TYR | 53 | 17.435 | −16.249 | 53.946 | 1.00 | 40.15 | B |
| 1979 | CZ | TYR | 53 | 18.306 | −16.488 | 54.992 | 1.00 | 40.03 | B |
| 1980 | OH | TYR | 53 | 18.397 | −17.752 | 55.521 | 1.00 | 39.76 | B |
| 1981 | C | TYR | 53 | 18.746 | −11.076 | 51.369 | 1.00 | 40.48 | B |
| 1982 | O | TYR | 53 | 19.054 | −9.967 | 51.807 | 1.00 | 40.28 | B |
| 1983 | N | LEU | 54 | 18.080 | −11.254 | 50.233 | 1.00 | 40.12 | B |
| 1984 | CA | LEU | 54 | 17.634 | −10.140 | 49.409 | 1.00 | 39.95 | B |
| 1985 | CB | LEU | 54 | 18.195 | −10.271 | 47.983 | 1.00 | 39.98 | B |
| 1986 | CG | LEU | 54 | 19.728 | −10.346 | 47.857 | 1.00 | 39.84 | B |
| 1987 | CD1 | LEU | 54 | 20.131 | −10.370 | 46.390 | 1.00 | 40.00 | B |
| 1988 | CD2 | LEU | 54 | 20.353 | −9.146 | 48.568 | 1.00 | 39.77 | B |
| 1989 | C | LEU | 54 | 16.108 | −10.168 | 49.373 | 1.00 | 39.95 | B |
| 1990 | O | LEU | 54 | 15.512 | −11.231 | 49.197 | 1.00 | 40.06 | B |
| 1991 | N | GLU | 55 | 15.473 | −9.015 | 49.554 | 1.00 | 39.84 | B |
| 1992 | CA | GLU | 55 | 14.017 | −8.954 | 49.520 | 1.00 | 39.83 | B |
| 1993 | CB | GLU | 55 | 13.540 | −7.505 | 49.619 | 1.00 | 39.82 | B |
| 1994 | CG | GLU | 55 | 12.101 | −7.355 | 50.074 | 1.00 | 39.79 | B |
| 1995 | CD | GLU | 55 | 11.643 | −5.912 | 50.094 | 1.00 | 40.01 | B |
| 1996 | OE1 | GLU | 55 | 12.508 | −5.004 | 50.125 | 1.00 | 39.92 | B |
| 1997 | OE2 | GLU | 55 | 10.414 | −5.683 | 50.089 | 1.00 | 40.17 | B |
| 1998 | C | GLU | 55 | 13.558 | −9.563 | 48.194 | 1.00 | 39.88 | B |
| 1999 | O | GLU | 55 | 14.249 | −9.448 | 47.178 | 1.00 | 39.68 | B |
| 2000 | N | ASP | 56 | 12.397 | −10.211 | 48.200 | 1.00 | 39.86 | B |
| 2001 | CA | ASP | 56 | 11.899 | −10.835 | 46.982 | 1.00 | 39.97 | B |
| 2002 | CB | ASP | 56 | 10.522 | −11.481 | 47.227 | 1.00 | 40.55 | B |
| 2003 | CG | ASP | 56 | 9.551 | −10.560 | 47.954 | 1.00 | 41.05 | B |
| 2004 | OD1 | ASP | 56 | 9.792 | −9.332 | 48.011 | 1.00 | 41.44 | B |
| 2005 | OD2 | ASP | 56 | 8.526 | −11.071 | 48.467 | 1.00 | 41.60 | B |
| 2006 | C | ASP | 56 | 11.837 | −9.887 | 45.781 | 1.00 | 39.66 | B |
| 2007 | O | ASP | 56 | 12.165 | −10.286 | 44.665 | 1.00 | 39.49 | B |
| 2008 | N | ILE | 57 | 11.442 | −8.636 | 46.002 | 1.00 | 39.41 | B |
| 2009 | CA | ILE | 57 | 11.359 | −7.678 | 44.900 | 1.00 | 39.38 | B |
| 2010 | CB | ILE | 57 | 10.753 | −6.333 | 45.350 | 1.00 | 39.45 | B |
| 2011 | CG2 | ILE | 57 | 9.325 | −6.548 | 45.835 | 1.00 | 39.63 | B |
| 2012 | CG1 | ILE | 57 | 11.623 | −5.697 | 46.441 | 1.00 | 39.32 | B |
| 2013 | CD1 | ILE | 57 | 11.202 | −4.280 | 46.795 | 1.00 | 39.16 | B |
| 2014 | C | ILE | 57 | 12.702 | −7.379 | 44.228 | 1.00 | 39.28 | B |
| 2015 | O | ILE | 57 | 12.751 | −6.685 | 43.213 | 1.00 | 39.13 | B |
| 2016 | N | ALA | 58 | 13.792 | −7.887 | 44.793 | 1.00 | 39.20 | B |
| 2017 | CA | ALA | 58 | 15.101 | −7.646 | 44.201 | 1.00 | 39.17 | B |
| 2018 | CB | ALA | 58 | 16.196 | −8.157 | 45.114 | 1.00 | 38.96 | B |
| 2019 | C | ALA | 58 | 15.202 | −8.314 | 42.828 | 1.00 | 39.20 | B |
| 2020 | O | ALA | 58 | 15.903 | −7.824 | 41.945 | 1.00 | 39.03 | B |
| 2021 | N | VAL | 59 | 14.503 | −9.431 | 42.646 | 1.00 | 39.35 | B |

TABLE 1-continued

| Atom | Atom Type | Res | # | X | Y | Z | OCC | B | Mol. |
|---|---|---|---|---|---|---|---|---|---|
| 2022 | CA | VAL | 59 | 14.550 | −10.130 | 41.360 | 1.00 | 39.57 | B |
| 2023 | CB | VAL | 59 | 13.663 | −11.400 | 41.368 | 1.00 | 39.70 | B |
| 2024 | CG1 | VAL | 59 | 13.666 | −12.059 | 39.979 | 1.00 | 39.75 | B |
| 2025 | CG2 | VAL | 59 | 14.182 | −12.380 | 42.413 | 1.00 | 39.86 | B |
| 2026 | C | VAL | 59 | 14.107 | −9.207 | 40.225 | 1.00 | 39.58 | B |
| 2027 | O | VAL | 59 | 14.806 | −9.072 | 39.216 | 1.00 | 39.68 | B |
| 2028 | N | ALA | 60 | 12.960 | −8.555 | 40.395 | 1.00 | 39.62 | B |
| 2029 | CA | ALA | 60 | 12.453 | −7.651 | 39.368 | 1.00 | 39.75 | B |
| 2030 | CB | ALA | 60 | 11.058 | −7.146 | 39.745 | 1.00 | 39.60 | B |
| 2031 | C | ALA | 60 | 13.400 | −6.470 | 39.168 | 1.00 | 39.86 | B |
| 2032 | O | ALA | 60 | 13.582 | −5.992 | 38.049 | 1.00 | 39.88 | B |
| 2033 | N | SER | 61 | 14.010 | −6.007 | 40.256 | 1.00 | 39.96 | B |
| 2034 | CA | SER | 61 | 14.930 | −4.883 | 40.182 | 1.00 | 40.10 | B |
| 2035 | CB | SER | 61 | 15.312 | −4.435 | 41.599 | 1.00 | 40.24 | B |
| 2036 | OG | SER | 61 | 16.106 | −3.268 | 41.565 | 1.00 | 40.32 | B |
| 2037 | C | SER | 61 | 16.190 | −5.238 | 39.387 | 1.00 | 40.20 | B |
| 2038 | O | SER | 61 | 16.623 | −4.491 | 38.511 | 1.00 | 39.93 | B |
| 2039 | N | LEU | 62 | 16.767 | −6.396 | 39.681 | 1.00 | 40.48 | B |
| 2040 | CA | LEU | 62 | 17.984 | −6.835 | 39.008 | 1.00 | 40.79 | B |
| 2041 | CB | LEU | 62 | 18.678 | −7.889 | 39.873 | 1.00 | 40.83 | B |
| 2042 | CG | LEU | 62 | 19.092 | −7.449 | 41.281 | 1.00 | 40.75 | B |
| 2043 | CD1 | LEU | 62 | 19.447 | −8.677 | 42.118 | 1.00 | 40.77 | B |
| 2044 | CD2 | LEU | 62 | 20.276 | −6.481 | 41.187 | 1.00 | 40.65 | B |
| 2045 | C | LEU | 62 | 17.770 | −7.403 | 37.597 | 1.00 | 41.21 | B |
| 2046 | O | LEU | 62 | 18.699 | −7.451 | 36.789 | 1.00 | 40.91 | B |
| 2047 | N | ALA | 63 | 16.545 | −7.829 | 37.306 | 1.00 | 41.76 | B |
| 2048 | CA | ALA | 63 | 16.226 | −8.428 | 36.014 | 1.00 | 42.24 | B |
| 2049 | CB | ALA | 63 | 14.758 | −8.854 | 35.987 | 1.00 | 42.07 | B |
| 2050 | C | ALA | 63 | 16.526 | −7.511 | 34.833 | 1.00 | 42.72 | B |
| 2051 | O | ALA | 63 | 17.105 | −7.942 | 33.838 | 1.00 | 42.73 | B |
| 2052 | N | ALA | 64 | 16.134 | −6.247 | 34.956 | 1.00 | 43.25 | B |
| 2053 | CA | ALA | 64 | 16.348 | −5.258 | 33.900 | 1.00 | 43.82 | B |
| 2054 | CB | ALA | 64 | 16.090 | −3.855 | 34.457 | 1.00 | 44.09 | B |
| 2055 | C | ALA | 64 | 17.746 | −5.323 | 33.289 | 1.00 | 43.99 | B |
| 2056 | O | ALA | 64 | 17.905 | −5.430 | 32.071 | 1.00 | 44.39 | B |
| 2057 | N | LYS | 65 | 18.758 | −5.296 | 34.143 | 1.00 | 43.95 | B |
| 2058 | CA | LYS | 65 | 20.142 | −5.309 | 33.691 | 1.00 | 44.01 | B |
| 2059 | CB | LYS | 65 | 20.988 | −4.413 | 34.604 | 1.00 | 43.63 | B |
| 2060 | CG | LYS | 65 | 20.598 | −2.951 | 34.605 | 1.00 | 43.43 | B |
| 2061 | CD | LYS | 65 | 21.298 | −2.185 | 35.727 | 1.00 | 43.05 | B |
| 2062 | CE | LYS | 65 | 22.818 | −2.233 | 35.597 | 1.00 | 42.89 | B |
| 2063 | NZ | LYS | 65 | 23.513 | −1.392 | 36.619 | 1.00 | 42.53 | B |
| 2064 | C | LYS | 65 | 20.841 | −6.659 | 33.620 | 1.00 | 44.17 | B |
| 2065 | O | LYS | 65 | 21.731 | −6.857 | 32.789 | 1.00 | 44.16 | B |
| 2066 | N | TRP | 66 | 20.438 | −7.590 | 34.475 | 1.00 | 44.43 | B |
| 2067 | CA | TRP | 66 | 21.143 | −8.856 | 34.560 | 1.00 | 44.80 | B |
| 2068 | CB | TRP | 66 | 21.572 | −9.045 | 36.017 | 1.00 | 44.39 | B |
| 2069 | CG | TRP | 66 | 22.255 | −7.805 | 36.513 | 1.00 | 44.15 | B |
| 2070 | CD2 | TRP | 66 | 23.492 | −7.269 | 36.030 | 1.00 | 43.98 | B |
| 2071 | CE2 | TRP | 66 | 23.682 | −6.018 | 36.662 | 1.00 | 43.97 | B |
| 2072 | CE3 | TRP | 66 | 24.449 | −7.716 | 35.108 | 1.00 | 43.86 | B |
| 2073 | CD1 | TRP | 66 | 21.767 | −6.893 | 37.408 | 1.00 | 44.00 | B |
| 2074 | NE1 | TRP | 66 | 22.619 | −5.815 | 37.502 | 1.00 | 43.86 | B |
| 2075 | CZ2 | TRP | 66 | 24.799 | −5.215 | 36.411 | 1.00 | 43.93 | B |
| 2076 | CZ3 | TRP | 66 | 25.559 | −6.916 | 34.857 | 1.00 | 43.93 | B |
| 2077 | CH2 | TRP | 66 | 25.720 | −5.676 | 35.504 | 1.00 | 43.94 | B |
| 2078 | C | TRP | 66 | 20.528 | −10.133 | 34.022 | 1.00 | 45.32 | B |
| 2079 | O | TRP | 66 | 21.208 | −11.157 | 33.954 | 1.00 | 45.20 | B |
| 2080 | N | LYS | 67 | 19.261 | −10.091 | 33.634 | 1.00 | 46.10 | B |
| 2081 | CA | LYS | 67 | 18.626 | −11.292 | 33.100 | 1.00 | 46.95 | B |
| 2082 | CB | LYS | 67 | 17.176 | −10.997 | 32.703 | 1.00 | 47.33 | B |
| 2083 | CG | LYS | 67 | 16.432 | −12.217 | 32.173 | 1.00 | 48.05 | B |
| 2084 | CD | LYS | 67 | 14.974 | −11.909 | 31.856 | 1.00 | 48.57 | B |
| 2085 | CE | LYS | 67 | 14.286 | −13.147 | 31.276 | 1.00 | 48.96 | B |
| 2086 | NZ | LYS | 67 | 12.860 | −12.897 | 30.895 | 1.00 | 49.49 | B |
| 2087 | C | LYS | 67 | 19.410 | −11.802 | 31.888 | 1.00 | 47.21 | B |
| 2088 | O | LYS | 67 | 19.902 | −11.013 | 31.083 | 1.00 | 47.25 | B |
| 2089 | N | GLY | 68 | 19.555 | −13.120 | 31.773 | 1.00 | 47.53 | B |
| 2090 | CA | GLY | 68 | 20.264 | −13.678 | 30.634 | 1.00 | 47.90 | B |
| 2091 | C | GLY | 68 | 21.770 | −13.809 | 30.773 | 1.00 | 48.24 | B |
| 2092 | O | GLY | 68 | 22.407 | −14.493 | 29.970 | 1.00 | 48.39 | B |
| 2093 | N | LYS | 69 | 22.346 | −13.159 | 31.780 | 1.00 | 48.41 | B |
| 2094 | CA | LYS | 69 | 23.785 | −13.222 | 32.014 | 1.00 | 48.60 | B |
| 2095 | CB | LYS | 69 | 24.231 | −12.018 | 32.841 | 1.00 | 48.88 | B |
| 2096 | CG | LYS | 69 | 24.030 | −10.681 | 32.143 | 1.00 | 49.27 | B |
| 2097 | CD | LYS | 69 | 25.263 | −10.277 | 31.361 | 1.00 | 49.77 | B |
| 2098 | CE | LYS | 69 | 24.912 | −9.242 | 30.306 | 1.00 | 50.02 | B |

TABLE 1-continued

| Atom | Atom Type | Res | # | X | Y | Z | OCC | B | Mol. |
|---|---|---|---|---|---|---|---|---|---|
| 2099 | NZ | LYS | 69 | 23.867 | −8.311 | 30.829 | 1.00 | 50.38 | B |
| 2100 | C | LYS | 69 | 24.135 | −14.510 | 32.754 | 1.00 | 48.62 | B |
| 2101 | O | LYS | 69 | 23.409 | −14.937 | 33.649 | 1.00 | 48.58 | B |
| 2102 | N | SER | 70 | 25.247 | −15.127 | 32.383 | 1.00 | 48.55 | B |
| 2103 | CA | SER | 70 | 25.667 | −16.358 | 33.031 | 1.00 | 48.64 | B |
| 2104 | CB | SER | 70 | 26.741 | −17.053 | 32.200 | 1.00 | 48.52 | B |
| 2105 | OG | SER | 70 | 27.937 | −16.293 | 32.193 | 1.00 | 48.58 | B |
| 2106 | C | SER | 70 | 26.230 | −16.045 | 34.411 | 1.00 | 48.68 | B |
| 2107 | O | SER | 70 | 26.568 | −14.897 | 34.709 | 1.00 | 48.64 | B |
| 2108 | N | SER | 71 | 26.331 | −17.070 | 35.248 | 1.00 | 48.70 | B |
| 2109 | CA | SER | 71 | 26.870 | −16.891 | 36.586 | 1.00 | 48.84 | B |
| 2110 | CB | SER | 71 | 26.760 | −18.197 | 37.382 | 1.00 | 48.74 | B |
| 2111 | OG | SER | 71 | 25.400 | −18.558 | 37.570 | 1.00 | 48.45 | B |
| 2112 | C | SER | 71 | 28.328 | −16.459 | 36.490 | 1.00 | 49.02 | B |
| 2113 | O | SER | 71 | 28.801 | −15.635 | 37.274 | 1.00 | 48.97 | B |
| 2114 | N | GLU | 72 | 29.031 | −17.015 | 35.510 | 1.00 | 49.24 | B |
| 2115 | CA | GLU | 72 | 30.436 | −16.702 | 35.299 | 1.00 | 49.50 | B |
| 2116 | CB | GLU | 72 | 31.000 | −17.565 | 34.167 | 1.00 | 50.10 | B |
| 2117 | CG | GLU | 72 | 30.731 | −19.074 | 34.306 | 1.00 | 51.11 | B |
| 2118 | CD | GLU | 72 | 29.272 | −19.459 | 34.048 | 1.00 | 51.70 | B |
| 2119 | OE1 | GLU | 72 | 28.670 | −18.953 | 33.078 | 1.00 | 52.50 | B |
| 2120 | OE2 | GLU | 72 | 28.721 | −20.286 | 34.803 | 1.00 | 52.20 | B |
| 2121 | C | GLU | 72 | 30.600 | −15.224 | 34.948 | 1.00 | 49.31 | B |
| 2122 | O | GLU | 72 | 31.546 | −14.567 | 35.397 | 1.00 | 49.38 | B |
| 2123 | N | GLU | 73 | 29.682 | −14.701 | 34.139 | 1.00 | 49.02 | B |
| 2124 | CA | GLU | 73 | 29.761 | −13.298 | 33.749 | 1.00 | 48.82 | B |
| 2125 | CB | GLU | 73 | 28.801 | −12.983 | 32.597 | 1.00 | 49.24 | B |
| 2126 | CG | GLU | 73 | 29.011 | −11.570 | 32.047 | 1.00 | 50.00 | B |
| 2127 | CD | GLU | 73 | 28.126 | −11.233 | 30.861 | 1.00 | 50.48 | B |
| 2128 | OE1 | GLU | 73 | 27.590 | −12.169 | 30.214 | 1.00 | 50.83 | B |
| 2129 | OE2 | GLU | 73 | 27.983 | −10.021 | 30.572 | 1.00 | 50.72 | B |
| 2130 | C | GLU | 73 | 29.439 | −12.401 | 34.937 | 1.00 | 48.32 | B |
| 2131 | O | GLU | 73 | 30.153 | −11.434 | 35.212 | 1.00 | 48.19 | B |
| 2132 | N | LEU | 74 | 28.360 | −12.723 | 35.640 | 1.00 | 47.81 | B |
| 2133 | CA | LEU | 74 | 27.957 | −11.938 | 36.800 | 1.00 | 47.37 | B |
| 2134 | CB | LEU | 74 | 26.719 | −12.559 | 37.455 | 1.00 | 47.26 | B |
| 2135 | CG | LEU | 74 | 25.433 | −12.529 | 36.630 | 1.00 | 47.22 | B |
| 2136 | CD1 | LEU | 74 | 24.321 | −13.215 | 37.400 | 1.00 | 47.15 | B |
| 2137 | CD2 | LEU | 74 | 25.057 | −11.085 | 36.320 | 1.00 | 47.11 | B |
| 2138 | C | LEU | 74 | 29.078 | −11.837 | 37.827 | 1.00 | 47.06 | B |
| 2139 | O | LEU | 74 | 29.380 | −10.754 | 38.324 | 1.00 | 46.87 | B |
| 2140 | N | LEU | 75 | 29.705 | −12.966 | 38.137 | 1.00 | 46.79 | B |
| 2141 | CA | LEU | 75 | 30.771 | −12.980 | 39.131 | 1.00 | 46.59 | B |
| 2142 | CB | LEU | 75 | 31.366 | −14.385 | 39.251 | 1.00 | 46.57 | B |
| 2143 | CG | LEU | 75 | 32.465 | −14.537 | 40.306 | 1.00 | 46.63 | B |
| 2144 | CD1 | LEU | 75 | 31.920 | −14.130 | 41.670 | 1.00 | 46.55 | B |
| 2145 | CD2 | LEU | 75 | 32.967 | −15.977 | 40.330 | 1.00 | 46.55 | B |
| 2146 | C | LEU | 75 | 31.881 | −11.969 | 38.849 | 1.00 | 46.50 | B |
| 2147 | O | LEU | 75 | 32.430 | −11.361 | 39.772 | 1.00 | 46.44 | B |
| 2148 | N | GLU | 76 | 32.210 | −11.779 | 37.574 | 1.00 | 46.41 | B |
| 2149 | CA | GLU | 76 | 33.270 | −10.844 | 37.205 | 1.00 | 46.29 | B |
| 2150 | CB | GLU | 76 | 34.048 | −11.381 | 35.995 | 1.00 | 47.04 | B |
| 2151 | CG | GLU | 76 | 33.176 | −12.071 | 34.936 | 1.00 | 48.20 | B |
| 2152 | CD | GLU | 76 | 33.934 | −12.441 | 33.654 | 1.00 | 48.84 | B |
| 2153 | OE1 | GLU | 76 | 35.182 | −12.559 | 33.696 | 1.00 | 49.33 | B |
| 2154 | OE2 | GLU | 76 | 33.272 | −12.626 | 32.600 | 1.00 | 49.21 | B |
| 2155 | C | GLU | 76 | 32.775 | −9.420 | 36.912 | 1.00 | 45.70 | B |
| 2156 | O | GLU | 76 | 33.538 | −8.580 | 36.438 | 1.00 | 45.76 | B |
| 2157 | N | THR | 77 | 31.507 | −9.145 | 37.199 | 1.00 | 44.89 | B |
| 2158 | CA | THR | 77 | 30.948 | −7.815 | 36.945 | 1.00 | 44.08 | B |
| 2159 | CB | THR | 77 | 29.638 | −7.920 | 36.156 | 1.00 | 44.08 | B |
| 2160 | OG1 | THR | 77 | 29.855 | −8.706 | 34.982 | 1.00 | 44.04 | B |
| 2161 | CG2 | THR | 77 | 29.148 | −6.536 | 35.760 | 1.00 | 44.00 | B |
| 2162 | C | THR | 77 | 30.682 | −7.043 | 38.230 | 1.00 | 43.44 | B |
| 2163 | O | THR | 77 | 29.687 | −7.281 | 38.913 | 1.00 | 43.38 | B |
| 2164 | N | LEU | 78 | 31.573 | −6.115 | 38.556 | 1.00 | 42.63 | B |
| 2165 | CA | LEU | 78 | 31.425 | −5.327 | 39.768 | 1.00 | 41.89 | B |
| 2166 | CB | LEU | 78 | 32.560 | −4.311 | 39.903 | 1.00 | 41.84 | B |
| 2167 | CG | LEU | 78 | 33.971 | −4.843 | 40.166 | 1.00 | 41.77 | B |
| 2168 | CD1 | LEU | 78 | 34.936 | −3.655 | 40.283 | 1.00 | 41.72 | B |
| 2169 | CD2 | LEU | 78 | 33.984 | −5.680 | 41.445 | 1.00 | 41.60 | B |
| 2170 | C | LEU | 78 | 30.101 | −4.591 | 39.796 | 1.00 | 41.50 | B |
| 2171 | O | LEU | 78 | 29.509 | −4.410 | 40.863 | 1.00 | 41.40 | B |
| 2172 | N | ASP | 79 | 29.641 | −4.166 | 38.625 | 1.00 | 40.76 | B |
| 2173 | CA | ASP | 79 | 28.391 | −3.436 | 38.537 | 1.00 | 40.19 | B |
| 2174 | CB | ASP | 79 | 28.133 | −2.994 | 37.099 | 1.00 | 39.93 | B |
| 2175 | CG | ASP | 79 | 27.021 | −1.973 | 37.005 | 1.00 | 39.73 | B |

TABLE 1-continued

| Atom | Atom Type | Res | # | X | Y | Z | OCC | B | Mol. |
|---|---|---|---|---|---|---|---|---|---|
| 2176 | OD1 | ASP | 79 | 27.080 | −.976 | 37.758 | 1.00 | 39.52 | B |
| 2177 | OD2 | ASP | 79 | 26.094 | −2.163 | 36.188 | 1.00 | 39.68 | B |
| 2178 | C | ASP | 79 | 27.222 | −4.274 | 39.046 | 1.00 | 39.95 | B |
| 2179 | O | ASP | 79 | 26.277 | −3.741 | 39.620 | 1.00 | 39.93 | B |
| 2180 | N | PHE | 80 | 27.290 | −5.584 | 38.833 | 1.00 | 39.65 | B |
| 2181 | CA | PHE | 80 | 26.238 | −6.479 | 39.298 | 1.00 | 39.49 | B |
| 2182 | CB | PHE | 80 | 26.535 | −7.914 | 38.848 | 1.00 | 39.69 | B |
| 2183 | CG | PHE | 80 | 25.635 | −8.947 | 39.471 | 1.00 | 39.88 | B |
| 2184 | CD1 | PHE | 80 | 26.171 | −9.978 | 40.232 | 1.00 | 39.84 | B |
| 2185 | CD2 | PHE | 80 | 24.257 | −8.893 | 39.290 | 1.00 | 39.82 | B |
| 2186 | CE1 | PHE | 80 | 25.349 | −10.944 | 40.804 | 1.00 | 39.98 | B |
| 2187 | CE2 | PHE | 80 | 23.427 | −9.854 | 39.857 | 1.00 | 39.99 | B |
| 2188 | CZ | PHE | 80 | 23.971 | −10.882 | 40.615 | 1.00 | 39.89 | B |
| 2189 | C | PHE | 80 | 26.141 | −6.419 | 40.822 | 1.00 | 39.23 | B |
| 2190 | O | PHE | 80 | 25.053 | −6.280 | 41.388 | 1.00 | 39.29 | B |
| 2191 | N | TYR | 81 | 27.281 | −6.513 | 41.494 | 1.00 | 38.84 | B |
| 2192 | CA | TYR | 81 | 27.268 | −6.466 | 42.947 | 1.00 | 38.60 | B |
| 2193 | CB | TYR | 81 | 28.603 | −6.960 | 43.500 | 1.00 | 38.64 | B |
| 2194 | CG | TYR | 81 | 28.822 | −8.407 | 43.146 | 1.00 | 38.74 | B |
| 2195 | CD1 | TYR | 81 | 29.522 | −8.766 | 41.993 | 1.00 | 38.91 | B |
| 2196 | CE1 | TYR | 81 | 29.624 | −10.097 | 41.598 | 1.00 | 38.98 | B |
| 2197 | CD2 | TYR | 81 | 28.236 | −9.418 | 43.901 | 1.00 | 38.88 | B |
| 2198 | CE2 | TYR | 81 | 28.330 | −10.756 | 43.514 | 1.00 | 38.83 | B |
| 2199 | CZ | TYR | 81 | 29.026 | −11.085 | 42.362 | 1.00 | 39.00 | B |
| 2200 | OH | TYR | 81 | 29.124 | −12.401 | 41.968 | 1.00 | 39.16 | B |
| 2201 | C | TYR | 81 | 26.915 | −5.090 | 43.491 | 1.00 | 38.39 | B |
| 2202 | O | TYR | 81 | 26.368 | −4.983 | 44.582 | 1.00 | 38.23 | B |
| 2203 | N | ARG | 82 | 27.209 | −4.036 | 42.735 | 1.00 | 38.27 | B |
| 2204 | CA | ARG | 82 | 26.855 | −2.700 | 43.194 | 1.00 | 38.20 | B |
| 2205 | CB | ARG | 82 | 27.430 | −1.615 | 42.277 | 1.00 | 38.62 | B |
| 2206 | CG | ARG | 82 | 28.948 | −1.499 | 42.343 | 1.00 | 39.18 | B |
| 2207 | CD | ARG | 82 | 29.415 | −.058 | 42.150 | 1.00 | 39.76 | B |
| 2208 | NE | ARG | 82 | 30.865 | .032 | 42.296 | 1.00 | 40.24 | B |
| 2209 | CZ | ARG | 82 | 31.732 | −.267 | 41.333 | 1.00 | 40.54 | B |
| 2210 | NH1 | ARG | 82 | 31.294 | −.660 | 40.142 | 1.00 | 40.61 | B |
| 2211 | NH2 | ARG | 82 | 33.039 | −.202 | 41.573 | 1.00 | 40.71 | B |
| 2212 | C | ARG | 82 | 25.335 | −2.610 | 43.218 | 1.00 | 37.97 | B |
| 2213 | O | ARG | 82 | 24.762 | −2.015 | 44.131 | 1.00 | 37.74 | B |
| 2214 | N | ASP | 83 | 24.683 | −3.209 | 42.220 | 1.00 | 37.78 | B |
| 2215 | CA | ASP | 83 | 23.223 | −3.189 | 42.175 | 1.00 | 37.70 | B |
| 2216 | CB | ASP | 83 | 22.690 | −3.795 | 40.873 | 1.00 | 37.72 | B |
| 2217 | CG | ASP | 83 | 22.784 | −2.835 | 39.699 | 1.00 | 37.89 | B |
| 2218 | OD1 | ASP | 83 | 22.683 | −1.604 | 39.917 | 1.00 | 38.14 | B |
| 2219 | OD2 | ASP | 83 | 22.931 | −3.306 | 38.556 | 1.00 | 37.83 | B |
| 2220 | C | ASP | 83 | 22.664 | −3.960 | 43.366 | 1.00 | 37.51 | B |
| 2221 | O | ASP | 83 | 21.676 | −3.559 | 43.958 | 1.00 | 37.53 | B |
| 2222 | N | ILE | 84 | 23.300 | −5.066 | 43.725 | 1.00 | 37.44 | B |
| 2223 | CA | ILE | 84 | 22.825 | −5.832 | 44.863 | 1.00 | 37.47 | B |
| 2224 | CB | ILE | 84 | 23.555 | −7.184 | 44.978 | 1.00 | 37.40 | B |
| 2225 | CG2 | ILE | 84 | 23.210 | −7.854 | 46.304 | 1.00 | 37.28 | B |
| 2226 | CG1 | ILE | 84 | 23.161 | −8.074 | 43.795 | 1.00 | 37.35 | B |
| 2227 | CD1 | ILE | 84 | 23.852 | −9.419 | 43.769 | 1.00 | 37.46 | B |
| 2228 | C | ILE | 84 | 23.021 | −5.035 | 46.150 | 1.00 | 37.47 | B |
| 2229 | O | ILE | 84 | 22.121 | −4.953 | 46.976 | 1.00 | 37.59 | B |
| 2230 | N | ILE | 85 | 24.191 | −4.428 | 46.311 | 1.00 | 37.43 | B |
| 2231 | CA | ILE | 85 | 24.481 | −3.646 | 47.511 | 1.00 | 37.40 | B |
| 2232 | CB | ILE | 85 | 25.951 | −3.156 | 47.512 | 1.00 | 37.47 | B |
| 2233 | CG2 | ILE | 85 | 26.181 | −2.201 | 48.678 | 1.00 | 37.29 | B |
| 2234 | CG1 | ILE | 85 | 26.905 | −4.352 | 47.594 | 1.00 | 37.36 | B |
| 2235 | CD1 | ILE | 85 | 28.350 | −3.996 | 47.266 | 1.00 | 37.35 | B |
| 2236 | C | ILE | 85 | 23.583 | −2.418 | 47.684 | 1.00 | 37.50 | B |
| 2237 | O | ILE | 85 | 23.046 | −2.178 | 48.770 | 1.00 | 37.33 | B |
| 2238 | N | SER | 86 | 23.420 | −1.636 | 46.620 | 1.00 | 37.58 | B |
| 2239 | CA | SER | 86 | 22.611 | −.426 | 46.719 | 1.00 | 37.89 | B |
| 2240 | CB | SER | 86 | 23.423 | .769 | 46.218 | 1.00 | 38.16 | B |
| 2241 | OG | SER | 86 | 24.648 | .859 | 46.930 | 1.00 | 38.50 | B |
| 2242 | C | SER | 86 | 21.277 | −.494 | 45.982 | 1.00 | 37.85 | B |
| 2243 | O | SER | 86 | 20.663 | .541 | 45.697 | 1.00 | 37.88 | B |
| 2244 | N | GLY | 87 | 20.833 | −1.712 | 45.684 | 1.00 | 37.83 | B |
| 2245 | CA | GLY | 87 | 19.570 | −1.901 | 44.993 | 1.00 | 37.79 | B |
| 2246 | C | GLY | 87 | 18.395 | −1.401 | 45.814 | 1.00 | 37.71 | B |
| 2247 | O | GLY | 87 | 18.460 | −1.388 | 47.042 | 1.00 | 37.67 | B |
| 2248 | N | PRO | 88 | 17.297 | −.997 | 45.157 | 1.00 | 37.71 | B |
| 2249 | CD | PRO | 88 | 17.139 | −1.053 | 43.692 | 1.00 | 37.67 | B |
| 2250 | CA | PRO | 88 | 16.080 | −.479 | 45.791 | 1.00 | 37.83 | B |
| 2251 | CB | PRO | 88 | 15.341 | .154 | 44.618 | 1.00 | 37.69 | B |
| 2252 | CG | PRO | 88 | 15.643 | −.807 | 43.510 | 1.00 | 37.64 | B |

TABLE 1-continued

| Atom | Atom Type | Res | # | X | Y | Z | OCC | B | Mol. |
|---|---|---|---|---|---|---|---|---|---|
| 2253 | C | PRO | 88 | 15.244 | −1.541 | 46.500 | 1.00 | 37.94 | B |
| 2254 | O | PRO | 88 | 14.056 | −1.713 | 46.216 | 1.00 | 37.87 | B |
| 2255 | N | PHE | 89 | 15.870 | −2.244 | 47.431 | 1.00 | 38.07 | B |
| 2256 | CA | PHE | 89 | 15.194 | −3.290 | 48.180 | 1.00 | 38.25 | B |
| 2257 | CB | PHE | 89 | 15.063 | −4.550 | 47.324 | 1.00 | 38.10 | B |
| 2258 | CG | PHE | 89 | 16.319 | −4.907 | 46.578 | 1.00 | 38.02 | B |
| 2259 | CD1 | PHE | 89 | 17.376 | −5.543 | 47.225 | 1.00 | 37.76 | B |
| 2260 | CD2 | PHE | 89 | 16.449 | −4.589 | 45.220 | 1.00 | 37.82 | B |
| 2261 | CE1 | PHE | 89 | 18.543 | −5.858 | 46.533 | 1.00 | 37.81 | B |
| 2262 | CE2 | PHE | 89 | 17.612 | −4.899 | 44.521 | 1.00 | 37.79 | B |
| 2263 | CZ | PHE | 89 | 18.662 | −5.536 | 45.180 | 1.00 | 37.99 | B |
| 2264 | C | PHE | 89 | 15.977 | −3.590 | 49.441 | 1.00 | 38.46 | B |
| 2265 | O | PHE | 89 | 17.172 | −3.309 | 49.529 | 1.00 | 38.42 | B |
| 2266 | N | GLU | 90 | 15.296 | −4.172 | 50.413 | 1.00 | 38.66 | B |
| 2267 | CA | GLU | 90 | 15.917 | −4.485 | 51.681 | 1.00 | 38.95 | B |
| 2268 | CB | GLU | 90 | 14.829 | −4.737 | 52.723 | 1.00 | 39.19 | B |
| 2269 | CG | GLU | 90 | 15.307 | −4.613 | 54.146 | 1.00 | 39.63 | B |
| 2270 | CD | GLU | 90 | 14.167 | −4.448 | 55.112 | 1.00 | 39.63 | B |
| 2271 | OE1 | GLU | 90 | 13.588 | −5.471 | 55.534 | 1.00 | 39.90 | B |
| 2272 | OE2 | GLU | 90 | 13.842 | −3.291 | 55.441 | 1.00 | 39.82 | B |
| 2273 | C | GLU | 90 | 16.828 | −5.692 | 51.591 | 1.00 | 39.01 | B |
| 2274 | O | GLU | 90 | 16.562 | −6.632 | 50.836 | 1.00 | 39.01 | B |
| 2275 | N | LYS | 91 | 17.929 | −5.646 | 52.333 | 1.00 | 38.99 | B |
| 2276 | CA | LYS | 91 | 18.838 | −6.778 | 52.389 | 1.00 | 39.10 | B |
| 2277 | CB | LYS | 91 | 20.238 | −6.431 | 51.873 | 1.00 | 39.04 | B |
| 2278 | CG | LYS | 91 | 20.282 | −5.909 | 50.435 | 1.00 | 39.18 | B |
| 2279 | CD | LYS | 91 | 20.188 | −4.385 | 50.407 | 1.00 | 39.16 | B |
| 2280 | CE | LYS | 91 | 20.294 | −3.844 | 48.993 | 1.00 | 39.09 | B |
| 2281 | NZ | LYS | 91 | 20.328 | −2.354 | 49.026 | 1.00 | 39.27 | B |
| 2282 | C | LYS | 91 | 18.892 | −7.138 | 53.865 | 1.00 | 39.23 | B |
| 2283 | O | LYS | 91 | 18.820 | −6.273 | 54.738 | 1.00 | 39.21 | B |
| 2284 | N | LEU | 92 | 18.986 | −8.423 | 54.146 | 1.00 | 39.40 | B |
| 2285 | CA | LEU | 92 | 19.034 | −8.876 | 55.522 | 1.00 | 39.58 | B |
| 2286 | CB | LEU | 92 | 17.745 | −9.628 | 55.873 | 1.00 | 39.62 | B |
| 2287 | CG | LEU | 92 | 17.642 | −10.163 | 57.300 | 1.00 | 39.75 | B |
| 2288 | CD1 | LEU | 92 | 17.771 | −9.027 | 58.303 | 1.00 | 39.86 | B |
| 2289 | CD2 | LEU | 92 | 16.304 | −10.867 | 57.465 | 1.00 | 39.95 | B |
| 2290 | C | LEU | 92 | 20.230 | −9.790 | 55.639 | 1.00 | 39.65 | B |
| 2291 | O | LEU | 92 | 20.281 | −10.847 | 55.013 | 1.00 | 39.55 | B |
| 2292 | N | ILE | 93 | 21.199 | −9.370 | 56.439 | 1.00 | 39.89 | B |
| 2293 | CA | ILE | 93 | 22.412 | −10.145 | 56.627 | 1.00 | 40.18 | B |
| 2294 | CB | ILE | 93 | 23.651 | −9.237 | 56.540 | 1.00 | 40.36 | B |
| 2295 | CG2 | ILE | 93 | 24.919 | −10.075 | 56.614 | 1.00 | 40.39 | B |
| 2296 | CG1 | ILE | 93 | 23.623 | −8.436 | 55.237 | 1.00 | 40.47 | B |
| 2297 | CD1 | ILE | 93 | 24.658 | −7.332 | 55.209 | 1.00 | 41.03 | B |
| 2298 | C | ILE | 93 | 22.390 | −10.806 | 57.996 | 1.00 | 40.37 | B |
| 2299 | O | ILE | 93 | 22.205 | −10.136 | 59.011 | 1.00 | 40.20 | B |
| 2300 | N | ARG | 94 | 22.561 | −12.122 | 58.030 | 1.00 | 40.70 | B |
| 2301 | CA | ARG | 94 | 22.578 | −12.813 | 59.304 | 1.00 | 41.11 | B |
| 2302 | CB | ARG | 94 | 21.511 | −13.905 | 59.378 | 1.00 | 41.34 | B |
| 2303 | CG | ARG | 94 | 21.391 | −14.492 | 60.776 | 1.00 | 41.86 | B |
| 2304 | CD | ARG | 94 | 21.838 | −15.945 | 60.864 | 1.00 | 42.47 | B |
| 2305 | NE | ARG | 94 | 20.839 | −16.837 | 60.298 | 1.00 | 42.93 | B |
| 2306 | CZ | ARG | 94 | 20.929 | −18.163 | 60.275 | 1.00 | 43.21 | B |
| 2307 | NH1 | ARG | 94 | 21.980 | −18.783 | 60.794 | 1.00 | 43.37 | B |
| 2308 | NH2 | ARG | 94 | 19.954 | −18.873 | 59.721 | 1.00 | 43.51 | B |
| 2309 | C | ARG | 94 | 23.930 | −13.447 | 59.561 | 1.00 | 41.29 | B |
| 2310 | O | ARG | 94 | 24.403 | −14.272 | 58.782 | 1.00 | 41.31 | B |
| 2311 | N | GLY | 95 | 24.559 | −13.031 | 60.650 | 1.00 | 41.47 | B |
| 2312 | CA | GLY | 95 | 25.831 | −13.608 | 61.021 | 1.00 | 41.78 | B |
| 2313 | C | GLY | 95 | 25.524 | −14.484 | 62.217 | 1.00 | 42.11 | B |
| 2314 | O | GLY | 95 | 24.856 | −14.038 | 63.148 | 1.00 | 41.97 | B |
| 2315 | N | SER | 96 | 25.968 | −15.734 | 62.180 | 1.00 | 42.50 | B |
| 2316 | CA | SER | 96 | 25.753 | −16.659 | 63.286 | 1.00 | 43.05 | B |
| 2317 | CB | SER | 96 | 24.888 | −17.839 | 62.845 | 1.00 | 43.13 | B |
| 2318 | OG | SER | 96 | 23.562 | −17.402 | 62.592 | 1.00 | 43.17 | B |
| 2319 | C | SER | 96 | 27.116 | −17.147 | 63.742 | 1.00 | 43.42 | B |
| 2320 | O | SER | 96 | 27.966 | −17.479 | 62.920 | 1.00 | 43.38 | B |
| 2321 | N | LYS | 97 | 27.326 | −17.181 | 65.053 | 1.00 | 43.78 | B |
| 2322 | CA | LYS | 97 | 28.613 | −17.601 | 65.594 | 1.00 | 44.33 | B |
| 2323 | CB | LYS | 97 | 28.782 | −17.055 | 67.016 | 1.00 | 43.97 | B |
| 2324 | CG | LYS | 97 | 29.334 | −15.636 | 67.063 | 1.00 | 43.61 | B |
| 2325 | CD | LYS | 97 | 28.487 | −14.660 | 66.262 | 1.00 | 43.15 | B |
| 2326 | CE | LYS | 97 | 29.113 | −13.271 | 66.287 | 1.00 | 42.99 | B |
| 2327 | NZ | LYS | 97 | 28.302 | −12.273 | 65.553 | 1.00 | 42.83 | B |
| 2328 | C | LYS | 97 | 28.888 | −19.094 | 65.599 | 1.00 | 44.89 | B |
| 2329 | O | LYS | 97 | 28.017 | −19.907 | 65.920 | 1.00 | 45.01 | B |

TABLE 1-continued

| Atom | Atom Type | Res | # | X | Y | Z | OCC | B | Mol. |
|---|---|---|---|---|---|---|---|---|---|
| 2330 | N | ILE | 98 | 30.111 | −19.446 | 65.218 | 1.00 | 45.54 | B |
| 2331 | CA | ILE | 98 | 30.547 | −20.832 | 65.227 | 1.00 | 46.25 | B |
| 2332 | CB | ILE | 98 | 31.464 | −21.135 | 64.031 | 1.00 | 46.31 | B |
| 2333 | CG2 | ILE | 98 | 32.038 | −22.541 | 64.159 | 1.00 | 46.33 | B |
| 2334 | CG1 | ILE | 98 | 30.663 | −20.998 | 62.732 | 1.00 | 46.41 | B |
| 2335 | CD1 | ILE | 98 | 31.501 | −21.063 | 61.460 | 1.00 | 46.56 | B |
| 2336 | C | ILE | 98 | 31.313 | −20.958 | 66.546 | 1.00 | 46.69 | B |
| 2337 | O | ILE | 98 | 31.185 | −21.955 | 67.258 | 1.00 | 46.81 | B |
| 2338 | N | ARG | 99 | 32.093 | −19.928 | 66.862 | 1.00 | 47.22 | B |
| 2339 | CA | ARG | 99 | 32.839 | −19.859 | 68.115 | 1.00 | 47.79 | B |
| 2340 | CB | ARG | 99 | 34.341 | −19.653 | 67.876 | 1.00 | 48.66 | B |
| 2341 | CG | ARG | 99 | 35.039 | −20.829 | 67.200 | 1.00 | 50.10 | B |
| 2342 | CD | ARG | 99 | 36.549 | −20.590 | 67.108 | 1.00 | 51.29 | B |
| 2343 | NE | ARG | 99 | 37.194 | −21.602 | 66.272 | 1.00 | 52.52 | B |
| 2344 | CZ | ARG | 99 | 37.376 | −22.872 | 66.630 | 1.00 | 52.95 | B |
| 2345 | NH1 | ARG | 99 | 36.967 | −23.293 | 67.821 | 1.00 | 53.15 | B |
| 2346 | NH2 | ARG | 99 | 37.957 | −23.727 | 65.791 | 1.00 | 53.37 | B |
| 2347 | C | ARG | 99 | 32.288 | −18.656 | 68.873 | 1.00 | 47.56 | B |
| 2348 | O | ARG | 99 | 31.841 | −17.685 | 68.263 | 1.00 | 47.62 | B |
| 2349 | N | GLU | 100 | 32.320 | −18.721 | 70.192 | 1.00 | 47.26 | B |
| 2350 | CA | GLU | 100 | 31.806 | −17.635 | 71.011 | 1.00 | 46.82 | B |
| 2351 | CB | GLU | 100 | 31.807 | −18.042 | 72.482 | 1.00 | 47.00 | B |
| 2352 | CG | GLU | 100 | 31.353 | −16.941 | 73.415 | 1.00 | 47.32 | B |
| 2353 | CD | GLU | 100 | 31.344 | −17.385 | 74.861 | 1.00 | 47.64 | B |
| 2354 | OE1 | GLU | 100 | 32.328 | −18.032 | 75.291 | 1.00 | 47.96 | B |
| 2355 | OE2 | GLU | 100 | 30.361 | −17.083 | 75.569 | 1.00 | 47.60 | B |
| 2356 | C | GLU | 100 | 32.613 | −16.363 | 70.831 | 1.00 | 46.46 | B |
| 2357 | O | GLU | 100 | 33.840 | −16.388 | 70.784 | 1.00 | 46.42 | B |
| 2358 | N | LEU | 101 | 31.911 | −15.244 | 70.730 | 1.00 | 45.98 | B |
| 2359 | CA | LEU | 101 | 32.542 | −13.945 | 70.558 | 1.00 | 45.58 | B |
| 2360 | CB | LEU | 101 | 32.636 | −13.575 | 69.074 | 1.00 | 45.63 | B |
| 2361 | CG | LEU | 101 | 33.666 | −14.276 | 68.178 | 1.00 | 45.72 | B |
| 2362 | CD1 | LEU | 101 | 33.383 | −13.944 | 66.717 | 1.00 | 45.66 | B |
| 2363 | CD2 | LEU | 101 | 35.072 | −13.833 | 68.564 | 1.00 | 45.72 | B |
| 2364 | C | LEU | 101 | 31.690 | −12.913 | 71.262 | 1.00 | 45.28 | B |
| 2365 | O | LEU | 101 | 30.467 | −12.924 | 71.133 | 1.00 | 45.19 | B |
| 2366 | N | SER | 102 | 32.328 | −12.029 | 72.016 | 1.00 | 44.93 | B |
| 2367 | CA | SER | 102 | 31.591 | −10.982 | 72.693 | 1.00 | 44.64 | B |
| 2368 | CB | SER | 102 | 32.470 | −10.285 | 73.728 | 1.00 | 44.63 | B |
| 2369 | OG | SER | 102 | 33.484 | −9.537 | 73.091 | 1.00 | 44.35 | B |
| 2370 | C | SER | 102 | 31.216 | −9.995 | 71.598 | 1.00 | 44.52 | B |
| 2371 | O | SER | 102 | 31.745 | −10.065 | 70.481 | 1.00 | 44.43 | B |
| 2372 | N | GLY | 103 | 30.309 | −9.080 | 71.913 | 1.00 | 44.33 | B |
| 2373 | CA | GLY | 103 | 29.899 | −8.098 | 70.931 | 1.00 | 44.23 | B |
| 2374 | C | GLY | 103 | 31.084 | −7.273 | 70.461 | 1.00 | 44.21 | B |
| 2375 | O | GLY | 103 | 31.335 | −7.179 | 69.257 | 1.00 | 43.93 | B |
| 2376 | N | PRO | 104 | 31.835 | −6.657 | 71.391 | 1.00 | 44.23 | B |
| 2377 | CD | PRO | 104 | 31.601 | −6.583 | 72.847 | 1.00 | 44.17 | B |
| 2378 | CA | PRO | 104 | 32.995 | −5.845 | 71.003 | 1.00 | 44.29 | B |
| 2379 | CB | PRO | 104 | 33.556 | −5.384 | 72.349 | 1.00 | 44.28 | B |
| 2380 | CG | PRO | 104 | 32.315 | −5.298 | 73.219 | 1.00 | 44.22 | B |
| 2381 | C | PRO | 104 | 34.018 | −6.640 | 70.184 | 1.00 | 44.41 | B |
| 2382 | O | PRO | 104 | 34.577 | −6.132 | 69.204 | 1.00 | 44.34 | B |
| 2383 | N | GLU | 105 | 34.252 | −7.888 | 70.583 | 1.00 | 44.57 | B |
| 2384 | CA | GLU | 105 | 35.211 | −8.744 | 69.889 | 1.00 | 44.86 | B |
| 2385 | CB | GLU | 105 | 35.313 | −10.107 | 70.589 | 1.00 | 45.23 | B |
| 2386 | CG | GLU | 105 | 36.169 | −10.108 | 71.864 | 1.00 | 45.87 | B |
| 2387 | CD | GLU | 105 | 35.997 | −11.374 | 72.700 | 1.00 | 46.21 | B |
| 2388 | OE1 | GLU | 105 | 35.568 | −12.412 | 72.141 | 1.00 | 46.29 | B |
| 2389 | OE2 | GLU | 105 | 36.303 | −11.328 | 73.919 | 1.00 | 46.63 | B |
| 2390 | C | GLU | 105 | 34.812 | −8.948 | 68.431 | 1.00 | 44.86 | B |
| 2391 | O | GLU | 105 | 35.628 | −8.784 | 67.521 | 1.00 | 44.82 | B |
| 2392 | N | TYR | 106 | 33.550 | −9.306 | 68.214 | 1.00 | 44.74 | B |
| 2393 | CA | TYR | 106 | 33.044 | −9.542 | 66.869 | 1.00 | 44.72 | B |
| 2394 | CB | TYR | 106 | 31.650 | −10.170 | 66.924 | 1.00 | 44.32 | B |
| 2395 | CG | TYR | 106 | 30.890 | −10.017 | 65.623 | 1.00 | 43.89 | B |
| 2396 | CD1 | TYR | 106 | 31.158 | −10.844 | 64.531 | 1.00 | 43.61 | B |
| 2397 | CE1 | TYR | 106 | 30.499 | −10.660 | 63.312 | 1.00 | 43.43 | B |
| 2398 | CD2 | TYR | 106 | 29.943 | −9.002 | 65.467 | 1.00 | 43.68 | B |
| 2399 | CE2 | TYR | 106 | 29.284 | −8.807 | 64.259 | 1.00 | 43.45 | B |
| 2400 | CZ | TYR | 106 | 29.565 | −9.634 | 63.185 | 1.00 | 43.44 | B |
| 2401 | OH | TYR | 106 | 28.934 | −9.412 | 61.981 | 1.00 | 43.19 | B |
| 2402 | C | TYR | 106 | 32.969 | −8.265 | 66.044 | 1.00 | 44.85 | B |
| 2403 | O | TYR | 106 | 33.394 | −8.239 | 64.895 | 1.00 | 44.94 | B |
| 2404 | N | SER | 107 | 32.428 | −7.207 | 66.637 | 1.00 | 45.03 | B |
| 2405 | CA | SER | 107 | 32.253 | −5.940 | 65.943 | 1.00 | 45.36 | B |
| 2406 | CB | SER | 107 | 31.366 | −5.008 | 66.772 | 1.00 | 45.31 | B |

TABLE 1-continued

| Atom | Atom Type | Res | # | X | Y | Z | OCC | B | Mol. |
|---|---|---|---|---|---|---|---|---|---|
| 2407 | OG | SER | 107 | 32.028 | −4.577 | 67.948 | 1.00 | 45.62 | B |
| 2408 | C | SER | 107 | 33.525 | −5.192 | 65.554 | 1.00 | 45.54 | B |
| 2409 | O | SER | 107 | 33.516 | −4.416 | 64.589 | 1.00 | 45.33 | B |
| 2410 | N | ARG | 108 | 34.614 | −5.411 | 66.289 | 1.00 | 45.82 | B |
| 2411 | CA | ARG | 108 | 35.862 | −4.707 | 65.998 | 1.00 | 46.19 | B |
| 2412 | CB | ARG | 108 | 37.010 | −5.245 | 66.860 | 1.00 | 46.83 | B |
| 2413 | CG | ARG | 108 | 38.393 | −4.627 | 66.567 | 1.00 | 47.97 | B |
| 2414 | CD | ARG | 108 | 39.447 | −5.200 | 67.510 | 1.00 | 48.98 | B |
| 2415 | NE | ARG | 108 | 39.228 | −6.632 | 67.687 | 1.00 | 50.09 | B |
| 2416 | CZ | ARG | 108 | 39.654 | −7.573 | 66.848 | 1.00 | 50.65 | B |
| 2417 | NH1 | ARG | 108 | 40.350 | −7.241 | 65.764 | 1.00 | 50.78 | B |
| 2418 | NH2 | ARG | 108 | 39.341 | −8.851 | 67.074 | 1.00 | 51.14 | B |
| 2419 | C | ARG | 108 | 36.253 | −4.758 | 64.522 | 1.00 | 46.00 | B |
| 2420 | O | ARG | 108 | 36.381 | −3.721 | 63.881 | 1.00 | 45.86 | B |
| 2421 | N | LYS | 109 | 36.429 | −5.957 | 63.982 | 1.00 | 45.88 | B |
| 2422 | CA | LYS | 109 | 36.824 | −6.105 | 62.585 | 1.00 | 45.94 | B |
| 2423 | CB | LYS | 109 | 37.112 | −7.574 | 62.269 | 1.00 | 46.46 | B |
| 2424 | CG | LYS | 109 | 37.774 | −7.804 | 60.906 | 1.00 | 47.39 | B |
| 2425 | CD | LYS | 109 | 39.186 | −7.201 | 60.841 | 1.00 | 48.10 | B |
| 2426 | CE | LYS | 109 | 39.836 | −7.472 | 59.481 | 1.00 | 48.60 | B |
| 2427 | NZ | LYS | 109 | 41.268 | −7.022 | 59.421 | 1.00 | 49.19 | B |
| 2428 | C | LYS | 109 | 35.760 | −5.565 | 61.630 | 1.00 | 45.63 | B |
| 2429 | O | LYS | 109 | 36.079 | −4.855 | 60.670 | 1.00 | 45.55 | B |
| 2430 | N | VAL | 110 | 34.497 | −5.886 | 61.894 | 1.00 | 45.16 | B |
| 2431 | CA | VAL | 110 | 33.410 | −5.414 | 61.051 | 1.00 | 44.73 | B |
| 2432 | CB | VAL | 110 | 32.028 | −5.853 | 61.593 | 1.00 | 44.71 | B |
| 2433 | CG1 | VAL | 110 | 30.907 | −5.239 | 60.748 | 1.00 | 44.63 | B |
| 2434 | CG2 | VAL | 110 | 31.929 | −7.369 | 61.574 | 1.00 | 44.80 | B |
| 2435 | C | VAL | 110 | 33.432 | −3.894 | 60.944 | 1.00 | 44.42 | B |
| 2436 | O | VAL | 110 | 33.358 | −3.342 | 59.846 | 1.00 | 44.16 | B |
| 2437 | N | MET | 111 | 33.544 | −3.219 | 62.081 | 1.00 | 44.16 | B |
| 2438 | CA | MET | 111 | 33.568 | −1.766 | 62.091 | 1.00 | 44.20 | B |
| 2439 | CB | MET | 111 | 33.521 | −1.241 | 63.526 | 1.00 | 44.23 | B |
| 2440 | CG | MET | 111 | 32.216 | −1.562 | 64.241 | 1.00 | 44.37 | B |
| 2441 | SD | MET | 111 | 32.026 | −.698 | 65.800 | 1.00 | 44.68 | B |
| 2442 | CE | MET | 111 | 33.149 | −1.674 | 66.836 | 1.00 | 44.57 | B |
| 2443 | C | MET | 111 | 34.795 | −1.223 | 61.365 | 1.00 | 44.19 | B |
| 2444 | O | MET | 111 | 34.722 | −.204 | 60.676 | 1.00 | 44.09 | B |
| 2445 | N | GLU | 112 | 35.919 | −1.913 | 61.523 | 1.00 | 44.23 | B |
| 2446 | CA | GLU | 112 | 37.159 | −1.521 | 60.865 | 1.00 | 44.24 | B |
| 2447 | CB | GLU | 112 | 38.259 | −2.551 | 61.153 | 1.00 | 44.74 | B |
| 2448 | CG | GLU | 112 | 39.006 | −2.344 | 62.463 | 1.00 | 45.81 | B |
| 2449 | CD | GLU | 112 | 40.078 | −3.403 | 62.683 | 1.00 | 46.41 | B |
| 2450 | OE1 | GLU | 112 | 40.665 | −3.867 | 61.674 | 1.00 | 47.00 | B |
| 2451 | OE2 | GLU | 112 | 40.345 | −3.760 | 63.857 | 1.00 | 46.99 | B |
| 2452 | C | GLU | 112 | 36.935 | −1.453 | 59.359 | 1.00 | 43.86 | B |
| 2453 | O | GLU | 112 | 37.242 | −.454 | 58.710 | 1.00 | 43.75 | B |
| 2454 | N | ASN | 113 | 36.394 | −2.544 | 58.824 | 1.00 | 43.53 | B |
| 2455 | CA | ASN | 113 | 36.133 | −2.674 | 57.400 | 1.00 | 43.29 | B |
| 2456 | CB | ASN | 113 | 35.655 | −4.086 | 57.066 | 1.00 | 43.39 | B |
| 2457 | CG | ASN | 113 | 36.726 | −5.126 | 57.312 | 1.00 | 43.65 | B |
| 2458 | OD1 | ASN | 113 | 37.915 | −4.822 | 57.266 | 1.00 | 43.96 | B |
| 2459 | ND2 | ASN | 113 | 36.318 | −6.355 | 57.557 | 1.00 | 43.65 | B |
| 2460 | C | ASN | 113 | 35.121 | −1.656 | 56.927 | 1.00 | 43.03 | B |
| 2461 | O | ASN | 113 | 35.241 | −1.141 | 55.821 | 1.00 | 43.01 | B |
| 2462 | N | CYS | 114 | 34.126 | −1.361 | 57.755 | 1.00 | 42.64 | B |
| 2463 | CA | CYS | 114 | 33.133 | −.374 | 57.364 | 1.00 | 42.52 | B |
| 2464 | CB | CYS | 114 | 31.963 | −.336 | 58.359 | 1.00 | 42.13 | B |
| 2465 | SG | CYS | 114 | 30.837 | −1.760 | 58.238 | 1.00 | 41.13 | B |
| 2466 | C | CYS | 114 | 33.771 | 1.005 | 57.283 | 1.00 | 42.70 | B |
| 2467 | O | CYS | 114 | 33.579 | 1.724 | 56.308 | 1.00 | 42.60 | B |
| 2468 | N | VAL | 115 | 34.526 | 1.372 | 58.313 | 1.00 | 42.95 | B |
| 2469 | CA | VAL | 115 | 35.173 | 2.676 | 58.337 | 1.00 | 43.35 | B |
| 2470 | CB | VAL | 115 | 35.923 | 2.917 | 59.668 | 1.00 | 43.35 | B |
| 2471 | CG1 | VAL | 115 | 36.626 | 4.277 | 59.630 | 1.00 | 43.27 | B |
| 2472 | CG2 | VAL | 115 | 34.945 | 2.870 | 60.836 | 1.00 | 43.13 | B |
| 2473 | C | VAL | 115 | 36.157 | 2.822 | 57.177 | 1.00 | 43.62 | B |
| 2474 | O | VAL | 115 | 36.255 | 3.893 | 56.577 | 1.00 | 43.60 | B |
| 2475 | N | ALA | 116 | 36.882 | 1.751 | 56.864 | 1.00 | 43.95 | B |
| 2476 | CA | ALA | 116 | 37.840 | 1.787 | 55.764 | 1.00 | 44.42 | B |
| 2477 | CB | ALA | 116 | 38.616 | .471 | 55.688 | 1.00 | 44.43 | B |
| 2478 | C | ALA | 116 | 37.087 | 2.033 | 54.456 | 1.00 | 44.80 | B |
| 2479 | O | ALA | 116 | 37.505 | 2.844 | 53.627 | 1.00 | 44.82 | B |
| 2480 | N | HIS | 117 | 35.971 | 1.335 | 54.270 | 1.00 | 45.02 | B |
| 2481 | CA | HIS | 117 | 35.182 | 1.517 | 53.059 | 1.00 | 45.36 | B |
| 2482 | CB | HIS | 117 | 33.978 | .577 | 53.042 | 1.00 | 45.33 | B |
| 2483 | CG | HIS | 117 | 32.889 | 1.029 | 52.119 | 1.00 | 45.35 | B |

TABLE 1-continued

| Atom | Atom Type | Res | # | X | Y | Z | OCC | B | Mol. |
|---|---|---|---|---|---|---|---|---|---|
| 2484 | CD2 | HIS | 117 | 31.675 | 1.569 | 52.371 | 1.00 | 45.40 | B |
| 2485 | ND1 | HIS | 117 | 33.023 | 1.008 | 50.746 | 1.00 | 45.38 | B |
| 2486 | CE1 | HIS | 117 | 31.935 | 1.516 | 50.194 | 1.00 | 45.41 | B |
| 2487 | NE2 | HIS | 117 | 31.100 | 1.865 | 51.156 | 1.00 | 45.50 | B |
| 2488 | C | HIS | 117 | 34.669 | 2.946 | 52.951 | 1.00 | 45.61 | B |
| 2489 | O | HIS | 117 | 34.781 | 3.581 | 51.895 | 1.00 | 45.59 | B |
| 2490 | N | LEU | 118 | 34.094 | 3.435 | 54.044 | 1.00 | 45.87 | B |
| 2491 | CA | LEU | 118 | 33.529 | 4.775 | 54.088 | 1.00 | 46.40 | B |
| 2492 | CB | LEU | 118 | 32.919 | 5.026 | 55.469 | 1.00 | 46.21 | B |
| 2493 | CG | LEU | 118 | 31.703 | 4.141 | 55.786 | 1.00 | 46.17 | B |
| 2494 | CD1 | LEU | 118 | 31.313 | 4.277 | 57.258 | 1.00 | 46.06 | B |
| 2495 | CD2 | LEU | 118 | 30.539 | 4.535 | 54.877 | 1.00 | 46.03 | B |
| 2496 | C | LEU | 118 | 34.555 | 5.854 | 53.746 | 1.00 | 46.94 | B |
| 2497 | O | LEU | 118 | 34.243 | 6.817 | 53.032 | 1.00 | 46.82 | B |
| 2498 | N | LYS | 119 | 35.772 | 5.700 | 54.257 | 1.00 | 47.41 | B |
| 2499 | CA | LYS | 119 | 36.820 | 6.667 | 53.958 | 1.00 | 48.19 | B |
| 2500 | CB | LYS | 119 | 38.048 | 6.421 | 54.845 | 1.00 | 48.24 | B |
| 2501 | CG | LYS | 119 | 37.827 | 6.759 | 56.311 | 1.00 | 48.48 | B |
| 2502 | CD | LYS | 119 | 39.053 | 6.419 | 57.167 | 1.00 | 48.89 | B |
| 2503 | CE | LYS | 119 | 38.859 | 6.868 | 58.620 | 1.00 | 49.08 | B |
| 2504 | NZ | LYS | 119 | 39.997 | 6.460 | 59.507 | 1.00 | 49.31 | B |
| 2505 | C | LYS | 119 | 37.184 | 6.505 | 52.480 | 1.00 | 48.60 | B |
| 2506 | O | LYS | 119 | 37.322 | 7.480 | 51.746 | 1.00 | 48.64 | B |
| 2507 | N | SER | 120 | 37.309 | 5.256 | 52.046 | 1.00 | 49.03 | B |
| 2508 | CA | SER | 120 | 37.644 | 4.951 | 50.665 | 1.00 | 49.52 | B |
| 2509 | CB | SER | 120 | 37.553 | 3.445 | 50.432 | 1.00 | 49.70 | B |
| 2510 | OG | SER | 120 | 37.802 | 3.131 | 49.075 | 1.00 | 50.40 | B |
| 2511 | C | SER | 120 | 36.742 | 5.669 | 49.665 | 1.00 | 49.72 | B |
| 2512 | O | SER | 120 | 37.223 | 6.277 | 48.709 | 1.00 | 49.97 | B |
| 2513 | N | VAL | 121 | 35.432 | 5.599 | 49.877 | 1.00 | 49.77 | B |
| 2514 | CA | VAL | 121 | 34.492 | 6.234 | 48.965 | 1.00 | 49.62 | B |
| 2515 | CB | VAL | 121 | 33.164 | 5.439 | 48.885 | 1.00 | 49.60 | B |
| 2516 | CG1 | VAL | 121 | 33.443 | 4.016 | 48.403 | 1.00 | 49.53 | B |
| 2517 | CG2 | VAL | 121 | 32.477 | 5.422 | 50.241 | 1.00 | 49.55 | B |
| 2518 | C | VAL | 121 | 34.203 | 7.678 | 49.347 | 1.00 | 49.56 | B |
| 2519 | O | VAL | 121 | 33.225 | 8.271 | 48.886 | 1.00 | 49.65 | B |
| 2520 | N | GLY | 122 | 35.059 | 8.237 | 50.199 | 1.00 | 49.41 | B |
| 2521 | CA | GLY | 122 | 34.902 | 9.620 | 50.617 | 1.00 | 49.04 | B |
| 2522 | C | GLY | 122 | 33.617 | 9.988 | 51.334 | 1.00 | 48.88 | B |
| 2523 | O | GLY | 122 | 33.131 | 11.113 | 51.202 | 1.00 | 48.83 | B |
| 2524 | N | THR | 123 | 33.061 | 9.057 | 52.101 | 1.00 | 48.62 | B |
| 2525 | CA | THR | 123 | 31.839 | 9.339 | 52.836 | 1.00 | 48.45 | B |
| 2526 | CB | THR | 123 | 30.636 | 8.568 | 52.257 | 1.00 | 48.43 | B |
| 2527 | OG1 | THR | 123 | 30.897 | 7.159 | 52.307 | 1.00 | 48.37 | B |
| 2528 | CG2 | THR | 123 | 30.391 | 8.986 | 50.804 | 1.00 | 48.46 | B |
| 2529 | C | THR | 123 | 32.002 | 8.979 | 54.306 | 1.00 | 48.42 | B |
| 2530 | O | THR | 123 | 31.298 | 8.115 | 54.833 | 1.00 | 48.20 | B |
| 2531 | N | TYR | 124 | 32.950 | 9.636 | 54.967 | 1.00 | 48.36 | B |
| 2532 | CA | TYR | 124 | 33.165 | 9.382 | 56.380 | 1.00 | 48.37 | B |
| 2533 | CB | TYR | 124 | 34.393 | 8.499 | 56.607 | 1.00 | 48.68 | B |
| 2534 | CG | TYR | 124 | 34.443 | 7.935 | 58.013 | 1.00 | 49.05 | B |
| 2535 | CD1 | TYR | 124 | 33.410 | 7.121 | 58.491 | 1.00 | 49.13 | B |
| 2536 | CE1 | TYR | 124 | 33.417 | 6.634 | 59.796 | 1.00 | 49.25 | B |
| 2537 | CD2 | TYR | 124 | 35.492 | 8.246 | 58.880 | 1.00 | 49.15 | B |
| 2538 | CE2 | TYR | 124 | 35.507 | 7.762 | 60.193 | 1.00 | 49.40 | B |
| 2539 | CZ | TYR | 124 | 34.465 | 6.959 | 60.643 | 1.00 | 49.37 | B |
| 2540 | OH | TYR | 124 | 34.458 | 6.493 | 61.941 | 1.00 | 49.50 | B |
| 2541 | C | TYR | 124 | 33.313 | 10.677 | 57.152 | 1.00 | 48.26 | B |
| 2542 | O | TYR | 124 | 34.405 | 11.031 | 57.595 | 1.00 | 48.28 | B |
| 2543 | N | GLY | 125 | 32.197 | 11.383 | 57.302 | 1.00 | 48.00 | B |
| 2544 | CA | GLY | 125 | 32.196 | 12.632 | 58.035 | 1.00 | 47.72 | B |
| 2545 | C | GLY | 125 | 31.789 | 12.370 | 59.471 | 1.00 | 47.48 | B |
| 2546 | O | GLY | 125 | 31.771 | 11.218 | 59.910 | 1.00 | 47.44 | B |
| 2547 | N | ASP | 126 | 31.455 | 13.425 | 60.206 | 1.00 | 47.17 | B |
| 2548 | CA | ASP | 126 | 31.060 | 13.259 | 61.597 | 1.00 | 46.93 | B |
| 2549 | CB | ASP | 126 | 30.799 | 14.613 | 62.260 | 1.00 | 47.09 | B |
| 2550 | CG | ASP | 126 | 32.027 | 15.509 | 62.267 | 1.00 | 47.31 | B |
| 2551 | OD1 | ASP | 126 | 33.165 | 14.988 | 62.358 | 1.00 | 47.24 | B |
| 2552 | OD2 | ASP | 126 | 31.842 | 16.738 | 62.191 | 1.00 | 47.53 | B |
| 2553 | C | ASP | 126 | 29.809 | 12.397 | 61.717 | 1.00 | 46.61 | B |
| 2554 | O | ASP | 126 | 29.712 | 11.554 | 62.605 | 1.00 | 46.57 | B |
| 2555 | N | ALA | 127 | 28.852 | 12.617 | 60.821 | 1.00 | 46.15 | B |
| 2556 | CA | ALA | 127 | 27.609 | 11.857 | 60.839 | 1.00 | 45.71 | B |
| 2557 | CB | ALA | 127 | 26.721 | 12.273 | 59.675 | 1.00 | 45.75 | B |
| 2558 | C | ALA | 127 | 27.884 | 10.361 | 60.781 | 1.00 | 45.32 | B |
| 2559 | O | ALA | 127 | 27.304 | 9.590 | 61.545 | 1.00 | 45.23 | B |
| 2560 | N | GLU | 128 | 28.777 | 9.958 | 59.883 | 1.00 | 44.95 | B |

TABLE 1-continued

| Atom | Atom Type | Res | # | X | Y | Z | OCC | B | Mol. |
|---|---|---|---|---|---|---|---|---|---|
| 2561 | CA | GLU | 128 | 29.122 | 8.550 | 59.733 | 1.00 | 44.76 | B |
| 2562 | CB | GLU | 128 | 29.907 | 8.324 | 58.438 | 1.00 | 44.56 | B |
| 2563 | CG | GLU | 128 | 29.083 | 8.501 | 57.157 | 1.00 | 44.48 | B |
| 2564 | CD | GLU | 128 | 28.644 | 9.932 | 56.933 | 1.00 | 44.62 | B |
| 2565 | OE1 | GLU | 128 | 29.523 | 10.822 | 56.881 | 1.00 | 44.61 | B |
| 2566 | OE2 | GLU | 128 | 27.424 | 10.175 | 56.809 | 1.00 | 44.46 | B |
| 2567 | C | GLU | 128 | 29.920 | 8.035 | 60.928 | 1.00 | 44.73 | B |
| 2568 | O | GLU | 128 | 29.732 | 6.894 | 61.369 | 1.00 | 44.60 | B |
| 2569 | N | ALA | 129 | 30.816 | 8.869 | 61.446 | 1.00 | 44.62 | B |
| 2570 | CA | ALA | 129 | 31.619 | 8.484 | 62.602 | 1.00 | 44.60 | B |
| 2571 | CB | ALA | 129 | 32.627 | 9.587 | 62.938 | 1.00 | 44.61 | B |
| 2572 | C | ALA | 129 | 30.677 | 8.243 | 63.780 | 1.00 | 44.49 | B |
| 2573 | O | ALA | 129 | 30.813 | 7.267 | 64.515 | 1.00 | 44.56 | B |
| 2574 | N | GLU | 130 | 29.714 | 9.137 | 63.951 | 1.00 | 44.45 | B |
| 2575 | CA | GLU | 130 | 28.739 | 9.011 | 65.026 | 1.00 | 44.48 | B |
| 2576 | CB | GLU | 130 | 27.858 | 10.256 | 65.078 | 1.00 | 45.14 | B |
| 2577 | CG | GLU | 130 | 28.598 | 11.486 | 65.547 | 1.00 | 46.35 | B |
| 2578 | CD | GLU | 130 | 27.778 | 12.747 | 65.390 | 1.00 | 47.07 | B |
| 2579 | OE1 | GLU | 130 | 26.533 | 12.654 | 65.497 | 1.00 | 47.63 | B |
| 2580 | OE2 | GLU | 130 | 28.379 | 13.830 | 65.179 | 1.00 | 47.40 | B |
| 2581 | C | GLU | 130 | 27.869 | 7.770 | 64.829 | 1.00 | 44.02 | B |
| 2582 | O | GLU | 130 | 27.526 | 7.081 | 65.791 | 1.00 | 43.83 | B |
| 2583 | N | ALA | 131 | 27.503 | 7.500 | 63.580 | 1.00 | 43.48 | B |
| 2584 | CA | ALA | 131 | 26.693 | 6.330 | 63.271 | 1.00 | 43.03 | B |
| 2585 | CB | ALA | 131 | 26.338 | 6.303 | 61.778 | 1.00 | 42.94 | B |
| 2586 | C | ALA | 131 | 27.486 | 5.080 | 63.649 | 1.00 | 42.74 | B |
| 2587 | O | ALA | 131 | 26.938 | 4.141 | 64.221 | 1.00 | 42.68 | B |
| 2588 | N | MET | 132 | 28.779 | 5.072 | 63.337 | 1.00 | 42.40 | B |
| 2589 | CA | MET | 132 | 29.617 | 3.925 | 63.658 | 1.00 | 42.20 | B |
| 2590 | CB | MET | 132 | 30.981 | 4.051 | 62.983 | 1.00 | 42.10 | B |
| 2591 | CG | MET | 132 | 30.948 | 3.863 | 61.473 | 1.00 | 41.85 | B |
| 2592 | SD | MET | 132 | 30.030 | 2.369 | 60.961 | 1.00 | 41.55 | B |
| 2593 | CE | MET | 132 | 31.020 | 1.045 | 61.669 | 1.00 | 41.45 | B |
| 2594 | C | MET | 132 | 29.798 | 3.746 | 65.167 | 1.00 | 42.24 | B |
| 2595 | O | MET | 132 | 30.032 | 2.636 | 65.642 | 1.00 | 42.08 | B |
| 2596 | N | GLN | 133 | 29.687 | 4.838 | 65.914 | 1.00 | 42.30 | B |
| 2597 | CA | GLN | 133 | 29.817 | 4.777 | 67.366 | 1.00 | 42.53 | B |
| 2598 | CB | GLN | 133 | 30.058 | 6.169 | 67.950 | 1.00 | 42.87 | B |
| 2599 | CG | GLN | 133 | 30.362 | 6.163 | 69.436 | 1.00 | 43.75 | B |
| 2600 | CD | GLN | 133 | 31.485 | 5.202 | 69.789 | 1.00 | 44.32 | B |
| 2601 | OE1 | GLN | 133 | 32.478 | 5.088 | 69.056 | 1.00 | 45.00 | B |
| 2602 | NE2 | GLN | 133 | 31.342 | 4.510 | 70.920 | 1.00 | 44.68 | B |
| 2603 | C | GLN | 133 | 28.514 | 4.210 | 67.915 | 1.00 | 42.32 | B |
| 2604 | O | GLN | 133 | 28.507 | 3.468 | 68.898 | 1.00 | 42.35 | B |
| 2605 | N | LYS | 134 | 27.409 | 4.573 | 67.276 | 1.00 | 42.03 | B |
| 2606 | CA | LYS | 134 | 26.112 | 4.063 | 67.689 | 1.00 | 41.86 | B |
| 2607 | CB | LYS | 134 | 25.005 | 4.728 | 66.878 | 1.00 | 41.92 | B |
| 2608 | CG | LYS | 134 | 23.614 | 4.381 | 67.347 | 1.00 | 42.04 | B |
| 2609 | CD | LYS | 134 | 22.575 | 5.239 | 66.649 | 1.00 | 42.11 | B |
| 2610 | CE | LYS | 134 | 21.173 | 4.882 | 67.129 | 1.00 | 42.16 | B |
| 2611 | NZ | LYS | 134 | 20.148 | 5.808 | 66.572 | 1.00 | 42.17 | B |
| 2612 | C | LYS | 134 | 26.156 | 2.566 | 67.411 | 1.00 | 41.63 | B |
| 2613 | O | LYS | 134 | 25.701 | 1.756 | 68.215 | 1.00 | 41.61 | B |
| 2614 | N | PHE | 135 | 26.730 | 2.219 | 66.263 | 1.00 | 41.35 | B |
| 2615 | CA | PHE | 135 | 26.898 | .832 | 65.829 | 1.00 | 41.15 | B |
| 2616 | CB | PHE | 135 | 27.687 | .831 | 64.513 | 1.00 | 41.27 | B |
| 2617 | CG | PHE | 135 | 27.818 | −.518 | 63.857 | 1.00 | 41.32 | B |
| 2618 | CD1 | PHE | 135 | 27.058 | −.826 | 62.731 | 1.00 | 41.46 | B |
| 2619 | CD2 | PHE | 135 | 28.757 | −1.441 | 64.305 | 1.00 | 41.29 | B |
| 2620 | CE1 | PHE | 135 | 27.231 | −2.032 | 62.051 | 1.00 | 41.47 | B |
| 2621 | CE2 | PHE | 135 | 28.941 | −2.650 | 63.637 | 1.00 | 41.40 | B |
| 2622 | CZ | PHE | 135 | 28.177 | −2.947 | 62.504 | 1.00 | 41.48 | B |
| 2623 | C | PHE | 135 | 27.672 | .068 | 66.917 | 1.00 | 40.97 | B |
| 2624 | O | PHE | 135 | 27.218 | −.966 | 67.422 | 1.00 | 40.60 | B |
| 2625 | N | ALA | 136 | 28.846 | .590 | 67.271 | 1.00 | 40.77 | B |
| 2626 | CA | ALA | 136 | 29.692 | −.025 | 68.295 | 1.00 | 40.78 | B |
| 2627 | CB | ALA | 136 | 30.960 | .810 | 68.493 | 1.00 | 40.74 | B |
| 2628 | C | ALA | 136 | 28.966 | −.182 | 69.634 | 1.00 | 40.78 | B |
| 2629 | O | ALA | 136 | 29.035 | −1.235 | 70.260 | 1.00 | 40.59 | B |
| 2630 | N | GLU | 137 | 28.281 | .871 | 70.073 | 1.00 | 40.99 | B |
| 2631 | CA | GLU | 137 | 27.557 | .836 | 71.343 | 1.00 | 41.43 | B |
| 2632 | CB | GLU | 137 | 26.864 | 2.176 | 71.621 | 1.00 | 42.20 | B |
| 2633 | CG | GLU | 137 | 27.792 | 3.326 | 72.023 | 1.00 | 43.67 | B |
| 2634 | CD | GLU | 137 | 28.600 | 3.022 | 73.277 | 1.00 | 44.55 | B |
| 2635 | OE1 | GLU | 137 | 27.989 | 2.739 | 74.335 | 1.00 | 45.15 | B |
| 2636 | OE2 | GLU | 137 | 29.854 | 3.062 | 73.204 | 1.00 | 45.31 | B |
| 2637 | C | GLU | 137 | 26.514 | −.278 | 71.396 | 1.00 | 41.11 | B |

TABLE 1-continued

| Atom | Atom Type | Res | # | X | Y | Z | OCC | B | Mol. |
|---|---|---|---|---|---|---|---|---|---|
| 2638 | O | GLU | 137 | 26.279 | −.857 | 72.454 | 1.00 | 41.14 | B |
| 2639 | N | ALA | 138 | 25.888 | −.577 | 70.262 | 1.00 | 40.77 | B |
| 2640 | CA | ALA | 138 | 24.858 | −1.616 | 70.210 | 1.00 | 40.34 | B |
| 2641 | CB | ALA | 138 | 24.142 | −1.581 | 68.856 | 1.00 | 40.48 | B |
| 2642 | C | ALA | 138 | 25.408 | −3.005 | 70.466 | 1.00 | 40.04 | B |
| 2643 | O | ALA | 138 | 24.699 | −3.863 | 70.986 | 1.00 | 39.85 | B |
| 2644 | N | PHE | 139 | 26.665 | −3.243 | 70.102 | 1.00 | 39.74 | B |
| 2645 | CA | PHE | 139 | 27.269 | −4.561 | 70.314 | 1.00 | 39.63 | B |
| 2646 | CB | PHE | 139 | 28.345 | −4.853 | 69.260 | 1.00 | 39.43 | B |
| 2647 | CG | PHE | 139 | 27.811 | −5.179 | 67.890 | 1.00 | 39.21 | B |
| 2648 | CD1 | PHE | 139 | 27.460 | −4.167 | 67.005 | 1.00 | 39.17 | B |
| 2649 | CD2 | PHE | 139 | 27.685 | −6.506 | 67.484 | 1.00 | 39.03 | B |
| 2650 | CE1 | PHE | 139 | 26.989 | −4.469 | 65.723 | 1.00 | 39.05 | B |
| 2651 | CE2 | PHE | 139 | 27.216 | −6.822 | 66.211 | 1.00 | 39.04 | B |
| 2652 | CZ | PHE | 139 | 26.867 | −5.804 | 65.326 | 1.00 | 38.97 | B |
| 2653 | C | PHE | 139 | 27.918 | −4.716 | 71.683 | 1.00 | 39.74 | B |
| 2654 | O | PHE | 139 | 28.161 | −5.836 | 72.125 | 1.00 | 39.68 | B |
| 2655 | N | LYS | 140 | 28.210 | −3.606 | 72.352 | 1.00 | 39.82 | B |
| 2656 | CA | LYS | 140 | 28.884 | −3.681 | 73.650 | 1.00 | 40.23 | B |
| 2657 | CB | LYS | 140 | 29.142 | −2.274 | 74.193 | 1.00 | 40.29 | B |
| 2658 | CG | LYS | 140 | 30.232 | −1.521 | 73.430 | 1.00 | 40.72 | B |
| 2659 | CD | LYS | 140 | 30.644 | −.267 | 74.150 | 1.00 | 41.15 | B |
| 2660 | CE | LYS | 140 | 31.701 | .493 | 73.377 | 1.00 | 41.49 | B |
| 2661 | NZ | LYS | 140 | 31.992 | 1.789 | 74.052 | 1.00 | 41.94 | B |
| 2662 | C | LYS | 140 | 28.231 | −4.543 | 74.729 | 1.00 | 40.23 | B |
| 2663 | O | LYS | 140 | 28.914 | −5.361 | 75.355 | 1.00 | 40.34 | B |
| 2664 | N | PRO | 141 | 26.922 | −4.415 | 74.954 | 1.00 | 40.31 | B |
| 2665 | CD | PRO | 141 | 25.967 | −3.418 | 74.428 | 1.00 | 40.32 | B |
| 2666 | CA | PRO | 141 | 26.297 | −5.235 | 76.005 | 1.00 | 40.41 | B |
| 2667 | CB | PRO | 141 | 25.105 | −4.395 | 76.414 | 1.00 | 40.39 | B |
| 2668 | CG | PRO | 141 | 24.665 | −3.838 | 75.091 | 1.00 | 40.45 | B |
| 2669 | C | PRO | 141 | 25.877 | −6.623 | 75.540 | 1.00 | 40.40 | B |
| 2670 | O | PRO | 141 | 25.189 | −7.342 | 76.263 | 1.00 | 40.38 | B |
| 2671 | N | VAL | 142 | 26.320 | −7.000 | 74.349 | 1.00 | 40.41 | B |
| 2672 | CA | VAL | 142 | 25.954 | −8.285 | 73.778 | 1.00 | 40.49 | B |
| 2673 | CB | VAL | 142 | 25.438 | −8.098 | 72.316 | 1.00 | 40.45 | B |
| 2674 | CG1 | VAL | 142 | 25.140 | −9.451 | 71.680 | 1.00 | 40.38 | B |
| 2675 | CG2 | VAL | 142 | 24.196 | −7.220 | 72.314 | 1.00 | 40.30 | B |
| 2676 | C | VAL | 142 | 27.108 | −9.278 | 73.754 | 1.00 | 40.66 | B |
| 2677 | O | VAL | 142 | 28.268 | −8.904 | 73.599 | 1.00 | 40.50 | B |
| 2678 | N | ASN | 143 | 26.771 | −10.551 | 73.919 | 1.00 | 40.87 | B |
| 2679 | CA | ASN | 143 | 27.760 | −11.614 | 73.836 | 1.00 | 41.19 | B |
| 2680 | CB | ASN | 143 | 28.002 | −12.273 | 75.193 | 1.00 | 41.32 | B |
| 2681 | CG | ASN | 143 | 29.095 | −13.323 | 75.129 | 1.00 | 41.65 | B |
| 2682 | OD1 | ASN | 143 | 30.185 | −13.068 | 74.598 | 1.00 | 41.53 | B |
| 2683 | ND2 | ASN | 143 | 28.816 | −14.511 | 75.668 | 1.00 | 41.69 | B |
| 2684 | C | ASN | 143 | 27.166 | −12.629 | 72.871 | 1.00 | 41.36 | B |
| 2685 | O | ASN | 143 | 25.950 | −12.825 | 72.856 | 1.00 | 41.16 | B |
| 2686 | N | PHE | 144 | 28.010 | −13.271 | 72.069 | 1.00 | 41.61 | B |
| 2687 | CA | PHE | 144 | 27.518 | −14.243 | 71.098 | 1.00 | 42.05 | B |
| 2688 | CB | PHE | 144 | 27.889 | −13.834 | 69.662 | 1.00 | 41.83 | B |
| 2689 | CG | PHE | 144 | 27.275 | −12.542 | 69.202 | 1.00 | 41.67 | B |
| 2690 | CD1 | PHE | 144 | 28.017 | −11.364 | 69.198 | 1.00 | 41.68 | B |
| 2691 | CD2 | PHE | 144 | 25.964 | −12.509 | 68.735 | 1.00 | 41.57 | B |
| 2692 | CE1 | PHE | 144 | 27.461 | −10.166 | 68.730 | 1.00 | 41.53 | B |
| 2693 | CE2 | PHE | 144 | 25.401 | −11.328 | 68.270 | 1.00 | 41.42 | B |
| 2694 | CZ | PHE | 144 | 26.153 | −10.149 | 68.266 | 1.00 | 41.44 | B |
| 2695 | C | PHE | 144 | 28.030 | −15.658 | 71.312 | 1.00 | 42.43 | B |
| 2696 | O | PHE | 144 | 29.108 | −16.011 | 70.833 | 1.00 | 42.44 | B |
| 2697 | N | PRO | 145 | 27.273 | −16.486 | 72.040 | 1.00 | 42.74 | B |
| 2698 | CD | PRO | 145 | 26.074 | −16.216 | 72.850 | 1.00 | 42.84 | B |
| 2699 | CA | PRO | 145 | 27.741 | −17.857 | 72.241 | 1.00 | 42.99 | B |
| 2700 | CB | PRO | 145 | 26.766 | −18.408 | 73.281 | 1.00 | 42.99 | B |
| 2701 | CG | PRO | 145 | 26.266 | −17.161 | 73.984 | 1.00 | 43.06 | B |
| 2702 | C | PRO | 145 | 27.564 | −18.516 | 70.875 | 1.00 | 43.22 | B |
| 2703 | O | PRO | 145 | 26.905 | −17.959 | 69.991 | 1.00 | 43.21 | B |
| 2704 | N | PRO | 146 | 28.154 | −19.697 | 70.669 | 1.00 | 43.41 | B |
| 2705 | CD | PRO | 146 | 28.924 | −20.582 | 71.555 | 1.00 | 43.53 | B |
| 2706 | CA | PRO | 146 | 27.956 | −20.302 | 69.351 | 1.00 | 43.39 | B |
| 2707 | CB | PRO | 146 | 28.683 | −21.641 | 69.467 | 1.00 | 43.46 | B |
| 2708 | CG | PRO | 146 | 28.663 | −21.930 | 70.936 | 1.00 | 43.66 | B |
| 2709 | C | PRO | 146 | 26.462 | −20.447 | 69.063 | 1.00 | 43.32 | B |
| 2710 | O | PRO | 146 | 25.681 | −20.780 | 69.954 | 1.00 | 43.39 | B |
| 2711 | N | GLY | 147 | 26.063 | −20.160 | 67.828 | 1.00 | 43.08 | B |
| 2712 | CA | GLY | 147 | 24.658 | −20.264 | 67.473 | 1.00 | 42.71 | B |
| 2713 | C | GLY | 147 | 23.951 | −18.930 | 67.579 | 1.00 | 42.36 | B |
| 2714 | O | GLY | 147 | 22.958 | −18.687 | 66.893 | 1.00 | 42.50 | B |

TABLE 1-continued

| Atom | Atom Type | Res | # | X | Y | Z | OCC | B | Mol. |
|---|---|---|---|---|---|---|---|---|---|
| 2715 | N | ALA | 148 | 24.455 | −18.058 | 68.440 | 1.00 | 41.98 | B |
| 2716 | CA | ALA | 148 | 23.857 | −16.739 | 68.605 | 1.00 | 41.52 | B |
| 2717 | CB | ALA | 148 | 24.539 | −15.994 | 69.742 | 1.00 | 41.54 | B |
| 2718 | C | ALA | 148 | 24.037 | −15.998 | 67.281 | 1.00 | 41.26 | B |
| 2719 | O | ALA | 148 | 24.953 | −16.299 | 66.511 | 1.00 | 41.14 | B |
| 2720 | N | SER | 149 | 23.177 | −15.020 | 67.015 | 1.00 | 40.78 | B |
| 2721 | CA | SER | 149 | 23.253 | −14.316 | 65.749 | 1.00 | 40.27 | B |
| 2722 | CB | SER | 149 | 22.179 | −14.852 | 64.790 | 1.00 | 40.27 | B |
| 2723 | OG | SER | 149 | 22.238 | −16.259 | 64.676 | 1.00 | 40.39 | B |
| 2724 | C | SER | 149 | 23.087 | −12.816 | 65.823 | 1.00 | 39.88 | B |
| 2725 | O | SER | 149 | 22.569 | −12.264 | 66.800 | 1.00 | 39.88 | B |
| 2726 | N | VAL | 150 | 23.544 | −12.169 | 64.761 | 1.00 | 39.35 | B |
| 2727 | CA | VAL | 150 | 23.392 | −10.743 | 64.608 | 1.00 | 38.82 | B |
| 2728 | CB | VAL | 150 | 24.735 | −9.980 | 64.563 | 1.00 | 38.79 | B |
| 2729 | CG1 | VAL | 150 | 25.670 | −10.565 | 63.504 | 1.00 | 38.52 | B |
| 2730 | CG2 | VAL | 150 | 24.453 | −8.512 | 64.276 | 1.00 | 38.56 | B |
| 2731 | C | VAL | 150 | 22.687 | −10.599 | 63.274 | 1.00 | 38.60 | B |
| 2732 | O | VAL | 150 | 22.990 | −11.308 | 62.308 | 1.00 | 38.40 | B |
| 2733 | N | PHE | 151 | 21.717 | −9.703 | 63.232 | 1.00 | 38.32 | B |
| 2734 | CA | PHE | 151 | 20.978 | −9.478 | 62.009 | 1.00 | 38.25 | B |
| 2735 | CB | PHE | 151 | 19.490 | −9.775 | 62.229 | 1.00 | 38.31 | B |
| 2736 | CG | PHE | 151 | 19.165 | −11.244 | 62.290 | 1.00 | 38.50 | B |
| 2737 | CD1 | PHE | 151 | 18.844 | −11.943 | 61.130 | 1.00 | 38.57 | B |
| 2738 | CD2 | PHE | 151 | 19.196 | −11.931 | 63.500 | 1.00 | 38.67 | B |
| 2739 | CE1 | PHE | 151 | 18.554 | −13.308 | 61.173 | 1.00 | 38.62 | B |
| 2740 | CE2 | PHE | 151 | 18.908 | −13.304 | 63.559 | 1.00 | 38.64 | B |
| 2741 | CZ | PHE | 151 | 18.587 | −13.989 | 62.393 | 1.00 | 38.59 | B |
| 2742 | C | PHE | 151 | 21.150 | −8.034 | 61.587 | 1.00 | 38.12 | B |
| 2743 | O | PHE | 151 | 20.826 | −7.121 | 62.351 | 1.00 | 37.93 | B |
| 2744 | N | TYR | 152 | 21.681 | −7.837 | 60.383 | 1.00 | 37.98 | B |
| 2745 | CA | TYR | 152 | 21.847 | −6.502 | 59.837 | 1.00 | 37.97 | B |
| 2746 | CB | TYR | 152 | 23.189 | −6.340 | 59.109 | 1.00 | 37.80 | B |
| 2747 | CG | TYR | 152 | 24.421 | −6.563 | 59.959 | 1.00 | 37.59 | B |
| 2748 | CD1 | TYR | 152 | 25.033 | −7.812 | 60.017 | 1.00 | 37.45 | B |
| 2749 | CE1 | TYR | 152 | 26.202 | −8.006 | 60.756 | 1.00 | 37.50 | B |
| 2750 | CD2 | TYR | 152 | 25.002 | −5.512 | 60.667 | 1.00 | 37.53 | B |
| 2751 | CE2 | TYR | 152 | 26.170 | −5.696 | 61.408 | 1.00 | 37.41 | B |
| 2752 | CZ | TYR | 152 | 26.760 | −6.941 | 61.442 | 1.00 | 37.42 | B |
| 2753 | OH | TYR | 152 | 27.922 | −7.121 | 62.145 | 1.00 | 37.70 | B |
| 2754 | C | TYR | 152 | 20.720 | −6.338 | 58.827 | 1.00 | 38.12 | B |
| 2755 | O | TYR | 152 | 20.657 | −7.048 | 57.822 | 1.00 | 37.99 | B |
| 2756 | N | ARG | 153 | 19.818 | −5.415 | 59.110 | 1.00 | 38.21 | B |
| 2757 | CA | ARG | 153 | 18.709 | −5.153 | 58.223 | 1.00 | 38.55 | B |
| 2758 | CB | ARG | 153 | 17.428 | −4.982 | 59.041 | 1.00 | 39.13 | B |
| 2759 | CG | ARG | 153 | 16.155 | −4.771 | 58.226 | 1.00 | 39.93 | B |
| 2760 | CD | ARG | 153 | 15.067 | −4.167 | 59.126 | 1.00 | 40.78 | B |
| 2761 | NE | ARG | 153 | 14.543 | −2.975 | 58.488 | 1.00 | 41.84 | B |
| 2762 | CZ | ARG | 153 | 14.398 | −1.795 | 59.070 | 1.00 | 42.20 | B |
| 2763 | NH1 | ARG | 153 | 14.730 | −1.609 | 60.341 | 1.00 | 42.29 | B |
| 2764 | NH2 | ARG | 153 | 13.926 | −.784 | 58.352 | 1.00 | 43.17 | B |
| 2765 | C | ARG | 153 | 19.056 | −3.861 | 57.489 | 1.00 | 38.47 | B |
| 2766 | O | ARG | 153 | 18.983 | −2.774 | 58.062 | 1.00 | 38.45 | B |
| 2767 | N | GLN | 154 | 19.459 | −3.989 | 56.232 | 1.00 | 38.38 | B |
| 2768 | CA | GLN | 154 | 19.817 | −2.830 | 55.432 | 1.00 | 38.51 | B |
| 2769 | CB | GLN | 154 | 20.923 | −3.170 | 54.444 | 1.00 | 38.40 | B |
| 2770 | CG | GLN | 154 | 21.385 | −1.991 | 53.598 | 1.00 | 38.16 | B |
| 2771 | CD | GLN | 154 | 22.381 | −2.404 | 52.527 | 1.00 | 38.27 | B |
| 2772 | OE1 | GLN | 154 | 23.205 | −3.307 | 52.736 | 1.00 | 37.97 | B |
| 2773 | NE2 | GLN | 154 | 22.319 | −1.738 | 51.375 | 1.00 | 37.83 | B |
| 2774 | C | GLN | 154 | 18.593 | −2.356 | 54.663 | 1.00 | 38.75 | B |
| 2775 | O | GLN | 154 | 18.205 | −2.949 | 53.655 | 1.00 | 38.54 | B |
| 2776 | N | SER | 155 | 17.987 | −1.286 | 55.149 | 1.00 | 39.11 | B |
| 2777 | CA | SER | 155 | 16.814 | −.708 | 54.519 | 1.00 | 39.50 | B |
| 2778 | CB | SER | 155 | 16.042 | .135 | 55.532 | 1.00 | 39.57 | B |
| 2779 | OG | SER | 155 | 15.119 | .981 | 54.876 | 1.00 | 40.10 | B |
| 2780 | C | SER | 155 | 17.237 | .159 | 53.358 | 1.00 | 39.71 | B |
| 2781 | O | SER | 155 | 18.228 | .889 | 53.423 | 1.00 | 39.77 | B |
| 2782 | N | PRO | 156 | 16.479 | .113 | 52.249 | 1.00 | 39.90 | B |
| 2783 | CD | PRO | 156 | 15.293 | −.728 | 51.977 | 1.00 | 39.90 | B |
| 2784 | CA | PRO | 156 | 16.861 | .946 | 51.099 | 1.00 | 40.02 | B |
| 2785 | CB | PRO | 156 | 16.011 | .379 | 49.948 | 1.00 | 39.96 | B |
| 2786 | CG | PRO | 156 | 14.811 | −.238 | 50.609 | 1.00 | 39.92 | B |
| 2787 | C | PRO | 156 | 16.629 | 2.434 | 51.368 | 1.00 | 40.13 | B |
| 2788 | O | PRO | 156 | 17.058 | 3.294 | 50.606 | 1.00 | 40.33 | B |
| 2789 | N | ASP | 157 | 15.970 | 2.717 | 52.490 | 1.00 | 40.28 | B |
| 2790 | CA | ASP | 157 | 15.667 | 4.081 | 52.914 | 1.00 | 40.49 | B |
| 2791 | CB | ASP | 157 | 14.391 | 4.083 | 53.750 | 1.00 | 40.92 | B |

TABLE 1-continued

| Atom | Atom Type | Res | # | X | Y | Z | OCC | B | Mol. |
|---|---|---|---|---|---|---|---|---|---|
| 2792 | CG | ASP | 157 | 13.192 | 3.535 | 52.985 | 1.00 | 41.43 | B |
| 2793 | OD1 | ASP | 157 | 12.330 | 2.899 | 53.628 | 1.00 | 41.85 | B |
| 2794 | OD2 | ASP | 157 | 13.115 | 3.745 | 51.752 | 1.00 | 41.53 | B |
| 2795 | C | ASP | 157 | 16.816 | 4.723 | 53.729 | 1.00 | 40.33 | B |
| 2796 | O | ASP | 157 | 16.605 | 5.720 | 54.410 | 1.00 | 40.34 | B |
| 2797 | N | GLY | 158 | 18.010 | 4.133 | 53.657 | 1.00 | 40.15 | B |
| 2798 | CA | GLY | 158 | 19.140 | 4.691 | 54.365 | 1.00 | 39.99 | B |
| 2799 | C | GLY | 158 | 19.208 | 4.408 | 55.854 | 1.00 | 40.01 | B |
| 2800 | O | GLY | 158 | 19.720 | 5.220 | 56.627 | 1.00 | 39.89 | B |
| 2801 | N | ILE | 159 | 18.691 | 3.260 | 56.270 | 1.00 | 39.97 | B |
| 2802 | CA | ILE | 159 | 18.712 | 2.894 | 57.678 | 1.00 | 40.14 | B |
| 2803 | CB | ILE | 159 | 17.291 | 2.866 | 58.288 | 1.00 | 40.25 | B |
| 2804 | CG2 | ILE | 159 | 17.342 | 2.297 | 59.717 | 1.00 | 40.47 | B |
| 2805 | CG1 | ILE | 159 | 16.699 | 4.270 | 58.296 | 1.00 | 40.50 | B |
| 2806 | CD1 | ILE | 159 | 15.253 | 4.319 | 58.750 | 1.00 | 40.85 | B |
| 2807 | C | ILE | 159 | 19.299 | 1.508 | 57.827 | 1.00 | 40.03 | B |
| 2808 | O | ILE | 159 | 19.093 | .652 | 56.974 | 1.00 | 40.19 | B |
| 2809 | N | LEU | 160 | 20.043 | 1.298 | 58.906 | 1.00 | 39.83 | B |
| 2810 | CA | LEU | 160 | 20.617 | −.002 | 59.190 | 1.00 | 39.58 | B |
| 2811 | CB | LEU | 160 | 22.143 | .065 | 59.282 | 1.00 | 39.62 | B |
| 2812 | CG | LEU | 160 | 22.798 | −1.270 | 59.656 | 1.00 | 39.78 | B |
| 2813 | CD1 | LEU | 160 | 22.595 | −2.268 | 58.535 | 1.00 | 39.75 | B |
| 2814 | CD2 | LEU | 160 | 24.282 | −1.076 | 59.920 | 1.00 | 39.82 | B |
| 2815 | C | LEU | 160 | 20.044 | −.429 | 60.535 | 1.00 | 39.57 | B |
| 2816 | O | LEU | 160 | 20.316 | .194 | 61.571 | 1.00 | 39.38 | B |
| 2817 | N | GLY | 161 | 19.233 | −1.478 | 60.510 | 1.00 | 39.51 | B |
| 2818 | CA | GLY | 161 | 18.649 | −1.985 | 61.738 | 1.00 | 39.53 | B |
| 2819 | C | GLY | 161 | 19.532 | −3.094 | 62.270 | 1.00 | 39.62 | B |
| 2820 | O | GLY | 161 | 19.982 | −3.950 | 61.514 | 1.00 | 39.47 | B |
| 2821 | N | LEU | 162 | 19.795 | −3.075 | 63.570 | 1.00 | 39.77 | B |
| 2822 | CA | LEU | 162 | 20.640 | −4.084 | 64.191 | 1.00 | 39.95 | B |
| 2823 | CB | LEU | 162 | 21.800 | −3.412 | 64.926 | 1.00 | 39.98 | B |
| 2824 | CG | LEU | 162 | 22.800 | −2.611 | 64.088 | 1.00 | 39.93 | B |
| 2825 | CD1 | LEU | 162 | 23.870 | −2.025 | 65.010 | 1.00 | 39.86 | B |
| 2826 | CD2 | LEU | 162 | 23.434 | −3.519 | 63.046 | 1.00 | 39.77 | B |
| 2827 | C | LEU | 162 | 19.845 | −4.915 | 65.185 | 1.00 | 40.25 | B |
| 2828 | O | LEU | 162 | 19.181 | −4.371 | 66.061 | 1.00 | 40.06 | B |
| 2829 | N | SER | 163 | 19.923 | −6.232 | 65.047 | 1.00 | 40.73 | B |
| 2830 | CA | SER | 163 | 19.225 | −7.140 | 65.948 | 1.00 | 41.50 | B |
| 2831 | CB | SER | 163 | 18.017 | −7.774 | 65.255 | 1.00 | 41.34 | B |
| 2832 | OG | SER | 163 | 17.060 | −6.787 | 64.940 | 1.00 | 41.93 | B |
| 2833 | C | SER | 163 | 20.177 | −8.229 | 66.394 | 1.00 | 41.90 | B |
| 2834 | O | SER | 163 | 21.069 | −8.628 | 65.649 | 1.00 | 41.79 | B |
| 2835 | N | PHE | 164 | 19.965 | −8.708 | 67.613 | 1.00 | 42.62 | B |
| 2836 | CA | PHE | 164 | 20.790 | −9.752 | 68.194 | 1.00 | 43.59 | B |
| 2837 | CB | PHE | 164 | 21.629 | −9.164 | 69.325 | 1.00 | 43.10 | B |
| 2838 | CG | PHE | 164 | 22.354 | −7.909 | 68.939 | 1.00 | 42.72 | B |
| 2839 | CD1 | PHE | 164 | 22.033 | −6.694 | 69.532 | 1.00 | 42.56 | B |
| 2840 | CD2 | PHE | 164 | 23.350 | −7.939 | 67.966 | 1.00 | 42.53 | B |
| 2841 | CE1 | PHE | 164 | 22.695 | −5.517 | 69.157 | 1.00 | 42.44 | B |
| 2842 | CE2 | PHE | 164 | 24.015 | −6.770 | 67.587 | 1.00 | 42.40 | B |
| 2843 | CZ | PHE | 164 | 23.684 | −5.560 | 68.186 | 1.00 | 42.30 | B |
| 2844 | C | PHE | 164 | 19.885 | −10.854 | 68.719 | 1.00 | 44.57 | B |
| 2845 | O | PHE | 164 | 18.927 | −10.593 | 69.440 | 1.00 | 44.62 | B |
| 2846 | N | SER | 165 | 20.192 | −12.086 | 68.343 | 1.00 | 45.81 | B |
| 2847 | CA | SER | 165 | 19.406 | −13.237 | 68.756 | 1.00 | 47.07 | B |
| 2848 | CB | SER | 165 | 18.740 | −13.869 | 67.534 | 1.00 | 47.20 | B |
| 2849 | OG | SER | 165 | 18.030 | −15.044 | 67.884 | 1.00 | 47.51 | B |
| 2850 | C | SER | 165 | 20.276 | −14.274 | 69.450 | 1.00 | 48.03 | B |
| 2851 | O | SER | 165 | 21.477 | −14.371 | 69.190 | 1.00 | 47.90 | B |
| 2852 | N | PRO | 166 | 19.680 | −15.053 | 70.367 | 1.00 | 48.99 | B |
| 2853 | CD | PRO | 166 | 18.371 | −14.808 | 70.991 | 1.00 | 49.16 | B |
| 2854 | CA | PRO | 166 | 20.412 | −16.093 | 71.101 | 1.00 | 49.70 | B |
| 2855 | CB | PRO | 166 | 19.505 | −16.375 | 72.303 | 1.00 | 49.59 | B |
| 2856 | CG | PRO | 166 | 18.671 | −15.115 | 72.421 | 1.00 | 49.47 | B |
| 2857 | C | PRO | 166 | 20.562 | −17.302 | 70.183 | 1.00 | 50.32 | B |
| 2858 | O | PRO | 166 | 21.460 | −18.124 | 70.361 | 1.00 | 50.60 | B |
| 2859 | N | ASP | 167 | 19.658 | −17.388 | 69.208 | 1.00 | 51.19 | B |
| 2860 | CA | ASP | 167 | 19.676 | −18.454 | 68.210 | 1.00 | 51.86 | B |
| 2861 | CB | ASP | 167 | 18.444 | −19.374 | 68.339 | 1.00 | 52.48 | B |
| 2862 | CG | ASP | 167 | 17.131 | −18.684 | 67.994 | 1.00 | 53.04 | B |
| 2863 | OD1 | ASP | 167 | 17.150 | −17.538 | 67.483 | 1.00 | 53.48 | B |
| 2864 | OD2 | ASP | 167 | 16.075 | −19.309 | 68.238 | 1.00 | 53.42 | B |
| 2865 | C | ASP | 167 | 19.739 | −17.856 | 66.803 | 1.00 | 52.05 | B |
| 2866 | O | ASP | 167 | 20.231 | −16.736 | 66.626 | 1.00 | 52.04 | B |
| 2867 | N | THR | 168 | 19.244 | −18.605 | 65.822 | 1.00 | 52.24 | B |
| 2868 | CA | THR | 168 | 19.275 | −18.160 | 64.438 | 1.00 | 52.52 | B |

TABLE 1-continued

| Atom | Atom Type | Res | # | X | Y | Z | OCC | B | Mol. |
|---|---|---|---|---|---|---|---|---|---|
| 2869 | CB | THR | 168 | 19.601 | −19.338 | 63.460 | 1.00 | 52.70 | B |
| 2870 | OG1 | THR | 168 | 18.426 | −20.136 | 63.264 | 1.00 | 52.94 | B |
| 2871 | CG2 | THR | 168 | 20.742 | −20.229 | 63.992 | 1.00 | 52.77 | B |
| 2872 | C | THR | 168 | 17.948 | −17.539 | 64.006 | 1.00 | 52.52 | B |
| 2873 | O | THR | 168 | 17.751 | −17.201 | 62.838 | 1.00 | 52.57 | B |
| 2874 | N | SER | 169 | 17.029 | −17.390 | 64.949 | 1.00 | 52.53 | B |
| 2875 | CA | SER | 169 | 15.732 | −16.808 | 64.630 | 1.00 | 52.52 | B |
| 2876 | CB | SER | 169 | 14.657 | −17.285 | 65.624 | 1.00 | 52.63 | B |
| 2877 | OG | SER | 169 | 14.862 | −16.745 | 66.921 | 1.00 | 52.94 | B |
| 2878 | C | SER | 169 | 15.855 | −15.301 | 64.685 | 1.00 | 52.30 | B |
| 2879 | O | SER | 169 | 16.604 | −14.771 | 65.501 | 1.00 | 52.37 | B |
| 2880 | N | ILE | 170 | 15.129 | −14.629 | 63.797 | 1.00 | 52.04 | B |
| 2881 | CA | ILE | 170 | 15.123 | −13.170 | 63.699 | 1.00 | 51.76 | B |
| 2882 | CB | ILE | 170 | 14.443 | −12.701 | 62.387 | 1.00 | 51.87 | B |
| 2883 | CG2 | ILE | 170 | 14.507 | −11.174 | 62.267 | 1.00 | 51.94 | B |
| 2884 | CG1 | ILE | 170 | 15.132 | −13.338 | 61.176 | 1.00 | 52.02 | B |
| 2885 | CD1 | ILE | 170 | 14.499 | −12.952 | 59.862 | 1.00 | 52.12 | B |
| 2886 | C | ILE | 170 | 14.355 | −12.538 | 64.866 | 1.00 | 51.42 | B |
| 2887 | O | ILE | 170 | 13.164 | −12.793 | 65.032 | 1.00 | 51.55 | B |
| 2888 | N | PRO | 171 | 15.021 | −11.700 | 65.679 | 1.00 | 51.00 | B |
| 2889 | CD | PRO | 171 | 16.459 | −11.373 | 65.694 | 1.00 | 50.87 | B |
| 2890 | CA | PRO | 171 | 14.330 | −11.065 | 66.804 | 1.00 | 50.58 | B |
| 2891 | CB | PRO | 171 | 15.406 | −10.155 | 67.391 | 1.00 | 50.62 | B |
| 2892 | CG | PRO | 171 | 16.660 | −10.934 | 67.127 | 1.00 | 50.76 | B |
| 2893 | C | PRO | 171 | 13.126 | −10.278 | 66.289 | 1.00 | 50.24 | B |
| 2894 | O | PRO | 171 | 13.166 | −9.720 | 65.190 | 1.00 | 50.16 | B |
| 2895 | N | GLU | 172 | 12.054 | −10.237 | 67.074 | 1.00 | 49.84 | B |
| 2896 | CA | GLU | 172 | 10.855 | −9.514 | 66.666 | 1.00 | 49.51 | B |
| 2897 | CB | GLU | 172 | 9.652 | −9.909 | 67.540 | 1.00 | 50.12 | B |
| 2898 | CG | GLU | 172 | 9.453 | −9.065 | 68.797 | 1.00 | 51.12 | B |
| 2899 | CD | GLU | 172 | 8.170 | −9.422 | 69.548 | 1.00 | 51.84 | B |
| 2900 | OE1 | GLU | 172 | 7.546 | −10.461 | 69.213 | 1.00 | 52.26 | B |
| 2901 | OE2 | GLU | 172 | 7.791 | −8.667 | 70.477 | 1.00 | 52.28 | B |
| 2902 | C | GLU | 172 | 11.103 | −8.012 | 66.753 | 1.00 | 48.81 | B |
| 2903 | O | GLU | 172 | 10.439 | −7.224 | 66.083 | 1.00 | 48.69 | B |
| 2904 | N | LYS | 173 | 12.064 | −7.619 | 67.583 | 1.00 | 48.05 | B |
| 2905 | CA | LYS | 173 | 12.407 | −6.207 | 67.734 | 1.00 | 47.37 | B |
| 2906 | CB | LYS | 173 | 12.023 | −5.696 | 69.126 | 1.00 | 47.74 | B |
| 2907 | CG | LYS | 173 | 10.515 | −5.552 | 69.338 | 1.00 | 48.42 | B |
| 2908 | CD | LYS | 173 | 10.177 | −4.903 | 70.678 | 1.00 | 48.90 | B |
| 2909 | CE | LYS | 173 | 8.668 | −4.655 | 70.794 | 1.00 | 49.33 | B |
| 2910 | NZ | LYS | 173 | 8.276 | −3.907 | 72.038 | 1.00 | 49.77 | B |
| 2911 | C | LYS | 173 | 13.896 | −5.987 | 67.503 | 1.00 | 46.60 | B |
| 2912 | O | LYS | 173 | 14.715 | −6.859 | 67.780 | 1.00 | 46.44 | B |
| 2913 | N | GLU | 174 | 14.243 | −4.820 | 66.986 | 1.00 | 45.80 | B |
| 2914 | CA | GLU | 174 | 15.640 | −4.514 | 66.730 | 1.00 | 45.06 | B |
| 2915 | CB | GLU | 174 | 15.769 | −3.670 | 65.466 | 1.00 | 44.62 | B |
| 2916 | CG | GLU | 174 | 15.225 | −4.386 | 64.245 | 1.00 | 44.00 | B |
| 2917 | CD | GLU | 174 | 15.485 | −3.643 | 62.962 | 1.00 | 43.55 | B |
| 2918 | OE1 | GLU | 174 | 14.992 | −2.505 | 62.820 | 1.00 | 43.16 | B |
| 2919 | OE2 | GLU | 174 | 16.187 | −4.202 | 62.096 | 1.00 | 43.38 | B |
| 2920 | C | GLU | 174 | 16.224 | −3.795 | 67.924 | 1.00 | 44.73 | B |
| 2921 | O | GLU | 174 | 15.503 | −3.129 | 68.659 | 1.00 | 44.71 | B |
| 2922 | N | ALA | 175 | 17.529 | −3.947 | 68.120 | 1.00 | 44.36 | B |
| 2923 | CA | ALA | 175 | 18.220 | −3.322 | 69.242 | 1.00 | 44.03 | B |
| 2924 | CB | ALA | 175 | 19.475 | −4.120 | 69.588 | 1.00 | 43.98 | B |
| 2925 | C | ALA | 175 | 18.590 | −1.875 | 68.956 | 1.00 | 43.77 | B |
| 2926 | O | ALA | 175 | 18.631 | −1.046 | 69.863 | 1.00 | 43.58 | B |
| 2927 | N | ALA | 176 | 18.866 | −1.576 | 67.694 | 1.00 | 43.60 | B |
| 2928 | CA | ALA | 176 | 19.241 | −.225 | 67.318 | 1.00 | 43.48 | B |
| 2929 | CB | ALA | 176 | 20.722 | .006 | 67.623 | 1.00 | 43.40 | B |
| 2930 | C | ALA | 176 | 18.965 | .065 | 65.848 | 1.00 | 43.40 | B |
| 2931 | O | ALA | 176 | 18.955 | −.844 | 65.015 | 1.00 | 43.29 | B |
| 2932 | N | LEU | 177 | 18.747 | 1.338 | 65.545 | 1.00 | 43.43 | B |
| 2933 | CA | LEU | 177 | 18.489 | 1.784 | 64.186 | 1.00 | 43.57 | B |
| 2934 | CB | LEU | 177 | 17.085 | 2.356 | 64.052 | 1.00 | 43.76 | B |
| 2935 | CG | LEU | 177 | 15.951 | 1.368 | 64.264 | 1.00 | 44.08 | B |
| 2936 | CD1 | LEU | 177 | 14.635 | 2.092 | 64.008 | 1.00 | 44.44 | B |
| 2937 | CD2 | LEU | 177 | 16.099 | .186 | 63.306 | 1.00 | 44.33 | B |
| 2938 | C | LEU | 177 | 19.474 | 2.876 | 63.820 | 1.00 | 43.52 | B |
| 2939 | O | LEU | 177 | 19.379 | 4.001 | 64.317 | 1.00 | 43.68 | B |
| 2940 | N | ILE | 178 | 20.415 | 2.553 | 62.951 | 1.00 | 43.26 | B |
| 2941 | CA | ILE | 178 | 21.397 | 3.530 | 62.542 | 1.00 | 42.90 | B |
| 2942 | CB | ILE | 178 | 22.727 | 2.836 | 62.291 | 1.00 | 42.96 | B |
| 2943 | CG2 | ILE | 178 | 23.773 | 3.844 | 61.862 | 1.00 | 42.91 | B |
| 2944 | CG1 | ILE | 178 | 23.124 | 2.096 | 63.574 | 1.00 | 43.04 | B |
| 2945 | CD1 | ILE | 178 | 24.397 | 1.325 | 63.482 | 1.00 | 43.38 | B |

TABLE 1-continued

| Atom | Atom Type | Res | # | X | Y | Z | OCC | B | Mol. |
|---|---|---|---|---|---|---|---|---|---|
| 2946 | C | ILE | 178 | 20.878 | 4.248 | 61.301 | 1.00 | 42.70 | B |
| 2947 | O | ILE | 178 | 20.779 | 3.662 | 60.226 | 1.00 | 42.77 | B |
| 2948 | N | GLU | 179 | 20.516 | 5.513 | 61.471 | 1.00 | 42.39 | B |
| 2949 | CA | GLU | 179 | 19.985 | 6.294 | 60.367 | 1.00 | 42.19 | B |
| 2950 | CB | GLU | 179 | 18.908 | 7.241 | 60.880 | 1.00 | 42.69 | B |
| 2951 | CG | GLU | 179 | 17.863 | 6.513 | 61.715 | 1.00 | 43.77 | B |
| 2952 | CD | GLU | 179 | 16.730 | 7.415 | 62.146 | 1.00 | 44.44 | B |
| 2953 | OE1 | GLU | 179 | 16.872 | 8.654 | 62.041 | 1.00 | 45.03 | B |
| 2954 | OE2 | GLU | 179 | 15.695 | 6.887 | 62.602 | 1.00 | 45.01 | B |
| 2955 | C | GLU | 179 | 21.088 | 7.062 | 59.667 | 1.00 | 41.66 | B |
| 2956 | O | GLU | 179 | 21.371 | 8.216 | 59.987 | 1.00 | 41.68 | B |
| 2957 | N | ASN | 180 | 21.703 | 6.399 | 58.698 | 1.00 | 40.93 | B |
| 2958 | CA | ASN | 180 | 22.783 | 6.986 | 57.925 | 1.00 | 40.29 | B |
| 2959 | CB | ASN | 180 | 24.087 | 6.933 | 58.731 | 1.00 | 40.39 | B |
| 2960 | CG | ASN | 180 | 25.235 | 7.594 | 58.011 | 1.00 | 40.49 | B |
| 2961 | OD1 | ASN | 180 | 25.828 | 7.016 | 57.103 | 1.00 | 40.54 | B |
| 2962 | ND2 | ASN | 180 | 25.545 | 8.830 | 58.402 | 1.00 | 40.58 | B |
| 2963 | C | ASN | 180 | 22.918 | 6.192 | 56.638 | 1.00 | 39.68 | B |
| 2964 | O | ASN | 180 | 23.260 | 5.008 | 56.653 | 1.00 | 39.49 | B |
| 2965 | N | LYS | 181 | 22.633 | 6.852 | 55.523 | 1.00 | 39.22 | B |
| 2966 | CA | LYS | 181 | 22.679 | 6.212 | 54.212 | 1.00 | 38.74 | B |
| 2967 | CB | LYS | 181 | 22.402 | 7.237 | 53.111 | 1.00 | 38.86 | B |
| 2968 | CG | LYS | 181 | 22.295 | 6.628 | 51.708 | 1.00 | 38.92 | B |
| 2969 | CD | LYS | 181 | 21.143 | 5.616 | 51.645 | 1.00 | 39.15 | B |
| 2970 | CE | LYS | 181 | 20.789 | 5.244 | 50.202 | 1.00 | 39.22 | B |
| 2971 | NZ | LYS | 181 | 19.618 | 4.328 | 50.153 | 1.00 | 39.40 | B |
| 2972 | C | LYS | 181 | 23.996 | 5.504 | 53.918 | 1.00 | 38.49 | B |
| 2973 | O | LYS | 181 | 24.010 | 4.323 | 53.582 | 1.00 | 38.22 | B |
| 2974 | N | ALA | 182 | 25.099 | 6.233 | 54.046 | 1.00 | 38.19 | B |
| 2975 | CA | ALA | 182 | 26.424 | 5.684 | 53.774 | 1.00 | 38.00 | B |
| 2976 | CB | ALA | 182 | 27.494 | 6.760 | 54.011 | 1.00 | 37.96 | B |
| 2977 | C | ALA | 182 | 26.723 | 4.456 | 54.613 | 1.00 | 37.86 | B |
| 2978 | O | ALA | 182 | 27.195 | 3.448 | 54.099 | 1.00 | 37.94 | B |
| 2979 | N | VAL | 183 | 26.455 | 4.541 | 55.910 | 1.00 | 37.80 | B |
| 2980 | CA | VAL | 183 | 26.715 | 3.420 | 56.800 | 1.00 | 37.67 | B |
| 2981 | CB | VAL | 183 | 26.640 | 3.864 | 58.282 | 1.00 | 37.56 | B |
| 2982 | CG1 | VAL | 183 | 26.752 | 2.659 | 59.211 | 1.00 | 37.39 | B |
| 2983 | CG2 | VAL | 183 | 27.782 | 4.847 | 58.575 | 1.00 | 37.59 | B |
| 2984 | C | VAL | 183 | 25.746 | 2.265 | 56.556 | 1.00 | 37.73 | B |
| 2985 | O | VAL | 183 | 26.120 | 1.094 | 56.687 | 1.00 | 37.63 | B |
| 2986 | N | SER | 184 | 24.513 | 2.587 | 56.176 | 1.00 | 37.66 | B |
| 2987 | CA | SER | 184 | 23.512 | 1.549 | 55.943 | 1.00 | 37.80 | B |
| 2988 | CB | SER | 184 | 22.197 | 2.170 | 55.438 | 1.00 | 37.71 | B |
| 2989 | OG | SER | 184 | 22.277 | 2.593 | 54.086 | 1.00 | 37.69 | B |
| 2990 | C | SER | 184 | 23.982 | .446 | 54.989 | 1.00 | 37.86 | B |
| 2991 | O | SER | 184 | 23.620 | −.718 | 55.162 | 1.00 | 38.03 | B |
| 2992 | N | SER | 185 | 24.807 | .791 | 54.001 | 1.00 | 37.91 | B |
| 2993 | CA | SER | 185 | 25.280 | −.213 | 53.048 | 1.00 | 38.02 | B |
| 2994 | CB | SER | 185 | 25.174 | .329 | 51.625 | 1.00 | 38.00 | B |
| 2995 | OG | SER | 185 | 26.058 | 1.422 | 51.448 | 1.00 | 38.14 | B |
| 2996 | C | SER | 185 | 26.715 | −.682 | 53.281 | 1.00 | 38.13 | B |
| 2997 | O | SER | 185 | 27.184 | −1.611 | 52.618 | 1.00 | 38.15 | B |
| 2998 | N | ALA | 186 | 27.410 | −.051 | 54.221 | 1.00 | 38.18 | B |
| 2999 | CA | ALA | 186 | 28.798 | −.402 | 54.489 | 1.00 | 38.35 | B |
| 3000 | CB | ALA | 186 | 29.361 | .471 | 55.626 | 1.00 | 38.24 | B |
| 3001 | C | ALA | 186 | 28.993 | −1.872 | 54.817 | 1.00 | 38.42 | B |
| 3002 | O | ALA | 186 | 29.856 | −2.525 | 54.240 | 1.00 | 38.53 | B |
| 3003 | N | VAL | 187 | 28.195 | −2.394 | 55.740 | 1.00 | 38.61 | B |
| 3004 | CA | VAL | 187 | 28.328 | −3.791 | 56.131 | 1.00 | 38.82 | B |
| 3005 | CB | VAL | 187 | 27.256 | −4.194 | 57.167 | 1.00 | 38.75 | B |
| 3006 | CG1 | VAL | 187 | 27.395 | −5.670 | 57.513 | 1.00 | 38.72 | B |
| 3007 | CG2 | VAL | 187 | 27.405 | −3.348 | 58.420 | 1.00 | 38.82 | B |
| 3008 | C | VAL | 187 | 28.257 | −4.741 | 54.937 | 1.00 | 38.98 | B |
| 3009 | O | VAL | 187 | 29.143 | −5.570 | 54.750 | 1.00 | 38.83 | B |
| 3010 | N | LEU | 188 | 27.214 | −4.625 | 54.123 | 1.00 | 39.29 | B |
| 3011 | CA | LEU | 188 | 27.088 | −5.510 | 52.966 | 1.00 | 39.62 | B |
| 3012 | CB | LEU | 188 | 25.748 | −5.291 | 52.264 | 1.00 | 39.52 | B |
| 3013 | CG | LEU | 188 | 25.445 | −6.212 | 51.080 | 1.00 | 39.49 | B |
| 3014 | CD1 | LEU | 188 | 25.559 | −7.676 | 51.495 | 1.00 | 39.46 | B |
| 3015 | CD2 | LEU | 188 | 24.064 | −5.899 | 50.559 | 1.00 | 39.39 | B |
| 3016 | C | LEU | 188 | 28.230 | −5.270 | 51.984 | 1.00 | 39.94 | B |
| 3017 | O | LEU | 188 | 28.705 | −6.191 | 51.322 | 1.00 | 39.83 | B |
| 3018 | N | GLU | 189 | 28.664 | −4.020 | 51.894 | 1.00 | 40.45 | B |
| 3019 | CA | GLU | 189 | 29.760 | −3.663 | 51.005 | 1.00 | 41.13 | B |
| 3020 | CB | GLU | 189 | 30.035 | −2.161 | 51.094 | 1.00 | 41.24 | B |
| 3021 | CG | GLU | 189 | 31.115 | −1.673 | 50.161 | 1.00 | 41.69 | B |
| 3022 | CD | GLU | 189 | 30.654 | −1.591 | 48.721 | 1.00 | 41.85 | B |

TABLE 1-continued

| Atom | Atom Type | Res | # | X | Y | Z | OCC | B | Mol. |
|---|---|---|---|---|---|---|---|---|---|
| 3023 | OE1 | GLU | 189 | 29.616 | −.949 | 48.461 | 1.00 | 41.80 | B |
| 3024 | OE2 | GLU | 189 | 31.335 | −2.163 | 47.847 | 1.00 | 42.32 | B |
| 3025 | C | GLU | 189 | 31.020 | −4.440 | 51.389 | 1.00 | 41.41 | B |
| 3026 | O | GLU | 189 | 31.725 | −4.961 | 50.523 | 1.00 | 41.54 | B |
| 3027 | N | THR | 190 | 31.303 | −4.518 | 52.689 | 1.00 | 41.79 | B |
| 3028 | CA | THR | 190 | 32.486 | −5.237 | 53.162 | 1.00 | 42.21 | B |
| 3029 | CB | THR | 190 | 32.727 | −5.026 | 54.673 | 1.00 | 42.24 | B |
| 3030 | OG1 | THR | 190 | 31.680 | −5.667 | 55.414 | 1.00 | 42.19 | B |
| 3031 | CG2 | THR | 190 | 32.762 | −3.534 | 55.012 | 1.00 | 42.05 | B |
| 3032 | C | THR | 190 | 32.354 | −6.736 | 52.934 | 1.00 | 42.52 | B |
| 3033 | O | THR | 190 | 33.318 | −7.478 | 53.076 | 1.00 | 42.62 | B |
| 3034 | N | MET | 191 | 31.159 | −7.189 | 52.580 | 1.00 | 42.82 | B |
| 3035 | CA | MET | 191 | 30.962 | −8.612 | 52.369 | 1.00 | 43.21 | B |
| 3036 | CB | MET | 191 | 29.681 | −9.046 | 53.056 | 1.00 | 43.46 | B |
| 3037 | CG | MET | 191 | 29.760 | −8.921 | 54.551 | 1.00 | 43.97 | B |
| 3038 | SD | MET | 191 | 28.164 | −9.202 | 55.245 | 1.00 | 44.79 | B |
| 3039 | CE | MET | 191 | 28.526 | −8.892 | 56.998 | 1.00 | 44.57 | B |
| 3040 | C | MET | 191 | 30.936 | −9.060 | 50.915 | 1.00 | 43.35 | B |
| 3041 | O | MET | 191 | 31.417 | −10.148 | 50.595 | 1.00 | 43.23 | B |
| 3042 | N | ILE | 192 | 30.370 | −8.237 | 50.039 | 1.00 | 43.58 | B |
| 3043 | CA | ILE | 192 | 30.291 | −8.591 | 48.625 | 1.00 | 43.98 | B |
| 3044 | CB | ILE | 192 | 28.853 | −9.000 | 48.217 | 1.00 | 43.85 | B |
| 3045 | CG2 | ILE | 192 | 28.439 | −10.249 | 48.966 | 1.00 | 43.73 | B |
| 3046 | CG1 | ILE | 192 | 27.882 | −7.845 | 48.475 | 1.00 | 43.66 | B |
| 3047 | CD1 | ILE | 192 | 26.485 | −8.087 | 47.922 | 1.00 | 43.56 | B |
| 3048 | C | ILE | 192 | 30.746 | −7.470 | 47.701 | 1.00 | 44.41 | B |
| 3049 | O | ILE | 192 | 30.623 | −7.574 | 46.481 | 1.00 | 44.24 | B |
| 3050 | N | GLY | 193 | 31.262 | −6.397 | 48.289 | 1.00 | 45.00 | B |
| 3051 | CA | GLY | 193 | 31.736 | −5.276 | 47.501 | 1.00 | 45.90 | B |
| 3052 | C | GLY | 193 | 33.059 | −5.577 | 46.821 | 1.00 | 46.58 | B |
| 3053 | O | GLY | 193 | 33.675 | −6.617 | 47.067 | 1.00 | 46.43 | B |
| 3054 | N | GLU | 194 | 33.502 | −4.655 | 45.975 | 1.00 | 47.35 | B |
| 3055 | CA | GLU | 194 | 34.749 | −4.833 | 45.247 | 1.00 | 48.29 | B |
| 3056 | CB | GLU | 194 | 35.106 | −3.555 | 44.492 | 1.00 | 48.33 | B |
| 3057 | CG | GLU | 194 | 36.206 | −3.739 | 43.460 | 1.00 | 48.56 | B |
| 3058 | CD | GLU | 194 | 36.792 | −2.418 | 42.979 | 1.00 | 48.66 | B |
| 3059 | OE1 | GLU | 194 | 36.092 | −1.381 | 43.061 | 1.00 | 48.60 | B |
| 3060 | OE2 | GLU | 194 | 37.952 | −2.416 | 42.506 | 1.00 | 48.79 | B |
| 3061 | C | GLU | 194 | 35.928 | −5.208 | 46.144 | 1.00 | 48.92 | B |
| 3062 | O | GLU | 194 | 36.695 | −6.121 | 45.827 | 1.00 | 49.02 | B |
| 3063 | N | HIS | 195 | 36.056 | −4.524 | 47.277 | 1.00 | 49.63 | B |
| 3064 | CA | HIS | 195 | 37.189 | −4.764 | 48.166 | 1.00 | 50.42 | B |
| 3065 | CB | HIS | 195 | 37.550 | −3.468 | 48.880 | 1.00 | 50.71 | B |
| 3066 | CG | HIS | 195 | 37.833 | −2.346 | 47.937 | 1.00 | 51.19 | B |
| 3067 | CD2 | HIS | 195 | 37.296 | −1.103 | 47.823 | 1.00 | 51.39 | B |
| 3068 | ND1 | HIS | 195 | 38.735 | −2.459 | 46.894 | 1.00 | 51.39 | B |
| 3069 | CE1 | HIS | 195 | 38.743 | −1.339 | 46.193 | 1.00 | 51.51 | B |
| 3070 | NE2 | HIS | 195 | 37.877 | −.502 | 46.741 | 1.00 | 51.64 | B |
| 3071 | C | HIS | 195 | 37.065 | −5.914 | 49.144 | 1.00 | 50.80 | B |
| 3072 | O | HIS | 195 | 37.977 | −6.154 | 49.935 | 1.00 | 50.97 | B |
| 3073 | N | ALA | 196 | 35.959 | −6.644 | 49.098 | 1.00 | 51.08 | B |
| 3074 | CA | ALA | 196 | 35.819 | −7.795 | 49.978 | 1.00 | 51.47 | B |
| 3075 | CB | ALA | 196 | 34.375 | −8.266 | 50.006 | 1.00 | 51.29 | B |
| 3076 | C | ALA | 196 | 36.711 | −8.858 | 49.335 | 1.00 | 51.73 | B |
| 3077 | O | ALA | 196 | 36.597 | −9.105 | 48.133 | 1.00 | 51.89 | B |
| 3078 | N | VAL | 197 | 37.599 | −9.477 | 50.106 | 1.00 | 52.04 | B |
| 3079 | CA | VAL | 197 | 38.465 | −10.489 | 49.519 | 1.00 | 52.26 | B |
| 3080 | CB | VAL | 197 | 39.826 | −10.623 | 50.254 | 1.00 | 52.51 | B |
| 3081 | CG1 | VAL | 197 | 40.691 | −11.638 | 49.512 | 1.00 | 52.65 | B |
| 3082 | CG2 | VAL | 197 | 40.556 | −9.282 | 50.270 | 1.00 | 52.53 | B |
| 3083 | C | VAL | 197 | 37.798 | −11.851 | 49.479 | 1.00 | 52.23 | B |
| 3084 | O | VAL | 197 | 37.899 | −12.566 | 48.482 | 1.00 | 52.40 | B |
| 3085 | N | SER | 198 | 37.107 | −12.220 | 50.548 | 1.00 | 52.13 | B |
| 3086 | CA | SER | 198 | 36.429 | −13.513 | 50.553 | 1.00 | 51.95 | B |
| 3087 | CB | SER | 198 | 35.740 | −13.764 | 51.886 | 1.00 | 52.14 | B |
| 3088 | OG | SER | 198 | 36.684 | −13.861 | 52.938 | 1.00 | 52.47 | B |
| 3089 | C | SER | 198 | 35.391 | −13.493 | 49.450 | 1.00 | 51.72 | B |
| 3090 | O | SER | 198 | 34.429 | −12.733 | 49.514 | 1.00 | 51.76 | B |
| 3091 | N | PRO | 199 | 35.577 | −14.320 | 48.415 | 1.00 | 51.44 | B |
| 3092 | CD | PRO | 199 | 36.784 | −15.079 | 48.038 | 1.00 | 51.39 | B |
| 3093 | CA | PRO | 199 | 34.610 | −14.333 | 47.318 | 1.00 | 51.14 | B |
| 3094 | CB | PRO | 199 | 35.457 | −14.735 | 46.130 | 1.00 | 51.27 | B |
| 3095 | CG | PRO | 199 | 36.344 | −15.754 | 46.744 | 1.00 | 51.36 | B |
| 3096 | C | PRO | 199 | 33.472 | −15.299 | 47.473 | 1.00 | 50.85 | B |
| 3097 | O | PRO | 199 | 32.655 | −15.381 | 46.564 | 1.00 | 50.87 | B |
| 3098 | N | ASP | 200 | 33.399 | −16.015 | 48.594 | 1.00 | 50.39 | B |
| 3099 | CA | ASP | 200 | 32.351 | −17.017 | 48.767 | 1.00 | 49.97 | B |

TABLE 1-continued

| Atom | Atom Type | Res | # | X | Y | Z | OCC | B | Mol. |
|---|---|---|---|---|---|---|---|---|---|
| 3100 | CB | ASP | 200 | 32.499 | −17.761 | 50.123 | 1.00 | 50.08 | B |
| 3101 | CG | ASP | 200 | 32.358 | −16.837 | 51.338 | 1.00 | 50.18 | B |
| 3102 | OD1 | ASP | 200 | 32.336 | −15.598 | 51.174 | 1.00 | 50.31 | B |
| 3103 | OD2 | ASP | 200 | 32.279 | −17.357 | 52.479 | 1.00 | 50.28 | B |
| 3104 | C | ASP | 200 | 30.925 | −16.488 | 48.590 | 1.00 | 49.64 | B |
| 3105 | O | ASP | 200 | 30.109 | −17.110 | 47.898 | 1.00 | 49.46 | B |
| 3106 | N | LEU | 201 | 30.613 | −15.346 | 49.188 | 1.00 | 49.24 | B |
| 3107 | CA | LEU | 201 | 29.267 | −14.804 | 49.061 | 1.00 | 49.02 | B |
| 3108 | CB | LEU | 201 | 29.046 | −13.648 | 50.044 | 1.00 | 49.14 | B |
| 3109 | CG | LEU | 201 | 28.857 | −14.062 | 51.513 | 1.00 | 49.23 | B |
| 3110 | CD1 | LEU | 201 | 28.846 | −12.833 | 52.390 | 1.00 | 49.11 | B |
| 3111 | CD2 | LEU | 201 | 27.558 | −14.833 | 51.680 | 1.00 | 49.22 | B |
| 3112 | C | LEU | 201 | 29.010 | −14.351 | 47.632 | 1.00 | 48.81 | B |
| 3113 | O | LEU | 201 | 27.945 | −14.612 | 47.086 | 1.00 | 48.56 | B |
| 3114 | N | LYS | 202 | 29.994 | −13.699 | 47.021 | 1.00 | 48.72 | B |
| 3115 | CA | LYS | 202 | 29.847 | −13.225 | 45.648 | 1.00 | 48.73 | B |
| 3116 | CB | LYS | 202 | 31.106 | −12.493 | 45.195 | 1.00 | 48.87 | B |
| 3117 | CG | LYS | 202 | 31.407 | −11.242 | 45.979 | 1.00 | 49.17 | B |
| 3118 | CD | LYS | 202 | 32.650 | −10.580 | 45.431 | 1.00 | 49.64 | B |
| 3119 | CE | LYS | 202 | 33.209 | −9.574 | 46.415 | 1.00 | 50.07 | B |
| 3120 | NZ | LYS | 202 | 34.703 | −9.507 | 46.342 | 1.00 | 50.51 | B |
| 3121 | C | LYS | 202 | 29.564 | −14.385 | 44.706 | 1.00 | 48.61 | B |
| 3122 | O | LYS | 202 | 28.737 | −14.277 | 43.804 | 1.00 | 48.42 | B |
| 3123 | N | ARG | 203 | 30.250 | −15.503 | 44.926 | 1.00 | 48.60 | B |
| 3124 | CA | ARG | 203 | 30.058 | −16.684 | 44.094 | 1.00 | 48.66 | B |
| 3125 | CB | ARG | 203 | 31.087 | −17.753 | 44.450 | 1.00 | 49.17 | B |
| 3126 | CG | ARG | 203 | 32.489 | −17.349 | 44.052 | 1.00 | 49.89 | B |
| 3127 | CD | ARG | 203 | 33.531 | −18.353 | 44.501 | 1.00 | 50.55 | B |
| 3128 | NE | ARG | 203 | 34.872 | −17.859 | 44.202 | 1.00 | 51.37 | B |
| 3129 | CZ | ARG | 203 | 35.996 | −18.463 | 44.578 | 1.00 | 51.84 | B |
| 3130 | NH1 | ARG | 203 | 35.945 | −19.596 | 45.274 | 1.00 | 52.02 | B |
| 3131 | NH2 | ARG | 203 | 37.174 | −17.931 | 44.263 | 1.00 | 52.02 | B |
| 3132 | C | ARG | 203 | 28.654 | −17.242 | 44.229 | 1.00 | 48.40 | B |
| 3133 | O | ARG | 203 | 28.025 | −17.598 | 43.229 | 1.00 | 48.32 | B |
| 3134 | N | CYS | 204 | 28.155 | −17.316 | 45.461 | 1.00 | 48.04 | B |
| 3135 | CA | CYS | 204 | 26.803 | −17.819 | 45.677 | 1.00 | 47.72 | B |
| 3136 | CB | CYS | 204 | 26.424 | −17.794 | 47.161 | 1.00 | 47.90 | B |
| 3137 | SG | CYS | 204 | 27.254 | −19.022 | 48.186 | 1.00 | 48.49 | B |
| 3138 | C | CYS | 204 | 25.828 | −16.949 | 44.911 | 1.00 | 47.34 | B |
| 3139 | O | CYS | 204 | 24.968 | −17.452 | 44.206 | 1.00 | 47.26 | B |
| 3140 | N | LEU | 205 | 25.969 | −15.636 | 45.057 | 1.00 | 46.97 | B |
| 3141 | CA | LEU | 205 | 25.089 | −14.698 | 44.382 | 1.00 | 46.69 | B |
| 3142 | CB | LEU | 205 | 25.493 | −13.267 | 44.742 | 1.00 | 46.40 | B |
| 3143 | CG | LEU | 205 | 25.144 | −12.876 | 46.184 | 1.00 | 46.24 | B |
| 3144 | CD1 | LEU | 205 | 25.849 | −11.584 | 46.574 | 1.00 | 45.98 | B |
| 3145 | CD2 | LEU | 205 | 23.631 | −12.735 | 46.309 | 1.00 | 45.95 | B |
| 3146 | C | LEU | 205 | 25.091 | −14.898 | 42.867 | 1.00 | 46.64 | B |
| 3147 | O | LEU | 205 | 24.035 | −14.908 | 42.236 | 1.00 | 46.55 | B |
| 3148 | N | ALA | 206 | 26.277 | −15.070 | 42.294 | 1.00 | 46.69 | B |
| 3149 | CA | ALA | 206 | 26.413 | −15.278 | 40.855 | 1.00 | 46.88 | B |
| 3150 | CB | ALA | 206 | 27.890 | −15.249 | 40.453 | 1.00 | 46.76 | B |
| 3151 | C | ALA | 206 | 25.789 | −16.608 | 40.449 | 1.00 | 47.02 | B |
| 3152 | O | ALA | 206 | 25.157 | −16.712 | 39.401 | 1.00 | 47.02 | B |
| 3153 | N | ALA | 207 | 25.950 | −17.615 | 41.299 | 1.00 | 47.19 | B |
| 3154 | CA | ALA | 207 | 25.420 | −18.944 | 41.024 | 1.00 | 47.39 | B |
| 3155 | CB | ALA | 207 | 26.029 | −19.947 | 42.001 | 1.00 | 47.39 | B |
| 3156 | C | ALA | 207 | 23.898 | −19.048 | 41.073 | 1.00 | 47.64 | B |
| 3157 | O | ALA | 207 | 23.280 | −19.643 | 40.189 | 1.00 | 47.61 | B |
| 3158 | N | ARG | 208 | 23.285 | −18.456 | 42.089 | 1.00 | 47.89 | B |
| 3159 | CA | ARG | 208 | 21.840 | −18.568 | 42.240 | 1.00 | 48.31 | B |
| 3160 | CB | ARG | 208 | 21.515 | −18.804 | 43.723 | 1.00 | 48.48 | B |
| 3161 | CG | ARG | 208 | 22.580 | −18.279 | 44.667 | 1.00 | 48.69 | B |
| 3162 | CD | ARG | 208 | 22.741 | −19.152 | 45.909 | 1.00 | 48.67 | B |
| 3163 | NE | ARG | 208 | 21.526 | −19.153 | 46.710 | 1.00 | 48.74 | B |
| 3164 | CZ | ARG | 208 | 21.111 | −20.176 | 47.448 | 1.00 | 48.57 | B |
| 3165 | NH1 | ARG | 208 | 21.812 | −21.300 | 47.504 | 1.00 | 48.42 | B |
| 3166 | NH2 | ARG | 208 | 19.973 | −20.072 | 48.114 | 1.00 | 48.59 | B |
| 3167 | C | ARG | 208 | 20.930 | −17.482 | 41.668 | 1.00 | 48.49 | B |
| 3168 | O | ARG | 208 | 19.725 | −17.699 | 41.540 | 1.00 | 48.40 | B |
| 3169 | N | LEU | 209 | 21.476 | −16.325 | 41.312 | 1.00 | 48.80 | B |
| 3170 | CA | LEU | 209 | 20.622 | −15.272 | 40.768 | 1.00 | 49.22 | B |
| 3171 | CB | LEU | 209 | 21.320 | −13.909 | 40.848 | 1.00 | 49.09 | B |
| 3172 | CG | LEU | 209 | 20.906 | −13.011 | 42.022 | 1.00 | 49.04 | B |
| 3173 | CD1 | LEU | 209 | 19.405 | −12.750 | 41.957 | 1.00 | 48.97 | B |
| 3174 | CD2 | LEU | 209 | 21.263 | −13.669 | 43.337 | 1.00 | 48.92 | B |
| 3175 | C | LEU | 209 | 20.123 | −15.500 | 39.338 | 1.00 | 49.67 | B |
| 3176 | O | LEU | 209 | 18.976 | −15.190 | 39.025 | 1.00 | 49.50 | B |

TABLE 1-continued

| Atom | Atom Type | Res | # | X | Y | Z | OCC | B | Mol. |
|---|---|---|---|---|---|---|---|---|---|
| 3177 | N | PRO | 210 | 20.971 | −16.046 | 38.452 | 1.00 | 50.19 | B |
| 3178 | CD | PRO | 210 | 22.389 | −16.414 | 38.618 | 1.00 | 50.27 | B |
| 3179 | CA | PRO | 210 | 20.533 | −16.273 | 37.070 | 1.00 | 50.82 | B |
| 3180 | CB | PRO | 210 | 21.692 | −17.062 | 36.472 | 1.00 | 50.64 | B |
| 3181 | CG | PRO | 210 | 22.879 | −16.463 | 37.178 | 1.00 | 50.46 | B |
| 3182 | C | PRO | 210 | 19.194 | −16.996 | 36.952 | 1.00 | 51.51 | B |
| 3183 | O | PRO | 210 | 18.291 | −16.530 | 36.258 | 1.00 | 51.48 | B |
| 3184 | N | ALA | 211 | 19.064 | −18.122 | 37.645 | 1.00 | 52.30 | B |
| 3185 | CA | ALA | 211 | 17.833 | −18.895 | 37.604 | 1.00 | 53.24 | B |
| 3186 | CB | ALA | 211 | 17.960 | −20.130 | 38.485 | 1.00 | 53.25 | B |
| 3187 | C | ALA | 211 | 16.635 | −18.062 | 38.037 | 1.00 | 53.94 | B |
| 3188 | O | ALA | 211 | 15.554 | −18.190 | 37.465 | 1.00 | 53.95 | B |
| 3189 | N | LEU | 212 | 16.818 | −17.211 | 39.045 | 1.00 | 54.79 | B |
| 3190 | CA | LEU | 212 | 15.722 | −16.363 | 39.512 | 1.00 | 55.73 | B |
| 3191 | CB | LEU | 212 | 16.049 | −15.749 | 40.875 | 1.00 | 55.73 | B |
| 3192 | CG | LEU | 212 | 16.141 | −16.680 | 42.083 | 1.00 | 55.92 | B |
| 3193 | CD1 | LEU | 212 | 16.463 | −15.855 | 43.322 | 1.00 | 55.87 | B |
| 3194 | CD2 | LEU | 212 | 14.822 | −17.431 | 42.271 | 1.00 | 55.95 | B |
| 3195 | C | LEU | 212 | 15.420 | −15.238 | 38.523 | 1.00 | 56.42 | B |
| 3196 | O | LEU | 212 | 14.264 | −14.901 | 38.286 | 1.00 | 56.37 | B |
| 3197 | N | LEU | 213 | 16.465 | −14.659 | 37.943 | 1.00 | 57.37 | B |
| 3198 | CA | LEU | 213 | 16.291 | −13.562 | 37.000 | 1.00 | 58.47 | B |
| 3199 | CB | LEU | 213 | 17.636 | −12.897 | 36.713 | 1.00 | 58.27 | B |
| 3200 | CG | LEU | 213 | 18.338 | −12.286 | 37.926 | 1.00 | 58.28 | B |
| 3201 | CD1 | LEU | 213 | 19.683 | −11.738 | 37.498 | 1.00 | 58.29 | B |
| 3202 | CD2 | LEU | 213 | 17.474 | −11.191 | 38.534 | 1.00 | 58.19 | B |
| 3203 | C | LEU | 213 | 15.650 | −13.999 | 35.687 | 1.00 | 59.34 | B |
| 3204 | O | LEU | 213 | 14.823 | −13.276 | 35.124 | 1.00 | 59.41 | B |
| 3205 | N | ASN | 214 | 16.027 | −15.180 | 35.205 | 1.00 | 60.39 | B |
| 3206 | CA | ASN | 214 | 15.492 | −15.684 | 33.943 | 1.00 | 61.55 | B |
| 3207 | CB | ASN | 214 | 16.411 | −16.765 | 33.357 | 1.00 | 61.91 | B |
| 3208 | CG | ASN | 214 | 16.403 | −18.053 | 34.170 | 1.00 | 62.38 | B |
| 3209 | OD1 | ASN | 214 | 15.530 | −18.262 | 35.017 | 1.00 | 62.69 | B |
| 3210 | ND2 | ASN | 214 | 17.372 | −18.936 | 33.899 | 1.00 | 62.65 | B |
| 3211 | C | ASN | 214 | 14.072 | −16.233 | 34.067 | 1.00 | 62.15 | B |
| 3212 | O | ASN | 214 | 13.566 | −16.860 | 33.134 | 1.00 | 62.30 | B |
| 3213 | N | GLU | 215 | 13.438 | −15.999 | 35.213 | 1.00 | 62.82 | B |
| 3214 | CA | GLU | 215 | 12.071 | −16.465 | 35.443 | 1.00 | 63.51 | B |
| 3215 | CB | GLU | 215 | 11.780 | −16.547 | 36.942 | 1.00 | 63.81 | B |
| 3216 | CG | GLU | 215 | 11.453 | −15.201 | 37.585 | 1.00 | 64.40 | B |
| 3217 | CD | GLU | 215 | 11.472 | −15.263 | 39.107 | 1.00 | 64.72 | B |
| 3218 | OE1 | GLU | 215 | 11.573 | −16.381 | 39.661 | 1.00 | 64.95 | B |
| 3219 | OE2 | GLU | 215 | 11.383 | −14.193 | 39.751 | 1.00 | 64.97 | B |
| 3220 | C | GLU | 215 | 11.099 | −15.479 | 34.800 | 1.00 | 63.76 | B |
| 3221 | OT1 | GLU | 215 | 11.556 | −14.377 | 34.424 | 1.00 | 63.97 | B |
| 3222 | OT2 | GLU | 215 | 9.899 | −15.810 | 34.682 | 1.00 | 63.98 | B |
| 3223 | OH2 | WAT | 1 | 31.093 | −4.250 | 43.359 | 1.00 | 38.31 | W |
| 3224 | OH2 | WAT | 2 | 22.205 | −3.369 | 72.055 | 1.00 | 41.07 | W |
| 3225 | OH2 | WAT | 3 | 20.554 | −.944 | 41.661 | 1.00 | 39.45 | W |
| 3226 | OH2 | WAT | 4 | 17.896 | −6.055 | 62.376 | 1.00 | 38.35 | W |
| 3227 | OH2 | WAT | 5 | 20.405 | 21.269 | 30.480 | 1.00 | 36.21 | W |
| 3228 | OH2 | WAT | 6 | 12.876 | −1.564 | 64.212 | 1.00 | 45.53 | W |
| 3229 | OH2 | WAT | 7 | 13.804 | 3.554 | 27.585 | 1.00 | 43.05 | W |
| 3230 | OH2 | WAT | 8 | 24.786 | −3.380 | 54.771 | 1.00 | 35.11 | W |
| 3231 | OH2 | WAT | 9 | 28.066 | 1.015 | 49.442 | 1.00 | 45.06 | W |
| 3232 | OH2 | WAT | 10 | 28.942 | .733 | 38.701 | 1.00 | 34.28 | W |
| 3233 | OH2 | WAT | 11 | 11.034 | 1.040 | 35.900 | 1.00 | 62.48 | W |
| 3234 | OH2 | WAT | 12 | 11.958 | −2.453 | 50.194 | 1.00 | 45.87 | W |
| 3235 | OH2 | WAT | 13 | 21.729 | 10.816 | 38.274 | 1.00 | 38.90 | W |
| 3236 | OH2 | WAT | 14 | 14.717 | 1.042 | 31.574 | 1.00 | 54.49 | W |
| 3237 | OH2 | WAT | 15 | 17.148 | 18.726 | 21.425 | 1.00 | 43.77 | W |
| 3238 | OH2 | WAT | 16 | 14.258 | −8.167 | 59.218 | 1.00 | 38.95 | W |
| 3239 | OH2 | WAT | 17 | 25.220 | 14.836 | 50.255 | 1.00 | 39.68 | W |
| 3240 | OH2 | WAT | 18 | 31.999 | −6.768 | 44.244 | 1.00 | 36.85 | W |
| 3241 | OH2 | WAT | 19 | 18.759 | −3.066 | 41.285 | 1.00 | 36.91 | W |
| 3242 | OH2 | WAT | 20 | 33.825 | −.369 | 44.325 | 1.00 | 46.84 | W |
| 3243 | OH2 | WAT | 21 | 21.027 | 6.946 | 63.895 | 1.00 | 39.53 | W |
| 3244 | OH2 | WAT | 22 | 26.841 | 26.528 | 37.222 | 1.00 | 41.75 | W |
| 3245 | OH2 | WAT | 23 | 25.367 | 9.122 | 54.856 | 1.00 | 37.37 | W |
| 3246 | OH2 | WAT | 24 | 25.067 | .794 | 29.176 | 1.00 | 43.46 | W |
| 3247 | OH2 | WAT | 25 | 19.710 | −3.614 | 38.582 | 1.00 | 41.87 | W |
| 3248 | OH2 | WAT | 26 | 17.814 | 2.392 | 46.303 | 1.00 | 43.24 | W |
| 3249 | OH2 | WAT | 27 | 25.147 | 24.525 | 18.999 | 1.00 | 37.60 | W |
| 3250 | OH2 | WAT | 28 | 27.097 | 13.442 | 48.534 | 1.00 | 41.43 | W |
| 3251 | OH2 | WAT | 29 | 27.483 | 37.303 | 38.185 | 1.00 | 49.70 | W |
| 3252 | OH2 | WAT | 30 | 29.357 | 14.737 | 45.872 | 1.00 | 46.90 | W |
| 3253 | OH2 | WAT | 31 | 17.807 | −7.527 | 69.022 | 1.00 | 44.13 | W |

TABLE 1-continued

| Atom | Atom Type | Res | # | X | Y | Z | OCC | B | Mol. |
|---|---|---|---|---|---|---|---|---|---|
| 3254 | OH2 | WAT | 32 | 21.345 | −13.823 | 34.901 | 1.00 | 44.32 | W |
| 3255 | OH2 | WAT | 33 | 35.351 | −17.312 | 50.704 | 1.00 | 55.78 | W |
| 3256 | OH2 | WAT | 34 | 26.136 | 26.351 | 20.833 | 1.00 | 40.13 | W |
| 3257 | OH2 | WAT | 35 | 32.708 | −13.771 | 75.135 | 1.00 | 43.56 | W |
| 3258 | OH2 | WAT | 36 | 12.775 | 2.758 | 37.403 | 1.00 | 45.67 | W |
| 3259 | OH2 | WAT | 37 | 25.576 | 21.447 | 40.719 | 1.00 | 44.80 | W |
| 3260 | OH2 | WAT | 38 | 22.179 | 22.412 | 44.230 | 1.00 | 40.57 | W |
| 3261 | OH2 | WAT | 39 | 27.629 | 1.078 | 29.037 | 1.00 | 46.71 | W |
| 3262 | OH2 | WAT | 40 | 15.214 | −8.497 | 63.801 | 1.00 | 38.34 | W |
| 3263 | OH2 | WAT | 41 | 33.570 | −1.687 | 70.758 | 1.00 | 40.60 | W |
| 3264 | OH2 | WAT | 42 | 31.914 | −2.489 | 45.115 | 1.00 | 43.00 | W |
| 3265 | OH2 | WAT | 43 | 23.695 | 2.255 | 70.078 | 1.00 | 43.19 | W |
| 3266 | OH2 | WAT | 44 | 29.791 | 12.761 | 49.741 | 1.00 | 48.56 | W |
| 3267 | OH2 | WAT | 45 | 15.071 | 9.940 | 29.979 | 1.00 | 40.83 | W |
| 3268 | OH2 | WAT | 46 | 6.237 | −10.540 | 53.081 | 1.00 | 48.79 | W |
| 3269 | OH2 | WAT | 47 | 20.476 | 3.837 | 40.323 | 1.00 | 42.14 | W |
| 3270 | OH2 | WAT | 48 | 29.765 | 5.450 | 42.949 | 1.00 | 41.40 | W |
| 3271 | OH2 | WAT | 49 | 23.422 | 10.111 | 60.106 | 1.00 | 41.64 | W |
| 3272 | OH2 | WAT | 50 | 20.860 | .481 | 49.642 | 1.00 | 46.53 | W |
| 3273 | OH2 | WAT | 51 | 5.256 | 8.767 | 49.027 | 1.00 | 55.74 | W |
| 3274 | OH2 | WAT | 52 | 24.018 | 33.664 | 24.223 | 1.00 | 52.13 | W |
| 3275 | OH2 | WAT | 53 | 21.760 | 30.910 | 22.406 | 1.00 | 47.05 | W |
| 3276 | OH2 | WAT | 54 | 19.585 | 14.021 | 16.441 | 1.00 | 56.45 | W |
| 3277 | OH2 | WAT | 55 | 20.975 | −19.597 | 38.847 | 1.00 | 49.49 | W |
| 3278 | OH2 | WAT | 56 | 13.251 | 1.391 | 60.383 | 1.00 | 54.19 | W |
| 3279 | OH2 | WAT | 57 | 23.704 | 7.874 | 64.123 | 1.00 | 44.28 | W |
| 3280 | OH2 | WAT | 58 | 15.256 | 7.236 | 51.233 | 1.00 | 43.50 | W |
| 3281 | OH2 | WAT | 59 | 24.722 | 14.018 | 57.391 | 1.00 | 45.21 | W |
| 3282 | OH2 | WAT | 60 | 26.451 | .059 | 45.352 | 1.00 | 44.50 | W |
| 3283 | OH2 | WAT | 61 | 34.911 | 7.400 | 28.623 | 1.00 | 49.87 | W |
| 3284 | OH2 | WAT | 62 | 16.024 | −8.090 | 61.241 | 1.00 | 39.36 | W |
| 3285 | OH2 | WAT | 63 | 24.783 | 9.796 | 62.406 | 1.00 | 46.71 | W |
| 3286 | OH2 | WAT | 64 | 31.166 | −2.930 | 69.992 | 1.00 | 41.41 | W |
| 3287 | OH2 | WAT | 65 | 10.893 | −9.636 | 41.973 | 1.00 | 44.07 | W |
| 3288 | OH2 | WAT | 66 | 28.314 | −12.912 | 62.930 | 1.00 | 41.86 | W |
| 3289 | OH2 | WAT | 67 | 24.853 | 17.293 | 49.467 | 1.00 | 38.69 | W |
| 3290 | OH2 | WAT | 68 | 36.526 | .983 | 63.657 | 1.00 | 46.65 | W |
| 3291 | OH2 | WAT | 69 | 18.777 | 3.199 | 43.897 | 1.00 | 57.05 | W |
| 3292 | OH2 | WAT | 70 | 28.000 | −.909 | 33.105 | 1.00 | 44.17 | W |
| 3293 | OH2 | WAT | 71 | 24.106 | 9.098 | 47.740 | 1.00 | 55.73 | W |
| 3294 | OH2 | WAT | 72 | 17.808 | 6.338 | 50.880 | 1.00 | 39.96 | W |
| 3295 | OH2 | WAT | 73 | 36.807 | 14.820 | 35.205 | 1.00 | 49.63 | W |
| 3296 | OH2 | WAT | 74 | 14.829 | 11.241 | 23.393 | 1.00 | 43.87 | W |
| 3297 | OH2 | WAT | 75 | 36.031 | 33.971 | 37.266 | 1.00 | 56.30 | W |
| 3298 | OH2 | WAT | 76 | 4.952 | −6.504 | 59.504 | 1.00 | 57.63 | W |
| 3299 | OH2 | WAT | 77 | 22.846 | 27.968 | 42.941 | 1.00 | 52.34 | W |
| 3300 | OH2 | WAT | 78 | 12.146 | −11.809 | 69.643 | 1.00 | 54.90 | W |
| 3301 | OH2 | WAT | 79 | 19.700 | 5.591 | 42.910 | 1.00 | 51.71 | W |
| 3302 | OH2 | WAT | 80 | 15.474 | .949 | 68.278 | 1.00 | 66.40 | W |
| 3303 | OH2 | WAT | 81 | 34.987 | 13.359 | 30.852 | 1.00 | 42.96 | W |
| 3304 | OH2 | WAT | 82 | 38.932 | 7.300 | 62.259 | 1.00 | 63.71 | W |
| 3305 | OH2 | WAT | 83 | 35.300 | 12.120 | 60.726 | 1.00 | 66.45 | W |
| 3306 | OH2 | WAT | 84 | 8.372 | 12.069 | 21.462 | 1.00 | 64.68 | W |
| 3307 | OH2 | WAT | 85 | 35.004 | −3.331 | 69.181 | 1.00 | 47.28 | W |
| 3308 | OH2 | WAT | 86 | 16.178 | −17.345 | 60.213 | 1.00 | 62.52 | W |
| 3309 | OH2 | WAT | 87 | 32.218 | −1.490 | 37.454 | 1.00 | 45.67 | W |
| 3310 | OH2 | WAT | 88 | 33.650 | −5.544 | 36.673 | 1.00 | 48.90 | W |
| 3311 | OH2 | WAT | 89 | 10.839 | 3.447 | 41.407 | 1.00 | 44.17 | W |
| 3312 | OH2 | WAT | 90 | 15.338 | 8.207 | 53.876 | 1.00 | 45.01 | W |
| 3313 | OH2 | WAT | 91 | 30.982 | −3.939 | 36.099 | 1.00 | 38.73 | W |
| 3314 | OH2 | WAT | 92 | 28.437 | −19.091 | 76.433 | 1.00 | 48.06 | W |
| 3315 | OH2 | WAT | 93 | 29.317 | −3.476 | 34.057 | 1.00 | 49.49 | W |
| 3316 | OH2 | WAT | 94 | 27.684 | 10.298 | 48.858 | 1.00 | 55.52 | W |
| 3317 | OH2 | WAT | 95 | 14.673 | −23.662 | 53.251 | 1.00 | 49.20 | W |
| 3318 | OH2 | WAT | 96 | 17.556 | 7.948 | 19.460 | 1.00 | 63.81 | W |
| 3319 | OH2 | WAT | 97 | 28.042 | 7.556 | 41.706 | 1.00 | 43.72 | W |
| 3320 | OH2 | WAT | 98 | 16.210 | 26.298 | 51.998 | 1.00 | 60.02 | W |
| 3321 | OH2 | WAT | 99 | 23.180 | 12.765 | 59.454 | 1.00 | 48.47 | W |
| 3322 | OH2 | WAT | 100 | 24.091 | 26.235 | 51.196 | 1.00 | 66.16 | W |
| 3323 | OH2 | WAT | 101 | 23.826 | 8.978 | 66.633 | 1.00 | 56.80 | W |
| 3324 | OH2 | WAT | 102 | 3.301 | 13.799 | 45.653 | 1.00 | 66.31 | W |
| 3325 | OH2 | WAT | 103 | 33.824 | 9.701 | 27.099 | 1.00 | 60.54 | W |
| 3326 | OH2 | WAT | 104 | 29.786 | 12.544 | 55.054 | 1.00 | 41.18 | W |
| 3327 | OH2 | WAT | 105 | 23.227 | −12.967 | 71.600 | 1.00 | 51.29 | W |
| 3328 | OH2 | WAT | 106 | 26.114 | 16.990 | 57.406 | 1.00 | 52.43 | W |
| 3329 | OH2 | WAT | 107 | 25.488 | 27.629 | 39.671 | 1.00 | 50.05 | W |
| 3330 | OH2 | WAT | 108 | 22.470 | 30.831 | 40.093 | 1.00 | 57.56 | W |

TABLE 1-continued

| Atom | Atom Type | Res | # | X | Y | Z | OCC | B | Mol. |
|---|---|---|---|---|---|---|---|---|---|
| 3331 | OH2 | WAT | 109 | 37.775 | 5.213 | 63.399 | 1.00 | 69.73 | W |
| 3332 | OH2 | WAT | 110 | 34.301 | −.031 | 38.944 | 1.00 | 45.56 | W |
| 3333 | OH2 | WAT | 111 | 27.597 | 2.887 | 47.690 | 1.00 | 60.49 | W |
| 3334 | OH2 | WAT | 112 | 17.992 | 3.627 | 67.907 | 1.00 | 58.51 | W |
| 3335 | OH2 | WAT | 113 | 34.212 | −2.513 | 48.565 | 1.00 | 47.94 | W |
| 3336 | OH2 | WAT | 114 | 9.142 | 3.223 | 51.976 | 1.00 | 57.69 | W |
| 3337 | OH2 | WAT | 115 | 19.903 | 1.345 | 25.038 | 1.00 | 68.54 | W |
| 3338 | OH2 | WAT | 116 | 20.188 | 2.209 | 52.296 | 1.00 | 42.73 | W |
| 3339 | OH2 | WAT | 117 | 28.947 | 5.592 | 51.018 | 1.00 | 40.39 | W |
| 3340 | OH2 | WAT | 118 | 16.572 | −11.398 | 70.607 | 1.00 | 46.52 | W |
| 3341 | OH2 | WAT | 119 | 22.371 | 28.957 | 16.258 | 1.00 | 55.29 | W |
| 3342 | OH2 | WAT | 120 | 20.120 | 12.380 | 14.024 | 1.00 | 58.21 | W |
| 3343 | OH2 | WAT | 121 | 30.963 | 2.318 | 25.429 | 1.00 | 48.38 | W |
| 3344 | OH2 | WAT | 122 | 21.073 | 3.484 | 45.639 | 1.00 | 56.45 | W |
| 3345 | OH2 | WAT | 123 | 34.100 | .809 | 70.341 | 1.00 | 50.51 | W |
| 3346 | OH2 | WAT | 124 | 18.016 | −1.735 | 72.545 | 1.00 | 53.41 | W |
| 3347 | OH2 | WAT | 125 | 32.760 | 17.849 | 19.769 | 1.00 | 51.60 | W |
| 3348 | OH2 | WAT | 126 | 20.014 | 35.120 | 27.688 | 1.00 | 68.27 | W |
| 3349 | OH2 | WAT | 127 | 39.302 | .999 | 59.401 | 1.00 | 41.72 | W |
| 3350 | OH2 | WAT | 128 | 33.457 | 4.342 | 66.754 | 1.00 | 67.39 | W |
| 3351 | OH2 | WAT | 129 | 11.112 | −.382 | 62.500 | 1.00 | 67.86 | W |
| 3352 | OH2 | WAT | 130 | 29.176 | −20.293 | 78.691 | 1.00 | 51.06 | W |
| 3353 | OH2 | WAT | 131 | 18.735 | 27.403 | 17.177 | 1.00 | 47.80 | W |
| 3354 | OH2 | WAT | 132 | 32.904 | 20.389 | 23.167 | 1.00 | 56.27 | W |
| 3355 | OH2 | WAT | 133 | 9.835 | −4.472 | 65.449 | 1.00 | 53.12 | W |
| 3356 | OH2 | WAT | 134 | 32.597 | 28.207 | 35.870 | 1.00 | 55.11 | W |
| 3357 | OH2 | WAT | 135 | 29.969 | −25.969 | 56.239 | 1.00 | 48.12 | W |
| 3358 | OH2 | WAT | 136 | 36.964 | −1.362 | 65.077 | 1.00 | 44.08 | W |
| 3359 | OH2 | WAT | 137 | 10.433 | 10.253 | 21.603 | 1.00 | 54.93 | W |
| 3360 | OH2 | WAT | 138 | 38.129 | 13.412 | 41.162 | 1.00 | 48.39 | W |
| 3361 | OH2 | WAT | 139 | 36.704 | 17.146 | 29.103 | 1.00 | 59.58 | W |
| 3362 | OH2 | WAT | 140 | 27.851 | −23.129 | 66.111 | 1.00 | 60.12 | W |
| 3363 | OH2 | WAT | 141 | 34.360 | 13.181 | 19.409 | 1.00 | 66.62 | W |
| 3364 | OH2 | WAT | 142 | 20.706 | −23.727 | 62.602 | 1.00 | 54.01 | W |
| 3365 | OH2 | WAT | 143 | 39.554 | 2.841 | 34.406 | 1.00 | 68.29 | W |
| 3366 | OH2 | WAT | 144 | 25.204 | −19.729 | 34.272 | 1.00 | 57.76 | W |
| 3367 | OH2 | WAT | 145 | 41.086 | −23.712 | 68.027 | 1.00 | 72.43 | W |
| 3368 | OH2 | WAT | 146 | 16.943 | 6.274 | 41.247 | 1.00 | 41.20 | W |
| 3369 | OH2 | WAT | 147 | 11.542 | −4.401 | 42.425 | 1.00 | 47.73 | W |
| 3370 | OH2 | WAT | 148 | 14.946 | 27.656 | 20.304 | 1.00 | 52.17 | W |
| 3371 | OH2 | WAT | 149 | 24.832 | 5.955 | 23.125 | 1.00 | 48.56 | W |
| 3372 | OH2 | WAT | 150 | 30.653 | 9.001 | 16.618 | 1.00 | 66.87 | W |
| 3373 | OH2 | WAT | 151 | 28.998 | 14.078 | 23.475 | 1.00 | 43.35 | W |
| 3374 | OH2 | WAT | 152 | 34.368 | 11.875 | 54.060 | 1.00 | 53.46 | W |
| 3375 | OH2 | WAT | 153 | 25.939 | 8.771 | 17.733 | 1.00 | 69.63 | W |
| 3376 | OH2 | WAT | 154 | 31.613 | 13.875 | 44.688 | 1.00 | 60.00 | W |
| 3377 | OH2 | WAT | 155 | 29.255 | .100 | 30.971 | 1.00 | 49.76 | W |
| 3378 | OH2 | WAT | 156 | 19.059 | 29.293 | 41.016 | 1.00 | 55.35 | W |
| 3379 | OH2 | WAT | 157 | 36.595 | −7.763 | 43.708 | 1.00 | 56.53 | W |
| 3380 | OH2 | WAT | 158 | 20.748 | −5.549 | 73.212 | 1.00 | 58.80 | W |
| 3381 | OH2 | WAT | 159 | 38.071 | −6.743 | 71.037 | 1.00 | 56.27 | W |
| 3382 | OH2 | WAT | 160 | 11.224 | 17.579 | 57.161 | 1.00 | 48.48 | W |
| 3383 | OH2 | WAT | 161 | 31.397 | 14.497 | 22.933 | 1.00 | 49.77 | W |
| 3384 | OH2 | WAT | 162 | 35.502 | −7.801 | 38.951 | 1.00 | 50.71 | W |
| 3385 | OH2 | WAT | 163 | 33.161 | −21.147 | 71.386 | 1.00 | 51.02 | W |
| 3386 | OH2 | WAT | 164 | 20.286 | 11.119 | 59.449 | 1.00 | 52.24 | W |
| 3387 | OH2 | WAT | 165 | 34.529 | 24.258 | 33.196 | 1.00 | 67.98 | W |
| 3388 | OH2 | WAT | 166 | 12.012 | 4.516 | 25.773 | 1.00 | 50.14 | W |
| 3389 | OH2 | WAT | 167 | 31.772 | 11.810 | 47.996 | 1.00 | 67.99 | W |
| 3390 | OH2 | WAT | 168 | 14.912 | 8.442 | 20.411 | 1.00 | 74.18 | W |
| 3391 | OH2 | WAT | 169 | 9.368 | 26.392 | 46.096 | 1.00 | 63.81 | W |
| 3392 | OH2 | WAT | 170 | 28.509 | 2.982 | 51.791 | 1.00 | 46.67 | W |
| 3393 | OH2 | WAT | 171 | 4.996 | 6.432 | 40.740 | 1.00 | 63.03 | W |
| 3394 | OH2 | WAT | 172 | 11.588 | 10.669 | 28.048 | 1.00 | 46.74 | W |
| 3395 | OH2 | WAT | 173 | 14.227 | 23.192 | 18.948 | 1.00 | 49.28 | W |
| 3396 | OH2 | WAT | 174 | 18.719 | 11.671 | 18.495 | 1.00 | 71.10 | W |
| 3397 | OH2 | WAT | 175 | 13.190 | −20.042 | 67.678 | 1.00 | 58.59 | W |
| 3398 | OH2 | WAT | 176 | 25.777 | −23.959 | 67.840 | 1.00 | 62.17 | W |
| 3399 | OH2 | WAT | 177 | 16.999 | 27.742 | 45.551 | 1.00 | 58.42 | W |
| 3400 | OH2 | WAT | 178 | 22.249 | .128 | 71.871 | 1.00 | 65.44 | W |
| 3401 | OH2 | WAT | 179 | 35.826 | −4.408 | 52.580 | 1.00 | 58.54 | W |
| 3402 | OH2 | WAT | 180 | 25.839 | .223 | 74.936 | 1.00 | 55.69 | W |
| 3403 | OH2 | WAT | 181 | 22.433 | 4.944 | 43.941 | 1.00 | 60.42 | W |
| 3404 | OH2 | WAT | 182 | 29.223 | −12.148 | 60.548 | 1.00 | 59.86 | W |
| 3405 | OH2 | WAT | 183 | 15.667 | 16.612 | 20.418 | 1.00 | 49.49 | W |
| 3406 | OH2 | WAT | 184 | 24.783 | −21.882 | 46.145 | 1.00 | 68.71 | W |
| 3407 | OH2 | WAT | 185 | 25.242 | 19.671 | 50.499 | 1.00 | 44.24 | W |

TABLE 1-continued

| Atom | Atom Type | Res | # | X | Y | Z | OCC | B | Mol. |
|---|---|---|---|---|---|---|---|---|---|
| 3408 | OH2 | WAT | 186 | 2.423 | 26.673 | 41.340 | 1.00 | 67.24 | W |
| 3409 | OH2 | WAT | 187 | 23.280 | 17.623 | 60.422 | 1.00 | 62.91 | W |
| 3410 | OH2 | WAT | 188 | 15.145 | 32.923 | 37.151 | 1.00 | 65.04 | W |
| 3411 | OH2 | WAT | 189 | 20.969 | 10.269 | 20.754 | 1.00 | 52.89 | W |
| 3412 | OH2 | WAT | 190 | 18.175 | −17.048 | 58.331 | 1.00 | 53.26 | W |
| 3413 | OH2 | WAT | 191 | 24.571 | −26.567 | 52.275 | 1.00 | 58.98 | W |
| 3414 | OH2 | WAT | 192 | 38.246 | −9.005 | 57.246 | 1.00 | 61.24 | W |
| 3415 | OH2 | WAT | 193 | 36.305 | −11.762 | 46.051 | 1.00 | 63.32 | W |
| 3416 | OH2 | WAT | 194 | 11.497 | 20.108 | 16.174 | 1.00 | 63.58 | W |
| 3417 | OH2 | WAT | 195 | 31.584 | −21.544 | 74.117 | 1.00 | 68.96 | W |
| 3418 | OH2 | WAT | 196 | 12.043 | −.744 | 48.184 | 1.00 | 52.26 | W |
| 3419 | OH2 | WAT | 197 | 11.989 | 14.143 | 21.333 | 1.00 | 61.32 | W |
| 3420 | OH2 | WAT | 198 | 12.839 | 1.264 | 29.315 | 1.00 | 69.48 | W |
| 3421 | OH2 | WAT | 199 | 11.860 | −15.478 | 45.332 | 1.00 | 65.32 | W |
| 3422 | OH2 | WAT | 200 | 20.430 | 13.555 | 61.068 | 1.00 | 59.82 | W |
| 3423 | OH2 | WAT | 201 | 23.643 | −4.606 | 32.061 | 1.00 | 64.48 | W |
| 3424 | OH2 | WAT | 202 | 38.517 | −25.787 | 70.646 | 1.00 | 76.00 | W |
| 3425 | OH2 | WAT | 203 | 15.297 | 31.145 | 28.851 | 1.00 | 66.25 | W |
| 3426 | OH2 | WAT | 204 | 15.159 | 2.605 | 25.487 | 1.00 | 60.04 | W |
| 3427 | OH2 | WAT | 205 | 28.077 | 23.607 | 35.404 | 1.00 | 67.09 | W |
| 3428 | OH2 | WAT | 206 | 32.761 | 39.897 | 39.324 | 1.00 | 57.67 | W |
| 3429 | OH2 | WAT | 207 | 36.641 | −2.074 | 53.768 | 1.00 | 57.82 | W |
| 3430 | OH2 | WAT | 208 | 34.353 | −1.946 | 73.339 | 1.00 | 50.05 | W |
| 3431 | OH2 | WAT | 209 | 27.589 | 2.824 | 43.260 | 1.00 | 70.02 | W |
| 3432 | OH2 | WAT | 210 | 12.853 | −.417 | 41.865 | 1.00 | 57.86 | W |
| 3433 | OH2 | WAT | 211 | 26.187 | 23.776 | 48.114 | 1.00 | 57.27 | W |
| 3434 | OH2 | WAT | 212 | 11.985 | −1.710 | 44.211 | 1.00 | 51.14 | W |
| 3435 | OH2 | WAT | 213 | 38.689 | 7.218 | 30.912 | 1.00 | 68.27 | W |
| 3436 | OH2 | WAT | 214 | 8.583 | 26.431 | 29.422 | 1.00 | 65.31 | W |
| 3437 | OH2 | WAT | 215 | 17.594 | 15.705 | 17.887 | 1.00 | 54.42 | W |
| 3438 | OH2 | WAT | 216 | 1.849 | 20.472 | 37.884 | 1.00 | 57.12 | W |
| 3439 | OH2 | WAT | 217 | 8.333 | −8.098 | 42.298 | 1.00 | 62.17 | W |
| 3440 | OH2 | WAT | 218 | 8.946 | −.483 | 52.167 | 1.00 | 57.91 | W |
| 3441 | OH2 | WAT | 219 | 29.333 | −23.629 | 74.187 | 1.00 | 70.25 | W |
| 3442 | OH2 | WAT | 220 | 6.604 | −3.624 | 52.392 | 1.00 | 62.34 | W |
| 3443 | OH2 | WAT | 221 | 12.983 | 25.059 | 21.917 | 1.00 | 53.69 | W |
| 3444 | OH2 | WAT | 222 | 38.735 | −18.849 | 48.176 | 1.00 | 64.01 | W |
| 3445 | OH2 | WAT | 223 | 8.728 | −2.184 | 62.901 | 1.00 | 65.88 | W |
| 3446 | OH2 | WAT | 224 | 8.411 | 4.504 | 49.068 | 1.00 | 60.02 | W |
| 3447 | OH2 | WAT | 225 | 31.938 | 15.968 | 55.305 | 1.00 | 58.81 | W |
| 3448 | OH2 | WAT | 226 | 32.527 | −20.621 | 52.265 | 1.00 | 60.11 | W |
| 3449 | OH2 | WAT | 227 | 9.073 | 30.520 | 40.192 | 1.00 | 59.71 | W |
| 3450 | OH2 | WAT | 228 | 20.976 | 8.564 | 67.698 | 1.00 | 67.06 | W |
| 3451 | OH2 | WAT | 229 | 40.435 | −5.021 | 47.043 | 1.00 | 69.13 | W |
| 3452 | OH2 | WAT | 230 | 11.670 | −2.733 | 39.421 | 1.00 | 59.51 | W |
| 3453 | OH2 | WAT | 231 | 33.789 | 14.958 | 43.047 | 1.00 | 67.65 | W |
| 3454 | OH2 | WAT | 232 | 35.687 | 3.313 | 26.142 | 1.00 | 74.71 | W |
| 3455 | OH2 | WAT | 233 | 38.617 | 1.882 | 62.137 | 1.00 | 66.43 | W |
| 3456 | OH2 | WAT | 234 | 16.871 | −20.946 | 65.437 | 1.00 | 60.62 | W |
| 3457 | OH2 | WAT | 235 | 7.222 | 21.869 | 30.683 | 1.00 | 71.14 | W |
| 3458 | OH2 | WAT | 236 | 29.336 | 18.254 | 60.245 | 1.00 | 72.61 | W |
| 3459 | OH2 | WAT | 237 | 5.178 | 1.864 | 39.450 | 1.00 | 60.41 | W |
| 3460 | OH2 | WAT | 238 | 12.637 | 1.590 | 57.377 | 1.00 | 69.21 | W |
| 3461 | OH2 | WAT | 239 | 38.338 | 13.267 | 36.482 | 1.00 | 50.89 | W |
| 3462 | OH2 | WAT | 240 | 19.406 | −4.325 | 29.852 | 1.00 | 63.56 | W |
| 3463 | OH2 | WAT | 241 | 15.305 | −4.423 | 71.898 | 1.00 | 67.37 | W |
| 3464 | OH2 | WAT | 242 | 11.386 | −15.025 | 65.042 | 1.00 | 67.69 | W |
| 3465 | OH2 | WAT | 243 | 24.769 | 3.511 | 50.789 | 1.00 | 54.60 | W |
| 3466 | OH2 | WAT | 244 | 8.493 | −8.294 | 50.615 | 1.00 | 58.19 | W |
| 3467 | OH2 | WAT | 245 | 34.390 | 2.967 | 64.355 | 1.00 | 70.20 | W |
| 3468 | OH2 | WAT | 246 | 36.585 | 8.991 | 63.426 | 1.00 | 64.27 | W |
| 3469 | OH2 | WAT | 247 | 28.778 | −21.201 | 45.284 | 1.00 | 66.53 | W |
| 3470 | OH2 | WAT | 248 | 19.928 | 29.712 | 46.272 | 1.00 | 68.79 | W |
| 3471 | OH2 | WAT | 249 | 36.168 | −15.643 | 42.609 | 1.00 | 62.80 | W |
| 3472 | OH2 | WAT | 250 | 6.443 | 29.483 | 39.025 | 1.00 | 71.20 | W |
| 3473 | OH2 | WAT | 251 | 14.585 | 1.334 | 34.064 | 1.00 | 64.66 | W |
| 3474 | OH2 | WAT | 252 | 37.851 | −23.772 | 62.225 | 1.00 | 71.61 | W |
| 3475 | OH2 | WAT | 253 | 13.134 | 10.148 | 21.360 | 1.00 | 70.24 | W |
| 3476 | OH2 | WAT | 254 | 30.268 | 22.816 | 36.964 | 1.00 | 51.51 | W |
| 3477 | OH2 | WAT | 255 | 37.927 | 3.391 | 40.343 | 1.00 | 57.64 | W |
| 3478 | OH2 | WAT | 256 | 42.938 | 10.339 | 36.942 | 1.00 | 66.82 | W |
| 3479 | OH2 | WAT | 257 | 28.860 | 7.512 | 45.386 | 1.00 | 63.93 | W |
| 3480 | OH2 | WAT | 258 | 24.155 | 4.617 | 71.176 | 1.00 | 64.96 | W |
| 3481 | OH2 | WAT | 259 | 13.549 | 7.501 | 55.948 | 1.00 | 53.90 | W |
| 3482 | OH2 | WAT | 260 | 12.203 | −3.194 | 66.196 | 1.00 | 45.03 | W |
| 3483 | OH2 | WAT | 261 | 39.578 | 9.149 | 32.471 | 1.00 | 64.60 | W |
| 3484 | OH2 | WAT | 262 | 25.827 | 6.707 | 70.171 | 1.00 | 63.75 | W |

TABLE 1-continued

| Atom | Atom Type | Res | # | X | Y | Z | OCC | B | Mol. |
|---|---|---|---|---|---|---|---|---|---|
| 3485 | OH2 | WAT | 263 | 13.063 | −9.369 | 70.044 | 1.00 | 61.85 | W |
| 3486 | OH2 | WAT | 264 | 22.769 | 38.693 | 34.425 | 1.00 | 69.39 | W |
| 3487 | OH2 | WAT | 265 | 24.833 | 4.824 | 42.490 | 1.00 | 46.49 | W |
| 3488 | OH2 | WAT | 266 | 25.434 | 32.148 | 40.949 | 1.00 | 70.08 | W |
| 3489 | OH2 | WAT | 267 | 17.356 | 3.009 | 24.217 | 1.00 | 66.40 | W |
| 3490 | OH2 | WAT | 268 | 33.379 | 16.174 | 58.540 | 1.00 | 69.39 | W |
| 3491 | OH2 | WAT | 269 | 28.851 | −.908 | 45.949 | 1.00 | 46.04 | W |
| 3492 | OH2 | WAT | 270 | 14.126 | −.572 | 35.803 | 1.00 | 64.61 | W |
| 3493 | OH2 | WAT | 271 | 18.950 | 27.610 | 56.135 | 1.00 | 66.68 | W |
| 3494 | OH2 | WAT | 272 | 23.906 | 6.480 | 20.580 | 1.00 | 63.73 | W |
| 3495 | OH2 | WAT | 273 | 33.719 | −8.571 | 43.438 | 1.00 | 51.28 | W |
| 3496 | OH2 | WAT | 274 | 24.311 | 26.011 | 16.450 | 1.00 | 43.15 | W |
| 3497 | OH2 | WAT | 275 | 21.426 | 20.152 | 32.573 | 1.00 | 47.14 | W |
| 3498 | OH2 | WAT | 276 | 26.446 | 8.758 | 44.029 | 1.00 | 51.61 | W |
| 3499 | OH2 | WAT | 277 | 12.889 | −21.632 | 53.500 | 1.00 | 52.81 | W |
| 3500 | OH2 | WAT | 278 | 41.069 | 38.032 | 31.898 | 1.00 | 57.66 | W |
| 3501 | OH2 | WAT | 279 | 23.117 | 28.163 | 40.325 | 1.00 | 44.59 | W |
| 3502 | OH2 | WAT | 280 | 26.857 | 12.778 | 56.394 | 1.00 | 49.45 | W |
| 3503 | OH2 | WAT | 281 | 30.368 | 17.578 | 41.493 | 1.00 | 55.61 | W |
| 3504 | OH2 | WAT | 282 | 13.016 | 29.422 | 25.555 | 1.00 | 48.14 | W |
| 3505 | OH2 | WAT | 283 | 19.874 | 29.181 | 52.014 | 1.00 | 71.41 | W |
| 3506 | OH2 | WAT | 284 | 28.920 | 16.418 | 43.716 | 1.00 | 51.39 | W |
| 3507 | OH2 | WAT | 285 | 18.685 | 1.850 | 48.511 | 1.00 | 51.50 | W |
| 3508 | OH2 | WAT | 286 | 29.129 | 25.983 | 19.126 | 1.00 | 57.44 | W |
| 3509 | OH2 | WAT | 287 | 13.978 | 25.840 | 18.608 | 1.00 | 60.66 | W |
| 3510 | OH2 | WAT | 288 | 33.677 | −18.113 | 32.020 | 1.00 | 60.74 | W |
| 3511 | OH2 | WAT | 289 | 22.914 | −20.293 | 70.652 | 1.00 | 58.51 | W |
| 3512 | OH2 | WAT | 290 | 31.910 | −12.638 | 49.166 | 1.00 | 53.02 | W |
| 3513 | OH2 | WAT | 291 | 27.439 | 24.079 | 17.763 | 1.00 | 49.94 | W |
| 3514 | OH2 | WAT | 292 | 32.424 | 16.265 | 40.423 | 1.00 | 49.57 | W |
| 3515 | OH2 | WAT | 293 | 21.240 | −8.372 | 30.296 | 1.00 | 63.65 | W |
| 3516 | OH2 | WAT | 294 | 11.765 | −10.836 | 37.034 | 1.00 | 71.61 | W |
| 3517 | OH2 | WAT | 295 | 40.879 | 5.315 | 51.721 | 1.00 | 61.78 | W |
| 3518 | OH2 | WAT | 296 | 2.507 | 23.113 | 38.112 | 1.00 | 60.11 | W |
| 3519 | OH2 | WAT | 297 | 11.474 | 1.699 | 43.768 | 1.00 | 55.91 | W |
| 3520 | OH2 | WAT | 298 | 13.539 | .130 | 66.634 | 1.00 | 59.35 | W |
| 3521 | OH2 | WAT | 299 | 41.707 | 2.695 | 55.851 | 1.00 | 53.29 | W |
| 3522 | OH2 | WAT | 300 | 18.341 | −15.413 | 75.839 | 1.00 | 63.84 | W |
| 3523 | OH2 | WAT | 301 | 12.349 | 10.624 | 30.772 | 1.00 | 57.13 | W |
| 3524 | OH2 | WAT | 302 | 10.595 | 2.398 | 47.881 | 1.00 | 62.67 | W |
| 3525 | OH2 | WAT | 303 | 40.012 | 3.605 | 58.475 | 1.00 | 64.07 | W |
| 3526 | OH2 | WAT | 304 | 18.383 | −20.177 | 41.953 | 1.00 | 68.55 | W |
| 3527 | OH2 | WAT | 305 | 21.609 | 30.526 | 44.140 | 1.00 | 74.34 | W |
| 3528 | OH2 | WAT | 306 | 14.691 | 28.352 | 47.650 | 1.00 | 70.27 | W |
| 3529 | OH2 | WAT | 307 | 33.449 | 2.986 | 71.701 | 1.00 | 69.46 | W |
| 3530 | OH2 | WAT | 308 | 13.414 | −6.967 | 32.790 | 1.00 | 65.31 | W |
| 3531 | OH2 | WAT | 309 | 33.466 | −3.525 | 30.583 | 1.00 | 62.35 | W |
| 3532 | OH2 | WAT | 310 | 16.536 | −26.252 | 50.513 | 1.00 | 59.40 | W |
| 3533 | OH2 | WAT | 311 | 12.868 | −17.768 | 46.259 | 1.00 | 64.49 | W |
| 3534 | OH2 | WAT | 312 | 38.794 | −23.819 | 72.570 | 1.00 | 80.28 | W |
| 3535 | OH2 | WAT | 313 | 8.998 | 18.417 | 30.866 | 1.00 | 68.82 | W |
| 3536 | OH2 | WAT | 314 | 34.911 | 8.822 | 19.832 | 1.00 | 73.20 | W |
| 3537 | OH2 | WAT | 315 | 8.915 | −3.801 | 49.634 | 1.00 | 61.40 | W |
| 3538 | OH2 | WAT | 316 | 38.660 | 11.497 | 31.752 | 1.00 | 68.73 | W |
| 3539 | OH2 | WAT | 317 | 16.707 | −21.982 | 69.442 | 1.00 | 60.76 | W |
| 3540 | OH2 | WAT | 318 | 12.028 | −10.177 | 28.742 | 1.00 | 70.20 | W |
| 3541 | OH2 | WAT | 319 | 5.774 | −5.828 | 54.505 | 1.00 | 65.34 | W |
| 3542 | OH2 | WAT | 320 | 39.266 | 1.301 | 38.833 | 1.00 | 58.62 | W |
| 3543 | OH2 | WAT | 321 | 18.343 | 27.444 | 61.597 | 1.00 | 62.10 | W |
| 3544 | OH2 | WAT | 322 | 20.903 | −21.561 | 66.845 | 1.00 | 63.88 | W |
| 3545 | OH2 | WAT | 323 | 34.493 | 10.466 | 21.876 | 1.00 | 70.53 | W |
| 3546 | OH2 | WAT | 324 | 15.691 | −1.283 | 30.803 | 1.00 | 63.76 | W |
| 3547 | OH2 | WAT | 325 | 26.634 | 8.299 | 68.122 | 1.00 | 62.31 | W |
| 3548 | OH2 | WAT | 326 | 25.919 | −3.163 | 33.600 | 1.00 | 59.63 | W |
| 3549 | OH2 | WAT | 327 | 38.618 | −14.348 | 44.238 | 1.00 | 73.50 | W |
| 3550 | OH2 | WAT | 328 | 11.465 | 2.147 | 50.403 | 1.00 | 60.62 | W |
| 3551 | OH2 | WAT | 329 | 28.096 | 32.068 | 40.827 | 1.00 | 76.59 | W |
| 3552 | OH2 | WAT | 330 | 36.452 | 12.479 | 48.769 | 1.00 | 62.77 | W |
| 3553 | OH2 | WAT | 331 | 30.966 | .750 | 44.943 | 1.00 | 51.62 | W |
| 3554 | OH2 | WAT | 332 | 21.804 | 7.976 | 19.945 | 1.00 | 67.83 | W |
| 3555 | OH2 | WAT | 333 | 15.722 | 32.585 | 24.096 | 1.00 | 68.69 | W |
| 3556 | OH2 | WAT | 334 | 21.998 | −17.667 | 32.451 | 1.00 | 71.85 | W |
| 3557 | OH2 | WAT | 335 | 16.570 | 28.743 | 18.262 | 1.00 | 55.46 | W |
| 3558 | OH2 | WAT | 336 | 15.355 | 29.463 | 26.907 | 1.00 | 56.68 | W |
| 3559 | OH2 | WAT | 337 | 8.856 | −4.842 | 42.494 | 1.00 | 57.55 | W |
| 3560 | OH2 | WAT | 338 | 15.673 | 11.399 | 16.679 | 1.00 | 70.26 | W |
| 3561 | OH2 | WAT | 339 | 30.499 | −19.038 | 31.070 | 1.00 | 70.97 | W |

TABLE 1-continued

| Atom | Atom Type | Res | # | X | Y | Z | OCC | B | Mol. |
|---|---|---|---|---|---|---|---|---|---|
| 3562 | OH2 | WAT | 340 | 27.359 | 6.348 | 14.986 | 1.00 | 76.17 | W |
| 3563 | OH2 | WAT | 341 | 30.716 | 22.063 | 48.368 | 1.00 | 68.15 | W |
| 3564 | OH2 | WAT | 342 | 17.680 | 32.354 | 47.113 | 1.00 | 74.87 | W |
| 3565 | OH2 | WAT | 343 | 35.483 | −23.224 | 64.528 | 1.00 | 67.43 | W |
| 3566 | OH2 | WAT | 344 | 11.697 | 33.674 | 34.831 | 1.00 | 62.19 | W |
| 3567 | OH2 | WAT | 345 | 35.198 | −13.847 | 37.632 | 1.00 | 62.48 | W |
| 3568 | OH2 | WAT | 346 | 10.971 | −16.646 | 58.283 | 1.00 | 62.08 | W |
| 3569 | OH2 | WAT | 347 | 35.865 | −19.311 | 48.930 | 1.00 | 81.00 | W |
| 3570 | OH2 | WAT | 348 | 28.051 | −8.076 | 32.451 | 1.00 | 59.05 | W |
| 3571 | OH2 | WAT | 349 | −.526 | 20.824 | 45.987 | 1.00 | 73.19 | W |
| 3572 | OH2 | WAT | 350 | 8.474 | 8.048 | 19.652 | 1.00 | 64.06 | W |
| 3573 | OH2 | WAT | 351 | 39.937 | 7.489 | 45.216 | 1.00 | 63.27 | W |
| 3574 | OH2 | WAT | 352 | 22.499 | 33.878 | 48.685 | 1.00 | 83.81 | W |
| 3575 | OH2 | WAT | 353 | 36.190 | −18.010 | 40.240 | 1.00 | 67.93 | W |
| 3576 | OH2 | WAT | 354 | 6.583 | 19.327 | 31.179 | 1.00 | 75.92 | W |
| 3577 | OH2 | WAT | 355 | 26.767 | −23.288 | 43.403 | 1.00 | 67.04 | W |
| 3578 | OH2 | WAT | 356 | 34.980 | 17.377 | 43.331 | 1.00 | 79.59 | W |
| 3579 | OH2 | WAT | 357 | 29.121 | 3.825 | 23.022 | 1.00 | 64.97 | W |
| 3580 | OH2 | WAT | 358 | 25.233 | 31.185 | 47.412 | 1.00 | 73.20 | W |
| 3581 | OH2 | WAT | 359 | 21.888 | −20.887 | 35.998 | 1.00 | 69.44 | W |
| 3582 | OH2 | WAT | 360 | 41.720 | −3.130 | 67.884 | 1.00 | 75.17 | W |
| 3583 | OH2 | WAT | 361 | 22.416 | −22.509 | 42.179 | 1.00 | 70.22 | W |
| 3584 | OH2 | WAT | 362 | 15.091 | −13.586 | 69.147 | 1.00 | 63.87 | W |
| 3585 | OH2 | WAT | 363 | 14.937 | −22.535 | 38.211 | 1.00 | 68.35 | W |
| 3586 | OH2 | WAT | 364 | 42.980 | −9.148 | 57.776 | 1.00 | 76.86 | W |
| 3587 | OH2 | WAT | 365 | 21.401 | −27.138 | 53.645 | 1.00 | 69.72 | W |
| 3588 | OH2 | WAT | 366 | 10.544 | −14.952 | 49.512 | 1.00 | 70.21 | W |
| 3589 | OH2 | WAT | 367 | 12.408 | 3.801 | 61.011 | 1.00 | 62.31 | W |
| 3590 | OH2 | WAT | 368 | 17.248 | 3.048 | 21.572 | 1.00 | 73.21 | W |
| 3591 | OH2 | WAT | 369 | 20.917 | 10.215 | 62.345 | 1.00 | 65.29 | W |
| 3592 | OH2 | WAT | 370 | 5.740 | −1.049 | 37.946 | 1.00 | 76.08 | W |
| 3593 | OH2 | WAT | 371 | 29.669 | 20.684 | 19.121 | 1.00 | 55.22 | W |
| 3594 | OH2 | WAT | 372 | 40.853 | −3.980 | 50.418 | 1.00 | 66.08 | W |
| 3595 | OH2 | WAT | 373 | 16.357 | 33.776 | 29.111 | 1.00 | 72.95 | W |
| 3596 | OH2 | WAT | 374 | 36.736 | −21.310 | 42.144 | 1.00 | 75.04 | W |
| 3597 | OH2 | WAT | 375 | 36.717 | −1.394 | 68.084 | 1.00 | 57.39 | W |
| 3598 | OH2 | WAT | 376 | 12.701 | 25.019 | 63.285 | 1.00 | 69.21 | W |
| 3599 | OH2 | WAT | 377 | 9.461 | .079 | 38.572 | 1.00 | 77.06 | W |
| 3600 | OH2 | WAT | 378 | 29.550 | −18.594 | 40.998 | 1.00 | 56.42 | W |
| 3601 | OH2 | WAT | 379 | 37.002 | 33.477 | 33.637 | 1.00 | 69.48 | W |
| 3602 | OH2 | WAT | 380 | 17.262 | −22.386 | 60.944 | 1.00 | 73.34 | W |
| 3603 | OH2 | WAT | 381 | 7.106 | −5.199 | 74.381 | 1.00 | 73.24 | W |
| 3604 | OH2 | WAT | 382 | 6.647 | 15.158 | 23.410 | 1.00 | 70.12 | W |
| 3605 | C1 | NAR | 501 | 26.934 | 18.860 | 35.807 | 1.00 | 61.49 | C |
| 3606 | C2 | NAR | 501 | 25.603 | 18.872 | 36.077 | 1.00 | 61.57 | C |
| 3607 | C3 | NAR | 501 | 24.640 | 19.829 | 35.382 | 1.00 | 61.65 | C |
| 3608 | C4 | NAR | 501 | 25.166 | 20.681 | 34.454 | 1.00 | 61.63 | C |
| 3609 | C5 | NAR | 501 | 26.686 | 20.701 | 34.114 | 1.00 | 61.58 | C |
| 3610 | C6 | NAR | 501 | 27.487 | 19.826 | 34.771 | 1.00 | 61.51 | C |
| 3611 | C7 | NAR | 501 | 24.264 | 21.692 | 33.683 | 1.00 | 61.64 | C |
| 3612 | C8 | NAR | 501 | 25.045 | 22.668 | 32.819 | 1.00 | 61.66 | C |
| 3613 | C9 | NAR | 501 | 26.289 | 22.040 | 32.224 | 1.00 | 61.75 | C |
| 3614 | O1 | NAR | 501 | 27.185 | 21.564 | 33.186 | 1.00 | 61.71 | C |
| 3615 | C10 | NAR | 501 | 26.971 | 23.031 | 31.318 | 1.00 | 61.82 | C |
| 3616 | C11 | NAR | 501 | 27.122 | 24.342 | 31.687 | 1.00 | 61.81 | C |
| 3617 | C12 | NAR | 501 | 27.816 | 25.322 | 30.758 | 1.00 | 61.88 | C |
| 3618 | C13 | NAR | 501 | 28.301 | 24.922 | 29.555 | 1.00 | 61.89 | C |
| 3619 | C14 | NAR | 501 | 28.134 | 23.466 | 29.145 | 1.00 | 61.92 | C |
| 3620 | C15 | NAR | 501 | 27.516 | 22.579 | 29.964 | 1.00 | 61.83 | C |
| 3621 | O2 | NAR | 501 | 23.058 | 21.704 | 33.750 | 1.00 | 61.67 | C |
| 3622 | O3 | NAR | 501 | 23.309 | 19.817 | 35.673 | 1.00 | 61.77 | C |
| 3623 | O4 | NAR | 501 | 27.748 | 17.997 | 36.444 | 1.00 | 61.35 | C |
| 3624 | O5 | NAR | 501 | 28.915 | 25.800 | 28.743 | 1.00 | 62.05 | C |
| 3625 | C1 | NAR | 502 | 33.796 | −8.354 | 57.778 | 1.00 | 89.25 | D |
| 3626 | C2 | NAR | 502 | 32.541 | −8.861 | 57.702 | 1.00 | 89.23 | D |
| 3627 | C3 | NAR | 502 | 32.089 | −10.035 | 58.559 | 1.00 | 89.22 | D |
| 3628 | C4 | NAR | 502 | 33.006 | −10.560 | 59.428 | 1.00 | 89.20 | D |
| 3629 | C5 | NAR | 502 | 34.440 | −10.025 | 59.563 | 1.00 | 89.20 | D |
| 3630 | C6 | NAR | 502 | 34.797 | −8.975 | 58.766 | 1.00 | 89.23 | D |
| 3631 | C7 | NAR | 502 | 32.694 | −11.745 | 60.364 | 1.00 | 89.18 | D |
| 3632 | C8 | NAR | 502 | 33.367 | −11.607 | 61.741 | 1.00 | 89.17 | D |
| 3633 | C9 | NAR | 502 | 34.687 | −10.819 | 61.746 | 1.00 | 89.16 | D |
| 3634 | O1 | NAR | 502 | 35.279 | −10.623 | 60.468 | 1.00 | 89.18 | D |
| 3635 | C10 | NAR | 502 | 35.618 | −11.507 | 62.726 | 1.00 | 89.13 | D |
| 3636 | C11 | NAR | 502 | 36.217 | −12.703 | 62.422 | 1.00 | 89.10 | D |
| 3637 | C12 | NAR | 502 | 37.149 | −13.377 | 63.431 | 1.00 | 89.06 | D |
| 3638 | C13 | NAR | 502 | 37.396 | −12.810 | 64.648 | 1.00 | 89.05 | D |

TABLE 1-continued

| Atom | Atom Type | Res | # | X | Y | Z | OCC | B | Mol. |
|---|---|---|---|---|---|---|---|---|---|
| 3639 | C14 | NAR | 502 | 36.727 | −11.482 | 64.979 | 1.00 | 89.06 | D |
| 3640 | C15 | NAR | 502 | 35.896 | −10.874 | 64.092 | 1.00 | 89.12 | D |
| 3641 | O2 | NAR | 502 | 31.989 | −12.680 | 60.059 | 1.00 | 89.20 | D |
| 3642 | O3 | NAR | 502 | 30.824 | −10.521 | 58.461 | 1.00 | 89.25 | D |
| 3643 | O4 | NAR | 502 | 34.142 | −7.311 | 56.993 | 1.00 | 89.32 | D |
| 3644 | O5 | NAR | 502 | 38.221 | −13.408 | 65.539 | 1.00 | 89.04 | D |
| 3645 | S1 | SUL | 601 | 29.329 | 15.428 | 57.928 | 1.00 | 72.96 | E |
| 3646 | O1 | SUL | 601 | 28.642 | 16.617 | 57.309 | 1.00 | 73.02 | E |
| 3647 | O2 | SUL | 601 | 28.473 | 14.847 | 58.999 | 1.00 | 73.02 | E |
| 3648 | O3 | SUL | 601 | 30.643 | 15.853 | 58.538 | 1.00 | 73.11 | E |
| 3649 | O4 | SUL | 601 | 29.610 | 14.436 | 56.850 | 1.00 | 73.00 | E |
| 3650 | S1 | SUL | 602 | 35.827 | −2.534 | 36.136 | 1.00 | 74.42 | F |
| 3651 | O1 | SUL | 602 | 35.316 | −1.739 | 37.305 | 1.00 | 74.49 | F |
| 3652 | O2 | SUL | 602 | 35.956 | −3.971 | 36.514 | 1.00 | 74.45 | F |
| 3653 | O3 | SUL | 602 | 37.188 | −2.019 | 35.723 | 1.00 | 74.53 | F |
| 3654 | O4 | SUL | 602 | 34.874 | −2.354 | 34.996 | 1.00 | 74.40 | F |
| 3655 | S1 | SUL | 603 | 23.022 | 36.796 | 31.551 | 1.00 | 84.30 | G |
| 3656 | O1 | SUL | 603 | 24.269 | 37.382 | 32.155 | 1.00 | 84.26 | G |
| 3657 | O2 | SUL | 603 | 22.893 | 35.383 | 31.991 | 1.00 | 84.22 | G |
| 3658 | O3 | SUL | 603 | 23.099 | 36.815 | 30.053 | 1.00 | 84.26 | G |
| 3659 | O4 | SUL | 603 | 21.855 | 37.634 | 31.971 | 1.00 | 84.28 | G |
| 3660 | S1 | SUL | 604 | 28.867 | 23.364 | 40.821 | 1.00 | 71.85 | H |
| 3661 | O1 | SUL | 604 | 28.898 | 22.850 | 39.401 | 1.00 | 71.90 | H |
| 3662 | O2 | SUL | 604 | 27.477 | 23.295 | 41.360 | 1.00 | 71.86 | H |
| 3663 | O3 | SUL | 604 | 29.322 | 24.801 | 40.860 | 1.00 | 71.98 | H |
| 3664 | O4 | SUL | 604 | 29.814 | 22.540 | 41.641 | 1.00 | 71.87 | H |
| 3665 | S1 | SUL | 605 | 37.472 | −10.233 | 53.632 | 1.00 | 90.38 | I |
| 3666 | O1 | SUL | 605 | 38.162 | −10.843 | 54.827 | 1.00 | 90.36 | I |
| 3667 | O2 | SUL | 605 | 36.461 | −11.177 | 53.085 | 1.00 | 90.34 | I |
| 3668 | O3 | SUL | 605 | 38.480 | −9.940 | 52.560 | 1.00 | 90.32 | I |
| 3669 | O4 | SUL | 605 | 36.839 | −8.942 | 54.058 | 1.00 | 90.34 | I |

"Structure coordinates" refers to Cartesian coordinates (x, y, and z positions) derived from mathematical equations involving Fourier synthesis as determined from patterns obtained via diffraction of a monochromatic beam of X-rays by the atoms (scattering centers) of an isomerase polypeptide in crystal form. Diffraction data are used to calculate electron density maps of repeating protein units in the crystal (unit cell). Electron density maps are used to establish the positions of individual atoms within a crystal's unit cell. The term "crystal structure coordinates" refers to mathematical coordinates derived from mathematical equations related to the patterns obtained on diffraction of a monochromatic beam of X-rays by the atoms (scattering centers) of an isomerase polypeptide (e.g., a chalcone isomerase protein molecule) in crystal form. The diffraction data are used to calculate an electron density map of the repeating unit of the crystal. The electron density maps are used to establish the positions of the individual atoms within the unit cell of the crystal. The crystal structure coordinates of an isomerase can be obtained from a chalcone isomerase protein crystal having space group P6$_5$22 (a=90.37 Å, c=352.86 Å with two molecules per asymmetric unit and a solvent content of 72%). The coordinates of the isomerase polypeptide can also be obtained by means of computational analysis.

The term "selenomethionine substitution" refers to the method of producing a chemically modified form of the crystal of an isomerase (e.g., a chalcone isomerase). The isomerase protein is expressed by bacteria in media that is depleted in methionine and supplement with selenomethionine. Selenium is thereby incorporated into the crystal in place of methionine sulfurs. The location(s) of selenium are determined by X-ray diffraction analysis of the crystal. This information is used to generate the phase information used to construct a three-dimensional structure of the protein.

"Heavy atom derivatizatiort" refers to a method of producing a chemically modified form of an isomerase crystal. In practice, a crystal is soaked in a solution containing heavy atom salts or organometallic compounds, e.g., lead chloride, gold thiomalate, thimerosal, uranyl acetate, and the like, which can diffuse through the crystal and bind to the protein's surface. Locations of the bound heavy atoms can be determined by X-ray diffraction analysis of the soaked crystal. This information is then used to construct phase information which can then be used to construct three-dimensional structures of the enzyme as described in Blundel, T. L., and Johnson, N. L., Protein Crystallography, Academic Press (1976), which is incorporated herein by reference.

"Unit cell" refers to a basic parallelepiped shaped block. Regular assembly of such blocks may construct the entire volume of a crystal. Each unit cell comprises a complete representation of the unit pattern, the repetition of which builds up the crystal.

"Space Group" refers to the arrangement of symmetry elements within a crystal.

"Molecular replacement" refers to generating a preliminary model of an isomerase whose structural coordinates are unknown, by orienting and positioning a molecule whose structural coordinates are known within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This in turn can be subject to any of the several forms of refinement to provide a final, accurate structure of the unknown crystal (Lattman, E., 1985, in Methods in Enzyrnology, 11 5.55-77; Rossmann, M G., ed., "The Molecular Replacement Method" 1972, Int, Sci. Rev. Ser., No. 13, Gordon & Breach, New York). Using structure coordinates of the isomerase provided herein, molecular replacement may be used to determine the structural coordinates of a crystalline mutant, homologue, or a different crystal form of an isomerase.

"Substrate" refers to chalcone and 6' deoxychalcone that are acted on by the chalcone isomerases and mutants thereof disclosed herein, and the like.

"Altered substrate specificity" includes a change in the ability of a mutant isomerase to produce a flavonoid product as compared to a non-mutated isomerase. Altered substrate specificity may include the ability of an isomerase to exhibit different enzymatic parameters relative to a non-mutated isomerase ($K_m$, $V_{max}$, etc.), use different substrates, and/or produce products that are different from those of known non-native isomerases.

A polypeptide is a chain of amino acids, regardless of length or post-translational modification (e.g., glycosylation or phosphorylation). A polypeptide or protein refers to a polymer in which the monomers are amino add residues, which are joined together through amide bonds. When the amino acids are alpha-amino acids, either the L-optical isomer or the D-optical isomer can be used, the L-isomers being typical. An isomerase polypeptide of the invention is intended to encompass an amino add sequence as set forth in SEQ ID NO:1 (see, Table 2) or SEQ ID NO:1 having one or more mutations, mutants, variants and conservative substitutions thereof comprising L- or D-amino acids and include modified sequences such as glycoproteins.

TABLE 2

(SEQ ID NO: 1)
```
maasitaitv enleypavvt spvtgksyfl ggagerglti egnfikftai gvylediava slaakwkgks seelletldf yrdiisgpfe klirgskire lsgpeysrkv mencvahlks vgtygdaeae amqkfaeafk pvnfppgasv fyrqspdgil glsfspdtsi pekeaalien kayssavlet migehayspd lkrclaarlp allnegafki gn
```

Accordingly, the polypeptides of the invention are intended to cover naturally occurring proteins, as well as those which are recombinantly or synthetically synthesized. Polypeptide or protein fragments are also encompassed by the invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general polypeptides of the invention include peptides, or full-length protein, that contains substitutions, deletions, or insertions into the protein backbone, that would still have an approximately 70%-90% homology to the original protein over the corresponding portion. A yet greater degree of departure from homology is allowed if like-amino adds, i.e. conservative amino acid substitutions, do not count as a change in the sequence.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine, and the like. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce other modifications, for example, deletion(s), replacement(s) or addition(s). Examples of such other modifications include incorporation of rare amino acids, dextra-amino acids, glycosylation sites, cytosine for specific disulfide bridge formation. The modified peptides can be chemically synthesized, or the isolated gene can be subjected to site-directed mutagenesis, or a synthetic gene can be synthesized and expressed in bacteria, yeast, baculovirus, tissue culture and so on.

Polypeptides of the invention include isomerase polypeptides (e.g., chalcone isomerase) from any number of plants, prokaryotes, eukaryotes, including, for example, invertebrates, mammals and humans and include sequences as set forth in SEQ ID NO:1 through SEQ ID NO:8, as well as sequences that have at least 70% homology to the sequence of SEQ ID NO:1 through SEQ ID NO:8, fragments, variants, or conservative substitutions of any of the foregoing sequences.

The term "variant" refers to polypeptides which are modified at one or more amino acid residues yet still retain the biological activity of an isomerase polypeptide. Variants can be produced by any number of means known in the art, including methods such as, for example, error-prone PCR, shuffling, oligonucleotide-directed mutagenesis, assembly PCR, sexual PCR mutagenesis, and the like, as well as any combination thereof.

By "substantially identical" is meant a polypeptide or nucleic acid exhibiting at least 50%, preferably 85%, more preferably 90%, and most preferably 95% homology to a reference amino acid or nucleic acid sequence.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of Person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment PROGRAM), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, available on the World Wide Web at weber.u.Washington.edu/~roach/human_genome_progress 2.html) (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the interne, for example, on the World Wide Web websites at tigr.org/tdb, genetics.wisc.edu, standford. edu/~ball, hiv-web.lanl.gov, ncbi.nlm.nih.gov, ebi.ac.uk, Pasteur.fr/other/biology, and genome.wi.mit.edu.

One example of a useful algorithm is BLAST and BLAST 2.0 algorithms, which are described in Altschul et al., Nuc. Acids Res: 25:3389-3402, 1977, and Altschul et al., J. Mol. Biol. 215:403-410, 1990, respectively. Software for performing BLAST analyses is publicly available through the National Center for Biotechnology Information (available on the World Wide Web website at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993). Less preferably, the PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine, e.g., on the World Wide Web at ncbi.nlm.nih.gov.

The parameters used with the above algorithms may be adapted depending on the sequence length and degree of homology studied. In some embodiments, the parameters may be the default parameters used by the algorithms in the absence of instructions from the user.

One aspect of the invention resides in obtaining crystals of the isomerase polypeptide (e.g., chalcone isomerase) of sufficient quality to determine the three dimensional (tertiary) structure of the protein by X-ray diffraction methods. The knowledge obtained concerning the three-dimensional structure of chalcone isomerase can be used in the determination of the three dimensional structure of other isomerase polypeptides in the polyketide synthesis or flavonoid pathway. The structural coordinates of chalcone isomerase can be used to develop new isomerase enzymes or isomerase binding agents (e.g., inhibitors or substrates) using various computer models. Based on the structural coordinates of the chalcone isomerase polypeptide (e.g., the three dimensional protein structure), as described herein, novel isomerases can be engineered. In addition, small molecules which mimic or are capable of interacting with a functional domain of an isomerase polypeptide, can be designed and synthesized to modulate chalcone isomerase and other isomerase biological functions as well as the biological functions of other flavanone-related isomerases. Accordingly, in one embodiment, the invention provides a method of "rational" enzyme or drug design.

Another approach to "rational" enzyme or drug design is based on a lead compound that is discovered using high throughput screens; the lead compound is further modified based on a crystal structure of the binding regions of the molecule in question. Accordingly, another aspect of the invention is to provide related protein sequences or material which is a starting material in the rational design of new isomerases or drugs which lead to the synthesis of new flavonoids or modify the flavonoid pathway.

The present invention relates to crystallized isomerases and mutants thereof from which the position of specific α-carbon atoms and R-groups associated therewith comprising the active site can be determined in three-dimensional space. The invention also relates to structural coordinates of said chalcone isomerases, use of said structural coordinates to develop structural information related to isomerase homologues, mutants, and the like, and to crystal forms of such isomerases. Furthermore, the invention, as disclosed herein, provides a method whereby the α-carbon structural coordinates specifically determined for atoms comprising the active site of the isomerase can be used to develop isomerases wherein R-groups associated with active site α-carbon atoms are different from the R-groups found in native CHI, e.g., are mutant isomerases. In addition, the present invention provides for production of mutant chalcone isomerases based on the structural information provided herein and for use of the mutant isomerases to make a variety of flavonoid or polyketide compounds using a variety of substrates.

The present invention further provides, for the first time, crystal isomerases, as exemplified by chalcone isomerase (CHI; PDB Accession No. 1EYP) see Table 1 for coordinates of native CHI.

Also provided are coordinates for crystals which are grown in the presence and absence of product and product analogues, thus allowing definition of the structural or atomic coordinates associated therewith. The structural coordinates allow determination of the α-carbon atoms comprising the active site, R-groups associated therewith, and the interaction of said α-carbons and said R-groups with each other. For example, CHI was co-crystallized with naringenin as a complex. Other crystallized complexes include CHI complexed with 5-deoxyflavanone and CHI complexed with 5,4'-dideoxyflavanone (PDB accession numbers 1FM7 and 1FM8, respectively, which were deposited on Aug. 16, 2000, all of which are incorporated herein by reference in their entirety) and CHI complexed with 4'-dihydroxyflavanone (Accession No. 1JEP, Protein Data Bank, which is incorporated herein by reference in its entirety). The crystals of CHI•naringenin belong to space group $P6_522$ having unit cell dimensions of a=89.47 Å; c=351.19 Å, α=β=90°, γ=120° with a single monomer per asymmetric unit.

Crystal structures are preferably obtained at a resolution of about 1.56 angstroms to about 3 angstroms for an isomerase in the presence and in the absence of bound product or product analog. Coordinates for an isomerase in the absence of a substrate bound in the active site have been deposited at the Brookhaven National Laboratory Protein Data Bank, accession number 1EYP. Those skilled in the art understand that a set of structure coordinates determined by X-ray crystallography is not without standard error. Therefore, for the purpose of this invention, any set of structure coordinates wherein the active site α-carbons of an isomerase, isomerase homologue, or mutants thereof, have a root mean square deviation less than ±2.3 angstroms when superimposed using the structural coordinates listed in Table 1 and PDB Accession No. 1EYP, shall be considered identical.

CHI is a functional monomer of approximately 220 residues and has been isolated from a variety of higher plants. The overall structure of CHI resembles an upside-down bouquet that adopts an open-faced β-sandwich fold (FIGS. 1B and 1C). A large β-sheet (β3a-β3f) and a layer of α-helices (α1-α7) comprise the core structure with three short β-strands (β1a, β1b, β2) on the opposite side of the large β-sheet. A search of the Protein Data Bank using DALI revealed no other structurally homologous folds. In addition, a PSI-BLAST search of sequence databases showed that CHI-like sequences are typically found in plants and these sequences display no detectable homology with other proteins. Amino acid sequence comparison of CHIs from a variety of advanced land plants reveals high homology (49% to 82% amino acid sequence identity) with regions of conservation spread uniformly throughout the primary structure (FIG. 1D). Interestingly, there is conservation of residues spanning β3a, β3b, α4, and α6 in the three-dimensional structure among CHIs from different species. Notably, these structural elements form the active site on the protein surface.

The active site α-carbons of chalcone isomerase generally are not all contiguous, i.e., are not adjacent to one another in the primary amino acid sequence of the isomerase due to intervening amino acid residues between various active site α-carbons. Nevertheless, it should be appreciated that certain active site α-carbons can be adjacent to one another in some instances.

An appropriate combination of R-groups, linked to active site α-carbons, can facilitate the formation of one or more desired reaction products. The combination of R-groups selected for use in an isomerase can be any combination other than the ordered arrangements of R-groups found in known native isomerases. Typically, R-groups found on active site α-carbons are those found in naturally occurring amino acids. In some embodiments, however, R-groups other than those found in naturally occurring amino acids can be used.

The present invention permits the use of molecular design techniques to design, select, and synthesize genes encoding mutant isomerases and chalcone isomerases that produce different and/or novel flavonoid compounds using various substrates. Mutant proteins of the present invention and nucleic acids encoding the same can be designed by genetic manipulation based on structural information provided herein for the first time regarding isomerases. For example, one or more R-groups associated with the active site α-carbon atoms of CHI can be changed by altering the nucleotide sequence of the corresponding CHI gene, thus making one or more mutant chalcone isomerases. Such genetic manipulations can be guided by structural information concerning the R-groups found in the active site α-carbons when substrate is bound to the protein upon crystallization.

Mutant proteins of the present invention may be prepared in a number of ways available to the skilled artisan. For example, the gene encoding wild-type CHI may be mutated at those sites identified herein as corresponding to amino acid residues identified in the active site by means currently available to the artisan skilled in molecular biology techniques. Such techniques include oligonucleotide-directed mutagenesis, deletion, chemical mutagenesis, and the like. The protein encoded by the mutant gene is then produced by expressing the gene in, for example, a bacterial or plant expression system.

Alternatively, isomerase mutants may be generated by site specific-replacement of a particular amino acid with an unnaturally occurring amino acid or mimetic. As such, isomerase mutants may be generated through replacement of an amino acid residue or a particular cysteine or methionine residue with selenocysteine or selenomethionine. This may be achieved by growing a host organism capable of expressing either the wild-type or mutant polypeptide on a growth medium depleted of natural cysteine or methionine or both and growing on medium enriched with either selenocysteine, selenomethionine, or both. These and similar techniques are described in Sambrook et al., (Molecular Cloning, A Laboratory Manual, $2^{nd}$ Ed. (1989) Cold Spring Harbor Laboratory Press).

Another suitable method of creating mutant isomerases of the present invention is based on a procedure described in Noel and Tsai, J. Cell. Biochem., 40:309-320, 1989. In so doing, the nucleic acids encoding the isomerase can be synthetically produced using oligonucleotides having overlapping regions, said oligonucleotides being degenerate at specific bases so that mutations are induced.

According to the present invention, nucleic acid sequences encoding a mutated polyketide isomerase can be produced by the methods described herein, or any alternative methods available to the skilled artisan. In designing the nucleic acid sequence of interest, it may be desirable to reengineer the gene for improved expression in a particular expression system. For example, it has been shown that many bacterially derived genes do not express well in plant systems. In some cases, plant-derived genes do not express well in bacteria. This phenomenon may be due to the non-optimal G+C content and/or A+T content of said gene relative to the expression system being used. For example, the very low G+C content of many bacterial genes results in the generation of sequences mimicking or duplicating plant gene control sequences that are highly A+T rich. The presence of A+T rich sequences within the genes introduced into plants (e.g., TATA box regions normally found in promoters) may result in aberrant transcription of the gene(s). In addition, the presence of other regulatory sequences residing in the transcribed mRNA (e.g. polyadenylation signal sequences (AAUAAA) or sequences complementary to small nuclear RNAs involved in pre-mRNA splicing) may lead to RNA instability. Therefore, one goal in the design of genes is to generate nucleic acid sequences that have a G+C content that affords raRNA stability and translation accuracy for a particular expression system.

Due to the plasticity afforded by the redundancy of the genetic code (i.e., some amino acids are specified by more than one codon), evolution of the genomes of different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. Therefore, in reengineering genes for expression, one may wish to determine the codon bias of the organism in which the gene is to be expressed. Looking at the usage of the codons as determined for genes of a particular organism deposited in GenBank can provide this information. After determining the bias thereof, the new gene sequence can be analyzed for restriction enzyme sites as well as other sites that could affect transcription such as exon:intron junctions, polyA addition signals, or RNA polymerase termination signals.

Genes encoding isomerases, such as chalcone isomerase, can be placed in an appropriate vector, depending on the artisan's interest, and can be expressed using a suitable expression system. An expression vector, as is well known in the art, typically includes elements that permit replication of said vector within the host cell and may contain one or more phenotypic markers for selection of cells containing the gene. The expression vector will typically contain sequences that control expression such as promoter sequences, ribosome binding sites, and translational initiation and termination sequences. Expression vectors may also contain elements such as subgenomic promoters, a repressor gene or various activator genes. The artisan may also choose to include nucleic acid sequences that result in secretion of the gene product, movement of said product to a particular organelle such as a plant plastid (see U.S. Pat. Nos. 4,762,785; 5,451, 513 and 5,545,817, which are incorporated herein by reference) or other sequences that increase the ease of peptide purification, such as an affinity tag.

A wide variety of expression control sequences are useful in expressing native or mutated isomerases when operably linked thereto. Such expression control sequences include, for example, the early and late promoters of SV40 for animal cells, the lac system, the trp system, major operator and promoter systems of phage S, and the control regions of coat proteins, particularly those from RNA viruses in plants. In E. coli, a useful transcriptional control sequence is the T7 RNA polymerase binding promoter, which can be incorporated into a pET vector as described by Studier et al., Methods Enzymology, 185:60-89, 1990, which is incorporated herein by reference.

For expression, a desired gene should be operably linked to the expression control sequence and maintain the appropriate reading frame to permit production to of the desired isomerase. Any of a wide variety of well-known expression vectors are of use to the present invention. These include, for example, vectors comprising segments of chromosomal, non-chromosomal and synthetic DNA sequences such as those derived from SV40, bacterial plasmids including those from *E. coli* such as col E1, pCR1, pBR322 and derivatives thereof, pMB9, wider host range plasmids such as RP4, phage DNA such as phage S, NM989, M13, and other such systems as described by Sambrook et al., (Molecular Cloning, A Laboratory Manual, $2^{nd}$ Ed. (1989) Cold Spring Harbor Laboratory Press), which is incorporated herein by reference.

A wide variety of host cells are available for expressing isomerase mutants of the present invention. Such host cells include, for example, bacteria such as *E. coli, Bacillus* and *Streptomyces*, fungi, yeast, animal cells, plant cells, insect cells, and the like. Preferred embodiments of the present invention include chalcone isomerase mutants that are expressed in *E. coli* or in plant cells. Said plant cells can either be in suspension culture or a transgenic plant.

In order to produce transgenic plants, vectors containing the nucleic acid construct encoding isomerases and mutants thereof are inserted into the plant genome. Preferably, these recombinant vectors are capable of stable integration into the plant genome. One variable in making a transgenic plant is the choice of a selectable marker. A selectable marker is used to identify transformed cells against a high background of untransformed cells. The preference for a particular marker is at the discretion of the artisan, but any of the selectable markers may be used along with any other gene not listed herein that could function as a selectable marker. Such selectable markers include aminoglycoside phosphotransferase gene of transposon Tn5 (Aph 11) (which encodes resistance to the antibiotics kanamycin), neomycin, G418, as well as those genes which code for resistance or tolerance to glyphosate, hygromycin, methotrexate, phosphinothricin, imidazolinones, sulfonylureas, triazolopyrimidine herbicides, such as chlorosulfuron, bromoxynil, dalapon, and the like. In addition to a selectable marker, it may be desirable to use a reporter gene. In some instances a reporter gene may be used with a selectable marker. Reporter genes allow the detection of transformed cells and may be used at the discretion of the artisan. A list of these reporter genes is provided in K. Wolsing et al., Ann. Rev. Genetics, 22:421, 1988.

The genes are expressed either by promoters expressing in all tissues at all times (constitutive promoters), by promoters expressing in specific tissues (tissue-specific promoters), promoters expressing at specific stages of development (developmental promoters), and/or promoters expressing in response to a stimulus or stimuli (inducible promoters). The choice of these is at the discretion of the artisan.

Several techniques exist for introducing foreign genes into plant cells, and for obtaining plants that stably maintain and express the introduced gene. Such techniques include acceleration of genetic material coated on a substrate directly into cells (U.S. Pat. No. 4,945,050 to Cornell): Plant cells may also be transformed using *Agrobacterium* technology (see, for example, U.S. Pat. Nos. 5,177,010 to University of Toledo, 5,104,310 to Texas A&M, U.S. Pat. Nos. 5,149,645, 5,469,976, 5,464,763, 4,940,838, and 4,693,976 to Schilperoot, European Patent Applications 116718, 290799, 320500 to Max Planck, European Patent Applications 604662, 627752 and U.S. Pat. No. 5,591,616 to Japan Tobacco, European Patent Applications 0267159, 0292435 and U.S. Pat. No. 5,231,011 to Ciba-Geigy, U.S. Pat. Nos. 5,463,174 and 4,762,785 to Calgene, and U.S. Pat. Nos. 5,004,863 and 5,159,135 to Agracetus). Other transformation technologies include whiskers technology (see U.S. Pat. Nos. 5,302,523 and 5,464,765 to Zeneca). Electroporation technology has also been used to transform plants (see WO 87106614 to Boyce Thompson Institute, 5,472,869 and 5,384,253 to Dakalb, and WO 92/09696 and WO 93/21335 to Plant Genetic Systems, all which are incorporated by reference). Viral vector expression systems can also be used such as those described in U.S. Pat. Nos. 5,316,931, 5,589,367, 5,811,653, and 5,866,785 to BioSource, which are incorporated herein by reference.

In addition to numerous technologies for transforming plants, the type of tissue that is contacted with the genes of interest may vary as well. Suitable tissue includes, for example, embryonic tissue, callus tissue, hypocotyl, meristem, and the like. Almost all plant tissues may be transformed during de-differentiation using the appropriate techniques described herein.

Regardless of the transformation system used, a gene encoding a mutant isomerase is preferably incorporated into a gene transfer vector adapted to express said gene in a plant cell by including in the vector an expression control sequence (e.g., a plant promoter regulatory element). In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter, and the like, may be used. Promoters of viral origin, such as the cauliflower mosaic virus (35S and 19S) are also desirable. Plant promoter regulatory elements also include ribulose-1,6-bisphosphate carboxylase small subunit promoter, beta-conglycinin promoter, phaseolin promoter, ADH promoter, heat-shock promoters, tissue specific promoters, and the like. Numerous promoters are available to skilled artisans for use at their discretion.

It should be understood that not all expression vectors and expression systems function in the same way to express the mutated gene sequences of the present invention. Neither do all host cells function equally well with the same expression system. However, one skilled in the art may make a selection among these vectors, expression control sequences, and host without undue experimentation and without departing from the scope of this invention.

Once an isomerase of the present invention is expressed, the protein obtained therefrom can be purified so that structural analysis, modeling, and/or biochemical analysis can be performed, as exemplified herein. The nature of the protein obtained can be dependent on the expression system used. For example, genes, when expressed in mammalian or other eukaryotic cells, may contain latent signal sequences that may result in glycosylation, phosphorylation, or other post-translational modifications, which may or may not alter function. Therefore, a preferred embodiment of the present invention is the expression of mutant isomerase genes in *E. coli* cells. Once the proteins are expressed, they can be easily purified using techniques common to the person having ordinary skill in the art of protein biochemistry, such as, for example, techniques described in Colligan at al., (1997) Current Protocols in Protein Science, Chanda, V. B., Ed., John Wiley & Sons, Inc., which is incorporated herein by reference. Such techniques often include the use of cation-exchange or anion-exchange chromatography, gel filtration-size exclusion chromatography, and the like. Another technique that may be commonly used is affinity chromatography. Affinity chromatography can include the use of antibodies, substrate analogs, or histidine residues (His-tag technology).

Once purified, mutants of the present invention may be characterized by any of several different properties. For example, such mutants may have altered active site surface charges of one or more charge units. In addition, the mutants may have altered substrate specificity or product capability relative to a non-mutated isomerase (e.g., a chalcone isomerase).

The present invention allows for the characterization of isomerase mutants by crystallization followed by X-ray diffraction. Polypeptide crystallization occurs in solutions where the polypeptide concentration exceeds it solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Compounds known as "precipitants" are often used to decrease the solubility of the polypeptide in a concentrated solution by forming an energetically unfavorable precipitating layer around the polypeptide molecules (Weber, Advances in Protein Chemistry, 41:1-36, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2,4-pentanediol, many of the polyglycols (such as polyethylene glycol), and the like.

Commonly used polypeptide crystallization methods include the following techniques: batch, hanging drop, seed initiation, dialysis, and the like. In each of these methods, it is important to promote continued crystallization after nucleation by maintaining a supersaturated solution. In the batch method, polypeptide is mixed with precipitants to achieve supersaturation, the vessel is sealed, and set aside until crystals appear. In the dialysis method, polypeptide is retained in a sealed dialysis membrane that is placed into a solution containing precipitant. Equilibration across the membrane increases the polypeptide and precipitant concentrations thereby causing the polypeptide to reach supersaturation levels.

In the preferred hanging drop technique (McPherson, J. Biol Chem, 6300-6306, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide will form.

Another method of crystallization involves introducing a nucleation site into a concentrated polypeptide solution. Generally, a concentrated polypeptide solution is prepared and a seed crystal of the polypeptide is introduced into this solution. If the concentration of the polypeptide and any precipitants are correct, the seed crystal will provide a nucleation site around which a larger crystal forms. In typical embodiments, the crystals of the present invention are formed in hanging drops with 15% PEG 8000; 200 mM magnesium acetate or magnesium chloride, 100 mM 3-(N-morpholino)-2-hydroxypropanesulfonic acid (pH 7.0), and 1 mM dithiothreitol as precipitant.

Some proteins may be recalcitrant to crystallization. However, several techniques are available to the skilled artisan. Quite often the removal of polypeptide segments at the amino or carboxy terminal end of the protein is necessary to produce crystalline protein samples. Said procedures involve either treatment of the protein with one of several proteases including trypsin, chymotrypsin, substilisin, and the like. This treatment often results in the removal of flexible polypeptide segments that are likely to negatively affect crystallization. Alternatively, the removal of coding sequences from the protein's gene facilitates the recombinant expression of shortened proteins that can be screened for crystallization.

The crystals so produced have a wide range of uses. For example, high quality crystals are suitable for X-ray or neutron diffraction analysis to determine the three-dimensional structure of mutant and native isomerases and to design additional mutants thereof. In addition, crystallization can serve as a further purification method. In some instances, a polypeptide or protein will crystallize from a heterogeneous mixture into crystals. Isolation of such crystals by filtration, centrifugation, etc., followed by redissolving the polypeptide affords a purified solution suitable for use in growing the high-quality crystals needed for diffraction studies. The high-quality crystals may also be dissolved in water and then formulated to provide an aqueous solution having other uses as desired.

Because isomerases may crystallize in more than one crystal form, the structural coordinates of α-carbons of an active site determined from an isomerase or portions thereof, as provided by this invention, are particularly useful to solve the structure of other crystal forms of isomerases. The structural coordinates, as provided herein, may also be used to solve the structure of isomerases having α-carbons positioned within the active sites in a manner similar to the wild-type isomerase, yet having R-groups that may or may not be identical to the wild-type isomerase.

Furthermore, the structural coordinates disclosed herein may be used to determine the structure of the crystalline form of other proteins with significant amino acid or structural homology to any functional domain of an isomerase. One method that may be employed for such purpose is molecular replacement. In this method, the unknown crystal structure, whether it is another crystal form of an isomerase, an isomerase having a mutated active site, or the crystal of some other protein with significant sequence and/or structural homology to an isomerase may be determined using the coordinates given in Table 1. This method provides sufficient structural form for the unknown crystal more efficiently than attempting to determine such information ab initio. In addition, this method can be used to determine whether or not a given isomerase in question falls within the scope of this invention.

As further disclosed herein, isomerases and mutants thereof may be crystallized in the presence or absence of substrates and substrate analogs. The crystal structures of a series of complexes may then be solved by molecular replacement and compared to that of the wild-type isomerase to assist in determination of suitable replacements for R-groups within the active site, thus making isomerase mutants according to the present invention.

All mutants of the present inventions may be modeled using the information disclosed herein without necessarily having to crystallize and solve the structure for each and every mutant. For example, one skilled in the art may use one of several specialized computer programs to assist in the process of designing isomerases having mutated active sites relative to the wild-type isomerase. Examples of such programs include: GRID (Goodford, 1985, J. Mod. Chem., 28:849-857), MCSS (Miranker and Karplus, 1991, Proteins: Structure, Function and Genetics, 11:29-34); AUTODOCK (Goodsell and Olsen, 1990, Proteins. Structure, Fumtion, and Genetics, 8:195-202); and DOCK (Kuntz et al., 1982, J. Mot Biol., 161:269-288), and the like, as well as those discussed in the Examples below. In addition, specific computer programs are also available to evaluate specific substrate-active site interactions and the deformation energies and electrostatic interactions resulting therefrom. MODELLER is a computer program often used for homology or comparative modeling of the three-dimensional structure of a protein. A. Saii & T. L. Blundell. J. Mol. Biol. 234:779-815, 1993. A sequence to be modeled is aligned with one or more known related structures and the MODELLER program is used to calculate a full-atom model, based on optimum satisfaction of spatial restraints. Such restraints can include, inter alia, homologous structures, site-directed mutagenesis, fluorescence spectroscopy, NMR experiments, or atom-atom potentials of mean force.

The present invention enables isomerase mutants to be made and the crystal structure thereof to be solved. Moreover, by virtue of the present invention, the location of the active site and the interface of substrate therewith permit the identification of desirable R-groups for introduction by mutagenesis.

The three-dimensional coordinates of the isomerases provided herein may additionally be used to predict the activity and or substrate specificity of a protein whose primary amino acid sequence suggests that it may have isomerase activity. The family of CHI-related enzymes is defined, in part, by a number of conserved amino acid residues including, for example, residues spanning β3a, β3b, α4, and α6 in the three-dimensional structure. By employing the three-dimensional coordinates disclosed herein and computer modeling programs, structural comparisons of CHI can be made with a putative enzyme. Differences between the two would provide the skilled artisan with information regarding the activity and/or substrate specificity of the putative enzyme.

Thus, in another embodiment of the invention, there is provided a method of predicting the activity and/or substrate specificity of an isomerase or putative isomerase comprising (a) generating a three-dimensional representation of a known isomerase (e.g., chalcone isomerase) using three-dimensional coordinate data, (b) generating a predicted three-dimensional representation of a putative isomerase, and (c) comparing the representation of the known isomerase with the representation of the putative isomerase, wherein the differences between the two representations are predictive of activity and/or substrate specificity of the putative isomerase.

In a further embodiment of the present invention, there is also provided a method of identifying a potential substrate of an isomerase comprising (a) defining the active site of an isomerase (e.g., chalcone isomerase) based on the atomic coordinates of the isomerase, (b) identifying a potential substrate that fits the defined active site, and (c) contacting the isomerase with the potential substrate of (b) and determining the activity thereon. Techniques for computer modeling and structural comparisons similar to those described herein for predicting putative isomerase activity and/or substrate specificity can be used to identify novel substrates for isomerases. The plurality of atomic coordinates that can be used to define the active site of an isomerase include those set forth in PDB Accession Nos: 1EYP, 1EYQ, 1FM7, 1FM8, 1JEP and Table 1. A subset or portion of these atomic coordinates can also be used, for example, those atomic coordinates defining the amino acid residues which comprise the enzymatic active site.

In addition, the structural coordinates and three-dimensional models disclosed herein can be used to design or identify isomerase inhibitors. Using the modeling techniques disclosed herein, potential inhibitor structures can be modeled with the isomerase active site and those that appear to interact therewith can subsequently be tested in activity assays in the presence of substrate.

Methods of using crystal structure data to design binding agents or substrates are known in the art. Thus, the crystal structure data provided herein can be used in the design of new or improved inhibitors, substrates or binding agents. For example, the isomerase polypeptide coordinates can be superimposed onto other available coordinates of similar enzymes to identify modifications in the active sites of the enzymes to create novel by-products of enzymatic activity or to modulate flavonoid synthesis. Alternatively, the isomerase polypeptide coordinates can be superimposed onto other available coordinates of similar enzymes which have substrates or inhibitors bound to them to give an approximation of the way these and related substrates or inhibitors might bind to an isomerase. Alternatively, computer programs employed in the practice of rational drug design can be used to identify compounds that reproduce interaction characteristics similar to those found between a isomerase polypeptide and a co-crystallized substrate. Furthermore, detailed knowledge of the nature of binding site interactions allows for the modification of compounds to alter or improve solubility, pharmacokinetics, etc. without affecting binding activity.

Computer programs are widely available that are capable of carrying out the activities necessary to design agents using the crystal structure information provided herein. Examples include, but are not limited to, the computer programs listed below:

Catalyst Databases™—an information retrieval program accessing chemical databases such as BioByte Master File, Derwent WDI and ACD;

Catalyst/HYPOT™—generates models of compounds and hypotheses to explain variations of activity with the structure of drug candidates;

Ludi™—fits molecules into the active site of a protein by identifying and matching complementary polar and hydrophobic groups;

Leapfrog™—"grows" new ligands using a genetic algorithm with parameters under the control of the user.

In addition, various general purpose machines may be used with programs written in accordance with the teachings herein, or it may be more convenient to construct more specialised apparatus to perform the operations. However, preferably the embodiment is implemented in one or more computer programs executing on programmable systems each comprising at least one processor, at least one data storage system (including volatile and non-volatile memory and/or storage elements), at least one input device, and at least one output device. The program is executed on the processor to perform the functions described herein.

Each such program may be implemented in any desired computer language (including machine, assembly, high level procedural, object oriented programming languages, or the like) to communicate with a computer system. In any case, the language may be a compiled or interpreted language. The computer program will typically be stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Figure 5:
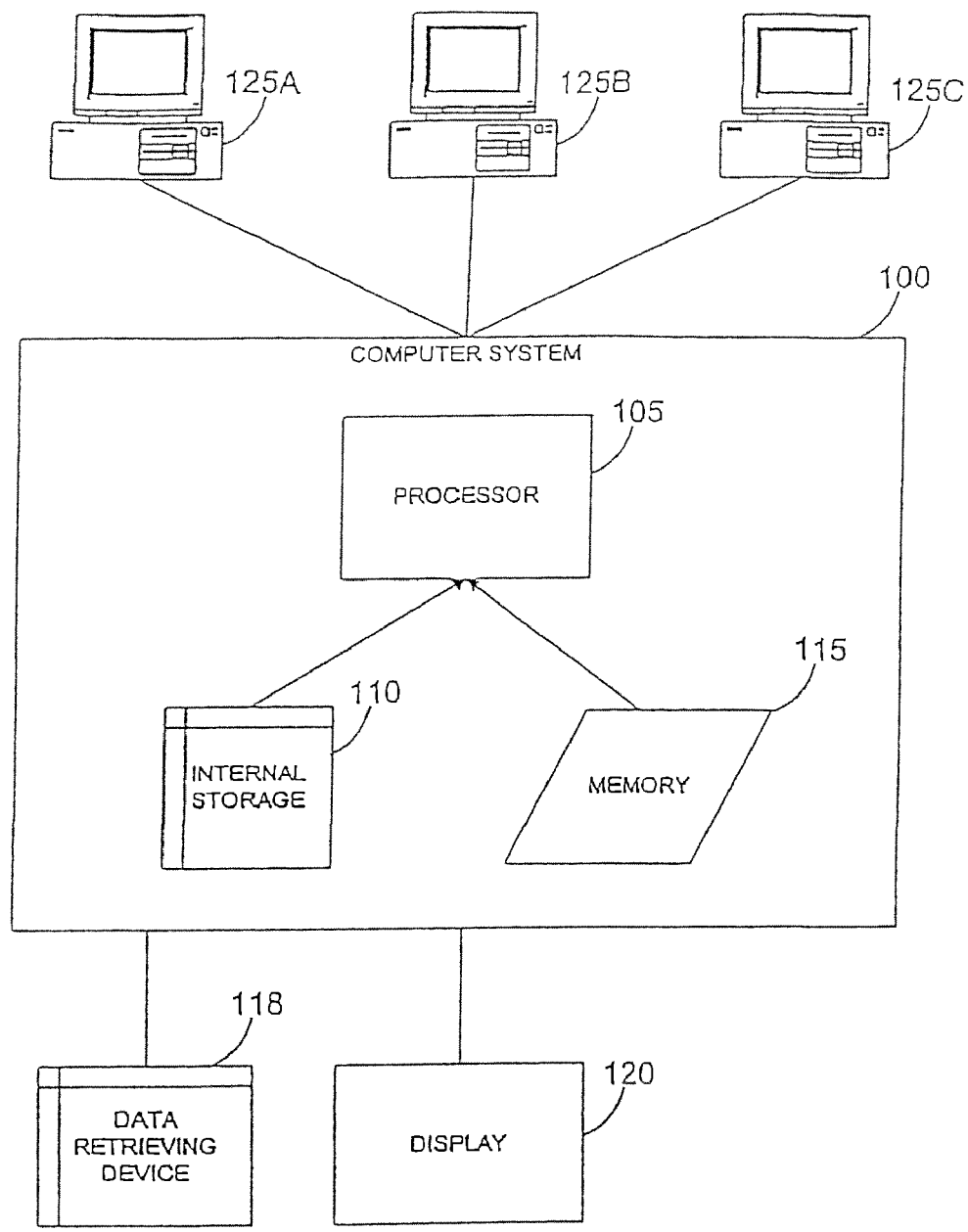
FIG. 5 shows an example of a computer system in block diagram form.

Embodiments of the invention include systems (e.g., internet based systems), particularly computer systems which store and manipulate the coordinate and sequence information described herein. One example of a computer system 100 is illustrated in block diagram form in FIG. 5. As used herein, "a computer system" refers to the hardware components, software components, and data storage components used to analyze the coordinates and sequences as set forth in Accession Nos. 1EYP, 1EYQ, 1FM7, 1FM8, and Table 1. The computer system 100 typically includes a processor for processing, accessing and manipulating the sequence data. The processor 105 can be any well-known type of central processing unit, such as, for example, the Pentium III from Intel Corporation, or similar processor from Sun, Motorola, Compaq, AMD or International Business Machines.

Typically the computer system 100 is a general purpose system that comprises the processor 105 and one or more internal data storage components 110 for storing data, and one or more data retrieving devices for retrieving the data stored on the data storage components. A skilled artisan can readily appreciate that any one of the currently available computer systems are suitable.

In one particular embodiment, the computer system 100 includes a processor 105 connected to a bus which is connected to a main memory 115 (preferably implemented as RAM) and one or more internal data storage devices 110, such as a hard drive and/or other computer readable media having data recorded thereon. In some embodiments, the computer system 100 further includes one or more data retrieving device 118 for reading the data stored on the internal data storage devices 110.

The data retrieving device 118 may represent, for example, a floppy disk drive, a compact disk drive, a magnetic tape drive, or a modem capable of connection to a remote data storage system (e.g., via the internet) etc. In some embodiments, the internal data storage device 110 is a removable computer readable medium such as a floppy disk, a compact disk, a magnetic tape, etc. containing control logic and/or data recorded thereon. The computer system 100 may advantageously include or be programmed by appropriate software for reading the control logic and/or the data from the data storage component once inserted in the data retrieving device.

The computer system 100 includes a display 120 which is used to display output to a computer user. It should also be noted that the computer system 100 can be linked to other computer systems 125a-c in a network or wide area network to provide centralized access to the computer system 100.

Software for accessing and processing the coordinate and sequences described herein, (such as search tools, compare tools, and modeling tools etc.) may reside in main memory 115 during execution.

For the first time, the present invention permits the use of molecular design techniques to design, select and synthesize novel enzymes, chemical entities and compounds, including inhibitory compounds, capable of binding to an isomerase polypeptide (e.g., a chalcone isomerase polypeptide), in whole or in part.

One approach enabled by this invention, is to use the structural coordinates as set forth in Accession Nos. 1EYP, 1EYQ, 1FM7, 1FM8, 1JEP, and Table 1 to design new enzymes capable of synthesizing novel flavonoids. For example, isomerases generate molecular diversity in their products by utilizing different starter molecules. The structural coordinates disclosed herein allow the elucidation of the nature by which isomerases achieve starter molecule selectivity and control flavonoid diversity and synthesis. Accordingly, the invention allows for the strategic development and biosynthesis of more diverse flavonoids and demonstrates a structural basis for control of flavonoid synthesis. In addition, the structural coordinates allow for the development of substrates or binding agents that bind to the polypeptide and alter the physical properties of the compounds in different ways, e.g., solubility.

In another approach an isomerase polypeptide crystal is probed with molecules composed of a variety of different chemical entities to determine optimal sites for interaction between candidate binding molecules (e.g., substrates) and the isomerase (e.g., chalcone isomerase).

In another embodiment, an approach made possible and enabled by this invention, is to screen computationally small molecule data bases for chemical entities or compounds that can bind in whole, or in part, to an isomerase polypeptide or fragment thereof. In this screening, the quality of fit of such entities or compounds to the binding site may be judged either by shape complementarity or by estimated interaction energy. Meng, E. C. et al., J. Comp. Chem., 13, pp. 505-524 (1992).

Chalcone isomerase is one member of a family of isomerase polypeptides, many of which have similar functional activity. In addition, many isomerase polypeptides may crystallize in more than one crystal form. Accordingly, the structural coordinates of chalcone isomerase, or portions thereof, as provided by this invention are particularly useful to solve the structure, function or activity of other crystal forms of isomerase polypeptides. They may also be used to solve the structure of an isomerase or a chalcone isomerase mutant.

One method that may be employed for this purpose is molecular replacement. In this method, the unknown crystal structure, whether it is another isomerase crystal form, chalcone isomerase, chalcone isomerase mutant, an isomerase complexed with a substrate or other molecule, or the crystal of some other protein with significant amino acid sequence homology to any isomerase polypeptide, may be determined using the structure coordinates as provided in Accession Nos. 1EYP, 1EYQ, 1FM7, 1FM8, 1JEP and Table 1. This method will provide an accurate structural form for the unknown crystal more quickly and efficiently than attempting to determine such information ab initio.

In addition, in accordance with the present invention, an isomerase, chalcone isomerase or chalcone isomerase mutant may be crystallized in association or complex with known isomerase binding agents, substrates, or inhibitors. The crystal structures of a series of such complexes may then be solved by molecular replacement and compared with that of wild-type isomerase polypeptides. Potential sites for modification within the isomerase polypeptide may thus be identified. This information provides an additional tool for determining the most efficient binding interactions between an isomerase and a chemical entity, substrate or compound.

All of the complexes referred to above may be studied using well-known X-ray diffraction techniques and may be refined to 2-3 Å resolution X-ray data to an R value of about 0.20 or less using computer software, such as X-PLOR (Yale University, 1992, distributed by Molecular Simulations, Inc.). See, e.g., Blundel & Johnson, supra; Methods in Enzymology, vol. 114 and 115, H. W. Wyckoff et al., eds., Academic Press (1985). This information may thus be used to optimize known classes of isomerase substrates or binding agents (e.g., inhibitors), and to design and synthesize novel classes of isomerases, substrates, and binding agents (e.g., inhibitors).

The design of substrates, compounds or binding agents that bind to or inhibit a chalcone isomerase polypeptide according to the invention generally involves consideration of two factors. First, the substrate, compound or binding agent must be capable of physically and structurally associating with the isomerase polypeptide. Non-covalent molecular interactions important in the association of a polyketide isomerase with a substrate include hydrogen bonding, van der Waals and hydrophobic interactions, and the like.

Second, the substrate, compound or binding agent must be able to assume a conformation that allows it to associate with an isomerase polypeptide. Although certain portions of the substrate, compound or binding agent will not directly participate in this association, those portions may still influence the overall conformation of the molecule. This, in turn, may have a significant impact on potency. Such conformational requirements include the overall three-dimensional structure and orientation of the chemical entity or compound in relation to all or a portion of the binding site, e.g., active site or accessory binding site of a polyketide isomerase (e.g., a chalcone isomerase polypeptide), or the spacing between functional groups of a substrate or compound comprising several chemical entities that directly interact with an isomerase.

The potential binding effect of a substrate or chemical compound on an isomerase or the activity of a newly synthesized or mutated isomerase might have on a known substrate may be analyzed prior to its actual synthesis and testing by the use of computer modeling techniques. For example, if the theoretical structure of the given substrate or compound suggests insufficient interaction and association between it and an isomerase, synthesis and testing of the compound may not be warranted. However, if computer modeling indicates a strong interaction, the molecule may then be tested for its ability to bind to, initiate catalysis or elongation of a flavonoid by an isomerase. Methods of assaying for isomerase activity are known in the art (as identified and discussed herein). Methods for assaying the effect of a newly created isomerase or a potential substrate or binding agent can be performed in the presence of a known binding agent or isomerase. For example, the effect of the potential binding agent can be assayed by measuring the ability of the potential binding agent to compete with a known substrate.

A mutagenized isomerase, novel isomerase, substrate or other binding compound of an isomerase may be computationally evaluated and designed by means of a series of steps in which chemical entities or fragments are screened and selected for their ability to associate with the individual binding pockets or other areas of the isomerase.

One skilled in the art may use one of several methods to screen chemical entities or fragments for their ability to associate with an isomerase and more particularly with the individual binding pockets of a chalcone isomerase polypeptide. This process may begin by visual inspection of, for example, the active site on the computer screen based on the coordinates in Accession Nos. 1EYP, 1E1Q, 1FM7, 1FM8, and Table 1. Selected fragments or substrates or chemical entities may then be positioned in a variety of orientations, or docked, within an individual binding pocket of an isomerase. Docking may be accomplished using software such as Quanta and Sybyl, followed by energy minimization and molecular dynamics with standard molecular mechanics forcefields, such as C and AMBER.

Specialized computer programs may also assist in the process of selecting fragments or chemical entities. These include:

1. GRID (Goodford, P. J., "A Computational Procedure for Determining Energetically Favorable Binding Sites on Biologically Important Macromolecules", J. Med. Chem., 28, pp. 849-857 (1985)). GRID is available from Oxford University, Oxford, UK.

2. MCSS (Miranker, A. and M. Karplus, "Functionality. Maps of Binding Sites: A Multiple Copy Simultaneous Search Method." Proteins: Structure. Function and Genetics, 11, pp. 29-34 (1991)). MCSS is available from Molecular Simulations, Burlington, Mass.

3. AUTODOCK (Goodsell, D. S, and A. J. Olsen, "Automated Docking of Substrates to Proteins by Simulated Annealing", Proteins: Structure. Function, and Genetics, 8, pp. 195-202 (1990)). AUTODOCK is available from Scripps Research Institute, La Jolla, Calif.

4. DOCK (Kuntz, I. D. et al., "A Geometric Approach to Macromolecule-Ligand Interactions", J. Mol. Biol., 161, pp. 269-288 (1982)). DOCK is available from University of California, San Francisco, Calif.

Once suitable substrates, chemical entities or fragments have been selected, they can be assembled into a single polypeptide, compound or binding agent (e.g., an inhibitor). Assembly may be performed by visual inspection of the relationship of the fragments to each other on the three-dimensional image displayed on a computer screen in relation to the structure coordinates of the molecules as set forth in Accession Nos. 1EYP, 1EYQ, 1FM7, 1FM8, and Table 1. This would be followed by manual model building using software such as Quanta or Sybyl.

Useful programs to aid one of skill in the art in connecting the individual chemical entities or fragments include:

1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., Royal Chem. Soc., 78, pp. 182-196 (1989)). CAVEAT is available from the University of California, Berkeley, Calif.

2. 3D Database systems such as MACCS-3D (MDL Information Systems, San Leandro, Calif.). This area is reviewed in Martin, Y. C., "3D Database Searching in Drug Design", J. Med. Chem., 35, pp. 2145-2154 (1992)).

3. HOOK (available from Molecular Simulations, Burlington, Mass.).

In addition to the method of building or identifying novel enzymes or an isomerase substrate or binding agent in a step-wise fashion one fragment or chemical entity at a time as described above, substrates, inhibitors or other isomerase interactions may be designed as a whole or "de novo" using either an empty active site or optionally including some portion(s) of known substrates, binding agents or inhibitors. These methods include:

1. LUDI (Bohm, H.-J., "The Computer Program LUDI: A New Method for the De Novo Design of Enzyme Inhibitors", J. Comp. Aid. Molec. Design, 6, pp. 61-78 (1992)). LUDI is available from Biosym Technologies, San Diego, Calif.

2. LEGEND (Nishibata, Y. and A. Itai, Tetrahedron, 47, p. 8985 (1991)). LEGEND is available from Molecular Simulations, Burlington, Mass.

3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry", J. Med. Chem., 33, pp. 883-894 (1990). See also, Navia, M. A. and M. A. Murcko, "The Use of Structural Information in Drug Design", Current Opinions in Structural Biology, 2, pp. 202-210 (1992).

Once a substrate, compound or binding agent has been designed or selected by the above methods, the efficiency with which that substrate, compound or binding agent may bind to an isomerase may be tested and optimized by computational evaluation.

A substrate or compound designed or selected as an isomerase binding agent may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the binding agent and the isomerase when the binding agent is bound to the isomerase, preferably make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., 1992); AMBER, version 4.0 (P. A. Kollman, University of California at San Francisco, 1994); QUANTA/CHARMM (Molecular Simulations, Inc., Burlington, Mass. 1994); and Insight II/Discover (Biosysm Technologies Inc., San Diego, Calif., 1994). These programs may be implemented, for example, using a Silicon Graphics workstation, IRIS 4D/35 or IBM RISC/6000 workstation model 550. Other hardware systems and software packages will be known to those skilled in the art of which the speed and capacity are continually modified Once an isomerase, isomerase substrate or isomerase binding agent has been selected or designed, as described above, substitutions may then be made in some of its atoms or side groups in order to improve or modify its binding properties. Generally, initial substitutions are conservative, e.g., the replacement group will have approximately the same size, shape, hydrophobicity and charge as the original group. Such substituted chemical compounds may then be analyzed for efficiency of fit to a polyketide isomerase substrate or fit of a modified substrate to an isomerase having a structure defined by the coordinates in Accession Nos. 1EYP, 1EYQ, 1FM7, 1FM8, 1JEP and Table 1, by the same computer methods described, above.

Conserved regions of the flavonoid family isomerases lend themselves to the methods and compositions of the invention. For example, a number of isomerases have conserved residues present within their active sites (as described more fully below). Accordingly, modification to the active site of chalcone isomerase or a chalcone isomerase substrate can be extrapolated to other conserved members of the family of isomerases, Functional fragments of isomerase polypeptides such as, for example, fragments of chalcone isomerase, can be designed based on the crystal structure and atomic coordinates described herein. Fragments of a chalcone isomerase polypeptide and the fragment's corresponding atomic coordinates can be used in the modeling described herein. In addition, such fragments may be used to design novel substrates or modified active sites to create new diverse flavonoids.

In one embodiment of the present invention, the crystal structure and atomic coordinates allow for the design of novel isomerases and novel isomerase substrates. The development of new isomerases will lead to the development a biodiverse library of flavonoids for use as therapeutics (e.g., as antibiotics, anti-cancer agents, anti-fungal agents) as described herein or known in the art. In vitro assay systems for production and determination of activity are known in the art. For example, antibiotic activities of novel products of the polyketide pathway and flavonoid pathway can be measured by any number of anti-microbial techniques currently used in hospitals and laboratories. In addition, anticancer activity can be determined by contacting cells having a cell proliferative disorder with a newly synthesized flavonoid and measuring the proliferation or apoptosis of the cells before and after contact with the flavonoid. Specific examples of apoptosis assays are provided in the following references: Lymphocyte: C. J. Li et al., Science, 268:429-431, 1995; D. Gibellini et al., Br. J. Haematol. 89:24-33, 1995; S. J. Martin et al., J. Immunol. 152:33042, 1994; C. Terai et al., J. Clin Invest. 87:1710-5, 1991; J. Dhein et al., Nature 373:438-441, 1995; P. D. Katsikis et al., J. Exp. Med. 1815:2029-2036, 1995; Michael O. Westendorp et al., Nature 375:497, 1995; DeRossi et al., Virology 198:234-44, 1994. Fibroblasts: H. Vossbeck et al., Int. J. Cancer 61:92-97, 1995; S. Goruppi et al., Oncogene 9:1537-44, 1994; A, Fernandez et al., Oncogene 9:2009-17, 1994; E. A. Harrington et al., Embo J. 13:3286-3295, 1994; N. Itoh et al., J. Biol. Chem. 268:10932-7, 1993. Neuronal Cells: G. Melino et al., Mol. Cell. Biol. 14:6584-6596, 1994; D. M. Rosenbaum et al., Ann. Neurol. 36:864-870, 1994; N. Sato et al., J. Neurobiol 25:1227-1234, 1994; G. Ferrari et al., J. Neurosci. 1516:2857-2866, 1995; A. K. Talley et al., Mol. Cell. Biol. 1585:2359-2366, 1995; A. K. Talley et al., Mol. and Cell. Biol. 15:2359-2366, 1995; G. Walkinshaw et al., J. Clin. Invest. 95:2458-2464, 1995. Insect Cells: R. J. Clem et al., Science 254:1388-90, 1991; N. E. Crook et al., J. Virol. 67:2168-74, 1993; S. Rabizadeh et al., J. Neurochem. 61:2318-21, 1993; M. J. Birnbaum et al., J. Virol 68:2521-8, 1994; R. J. Clem et al., Mol. Cell. Biol. 14:5212-5222, (1994). Other assays are well within the ability of those of skill in the art.

Production of novel flavonoids or isomerases can be carried out in culture. For example, mammalian expression constructs carrying isomerases can be introduced into various cell lines such as CHO, 3T3, HL60, Rat-1, or Jurkart cells, for example. In addition, SF21 insect cells may be used in which case the isomerase gene is expressed using an insect heat shock promotor.

In another embodiment of the present invention, once a novel substrate or binding agent is developed by the computer methodology discussed above, the invention provides a method for determining the ability of the substrate or agent to be acted upon by an isomerase. The method includes contacting components comprising the substrate or agent and an isomerase, or a recombinant cell expressing an isomerase, under conditions sufficient to allow the substrate or agent to interact and determining the affect of the agent on the activity of the polypeptide. The term "affect", as used herein, encompasses any means by which protein activity can be modulated, and includes measuring the interaction of the agent with the isomerase polypeptide by physical means including, for example, fluorescence detection of the binding of an agent to the polypeptide. Such agents can include, for example, polypeptides, peptidomimetics, chemical compounds, small molecules, substrates and biologic agents as described herein. Examples of small molecules include but are not limited to small peptides or peptide-like molecules.

Contacting or incubating includes conditions which allow contact between the test agent or substrate and an isomerase or modified isomerase polypeptide or a cell expressing an isomerase or modified isomerase polypeptide. Contacting includes in solution and in solid phase. The substrate or test agent may optionally be a combinatorial library for screening a plurality of substrates or test agents. Agents identified in the method of the invention can be further evaluated by chromatography, cloning, sequencing, and the like.

In yet another embodiment, the present invention provides a computer for producing a three-dimensional representation of a molecule or molecular complex or a homologue of said molecule or molecular complex, wherein said molecule or molecular complex or a homologue of said molecule or molecular complex comprises an active site defined by atomic coordinates are as set forth in PDB Accession Nos: 1EYP, 1EYQ, 1FM7, 1FM8, 1JEP, or Table 1, wherein said computer comprises:
  (i) a computer-readable data storage medium comprising a data storage material encoded with computer-readable data, wherein said data comprises atomic coordinates are as set forth in PDB Accession Nos: 1EYP, 1EYQ, 1FM7, 1FM8, 1JEP, or Table 1;
  (ii) a working memory for storing instructions for processing said computer-readable data;
  (iii) a central-processing unit coupled to said working memory and to said computer-readable data storage medium for processing said computer-machine readable data into said three-dimensional representation; and
  (iv) a display coupled to said central-processing unit for displaying said three-dimensional representation.

Such a computer could also be used to determine at least a portion of the atomic coordinates corresponding to X-ray diffraction data obtained from a molecule or molecular complex or a homologue of said molecule or molecular complex.

In yet another embodiment, the present invention provides methods of screening compounds to determine whether they are isomerase substrates, said method comprising:
  a) determining the points of interaction between an isomerase and a substrate or product therefor;
  b) selecting compound(s) having similar interaction with said isomerase; and
  c) testing the selected compound for the ability to be converted by said isomerase.

An alternative method of screening compounds to determine whether they are isomerase substrates comprises:
  a) selecting compound(s) having points of interaction with said isomerase, wherein similar points of interaction have been determined between said isomerase and a substrate or product therefor; and
  b) testing the selected compound for the ability to be converted by said isomerase.

Another alternative method of screening compounds to determine whether they are isomerase substrates comprises:
  testing a compound for the ability to be converted by said isomerase,
  wherein said compound has been selected as having points of interaction with said isomerase, and
  wherein similar points of interaction have been determined between said isomerase and a substrate or product therefor.

In another embodiment, the present invention provides methods for screening for compounds that inhibit an isomerase comprising:
  a) determining the points of interaction between an isomerase and a substrate or product therefor;
  b) selecting compound(s) having similar interaction with said isomerase; and
  c) testing the selected compound for the ability to inhibit the activity of said isomerase.

An alternative method for screening for compounds that inhibit an isomerase comprises:
  a) selecting compound(s) having points of interaction with an isomerase, wherein similar points of interaction have been determined between said isomerase and a substrate or product therefor; and
  b) testing the selected compound for the ability to inhibit the activity of said isomerase.

Another alternative method for screening for compounds that inhibit an isomerase comprises:
  testing a compound for the ability to inhibit the activity of said isomerase,
  wherein said compound has been selected as having points of interaction with said isomerase, and
  wherein similar points of interaction have been determined between said isomerase and a substrate or product therefor.

The present invention also claims a compound identified by these methods and a composition comprising such a compound and an acceptable carrier therefor.

Although methods and materials similar or equivalent to those described herein can be used to practice the invention, suitable methods and materials are described below. All publications, patent applications, patents and other references mentioned herein are incorporated by reference in their entirety. The invention will now be described in greater detail by reference to the following non-limiting examples.

EXAMPLES

Expression, Mutagenesis, and Purification

Alfalfa CHI cDNA was PCR amplified and inserted into the pHIS8 expression vector (Jez et al., Biochemistry 39:890-902, 2000). The CHI Y106F mutant was generated with the QuikChange (Stratagene) PCR method. N-terminal His-tagged protein was expressed in *E. coli* BL21(DE3) cells. Tagged CHI was purified from sonicates using a $Ni^{2+}$-NTA (Qiagen) column. Thrombin digestion removed the histidine tag, and the protein was passed over a $Ni^{2+}$-NTA column. Digested CHI was depleted of thrombin using a benzamidine-Sepharose column. Gel filtration on a Superdex-75 (Pharmacia) FPLC column was the final purification step.

Enzyme Assays

CHI assays were performed at 25° C. in a 0.5 ml reaction volume containing 0.05 M Hepes (pH 7.5), 50 µM 6'-deoxychalcone, and 3% ethanol as co-solvent. Time-dependent decreases in 6'-deoxychalcone absorbance ($\lambda_{max}$=390 nm; $\epsilon$=29,400 $M^{-1}$ $cm^{-1}$) were monitored with a Beckman DU-640 spectrophotometer. Determination of steady-state kinetic constants used the standard assay system with varied concentrations of substrate (2-50 µM) following fitting to the Michaelis-Menton equation using Kaleidagraph (Abelbeck Software).

Crystallization, Structure Determination, and Refinement of the Native Structure Crystals of CHI were grown at 4° C. by vapor diffusion using the hanging drop method. A 2 µl drop containing a 1:1 mixture of 25 mg ml$^{-1}$ CHI and Crystallization buffer (25% glycerol, 1.8-2.0 M ammonium sulfate and 0.05 M PIPES, pH 6.5) yielded diffraction quality crystals within a few days at 4° C. Crystals grew in space group P6$_5$22 with unit cell dimensions of a=90.37 Å; c=352.86 Å with two molecules per asymmetric unit and a solvent content of 72%. Native CHI diffraction data (105 K) were collected at beamline 7-1 of the Stanford Synchrotron Radiation Source (SSRL 7-1) on a 30 cm MAR imaging plate system. For generation of heavy atom derivatives, CHI crystals were soaked in mother liquor with either 1.2 mM K$_2$OsCl$_6$ or 1 mM HgCl$_2$ for 12-16 hours. Heavy atom data (105 K) were collected at SSRL 9-1 on a 30 cm MAR imaging plate system. All images were indexed and integrated using DENZO and the reflections merged with SCALEPACK (Otwinowski, Z. & Minor, W., Methods Enzymol. 276:307-326, 1997). Data reduction was completed using programs from CCP4 (Collaborative Computational Project 4 (CCP4) Acta Crystallogr. D53:240-255, 1994) (See Table 3). Heavy atom sites were located with SOLVE (Terwilliger, T. C. & Berendzen, J. Acta Crystallogr. D55:849-861, 1999) Refinement of sites and location of additional sites used MLPHARE (Otwinowski, Z. ML-PHARE in Daresbary Study Weekend Proceedings (CCP4, SERC Daresbary Laboratory, Warrington, UK; 1991). SHARP was used for phase calculation and heavy atom refinement (de La Fortelle, E. & Bricogne, G. Methods Enzymol. 276:472-494, 1997). This set of experimental phases was improved and extended using solvent flipping with SOLOMON (Abrahams, J. P. & Leslie, A. G. W. Acta Crystallogr. D52:30-42, 1996). Model building was performed with O. CNS was used for refinement (Bringer, A. T. et al. Acta Crystallogr. D54:905-921, 1998). The initial model was subjected to simulated annealing, positional refinement, and group B-factor refinement with strict non-crystallographic symmetry maintained between both molecules in the asymmetric unit. In subsequent rounds of model building and refinement, non-crystallographic constraints were released and water molecules were added using CNS to yield the R-factors shown in Table 3. The final model included residues 4 to 215 of monomer A, residues 3 to 38 and 45 to 215 of monomer B. The quality of the CHI model was checked with PROCHECK (Laskowski, R. A., MacArthur, M. W., Moss, D. S., & Thornton, J. M. J. Appl. Crystallogr, 26:283-291, 1993). A total of 89.6% of the residues in CHI are in the most favored regions of the Ramachandran plot and 10.4% are in the additional allowed region.

Overall Structure

Expression of alfalfa CHI[15] in E. coli yielded active enzyme that was purified and crystallized. The overall structure of CHI resembles an upside-down bouquet that adopts an open-faced β-sandwich fold (FIGS. 1B and 1C). A large β-sheet (β3a-β3f) and a layer of α-helices (α1-α7) comprise the core structure with three short β-strands (β1a, β1b, β2) on the opposite side of the large β-sheet. A search of the Protein Data Bank using DALI revealed no other structurally homologous folds. In addition, a PSI-BLAST search of sequence databases showed that CHI-like sequences are currently found typically in plants and these sequences display no detectable homology with other proteins. These results imply that the CHI three-dimensional fold and enzymatic activity are typically found in the plant kingdom. Amino acid sequence comparison of CHIs from a variety of advanced land plants reveals high homology (49% to 82% amino acid sequence identity) with regions of conservation spread uniformly throughout the primary structure (FIG. 1D). Interestingly, there is conservation of residues spanning β3a, β3b, α4, and α6 in the three-dimensional structure among CHIs from different species. Notably, these structural elements form the active site on the protein surface.

Accumulating data suggests that co-localization of proteins in loosely associated macromolecular complexes is a fundamental component of cellular processes, including flavonoid biosynthesis. CHI and other flavonoid biosynthetic enzymes may associate to provide efficient channeling of substrates and products as shown recently in Arabidopsis thaliana. Although the three short β-strands (β1a, β1b, β2) on the backside of the CHI structure form a relatively flat surface that would be ideal for protein-protein interactions, both gel filtration and analytical ultracentrifugation experiments failed to detect association of alfalfa CHI and alfalfa chalcone synthase 2 in vitro.

TABLE 3

Crystallographic data, phasing, and refinement information

| | Native | K$_2$OsCl$_6$ | HgCl$_2$ | Naringenin |
|---|---|---|---|---|
| Wavelength (Å) | 1.08 | 0.98 | 0.98 | 0.95 |
| Resolution range (Å) | 38.1-2.50 | 78.0-3.24 | 76.0-3.26 | 46.7-1.85 |
| Observations | 86,781 | 44,070 | 39,193 | 697,121 |
| Unique reflections | 27,863 | 24,966 | 22,238 | 70,889 |
| Completeness[1] (%) | 90.7 (61.7) | 99.2 (99.6) | 95.8 (98.2) | 85.5 (60.6) |
| I/□[1] | 19.4 (2.0) | 9.3 (2.6) | 17.5 (7.4) | 28.0 (2.0) |
| $R_{sym}$[1,2] (%) | 5.4 (36.5) | 10.3 (31.2) | 5.8 (12.0) | 4.8 (45.4) |
| POP[3] (acentric/centric) | | 2.55/1.85 | 1.58/1.07 | |
| $R_{cullis}$[4] (iso/ano) | | 0.52/0.76 | 0.72/0.81 | |
| $R_{cryst}$[5]/$R_{free}$[6] (%) | 24.9/28.0 | | | 23.7/26.2 |
| Protein atoms | 3181 | | | 3222 |
| Water molecules | 94 | | | 382 |
| Ligand atoms[7] | | | | 40 nar/20 sul |
| R.m.s.d. bonds (Å) | 0.019 | | | 0.019 |
| R.m.s.d. angles (°) | 2.0 | | | 2.1 |
| average B-factor -- protein (Å$^2$) | 60.6 | | | 46.8 |
| average B-factor -- water (Å$^2$) | 62.7 | | | 50.1 |

[1]Number in parenthesis is for highest resolution shell;
[2]$R_{sym} = \Sigma|I_h - <I_h>|/\Sigma I_h$, where $<I_h>$ is the average intensity over symmetry equivalent reflections;
[3]Power of Phasing = $<|F_{H(calc)}/|E|>$, where $F_{H(calc)}$ is the calculated difference and E is the lack of closure;
[4]$R_{cullis} = \Sigma|E|/\Sigma|F_{PH} - F_P|$;
[5]R-factor = $\Sigma|F_{obs} - F_{calc}|/\Sigma F_{obs}$, where summation is over the data used for refinement;
[6]$R_{free}$-factor was calculated using 5% of data excluded from refinement;
[7]nar = naringenin and sul = sulfate.

Crystallization, Structure Determination, and Refinement of the CHI•Naringenin Complex Structure Crystals of the CHI•naringenin complex (P6₅22; a=89.47 Å; c=351.19 Å) (and other co-complexes) were grown as above from a crystallization buffer containing 2.5 mM (2S/2R)-naringenin and 5% ethanol. Data (105 K) were collected at SSRL 9-2 with a Quantum 4 CCD detector. Images were processed as above. Following rigid-body refinement with CNS, electron density resembling naringenin was observed in each monomer and modeled as such. In subsequent rounds of refinement and rebuilding, the R-factors converged to those listed in Table 3. The final model includes residues 4 to 215 of both monomers.

(2S)-Naringenin Binding and Reaction Stereoselectivity

The location of (2S)-naringenin in the CHI structure defines the active site (FIG. 2). Although a commercially obtained mixture of (2S)- and (2R)-naringenin was used for co-crystallisation, only the (2S)-isomer bound the CHI active site. The position of the (2S)-naringenin binding cleft is consistent with inactivation studies that suggested a cysteine residue (Cys 114 in alfalfa CHI) is proximal to the active site. In the CHI structure, Cys 114 is near the binding cleft but does not directly contact (2S)-naringenin. The active site cleft is largely apolar and consists of residues from β3a (Arg 36, Gly 37, Leu 38), β3b (Phe 47, Thr 48, Ile 50), α4 (Tyr 106, Lys 109, Val 110, Asn 113), and α6 (Thr 190, Met 191) (FIG. 2B). The apolar methylene carbons of Arg 36 are positioned by a restraining charge-charge interaction from the δ-guanido group to Glu 200. In addition, the methylene carbons of Lys 109 are fixed by a charge-charge interaction between the side chain amine and Glu 112. Except for Thr 190 and Met 191, the residues contacting (2S)-naringenin are identical among CHIs from different plants (FIG. 1D). Although van der Waals contacts dominate the interactions between CHI and (2,5)-naringenin, two hydrogen bond interactions exist. The first is mediated by the side chain hydroxyl moiety of Thr 48 bound to the 4'-hydroxyl group of (2S)-naringenin. The second interaction is between a water molecule and the ligand ketone (FIG. 2B). This water molecule and its connected network of hydrogen bonds occupy the same position in the apoenzyme structure. The overall surface topology of the cleft tightly sequesters the (2S)-naringenin molecule (FIG. 2C). The CHI•naringenin complex explains the stereochemical preference of the cyclization reaction; moreover, it suggests why CHIs from different species show moderate selectivity for chalcone and 6'-deoxychalcone as substrates.

Modeling of chalcone, based on the position of (2S)-naringenin, shows that a slight rotation of the trihydroxyl-ring outward in the direction of the active site opening places the 2'-hydroxyl group in position for nucleophilic attack on the α,β-unsaturated double bond of the coumaroyl moiety (FIG. 3A). This rotation preserves the position of the chalcone backbone and the hydrogen bonds between Thr 190 and the water molecule at the backside of the binding site. Formation of (2R)-naringenin would require substantial rearrangements in the active site of CHI due to significant steric clashes between the trihydroxyl-ring and CHI side chains. Although rotation of the trihydroxyl-ring away from the active site entrance could reposition the 2'-hydroxyl group for attack on the opposite face of the α,β-double bond, the side chain of Val 110 sterically prevents this movement from occurring (FIG. 3B). In addition, the opposite side of the substrate double bond could be positioned for attack by the 2'-hydroxyl group in the formation of (2R)-naringenin. This alternative cyclization would be accomplished by rotation of the coumaroyl moiety outward towards the solvent accessible active site entrance. However, Leu 38 and Lys 109 constrain the orientation of the coumaroyl moiety in the binding cleft. Architecturally, the CHI active site limits the substrate's available conformations to ensure stereospecific product formation.

Subtle variations in substrate preference reflected in the $K_m$ values for chalcone versus 6'-deoxychalcone exist between CHIs of different species. CHIs from legumes, such as alfalfa, prefer 6'-deoxychalcone as a substrate but the enzymes from non-legumes, like petunia, optimally use chalcone. The structure of the CHI•naringenin complex, viewed with reference to the amino acid sequences of different CHIs, suggests that Thr 190 and Met 191 may partially modulate substrate preference. In the CHIs from non-legumes, a serine and an isoleucine replace Thr 190 and Met 191, respectively. These two differences may better accommodate the 6'-hydroxyl moiety of chalcone due to a modest increase in active site volume in the vicinity of the trihydroxyl ring.

Catalytic Mechanism

CHI catalyzes an intramolecular reaction utilizing a substrate-derived nucleophile and a carbon-carbon double bond as a Michael acceptor. Two reaction mechanisms have been proposed for (2S)-naringenin formation by CHI. One involves nucleophilic catalysis by an active site residue that forms a covalent intermediate that is released after a $SN_2$ displacement by the 2'-O⁻ of chalcone. The other mechanism invokes general acid-base catalysis employing an enol intermediate. The structure of CHI clearly supports the latter mechanism.

Examination of the CHI•naringenin complex structure reveals a hydrogen bond network at the bottom of the binding cleft centered about the water molecule that contacts the ketone of (2S)-naringenin (FIGS. 4A and 4B). Of the five amino acids contributing to this network, only Thr 48 and Tyr 106 are conserved in all CHIs. The position of the water molecule between (2S)-naringenin and Tyr 106 suggests a reaction mechanism in which the tyrosine activates the water, allowing it to serve as a general acid in the cyclization reaction (FIG. 4C). In the proposed reaction mechanism, the 2-O⁻ ($pK_a$~7-8) forms in solution as suggested by studies on the spontaneous cyclization of chalcones. The negatively charged oxygen then attacks the carbon-carbon double bond utilizing a Michael addition with the water molecule at the backside of the active site acting as the general acid in the transient protonation of the intermediate enolate.

To test this reaction mechanism, Tyr 106 was substituted by phenylalanine and the properties of the mutant CHI compared to the wild-type enzyme. The kinetics for the cyclization of 6'-deoxychalcone by wild-type CHI ($k_{cat}$=4384 min⁻¹; $K_m$=25.7 μM; $k_{cat}/K_m$=1.71×10⁸ M⁻¹ min⁻¹) versus those of the reaction catalyzed by the CHI Y106F mutant ($k_{cat}$=69.0 min⁻¹; $K_m$=29.1 μM; $k_{cat}/K_m$=2.37×10⁶ M⁻¹ min⁻¹) demonstrate that the tyrosine residue contributes to the stabilization of the transition state. The 100-fold reduction in reaction rate is consistent with the decrease in rate associated with the loss of a general acid. However, the observed reaction rate with the mutant remains greater than that of the uncatalyzed cyclization reaction. It is suggested that the structural complementarity of the binding cleft to the transition state of the reaction contributes additional levels of catalytic rate enhancement.

A major contribution to rate enhancement in enzymatic reactions results from bringing substrates or reactive centers in the same molecule together in space. As described above, the topology of the binding cleft limits the flexibility of chalcone and eliminates catalytically unproductive orientations by spatially defining an optimal geometry for (2S)-naringenin formation. This effectively channels the ground state conformation of the substrate into a catalytically productive conformation. Together with contributions from general acid-base catalysis, shape complementarity between the CHI binding pocket and chalcone accelerates the cyclization of chalcone $10^7$-fold over the spontaneous reaction rate.

TABLE 4

Kinetic constants for wild-type and Y106F mutant CHI

| | $k_{cat}$ (min$^{-1}$) | $K_m$ (μM) | $k_{cat}/K_m$ (M$^{-1}$ min$^{-1}$) |
|---|---|---|---|
| CHI wild-type | 4384 ± 517 | 25.7 ± 5.4 | 1.71 × 10$^8$ |
| CHIY106F | 69.0 ± 5.1 | 29.1 ± 3.7 | 2.37 × 10$^6$ |

The three-dimensional structure of CHI, together with the structure of chalcone synthase, provides a useful template for engineering isomerases to develop, diversify and modify flavonoid biosynthetic pathways for crop and food sources, as well as providing novel flavanones for intermediates and leads in drug discovery. All figures were prepared with MOL-SCRIPT or GRASP and rendered with POV-Ray.

While the foregoing has been presented with reference to particular embodiments of the invention, it will be appreciated by those skilled in the art that changes in these embodiments may be made without departing from the principles and spirit of the invention, the scope of which is defined by the appended claims.

What is claimed is:

1. An isolated polypeptide comprising an amino acid sequence that has at least 85% amino acid sequence identity to the amino acid sequence set forth in SEQ ID NO:1,
wherein the isolated polypeptide has Met, Lys, Ala, His, or Gln at the position corresponding to amino acid 36 of SEQ ID NO:1, and
wherein the isolated polypeptide has chalcone isomerase enzymatic activity.

2. The isolated polypeptide of claim 1, wherein the amino acid located at the position corresponding to amino acid 36 of SEQ ID NO:1 is Met.

3. The isolated polypeptide of claim 1, wherein the amino acid located at the position corresponding to amino acid 36 of SEQ ID NO:1 is Ala.

4. The isolated polypeptide of claim 1, wherein the amino acid located at the position corresponding to amino acid 36 of SEQ ID NO:1 is His.

5. The isolated polypeptide of claim 1, wherein the amino acid located at the position corresponding to amino acid 36 of SEQ ID NO:1 is Gln.

6. The isolated polypeptide of claim 1, wherein the amino acid located at the position corresponding to amino acid 36 of SEQ ID NO:1 is Lys.

7. The isolated polypeptide of claim 1, wherein said polypeptide has at least 90% amino acid sequence identity to the amino acid sequence set forth in SEQ ID NO:1.

8. The isolated polypeptide of claim 1, wherein said polypeptide has at least 95% amino acid sequence identity to the amino acid sequence set forth in SEQ ID NO:1.

9. A crystal of an unliganded chalcone isomerase polypeptide, the crystal having the space group $P6_522$ and unit cell dimensions of a=90.37 Å and c=352.86 Å,
wherein the chalcone isomerase polypeptide has the amino acid sequence set forth in SEQ ID NO:1 with R at position 36, L at position 38, T at position 48, Y at position 106, K at position 109, V at position 110, N at position 113, T at position 190, and M at position 191, respectively, of SEQ ID NO:1.

10. A crystal of a chalcone isomerase polypeptide in complex with (2S)-naringenin, the crystal having the space group $P6_522$ and unit cell dimensions of a=89.47 Å and c=351.19 Å,
wherein the chalcone isomerase polypeptide has the amino acid sequence set forth in SEQ ID NO:1 with R at position 36, L at position 38, T at position 48, Y at position 106, K at position 109, V at position 110, N at position 113, T at position 190, and M at position 191, respectively, of SEQ ID NO:1.

* * * * *